US011892452B2

(12) United States Patent
Fong et al.

(10) Patent No.: US 11,892,452 B2
(45) Date of Patent: Feb. 6, 2024

(54) DISEASE-ASSOCIATED ANTIGENS AND METHODS OF USE THEREOF

(71) Applicant: The Regents of the University of California, Oakland, CA (US)

(72) Inventors: Lawrence H. Fong, Palo Alto, CA (US); Serena Kwek MacPhee, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 96 days.

(21) Appl. No.: 17/328,364

(22) Filed: May 24, 2021

(65) Prior Publication Data

US 2022/0099676 A1 Mar. 31, 2022

Related U.S. Application Data

(60) Continuation of application No. 15/954,324, filed on Apr. 16, 2018, now Pat. No. 11,016,093, which is a continuation of application No. 14/977,359, filed on Dec. 21, 2015, now Pat. No. 9,945,864, which is a division of application No. 13/124,922, filed as application No. PCT/US2009/062320 on Oct. 28, 2009, now abandoned.

(60) Provisional application No. 61/109,428, filed on Oct. 29, 2008.

(51) Int. Cl.
| | |
|---|---|
| C07K 14/705 | (2006.01) |
| C07K 16/30 | (2006.01) |
| G01N 33/564 | (2006.01) |
| A61P 35/00 | (2006.01) |
| A61P 37/04 | (2006.01) |
| G01N 33/574 | (2006.01) |
| A61K 39/395 | (2006.01) |
| C07K 14/47 | (2006.01) |
| A61K 39/00 | (2006.01) |

(52) U.S. Cl.
CPC .... *G01N 33/57434* (2013.01); *A61K 39/0011* (2013.01); *A61K 39/001193* (2018.08); *A61K 39/39558* (2013.01); *C07K 14/4748* (2013.01); *C07K 14/705* (2013.01); *C07K 16/30* (2013.01); *G01N 33/564* (2013.01); *C07K 2317/24* (2013.01); *G01N 2800/042* (2013.01); *G01N 2800/104* (2013.01); *G01N 2800/50* (2013.01); *G01N 2800/52* (2013.01); *Y02A 50/30* (2018.01)

(58) Field of Classification Search
CPC ......... G01N 33/57434; A61K 39/0011; A61K 39/001193; A61K 39/39558; C07K 14/4748; C07K 14/705; C07K 16/30

USPC ....................................................... 424/184.1
See application file for complete search history.

(56) References Cited

U.S. PATENT DOCUMENTS

| | | |
|---|---|---|
| 2002/0090372 A1 | 7/2002 | Xu et al. |
| 2003/0083481 A1 | 5/2003 | Birse et al. |
| 2003/0096327 A1 | 5/2003 | Magnani |
| 2004/0023242 A1 | 2/2004 | Yue et al. |
| 2005/0125852 A1 | 6/2005 | Caenepeel et al. |
| 2006/0194730 A1 | 8/2006 | Eisenhach et al. |
| 2007/0020687 A1 | 1/2007 | Cheng et al. |
| 2007/0083334 A1 | 4/2007 | Mintz et al. |
| 2007/0128633 A1 | 6/2007 | Zozulya et al. |
| 2008/0171061 A1 | 7/2008 | Nixon et al. |
| 2010/0247552 A1 | 9/2010 | Tonegawa et al. |
| 2010/0322896 A1 | 12/2010 | Hill et al. |

FOREIGN PATENT DOCUMENTS

| | | |
|---|---|---|
| WO | WO 2000/033870 | 6/2000 |
| WO | WO 200153793 | * 7/2001 |
| WO | WO 2002/079449 | 10/2002 |

OTHER PUBLICATIONS

Atwell, et al.; "A Novel Mode of Gleevec Binding is Revealed by the Structure of Spleen Tyrosine Kinase"; The Journal of Biological Chemistry; vol. 279, No. 53, pp. 55827-55832 (2004).
Eswaran, et al.; "Crystal Structures of the p21-Activated Kinases PAK4, PAK5, and PAK6 Reveal Catalytic Domain Plasticity of Active Group II PAKs"; Structure; vol. 15, pp. 201-2013 (Feb. 2007).
GenBank AAH35596.1; PAK6 protein [*Homo sapiens*]; 3 pages (Jan. 4, 2017).
Lampasona et al., "Antibodies to tissue transglutaminase C in Type I diabetes", Diabetologia 42:1195-1198 (1999).
Kaur et al.; "Increased PAK6 Expression in Prostate Cancer and Identification of PAK6 Associated Proteins"; The Prostate; vol. 68, pp. 1510-1516 (2008).
Kwek, et al.; "Diversity of Antigen-Specific Responses Induced In Vivo with CTLA-4 Blockade in Prostate Cancer Patients"; The Journal of Immunology; vol. 189, pp. 3759-3766 (2012).
Sada, et al.; "Structure and Function of Syk Protein-Tyrosine Kinase"; J. Biochem.; vol. 130, pp. 177-186 (2001).
Yang, et al.; "Androgen Receptor Specifically Interacts with a Novel p21-activated Kinase, PAK6*"; The Journal of Biological Chemistry; vol. 276, No. 18, pp. 15345-15353 (2001).

\* cited by examiner

*Primary Examiner* — Yan Xiao
(74) *Attorney, Agent, or Firm* — Mandar A. Joshi; Bozicevic, Field & Francis LLP

(57) ABSTRACT

The present disclosure provides synthetic antibodies specific for a disease-associated antigen, and methods of using the antibodies in disease therapy. The present disclosure further provides diagnostic assays involving detecting the presence and/or level in biological sample of an antibody specific for a disease-associated antigen.

14 Claims, 4 Drawing Sheets
Specification includes a Sequence Listing.

pr125 m3 400x
low grade tumor pr328-T 400x
high grade tumor

Patient 20 400x
tumor biopsy zs06-6327 200x
tumor region zs06-6327 200x
benign region Patient 24 200x
tumor biopsy p801-4 200x
tumor region p801-4 200x
benign region zs06-4762 200x
tumor and benign region

DISEASE-ASSOCIATED ANTIGENS AND METHODS OF USE THEREOF

CROSS-REFERENCE

This application is a continuation of U.S. patent application Ser. No. 15/954,324, filed, Apr. 16, 2018, now U.S. Pat. No. 11,016,093, which is a continuation of U.S. patent application Ser. No. 14/977,359, filed Dec. 21, 2015, no U.S. Pat. No. 9,945,864, which is a divisional of U.S. patent application Ser. No. 13/124,922, filed Jun. 29, 2011, which is a national stage filing under 35 U.S.C. § 371 of PCT/US2009/062320, filed Oct. 28, 2009, which claims the benefit of U.S. Provisional Patent Application No. 61/109,428, filed Oct. 29, 2008, each of which applications is incorporated herein by reference in its entirety.

STATEMENT REGARDING FEDERALLY SPONSORED RESEARCH

The U.S. government has certain rights in this invention, pursuant to grant nos. R01 CA 102303 and U19 AI056388 awarded by the National Institutes of Health.

BACKGROUND

Worldwide, prostate cancer is the fourth most prevalent cancer in men. In North America and Northern Europe, it is by far the most common cancer in males and is the second leading cause of cancer death in men. In the United States alone, well over 30.000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

Systemic lupus erythematosus (SLE) is an autoimmune disease that can affect many different tissues. The diagnosis and assessment of this disease relics primarily on clinical findings including the scoring of manifestations according to the SLE disease activity index (SLEDAI). Aside from the presence of an array of clinical symptoms, the only widely used biological assay to diagnose lupus involves detecting auto-antibodies to nuclear components of cells such as to dsDNA and ribonucleoproteins, which is not completely reliable. Type 1 insulin dependent diabetes mellitus is a chronic metabolic syndrome with an autoimmune component. Current diagnostic methods are based primarily on the detection of hyperglycemia and related conditions which develop as a result of significant damage to beta islet cells. There is a need in the art for new approaches to the diagnosis and assessment of autoimmune diseases such as SLE and type 1 insulin dependent diabetes mellitus.

SUMMARY OF THE INVENTION

The present disclosure provides synthetic antibodies specific for a disease-associated antigen, and methods of using the antibodies in disease therapy. The present disclosure further provides diagnostic assays involving detecting the presence and/or level in biological sample of an antibody specific for a disease-associated antigen.

DEFINITIONS

Figure 1:
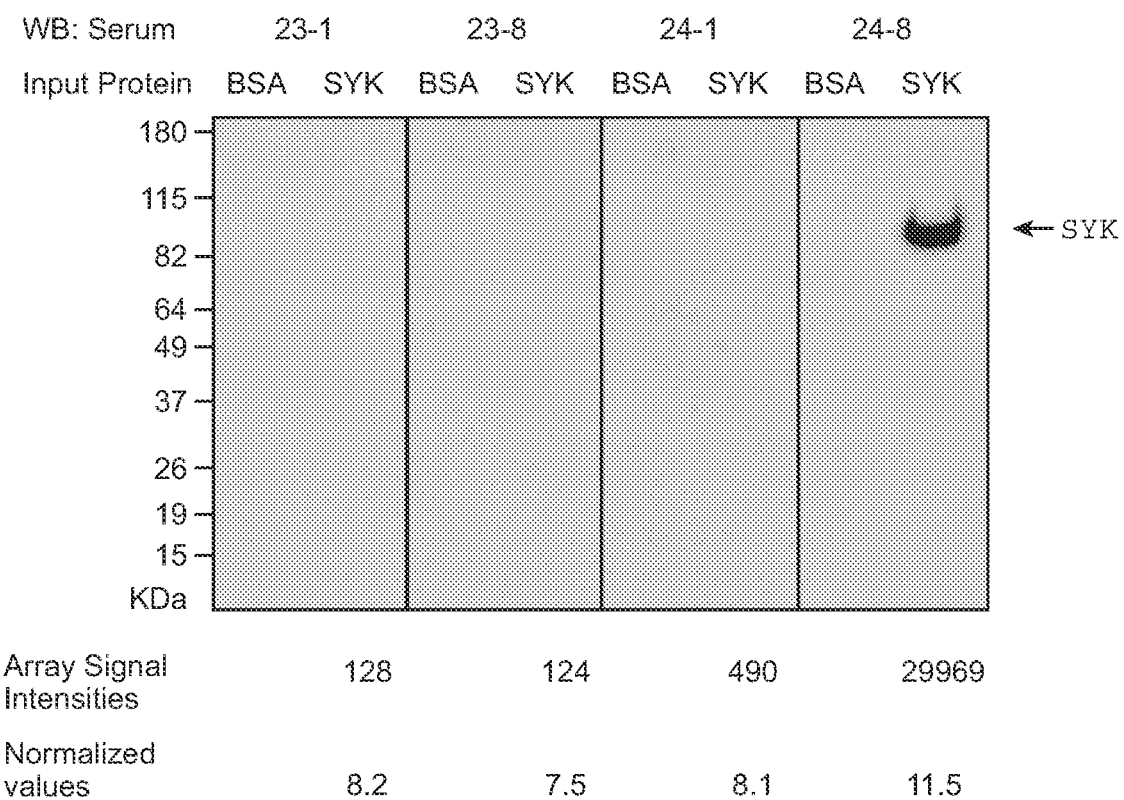
FIG. 1 shows the results of a western blot assay designed to validate an exemplary target antigen.
Figure 2A:
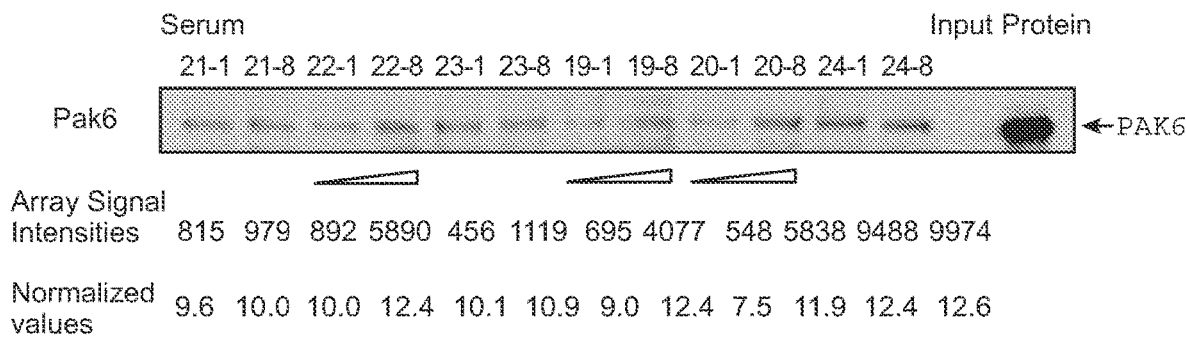
FIGS. 2A-D show the results of immunoprecipitation assays designed to validate exemplary target antigens.
Figure 2B:
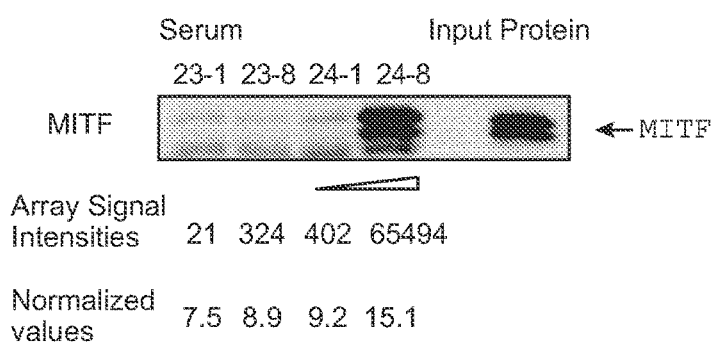
Figure 2C:
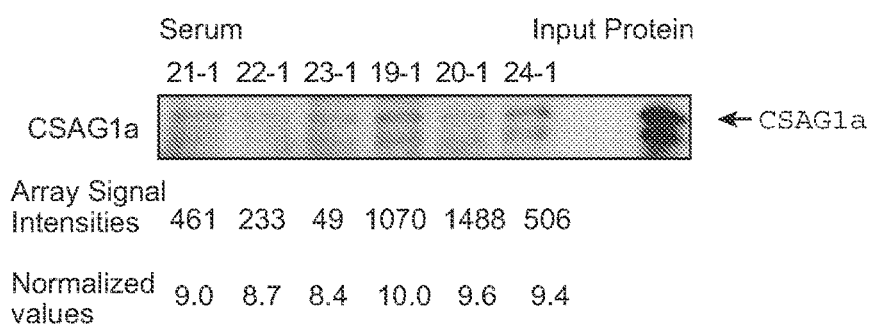
Figure 2D:
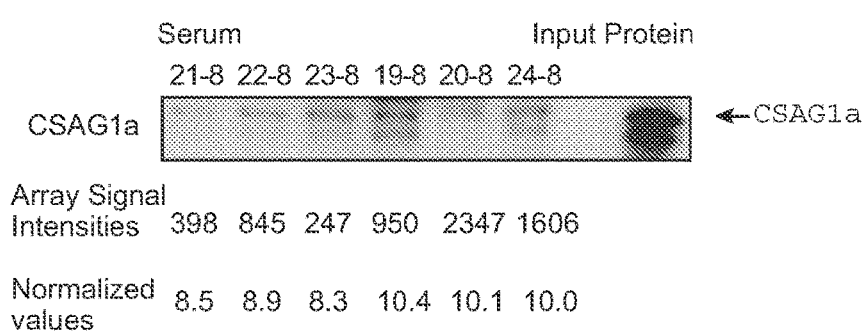

As used herein, a "biological sample" encompasses a variety of sample types obtained from an individual and can be used in a diagnostic or monitoring assay. The term "biological sample" encompasses blood and other liquid samples of biological origin, solid tissue samples such as a biopsy specimen or tissue cultures or cells derived therefrom and the progeny thereof. The term "biological sample" also includes samples that have been manipulated in any way after their procurement, such as by treatment with reagents; washed; or enrichment for certain cell populations, such as $CD4^+$ T lymphocytes. $CD8^+$ T lymphocytes, glial cells, macrophages, tumor cells, peripheral blood mononuclear cells (PBMC), cancer cells, and the like. The term "biological sample" encompasses a clinical sample, and also includes cells in culture, cell supernatants, tissue samples, organs, bone marrow, blood, plasma, serum, cerebrospinal fluid, and the like.

The terms "polypeptide," "peptide," and "protein." used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, J. Biol. Chem., 243 (1969), 3552-59 is used.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like. The term "fluorescer" refers to a substance or a portion thereof which is capable of exhibiting fluorescence in the detectable range.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art. An isolated polypeptide will in some embodiments be purified.

By "purified" is meant a compound of interest (e.g., a polypeptide) has been separated from components that accompany it in nature. "Purified" can also be used to refer to a compound of interest (e.g., a polypeptide) separated from components that can accompany it during manufacture (e.g., in chemical synthesis). In some embodiments, a compound (e.g., a polypeptide) is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. Thus, e.g., a subject polypeptide that is "purified" is present in a composition where the polypeptide is present in an amount of at least 75%, at least 90%, at least 95%, or at least 99%, by weight, of the composition. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, high performance liquid chromatography analysis, etc.

An "antigen" is a term that is well understood in the art, and includes any substance that may be specifically bound by an antigen-binding site of an antibody molecule or a T cell receptor. An "immunogen" is an antigen that is capable of initiating lymphocyte activation resulting in an antigen-specific immune response.

By "epitope" is meant a site on an antigen to which specific B cells and/or T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments of the polymer that are discontinuous in the linear sequence but are continuous in the folded conformation(s). Epitopes that are composed of single segments of biopolymers or other molecules are termed continuous or linear epitopes. T cell epitopes are generally linear peptides. Antibodies that recognize the same epitope can be identified in a simple immunoassay showing the ability of one antibody to block the binding of another antibody to a target antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts The monoclonal antibodies included within the scope of the invention include hybrid and recombinant antibodies (e.g. "humanized" antibodies) regardless of species of origin or immunoglobulin class or subclass designation, as well as antibody fragments (e.g., Fab, F(ab')$_2$, and Fv), so long as they are capable of binding specifically to a target antigen as described herein. Cabilly, et al., U.S. Pat. No. 4,816,567; Mage & Lamoyi, in Monoclonal Antibody Production Techniques and Applications, pp. 79-97 (Marcel Dekker, Inc., New York, 1987).

Thus, the modifier "monoclonal" indicates the character of the antibody as being obtained from such a substantially homogeneous population of antibodies, and is not to be construed as requiring production of the antibody by any particular method. For example, a monoclonal antibody can be made using the hybridoma method first described by Kohler & Milstein, Nature 256:495 (1975), or may be made by recombinant DNA methods. Cabilly, et al., U.S. Pat. No. 4,816,567.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cells of interest for treatment in the present application include precancerous, malignant, pre-metastatic, metastatic, and non-metastatic cells, as well as carcinoma in situ.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

The terms "subject," "individual," "host," and "patient" are used interchangeably herein to refer to a mammal, including, but not limited to, murines (rats, mice), felines, non-human primates (e.g., simians), humans, canines, ungulates, etc.

The terms "treatment." "treating." "treat." and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

As used herein in the context of patient response to treatment with an immunomodulatory treatment regimen, the terms "beneficial response," "beneficial patient response," and "clinically beneficial response," "clinical benefit," and the like, are used interchangeably and include partial response (PR), complete response (CR), and stabilization of disease (SD).

Beneficial response to treatment with an immunomodulatory treatment regimen can be assessed according to whether an individual patient experiences a desirable change in disease status. Examples of desirable change in disease status in cancer include loss of detectable tumor (complete response. CR), decrease in tumor size and/or cancer cell number (partial response, PR), and tumor growth arrest (stable disease, SD). Continued increase in tumor size and/or cancer cell number and/or tumor metastasis is indicative of lack of beneficial response to treatment.

As used herein, in the context of prostate cancer, the term "responder" refers to a patient who has prostate cancer, and who exhibits a beneficial clinical response following treatment with an immunomodulatory treatment regimen.

As used herein, in the context of prostate cancer, the term "non-responder" refers to a patient who has prostate cancer, and who has not shown a beneficial response following treatment with an immunomodulatory treatment regimen.

As used herein, the term "correlates." or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The term "substantially similar" as used in the context of nucleic acid or amino acid sequence identity refers to two or more sequences which have at least about 50%, at least about 60%, at least about 70%, at least about 75%, at least about 80%, at least about 85%, at least about 90%, at least about 95%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory (EMBL). This tool is accessible at the website located by placing "www." in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antigen" includes a plurality of such antigens and reference to "the antibody" includes reference to one or more antibodies and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides synthetic antibodies specific for a disease-associated antigen, and methods of using the antibodies in disease therapy. The present disclosure further provides diagnostic assays involving detecting the presence and/or level in biological sample of an antibody specific for a disease-associated antigen. The present disclosure further provides immunogenic compositions comprising disease-associated antigens.

Prostate Cancer Antigens

The present disclosure relates to the observation that individuals who exhibit a clinically beneficial response to an immunomodulatory treatment for prostate cancer can mount an immune response to one or more antigens associated with prostate cancer cells. Identification of the antigens that are the target of such an immune response allows the development of a diagnostic method for determining the likelihood that an individual who has been diagnosed with prostate cancer will exhibit a clinically beneficial response to treatment with an immunomodulatory treatment regimen. Identification of the target antigens also provides for the development of immunogenic compositions comprising a target antigen or a variant or fragment of a target antigen, where administration of such an immunogenic composition to an individual, who has prostate cancer and who has been determined to be less likely to respond to treatment with an immunomodulatory treatment regimen, increases the likelihood that the individual will respond to treatment with an immunomodulatory treatment regimen. Furthermore, identification of target antigens allows generation of therapeutic antibodies for the treatment of prostate cancer.

Target antigens that are the target of an immune response generated in an individual who has prostate cancer and who has exhibited a clinically beneficial response to treatment with an immunomodulatory treatment regimen are also referred to herein as "response indicator antigens" or "prostate cancer-associated target antigens." Antibodies generated in an individual in response to such antigens are referred to herein as "response indicator antibodies" or "prostate cancer-associated response indicator antibodies."

Target antigens are useful in diagnostic assays, as described below, to detect an antibody response in a prostate cancer patient undergoing treatment, e.g., to determine likelihood of beneficial clinical response to treatment with an immunomodulatory treatment regimen. Target antigens are also useful in diagnostic assays, as described below, to detect an antibody response in a prostate cancer patient who has not yet undergone treatment for the prostate cancer, e.g., to determine likelihood of beneficial clinical response to treatment with an immunomodulatory treatment regimen. Target antigens are also useful in immunogenic compositions, to induce an immune response to the target antigen, e.g., in an individual who is determined to be less likely to respond to treatment with an immunomodulatory treatment regimen.

Target antigens are also useful for generating therapeutic antibodies, which antibodies are useful for treating prostate cancer.

Immunomodulatory Treatment Regimen

The present disclosure provides methods of assessing the likelihood that a patient having prostate cancer will exhibit a beneficial response to treatment with an immunomodulatory treatment regimen. Patients subject to such an assessment include: 1) patients who have prostate cancer and who have been treated with an immunomodulatory treatment regimen, where treatment with the immunomodulatory treatment regimen was prescribed as a treatment for the prostate cancer; 2) patients who have prostate cancer, who failed treatment with an agent other than an immunomodulatory treatment regimen, and who have begun treatment with an immunomodulatory treatment regimen (e.g., patients with metastatic hormone-refractory prostate cancer); and 3) prostate cancer patient who have not yet received any treatment for the prostate cancer, including prostate cancer patients at any stage of the disease.

In some embodiments, a patient who is being assessed using a subject method is one who is being treated with an immunomodulatory treatment regimen for prostate cancer. Immunomodulatory treatment regimens for the treatment of prostate cancer include any treatment for prostate cancer that modulates an immune response in the individual, e.g., an immune response to a prostate cancer cell. Immunomodulatory treatment regimens include, e.g., hormone therapy, radiation therapy, and immunomodulatory agent therapy.

Hormone therapy for prostate cancer has been reported to have an immunomodulatory effect. See, e.g., Nesslinger et al. (2007) *Clin. Cancer Res.* 13:1493; and Mercader et al. (2001) *Proc. Natl. Acad. Sci USA* 98:14565. Hormone therapy for prostate cancer includes, e.g., luteinizing hormone releasing hormone (LHRH) agonists (e.g., leuprolide (Eligard, Lupron, Viadur); goserelin (Zoladex), triptorelin (Trelstar), etc.); and anti-androgens (e.g., bicalutamide (Casodex), flutamide (Eulexin), nilutamide (Nilandron), etc.).

Immunomodulatory agents for the treatment of prostate cancer include, but are not limited to, an antibody, e.g., anti-CTLA4 (Ipilimumab), CYT 356 (Deb et al. (1996) *Clin Cancer Res* 2: 1289-97), CC49 (see, e.g., Agnese et al. (2004) *Annals Surg. Oncol.* 11:197), C225 (Cetuximab), MT201 (adecatumumab), MLN2704 (anti-PSMA), anti-Ox40 antibody, etc.; a cytokine, e.g., granulocyte-macrophage colony stimulating factor (GM-CSF); and the like. In some embodiments, the antibody is specific for a prostate cancer antigen or epitope, e.g., prostate-specific membrane antigen (PSMA); see, e.g., U.S. Pat. No. 6,107,090. In other embodiments, the antibody is specific for an Ep-CAM (CD326) antigen.

In some embodiments, "an immunomodulatory treatment regimen" includes treatment with two or more agents, one or more of which is an immunomodulatory agent. For example, in some embodiments, "treatment with an immunomodulatory agent" includes treatment with an anti-CTLA4 antibody and GM-CSF. For example, in some embodiments, "treatment with an immunomodulatory agent" includes treatment with an antibody for the treatment of prostate cancer, and a small molecule anti-cancer chemotherapeutic agent. In some embodiments, "an immunomodulatory treatment regimen" includes a combination of radiation therapy and hormone therapy. In some embodiments, "an immunomodulatory treatment regimen" includes a combination of radiation therapy and treatment with one or more immunomodulatory agents. In some embodiments, "an immunomodulatory treatment regimen" includes a combination of hormone therapy and treatment with one or more immunomodulatory agents.

Antigens

Target antigens that are the target of an immune response generated in an individual who has prostate cancer and who has exhibited a clinically beneficial response to treatment with an immunomodulatory treatment regimen include, but are not limited to, those shown in Table 1, below.

TABLE 1

| Name | GenBank Accession No. |
|---|---|
| NTRK3 | NM_002530 |
| AURKB | NM_004217 |
| PLK3 | NM_004073 |
| MPG | BC014991 |
| NEK2 | NM_002497 |
| SNURF | NM_005678 |
| ACLY | BC006195 |
| CaMKIId | NM_001221 |
| PAK6 | NM_020168 |
| CSNK1D | NM_001893 |
| CSNK1G2 (CK1g2) | NM_001319 |
| SMTNL2 | NM_198501 |
| MARK4 | NM_031417 |
| GTSF1 | NM_144594 |
| MLLT6/ AF-7 | BC064612 |
| RET | NM_020630 |
| CSAG1a | BG059947 |
| WAC | B010356 |
| TMEPAI | NM_0201182 |
| AKT2 | NM_001626 |
| AIF1 | NM_001623 |
| AFF4 | BC025700 |
| CDK9 | NM_001240 |
| TPRXL | BC027729 |
| STK22B | NM_053006 |
| NUAK1 | NM_014840 |
| MARK2 | NM_001039468 |
| AXL | NM_001699 |
| CDK1 | NM_001786 |
| G3BP1 | NM_198395 |
| MPG | BC014991 |
| SLAIN | BC031691 |
| PPID | NM_005038 |
| C3orf37 | BC010125 |
| MAPK13 | NM_002754 |
| IKBIP | NM_201613 |
| KIR3DX1 | BC033195 |
| LMCD1 | NM_014583 |
| C1orf116 | NM_023938.4 |
| GSK3B | NM_002093 |
| sulfatase 1 | BC012997.2 |
| MRPL19 | NM_014763 |
| MITF | BC011461 |
| C15orf38 | BC053602 |
| HN1 | NM_016185 |
| DCAMKL2 | NM_152619 |
| SYK | NM_003177 |
| MGC11082 | NM_032691 |
| CAMK2N2 | NM_033259 |
| AMMECR1L | NM_031445 |
| UBE2V1 | BC000468 |
| ZNF434 | BC002859 |
| IKIP | NM_201613 |
| AKT1 | BC000479 |
| CAMKIIN1 | NM_018584 |
| AXL | NM_001699 |
| AURKA | NM_003600 |
| KIT | NM_000222 |
| CSNK1G1 | NM_022048 |
| CSNK1E | NM_001894 |
| CCNT1 | NM_001240 |
| PAK4 | NM_005884 |
| C19orf57 | BC012945.1 |

TABLE 1-continued

| Name | GenBank Accession No. |
|---|---|
| Tox2 | NM_032883.1 |
| ASPSCR1 | BC018722.1 |
| GSK3A | NM_019884 |
| RSK1 | NM_001006665 |
| FGF21 | BC018404.1 |
| RIPPLY1 | NM_138382 |
| ALDH7A1 | NM_001182.2 |
| UBXN10 | NM_152376.2 |
| CAMK2B | NM_001220 |
| BAG5 | BC050551.1 |
| FAM129A | NM_052966 |
| cortactin (CTTN) | NM_138565.1 |
| ErbB2 (HER2) | NM_001005862 |
| TPM1 | BC053545.1 |
| ANKS6 | BC064367.1 |
| ITGA6 | NM_000210.1 |
| TCEAL2 | NM_080390.3 |
| IGKV1-5 | BC030814.1 |
| TPM2 | BC011776.1 |

The present disclosure provides an isolated target antigen, antigenic fragments of a target antigen, and variants of a target antigen. In some embodiments, a subject target antigen is synthetic, e.g., a subject synthetic target antigen is synthesized chemically in a laboratory.

In some embodiments, a subject target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of the following GenBank Accession Numbers: NM_002530, NM_004217, NM_004073, BC014991, NM_002497, NM_005678, BC006195, NM_001221, NM_020168, NM_001893, NM_001319, NM_198501, NM_031417, NM_144594, BC064612. NM_020630, BC059947, B010356, NM_0201182, NM_001626, NM_001623, NM_014763, BC011461, BC053602, NM_016185, NM_152619, NM_003177, NM_032691, NM_033259, NM_031445, BC000468, BC002859, NM_201613, BC000479, NM_018584, NM_001699, NM_003600, NM_000222, NM_022048, NM_001894, NM_001240, NM_005884, BC025700, NM_001240, BC027729, NM_053006, NM_014840, NM_001039468, NM_001699, NM_001786, NM_198395, BC014991, BC031691, NM_005038, BC010125, NM_002754, NM_201613, BC033195, NM_014583, NM_023938.4, NM_002093, BC012997.2, BC012945.1, NM_032883.1, BC018722.1, NM_019884, NM_001006665, BC018404.1, NM_138382, NM_001182.2, NM_152376.2, NM_001220, BC050551.1, NM_052966, NM_138565.1, NM_001005862, BC053545.1, BC064367.1, NM_000210.1, NM_080390.3, BC030814.1, and BC011776.1.

In some embodiments, a subject target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NOs:1-42 and 108-147.

For example, in some embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 50) aa, from about 500 aa to about 750 aa, from about 750 aa to about 800 aa, or from about 800 aa to about 825 aa, of the amino acid sequence set forth in SEQ ID NO:1 (NTRK3). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 750 aa, from about 750 aa to about 800 aa, or from about 800 aa to about 825 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 344 aa, of the amino acid sequence set forth in SEQ ID NO:2 (AURKB). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 au to about 250 aa, from about 250 aa to about 3M) aa, or from about 300 aa to about 344 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 646 aa, of the amino acid sequence set forth in SEQ ID NO:3 (PLK3). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 646 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 293 aa, of the amino acid sequence set forth in SEQ ID NO:4 (MPG). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 293 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 445 aa, of the amino acid sequence set forth in SEQ ID NO:5 (NKE2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 445 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, or from about 50 aa to about 71 aa, of the amino acid sequence set forth in SEQ ID NO:6 (SNURF). In some of these embodiments, the target antigen will have a length of from about 5 aa to about 10 aa, from about 10 aa to about 25 aa, from about 25 aa to about 50 aa, or from about 50 aa to about 71 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, from about 900 aa to about 1000 aa, or from about 1000 aa to about 1101 aa, of the amino acid sequence set forth in SEQ ID NO:7 (ACLY). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, from about 900 aa to about 1000 aa, or from about 1000 aa to about 1101 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 499 aa, of the amino acid sequence set forth in SEQ ID NO:8 (CaMKIId). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 499 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, or from about 600 aa to about 681 aa, of the amino acid sequence set forth in SEQ ID NO:9 (PAK6). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, or from about 600 aa to about 681 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 415 aa, of the amino acid sequence set forth in SEQ ID NO:10 (CSNK1D). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 415 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 415 aa, of the amino acid sequence set forth in SEQ ID NO: 11 (CSNK1G2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 415 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 317 aa, of the amino acid sequence set forth in SEQ ID NO:12 (SMTNL2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 317 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 317 aa, of the amino acid sequence set forth in SEQ ID NO:13 (MARK4). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa; from about 400 aa to about 500 aa, from about 500 aa to about 600 aa, or from about 600 aa to about 688 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, or from about 150 aa to about 167 aa, of the amino acid sequence set forth in SEQ ID NO:14 (GTSF1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, or from about 150 aa to about 167 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 325 aa, of the amino acid sequence set forth in SEQ ID NO:15 (MLLT6/AF-7). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 325 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, from about 900 aa to about 1000 aa, or from about 1000 aa to about 1072 aa, of the amino acid sequence set forth in SEQ ID NO:16 (RET). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, from about 900 aa to about 1000 aa, or from about 1000 aa to about 1072 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 75 aa, or from about 75 aa to about 78 aa, of the amino acid sequence set forth in SEQ ID NO:17 (CSAG1a). In some of these embodiments, the target antigen will have a length of from about 5 aa to about 10 aa, from about 10 aa to about 25 aa, from about 25 aa to about 50 aa, from about 50 aa to about 75 aa, or from about 75 aa to about 78 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 210 aa, of the amino acid sequence set forth in SEQ ID NO:18 (WAC). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 210 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 287 aa, of the amino acid sequence set forth in SEQ ID NO:19 (TMEPAI). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 287 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa from about 300 aa to about 400 aa, or from about 400 aa to about 481 aa, of the amino acid sequence set forth in SEQ ID NO:20 (AKT2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, or from about 400 aa to about 481 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, or from about 100 aa to about 147 aa, of the amino acid sequence set forth in SEQ ID NO:21 (AIF1). In some of these embodiments, the target antigen will have a length of from about 5 aa to about 10 aa, from about 10 aa to about 25 aa, from about 25 aa to about 50 aa, from about 50 aa to about 100 aa, or from about 100 aa to about 147 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 292, of the amino acid sequence set forth in SEQ ID NO:22 (MRPL19). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 292.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 15 aa, from about 15 aa to about 20 aa, or from about 20 aa to about 23 aa, of the amino acid sequence set forth in SEQ ID NO:23 (MITF). In some of these embodiments, the target antigen will have a length of from about 5 aa to about 10 aa, from about 10 aa to about 15 aa, from about 15 aa to about 20 aa, or from about 20 aa to about 23 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 226 aa, of the amino acid sequence set forth in SEQ ID NO:24 (C15orf38). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 226 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, or from about 150 aa to about 154 aa, of the amino acid sequence set forth in SEQ ID NO:25 (HN1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, or from about 150 aa to about 154 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa; from about 500 aa to about 600 aa, or from about 600 aa to about 695 aa, of the amino acid sequence set forth in SEQ ID NO:26 (DCAMKL2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa; from about 500 aa to about 600 aa, or from about 600 aa to about 695 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa; from about 500 aa to about 600 aa, or from about 600 aa to about 635 aa, of the amino acid sequence set forth in SEQ ID NO:27 (SYK). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa; from about 500 aa to about 600 aa, or from about 600 aa to about 635 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 75 aa, or from about 75 aa to about 88 aa, of the amino acid sequence set forth in SEQ ID NO:28 (MGC11082). In some of these embodiments, the target antigen will have a length of from about 5 aa to about 10 aa, from about 10 aa to about 25 aa, from about 25 aa to about 50 aa, from about 50 aa to about 75 aa, or from about 75 aa to about 88 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 75 aa, or from about 75 aa to about 79 aa, of the amino acid sequence set forth in SEQ ID NO:29 (CAMK2N2). In some of these embodiments, the target antigen will have a length of from about 5 aa to about 10 aa, from about 10 aa to about 25 aa, from about 25 aa to about 50 aa, from about 50 aa to about 75 aa, or from about 75 aa to about 79 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, or from about 300 aa to about 310 aa, of the amino acid sequence set forth in SEQ ID NO:30 (AMMECR1L). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, or from about 300 aa to about 310 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, or from about 100 aa to about 147 aa, of the amino acid sequence set forth in SEQ ID NO:31 (UBE2V1). In some of these embodiments, the target antigen will have a length of from about 5 aa to about 10 aa, from about 10 aa to about 25 aa, from about 25 aa to about 50 aa, from about 50 aa to about 100 aa, or from about 100 aa to about 147 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 256 aa, of the amino acid sequence set forth in SEQ ID NO:32 (ZNF434). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 256 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 60 aa, or from about 60 aa to about 70 aa, of the amino acid sequence set forth in SEQ ID NO:33 (IKIP). In some of these embodiments, the target antigen will have a length of from about 5 aa to about 10 aa, from about 10 aa to about 25 aa, from about 25 aa to about 50 aa, from about 50 aa to about 60 aa, or from about 60 aa to about 70 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, or from about 400 aa to about 480 aa, of the amino acid sequence set forth in SEQ ID NO:34 (AKT1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, or from about 400 aa to about 480 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 60 aa, from about 60 aa to about 70 aa, or from about 70 aa to about 78 aa, of the amino acid sequence set forth in SEQ ID NO:35 (CAMKIIN1). In some of these embodiments, the target antigen will have a length of from about 5 aa to about 10 aa, from about 10 aa to about 25 aa, from about 25 aa to about 50 aa, from about 50 aa to about 60 aa, from about 60 aa to about 70 aa, or from about 70 aa to about 78 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, from about 500 aa to about 600 aa, from about 600 aa to about 700 aa, from about 700 aa to about 800 aa, or from about 800 aa to about 885 aa, of the amino acid sequence set forth in SEQ ID NO:36 (AXL). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, from about 500 aa to about 600 aa, from about 600 aa to about 700 aa, from about 700 aa to about 800 aa, or from about 800 aa to about 885 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, or from about 300 aa to about 403 aa, of the amino acid sequence set forth in SEQ ID NO:37 (AURKA). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, or from about 300 aa to about 403 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, or from about 900 aa to about 976 aa, of the amino acid sequence set forth in SEQ ID NO:38 (KIT). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, or from about 900 aa to about 976 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 20 aa to about 300 aa, from about 300 aa to about 400 aa, or from about 400 aa to about 422 aa, of the amino acid sequence set forth in SEQ ID NO:39 (CSNK1G1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, or from about 400 aa to about 422 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, or from about 400 aa to about 416 aa, of the amino acid sequence set forth in SEQ ID NO:40 (CSNK1E). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, or from about 400 aa to about 416 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, from about 500 aa to about 600 aa, from about 600 aa to about 700 aa, or from about 700 aa to about 726 aa, of the amino acid sequence set forth in SEQ ID NO:41 (CCNT1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, from about 500 aa to about 600 aa, from about 600 aa to about 700 aa, or from about 700 aa to about 726 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, or from about 500 aa to about 591 aa, of the amino acid sequence set forth in SEQ ID NO:42 (PAK4). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 300 aa, from about 300 aa to about 400 aa, from about 400 aa to about 500 aa, or from about 500 aa to about 591 aa.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 365 aa, of the amino acid sequence set forth in SEQ ID NO: 108 (AFF4). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 365 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, or from about 600 aa to about 726 aa of the amino acid sequence set forth in SEQ ID NO: 109 (CDK9). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, or from about 600 aa to about 726 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 258 aa of the amino acid sequence set forth in SEQ ID NO: 110 (TPRXL). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 258 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 358 aa, of the amino acid sequence set forth in SEQ ID NO: 111 (STK22B). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 358 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 661 aa, of the amino acid sequence set forth in SEQ ID NO: 112 (NUAK1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 661 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600, from about 600 aa to about 700 aa, or from about 700 aa to about 724 aa, of the amino acid sequence set forth in SEQ ID NO: 113 (MARK2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600, from about 600 aa to about 700, or from about 700 to about 724 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 700 aa, from about 700 aa to about 800 aa, or from about 800 aa to about 885 aa, of the amino acid sequence set forth in SEQ ID NO: 114 (AXL). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 700 aa, from about 700 aa to about 800 aa, or from about 800 aa to about 885 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 297 aa, of the amino acid sequence set forth in SEQ ID NO: 115 (CDK1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 297 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 466 aa, of the amino acid sequence set forth in SEQ ID NO: 116 (G3BP1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 466 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 298 aa, of the amino acid sequence set forth in SEQ ID NO: 117 (MPG). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 298 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 581 aa, of the amino acid sequence set forth in SEQ ID NO: 118 (SLAIN). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 581 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 370 aa, of the amino acid sequence set forth in SEQ ID NO: 119 (PPID). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 370 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 354 aa, of the amino acid sequence set forth in SEQ ID NO: 120 (C3orf37). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 354 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 365 aa, of the amino acid sequence set forth in SEQ ID NO: 121 (MAPK13). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 365 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, or from about 50 aa to about 77 aa, of the amino acid sequence set forth in SEQ ID NO: 122 (IKBIP). In some of these embodiments, the target antigen will have a length of from about 5 aa to about 10 aa, from about 10 aa to about 25 aa, from about 25 aa to about 50 aa, or from about 50 aa to about 77 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 352 aa, of the amino acid sequence set forth in SEQ ID NO: 123 (KIR3DX1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 352 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 365 aa, of the amino acid sequence set forth in SEQ ID NO: 124 (LMCD1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 365 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 601 aa, of the amino acid sequence set forth in SEQ ID NO: 125 (C1orf116). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 601 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 433 aa, of the amino acid sequence set forth in SEQ ID NO: 126 (GSK3B). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400, or from about 400 aa to about 433 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, or from about 25 aa to about 44 aa, of the amino acid sequence set forth in SEQ ID NO: 127 (sulfatase 1). In some of these embodiments, the target antigen will have a length of from about 5 aa to about 10 aa, from about 10 aa to about 25 aa, or from about 25 aa to about 44 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 546 aa, of the amino acid sequence set forth in SEQ ID NO: 128 (C19orf57). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 546 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 553 aa, of the amino acid sequence set forth in SEQ ID NO: 129 (Tox2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400, or from about 400 aa to about 553 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 553 aa, of the amino acid sequence set forth in SEQ ID NO: 130 (ASPSCR1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 553 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or about 400 aa to about 483 aa, of the amino acid sequence set forth in SEQ ID NO: 131 (GSK3A). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 483 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 700 aa, or from about 700 aa to about 744 aa, of the amino acid sequence set forth in SEQ ID NO: 132 (RSK1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 700 aa, or from about 700 aa to about 744 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, or from about 150 aa to about 209 aa, of the amino acid sequence set forth in SEQ ID NO: 133 (FGF21). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, or from about 150 aa to about 209 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, or from about 100 aa to about 151 aa, of the amino acid sequence set forth in SEQ ID NO: 134 (RIPPLY1). In some of these embodiments, the target antigen will have a length of from about 5 aa to about 10 aa, from about 10 aa to about 25 aa, from about 25 aa to about 50 aa, or from about 50 aa to about 100 aa, from about 100 aa to about 151 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 511 aa, of the amino acid sequence set forth in SEQ ID NO: 135 (ALDH7A1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 511 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 280 aa, of the amino acid sequence set forth in SEQ ID NO: 136 (UBXN10). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 280 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, or from about 600 aa to about 666 aa, of the amino acid sequence set forth in SEQ ID NO: 137 (CAMK2B). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, or from about 600 aa to about 666 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 488 aa, of the amino acid sequence set forth in SEQ ID NO: 138 (BAGS). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 400 aa, or from about 400 aa to about 488 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 800 aa, or from about 800 aa to about 928 aa, of the amino acid sequence set forth in SEQ ID NO: 139 (FAM129A). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200) aa, from about 200 aa to about 250 aa, from about 250 aa to about 500 aa, from about 500 aa to about 60) aa, from about 600 aa to about 800 aa, or from about 800 aa to about 928 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 550 aa, of the amino acid sequence set forth in SEQ ID NO: 140 (cortactin). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 550 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 600 aa, from about 600 aa to about 800 aa, from about 800 aa to about 1000 aa, or from about 1000 aa to about 1255 aa, of the amino acid sequence set forth in SEQ ID NO: 141 (ErbB2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 800 aa, from about 800 aa to about 1000 aa, or from about 1000 aa to about 1255 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 284 aa, of the amino acid sequence set forth in SEQ ID NO: 142 (TPM1). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 284 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 471 aa, of the amino acid sequence set forth in SEQ ID NO: 143 (ANKS6). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, or from about 300 aa to about 471 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, or from about 500 aa to about 600 aa, from about 600 aa to about 800 aa, from about 800 aa to about 1000 aa, or from about 1000 aa to about 1073 aa, of the amino acid sequence set forth in SEQ ID NO: 144 (ITGA6). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 500 aa, from about 500 aa to about 600 aa, from about 600 aa to about 800 aa, from about 800 aa to about 1000 aa, or from about 1000 aa to about 1073 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 227 aa, of the amino acid sequence set forth in SEQ ID NO: 145 (TCEAL2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, or from about 200 aa to about 227 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, or from about 100 aa to about 117 aa, of the amino acid sequence set forth in SEQ ID NO: 146 (IGKV1-5). In some of these embodiments, the target antigen will have a length of from about 5 aa to about 10 aa, or from about 10 aa to about 25 aa, from about 25 aa to about 50 aa, from about 50 aa to about 100 aa, from about 100 aa to about 117 amino acids.

In other embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to a contiguous stretch of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 284 aa, of the amino acid sequence set forth in SEQ ID NO: 147 (TPM2). In some of these embodiments, the target antigen will have a length of from about 5 aa to about 10 aa, from about 10 aa to about 25 aa, from about 25 aa to about 50 aa, from about 50 aa to about 100 aa, from about 100 aa to about 150 aa, from about 150 aa to about 200 aa, from about 200 aa to about 250 aa, or from about 250 aa to about 284 amino acids.

A subject target antigen will in some embodiments have a length of from about 5 amino acids to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, a subject target antigen will have a length of from about 50 aa to about 75 aa, from about 75 aa to about 100 aa, from about 100 aa to about 150 aa, or from about 150 aa to about 200 aa.

In some embodiments, a subject prostate cancer-associated target antigen differs in amino acid sequence by 1, 2, 3, 4, 5, 6, 7, 8, 9, 10, from 10 to 15, from 15 to 20, or from 20 to 25, amino acids compared to the amino acid sequence set forth in any one of SEQ ID NOs: 1-42 and 108-147.

Panel

The present disclosure provides a panel of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, about 45, about 50, about 60, about 70, or about 82 of the above-described prostate cancer-associated target antigens or isolated target antigens. A subject panel is useful for detecting in a biological sample the presence of antibody to the two or more antigens.

In some embodiments, two or more of the target antigens will be detectably labeled with distinguishable detectable labels, e.g., a first target antigen is labeled with a first detectable label, a second target antigen is labeled with a second detectable label, etc., where the first and the second (and any additional) detectable labels are distinguishable from one another.

In some embodiments, a subject panel comprises two or more prostate cancer-associated target antigens, where the antigens are immobilized on an insoluble support.

Detectable Labels

In some embodiments, a subject target antigen comprises a detectable label. Suitable labels include radioisotopes (e.g., $^{125}$I; $^{35}$S, and the like): enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like: bioluminescent compounds, e.g., luciferin; fluorescent proteins; and the like. Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

Carriers

In some embodiments, a subject target antigen is linked to a carrier. The term "linked," as used herein interchangeably with the term "coupled," refers to proximately associated, e.g., the subject target antigen and the carrier are in close spatial proximity. In some embodiments, the linkage is a covalent linkage. In other embodiments, the linkage is a non-covalent linkage. In some embodiments, the subject target antigen is linked directly to the carrier. In other embodiments, the subject target antigen is linked indirectly, e.g., via a linker molecule.

Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like: amino acid copolymers; inactivated virus particles; inactivated bacterial toxins such as toxoid from diphtheria, tetanus, cholera, leukotoxin molecules; liposomes; inactivated bacteria; dendritic cells; and the like. Carriers are described in further detail below.

Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and *Bacillus* Calmette-Guerin (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers, and for methods of conjugating peptides to carriers.

*Pseudomonas aeruginosa* exotoxin A (toxin A) has been used effectively as a carrier in conjugate vaccines. *Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalently couple a polypeptide to toxin A. Toxin A may also be coupled to a polypeptide using a carbodiimide reagent.

PPD-peptide conjugates are conveniently prepared with glutaraldehyde as coupling agent. See, e.g., Rubinstein et al. (1995) AIDS 9:243-51.

The methods by which a subject polypeptide is conjugated with a carrier include disulfide linkages through a C terminal peptide cysteine linkage, coupling with glutaraldehyde solution for two hours, coupling with tyrosine, or coupling with water soluble carbodiimide.

In some embodiments, a subject target antigen is lipidated. Lipidation increases a cytotoxic T cell (CTL) response to the peptide that is linked to the lipid. The lipid residue, such as palmitic acid or the like, is attached to the amino terminus of the peptide. The lipid can be attached directly to the peptide, or, indirectly via a linkage, such as a Scr-Scr, Gly, Gly-Gly, Ser linkage or the like. As another example, *E. coli* lipoprotein, such as tripalmitoyl-S-glycerylcysteine-seryl-serine (P, CSS), can be used to prime specific (TI when covalently attached to the peptide. See, Deres et al., Nature 342:561-564 (1989). A subject target antigen can be conjugated with uncharged fatty acid residues of different chain lengths and degrees of unsaturation, ranging from acetic to stearic acid as well as to negatively charged succinyl residues via the appropriate carboxylic acid anhydrides. See, e.g., U.S. Pat. No. 6,419,931.

A subject target antigen may be conjugated directly or indirectly, e.g., via a linker molecule, to a carrier. A wide variety of linker molecules are known in the art and can be used in the conjugates. The linkage from the peptide to the carrier may be through a peptide reactive side chain, or the N- or C-terminus of the peptide. A linker may be an organic, inorganic, or semi-organic molecule, and may be a polymer of an organic molecule, an inorganic molecule, or a copolymer comprising both inorganic and organic molecules.

If present, the linker molecules are generally of sufficient length to permit the subject target antigen and a linked carrier to allow some flexible movement between the subject target antigen and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Compositions

The present disclosure provides compositions comprising a subject target antigen. Compositions comprising a subject target antigen can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MFS), 3-(N-Morpholino)propanesulfinic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.: a protease inhibitor; and the like. In some embodiments, as described in more detail below, a subject target antigen composition is an immunogenic composition. In other embodiments, as described in more detail below, a subject target antigen composition is a pharmaceutical composition, e.g., a composition comprising a subject target antigen and a pharmaceutically acceptable excipient.

Diagnostic Methods

The present disclosure provides methods of determining the likelihood that a patient who has been diagnosed with prostate cancer will exhibit a clinically beneficial response to treatment with an immunomodulatory treatment regimen. The methods generally involve determining an antibody response profile in the individual to one or more of the above-mentioned target antigens. As noted above, antibodies specific for one or more of the above-mentioned target antigens ("response indicator antigens"), where the antibodies are endogenous antibodies generated in an individual who has prostate cancer, and who exhibits a clinically beneficial response to treatment with an immunomodulatory treatment regimen, are referred to herein as "response indicator antibodies."

An antibody profile is detected in a biological sample (e.g., blood or a blood product such as serum, plasma, etc.), and the antibody profile either correlates directly with or is inversely correlated with, a clinically beneficial response to treatment with an immunomodulatory treatment regimen.

A level of an antibody, present in a biological sample from an individual who has prostate cancer and who has undergone treatment with an immunomodulatory treatment regimen for the prostate cancer, to one or more response indicator antigens, (a "response indicator antibody"), that is substantially higher than the level of the antibody in the individual before treatment with the immunomodulatory treatment regimen, indicates an increased likelihood that the individual will exhibit a clinically beneficial response to treatment with the immunomodulatory treatment regimen.

For example, the level in an individual, who has prostate cancer and who has been treated with an immunomodulatory treatment regimen, of a response indicator antibody that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a control level of the antibody (e.g., the level of the antibody in the individual before treatment with the immunomodulatory treatment regimen), indicates an increased likelihood that the individual will exhibit a clinically beneficial response to treatment with the immunomodulatory treatment regimen.

For example, the level in an individual, who has prostate cancer and who has been treated with an immunomodulatory treatment regimen, of a response indicator antibody that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a control level (e.g., the level of the antibody in the individual before treatment with the immunomodulatory treatment regimen), indicates an at least about 10%, at least about 20%, at least about 25%, at least about 30%, at least about 40%, at least about 50%, at least about 60%, at least about 70%, at least about 80%, or greater than 80%, increased likelihood that the individual will exhibit a clinically beneficial response to treatment with the immunomodulatory treatment regimen.

A level of an antibody, present in a biological sample from an individual who has prostate cancer, to one or more response indicator antigens, that is substantially higher than a non-responder control level, indicates an increased likelihood that the individual will exhibit a clinically beneficial response to treatment with an immunomodulatory treatment regimen.

For example, the level in an individual who has prostate cancer (and who has not yet been treated for the prostate cancer) of a response indicator antibody that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a non-responder control level, indicates an increased likelihood that the individual will exhibit a clinically beneficial response to treatment with an immunomodulatory treatment regimen.

For example, the level in an individual who has prostate cancer (and who has not yet been treated for the prostate cancer) of a response indicator antibody that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a non-responder control level indicates an at least about 10%, at least about 20%, at least about 25%, at least about 30%, at least about 35%, at least about 40%, at least about 45%, at least about 50%, at least about 60%, at least about 70%, at least about 80%, or greater than 80%, increased likelihood that the individual will exhibit a clinically beneficial response to treatment with an immunomodulatory treatment regimen.

A non-responder control level of an antibody can be readily determined by determining the level of a response indicator antibody in a statistically significant number of individuals who have prostate cancer and who did not exhibit a clinically beneficial response to an immunomodulatory treatment regimen. A non-responder control level is a range of level of a response indicator antibody detected in in a statistically significant number of individuals who have prostate cancer and who did not exhibit a clinically beneficial response to an immunomodulatory treatment regimen.

In some embodiments, the level of response indicator antibody to two or more prostate cancer-associated target antigens is determined. For example, in some embodiments, the level of response indicator antibody to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, from about 42 to about 45, from about 45 to about 50, from about 50 to about 60, from about 60 to about 70, or from about 70 to about 82 of the antigens listed in Table 1 is determined. Where the level of response indicator antibody to two or more prostate cancer-associated target antigens is determined, the two or more antibody levels are collectively referred to as an "antibody profile."

In some embodiments, the level of a response indicator antibody is expressed as a "normalized level." For example, either Quantile Normalization or Robust Linear Normalization can be utilized to obtain a "normalized level". In one embodiment, Quantile Normalization is utilized to obtain a normalized response level. In the context of protein arrays, this method forces the arrays to have identical intensity distribution to allow comparison between arrays that may have systematic measurement errors.

In another embodiment. Robust Linear Normalization is utilized to obtain a normalized response level. This method uses a statistical linear model and positive control proteins, e.g., IgG and V5 to fit the model and also removes systematic measurement errors.

A level in an individual, who has prostate cancer and who has been treated with an immunomodulatory treatment regimen, of a response indicator antibody(ies) that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than the level of the antibody in the individual before treatment with the immunomodulatory treatment regimen, indicates that the individual has an increased likelihood of exhibiting a clinically beneficial response to treatment with the immunomodulatory treatment regimen. In other words, a level in an individual, who has prostate cancer and who has been treated with an immunomodulatory treatment regimen, of a response indicator antibody(ies) that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than the level of the antibody in the individual before treatment with the immunomodulatory treatment regimen, indicates that the individual has an at least about 10%, at least about 15%, at least about 20%, at least about 25%, at least about 30%, at least about 40%, at least about 50%, at least about 60%, at least about 70%, at least about 80%, or greater than 80%, increased likelihood of exhibiting a clinically beneficial response to treatment with the immunomodulatory treatment regimen, compared to an individual who does not exhibit an increased level of the response indicator antibody(ies).

A level in an individual, who has prostate cancer and who has not yet been treated for the prostate cancer, of a response indicator antibody(ies) that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a non-responder control level of the antibody, indicates that the individual has an increased likelihood of exhibiting a clinically beneficial response to treatment with an immunomodulatory treatment regimen. In other words, a level in an individual, who has prostate cancer and who has not yet been treated for the prostate cancer, of a response indicator antibody(ies) that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a non-responder control level of the antibody, indicates that the individual has an at least about 10%, at least about 15%, at least about 20%, at least about 25%, at least about 30%, at least about 40%, at least about 50%, at least about 60%, at least about 70%, at least about 80%, or greater than 80%, increased likelihood of exhibiting a clinically beneficial response to treatment with an immunomodulatory treatment regimen, compared to the likelihood of a non-responder control.

The level of an antibody to a target antigen can be determined using any of a number of immunological assays. For example, a detectably labeled subject target antigen, or a panel of detectably labeled target antigens, can be employed, where the level of signal produced in an immunological assay is proportional to the amount of antibody in a biological sample. Suitable assays include, e.g., enzyme-linked immunosorbent assays (ELISA), radioimmunoassay (RIA), and the like.

In some embodiments, the assay is a sandwich assay, in which an antibody specific for the Fe portion of human antibody is immobilized on an insoluble support; a biological sample from a test individual (e.g., an individual having prostate cancer: an individual having prostate cancer who has been treated with an immunomodulatory treatment regimen, an individual having prostate cancer who has not yet been treated for the cancer) is contacted with the immobilized antibody, forming a complex between antibodies present in the biological sample and the immobilized antibody; and the complex is contacted with a subject detectably labeled prostate cancer-associated antigen. The level of signal produced by the detectably labeled prostate cancer-associated antigen indicates the level of antibody in the biological sample that is specific for a subject prostate cancer-associated antigen. Suitable insoluble support materials include, e.g., agarose, sepharose, nitrocellulose, silica, polystyrene, and the like. The insoluble support can be in any of a variety of forms, including, e.g., beads, magnetic beads, films, strips, chips, multi-well plates, and the like.

Immunogenic Compositions

The present disclosure provides an immunogenic composition comprising a subject target antigen. A subject immunogenic composition is useful for inducing in an individual an immune response to a subject target antigen.

In some embodiments, a subject immunogenic composition comprises a subject target antigen, and an adjuvant. Suitable adjuvants include those suitable for use in humans. Examples of known suitable adjuvants that can be used in humans include, but are not necessarily limited to, alum, aluminum phosphate, aluminum hydroxide. MF59 (4.3% w/v squalene, 0.5% w/v polysorbate 80 (Tween 80), 0.5% w/v sorbitan trioleate (Span 85)), a CpG-containing nucleic acid (where the cytosine is unmethylated), QS21 (saponin adjuvant), MPL (Monophosphoryl Lipid A), 3DMPL (3-O- deacylated MPL), extracts from Aquilla, ISCOMS (see, e.g., Sjölander et al. (1998) J. Leukocyte Biol. 64:713), LT/CT mutants, poly(D,L-lactide-co-glycolide) (PLG) microparticles, Quil A, interleukins, and the like. For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman. Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer. (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, MT) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (DETOX™); (2) saponin adjuvants, such as QS21 or STIMULON™ (Cambridge Bioscience, Worcester, MA) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), other TNF superfamily molecules (e.g., CH40L, OX40L, and the like), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL, with, for example, QS21 and/or oil-in-water emulsions e.g. EP-A-0835318, EP-A-0735898. EP-A-0761231; (7) oligonucleotides comprising CpG motifs [Krieg Vaccine 2000, 19, 618-622; Krieg *Curr Opin Mol Ther* 2001 3:15-24; Roman et al., *Nat. Med.*, 1997, 3, 849-854; Weiner et al., *PNAS USA*, 1997, 94, 10833-10837; Davis et al, *J. Immunol*, 1998, 160, 870-876; Chu et al., J. Ep. Med, 1997, 186, 1623-1631; Lipford et al, *Eur. J. Immunol.*, 1997, 27, 2340-2344; Moldoveanu et al., *Vaccine*. 1988, 16, 1216-1224. Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al. *J. Immunol*, 1996, 156, 4570-4575; Halpern et al, *Cell Immunol*, 1996, 167, 72-78; Yamamoto et al. *Jpn. J. Cancer Res.*, 1988, 79, 866-873: Stacey et al, *J. Immunol.*, 1996, 157, 2116-2122; Messina et al, *J. Immunol,* 1991, 147, 1759-1764; Yi et al, *J. Immunol,* 1996, 157, 4918-4925; Yi et al, *J. Immunol,* 1996, 157, 5394-5402; Yi et al, *J. Immunol,* 1998, 160, 4755-4761; and Yi et al, *J. Immunol,* 1998, 160, 5898-5906; International patent applications WO96/02555, WO98/16247, WO98/18810, WO98/40100, WO98/55495. WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

A subject immunogenic composition can include a conventional pharmaceutically acceptable excipient, such as pharmaceutical grades of mannitol, lactose, starch, magnesium stearate, sodium saccharin, talcum, cellulose, glucose, sucrose, magnesium, carbonate, and the like. A subject immunogenic composition can include one or more pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen (e.g., a subject target antigen) in these formulations can vary widely, and can be selected based on various factors such as fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The protein concentration of a subject immunogenic composition in the pharmaceutical formulations can vary widely, e.g., less than about 0.1%, from about 0.1% to about 2%, from about 2% to 20%, or from about 20% to about 50%, or more, by weight, and will be selected on the basis of various factors such as fluid volumes, viscosities, etc., in accordance with the particular mode of administration selected.

Methods of Inducing an Immune Response

The present disclosure provides a method of inducing an immune response in an individual to a target antigen associated with prostate cancer. The methods generally involve administering to an individual having prostate cancer a subject prostate cancer-associated target antigen in an amount effective to induce an immune response to the target antigen. Suitable immune responses include, e.g., an antibody response, a CD4$^+$ T cell response, and a cytotoxic T cell (CTL) response. In some embodiments, a subject method of inducing an immune response in an individual to a prostate cancer-associate target antigen involves administering to the individual an effective amount of a subject immunogenic composition (e.g., a composition comprising a subject prostate cancer-associated target antigen and an adjuvant).

In some embodiments, a subject method of inducing an immune response in an individual increases the likelihood that the individual will respond to treatment for prostate cancer with an immunomodulatory treatment regimen.

A subject prostate cancer-associated target antigen, or a subject immunogenic composition comprising a subject prostate cancer-associated target antigen, is administered to an individual in one or more doses. Suitable amounts of a subject prostate cancer-associated target antigen per dose range from about 100 µg to about 100 mg, e.g., from about 100 µg to about 250 µg, from about 250 µg to about 500 µg, from about 500 µg to about 1 mg, from about 1 mg to about 10 mg, from about 10 mg to about 25 mg, from about 25 mg to about 50 mg, from about 50 mg to about 75 mg, or from about 75 mg to about 100 mg.

Antibodies Specific for Target Antigens

The present disclosure provides antibodies specific for a subject prostate cancer-associated target antigen. In certain embodiments, a subject prostate cancer-associated target antigen-specific antibody is isolated, e.g., is in an environment other than its naturally-occurring environment. Suitable antibodies specific for a subject prostate cancer-associated target antigen include antibodies of any isotype; single-chain Fv; Fab; Fab; Fv; F(ab')$_2$; artificial antibodies; humanized antibodies; and the like. In some embodiments, a subject antibody is specific for a mutant prostate-associated target antigen.

Suitable antibodies are obtained by immunizing a host animal with peptides comprising all or a portion of a subject prostate cancer-associated target antigen. Suitable host animals include mouse, rat sheep, goat, hamster, rabbit, etc. The host animal will generally be from a different species than the immunogen where the immunogen is from a naturally occurring source, e.g., a human sample, where representative host animals include, but are not limited to, e.g., rabbits, goats, mice, etc.

The immunogen may comprise the complete protein, or fragments and derivatives thereof. Generally, immunogens comprise all or a part of the protein, where these residues contain any post-translation modifications found on the native target protein. Immunogens are produced in a variety of ways known in the art, e.g., expression of cloned genes using conventional recombinant methods, preparation of fragments of a subject deacylase protein using well-known methods, etc.

For preparation of polyclonal antibodies, the first step is immunization of the host animal with the target protein, where the target protein can be in substantially pure form, comprising less than about 1% contaminant. The immunogen may comprise the complete prostate cancer-associated target antigen protein, fragments or derivatives thereof. To increase the immune response of the host animal, the prostate cancer-associated target antigen protein may be combined with an adjuvant, where suitable adjuvants include alum, dextran, sulfate, large polymeric anions, and oil-and-water emulsions, e.g. Freund's adjuvant, Freund's complete adjuvant, and the like. A subject prostate cancer-associated target antigen protein may also be conjugated to synthetic carrier proteins or synthetic antigens. A variety of hosts may be immunized to produce polyclonal antibodies. Such hosts include rabbits, guinea pigs, rodents, e.g. mice, rats, sheep, goats, and the like. A subject prostate cancer-associated target antigen protein is administered to the host, e.g., intradermally or intramuscularly, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAF chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies include mouse, rat, hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Antibodies specific for a subject prostate cancer-associated target antigen also include "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516.637; 5,223,409; 5,658,727; 5,667,988; 5,498,538; 5,403,484; 5,571,698; and 5,625,033.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CHI domain and hinge region of the H chain, followed by a translational stop codon to yield the truncated molecule.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Bio. 3:280), Rous sarcoma virus LTR (Gorman e al. (1982)

P.N.A.S. 79:6777), and moloney murine leukemia virus LTR (Grossehedl et al. (1985) Cell 41:885); native Ig promoters, etc.

A subject antibody specific for a subject prostate cancer-associated target antigen will in some embodiments be detectably labeled, e.g., with a radioisotope, an enzyme which generates a detectable product, a fluorescent protein, a chromogenic protein, and the like. An antibody specific for a subject prostate cancer-associated target antigen may be further conjugated to other moieties, such as members of specific binding pairs, e.g., biotin (member of biotin-avidin specific binding pair), and the like. An antibody specific for a subject prostate cancer-associated target antigen may also be bound to a solid support, including, but not limited to, polystyrene plates or beads, magnetic beads, test strips, membranes, and the like.

In some embodiments, an antibody specific for a subject prostate cancer-associated target antigen is detectably labeled, either directly or indirectly. Direct labels include radioisotopes (e.g., $^{125}$I; $^{35}$S, and the like): enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include second antibodies specific for a subject antibody, wherein the second antibody is labeled as described above; and members of specific binding pairs, e.g., biotin-avidin, and the like.

In some embodiments, a subject antibody comprises, covalently linked to the antibody, a protein that provides for a detectable signal. Suitable proteins include, but are not limited to, fluorescent proteins and enzymes (e.g., β-galactosidase, luciferase, horse radish peroxidase, alkaline phosphatase, etc.). Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis*, *Renilla mulleri*, or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; a yellow fluorescent protein; a blue fluorescent protein; and the like.

A subject antibody can be coupled to one or more of a therapeutic drug; a compound emitting radiation; a molecule of plants, fungal, or bacterial origin; and a biological protein. The cytotoxic drugs can be intracellularly acting cytotoxic drugs, such as short-range radiation emitters, including, for example, short-range, high-energy α-emitters.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins. *Phytolacca americana* proteins (PAP, PAPII and PAP-S), *Momordica charantia* inhibitor, curcin, crotin, *Saponaria officinalis* inhibitor, gelonin, mitogillin, restrictocin, phenomycin, and enomycin, for example. Procedures for preparing active polypeptides of the immunotoxins are described in WO84/03508 and WO85/03508. Certain cytotoxic moieties are derived from adriamycin, chlorambucil, daunomycin, methotrexate, neocarzinostatin, and platinum, for example.

Methods of Treating Prostate Cancer

The present disclosure provides methods of treating prostate cancer in an individual having prostate cancer, the methods generally involving administering to the individual an effective amount of a subject antibody, i.e., an antibody specific for a prostate cancer-associated target antigen.

In some embodiments, an effective amount of a subject antibody is an amount that is effective, when administered in one or more doses, to reduce the number of prostate cancer cells in an individual by at least about 10%, at least about 20%, at least about 25%, at least about 30%, at least about 40%, at least about 50%, at least about 60%, at least about 70%, at least about 80%, or more than 80%, compared to the number of prostate cancer cells in the untreated individual.

For therapeutic applications, a subject antibody can be administered to a mammal, e.g., a human (e.g., a male having prostate cancer), in a pharmaceutically acceptable dosage form, including those that may be administered to a human intravenously as a bolus or by continuous infusion over a period of time, by intramuscular, subcutaneous, intra-articular, intrasynovial, intrathecal, oral, topical, or inhalation routes. A subject antibody is also suitably administered by intratumoral, peritumoral, intralesional, or perilesional routes, to exert local as well as systemic therapeutic effects.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride-mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/nil to 100 mg/ml.

For the prevention or treatment of prostate cancer, the appropriate dosage of antibody will depend on the type of disease to be treated, as defined above, the severity and course of the disease, whether the antibodies are administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 0.015 to 15 mg/kg of antibody is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful.

According to another embodiment of the invention, the effectiveness of the antibody in preventing or treating disease may be improved by administering the antibody serially or in combination with another agent that is effective for those purposes, such as another antibody directed against a different epitope or neutralizing a different protein than the first antibody, or one or more conventional therapeutic agents such as, for example, anti-cancer chemotherapeutic agents. Such other agents may be present in the composition being administered or may be administered separately. Also, the antibody is suitably administered serially or in combination with radiological treatments, whether involving irradiation or administration of radioactive substances.

A subject antibody can be used in conjunction with other therapeutic treatment modalities. Such other treatments include surgery, radiation, cryosurgery, thermotherapy, hormone treatment, chemotherapy, vaccines, and other immunotherapies.

Treatment in accordance with the present disclosure can be effectively monitored with clinical parameters such as serum prostate specific antigen and/or pathological features of a patient's cancer, including stage, Gleason score, extracapsular, seminal, vesicle or perineural invasion, positive margins, involved lymph nodes, etc. Alternatively, these parameters can be used to indicate when such treatment should be employed.

Target Antigens in Autoimmune Disorders

The present disclosure relates to the observation that individuals affected with autoimmune disorders (e.g., systemic lupus erythematosus (SLE) and type 1 diabetes mellitus) can mount an immune response to one or more self-antigens.

SLE-Associated Self-Antigens

Self-antigens that are the target of an immune response generated in an individual who has SLE (referred to herein as "SLE-associated self antigens") include, but are not limited to, those shown in Table 2, below.

TABLE 2

| Name | GenBank Accession No. |
|---|---|
| MAPK9 (JNK2) | NM_002752 |
| ATF2 | BC026175 |
| ITGA6 | NM_000210 |
| PIP5K2C | NM_024779 |
| ZAP-70 | NM_001079 |
| NOLC1 | BC006769 |
| SII3GL2 | BC032825 |
| RPAP3 | BC056415 |
| NECAB3 | BC047673 |
| ISG20 | NM_002201 |
| C19orf33 | BC060319 |
| TRIM21 | NM_003141 |
| SMCR7 | NM_139162 |
| SNRPA | NM_004596 |
| RPLP2 | NM_001004 |
| CASZ1 | BC004410 |
| SNRP70 | NM_003089 |
| SNRPC | NM_003093 |
| FGF12 | NM_004113 |
| CAMK2N1 | NM_018584 |
| IFI6 | BC024289 |
| KIAA0515 | BC012289 |
| LOC400027 | XM_378350.2; BC047417 |
| CTNNA1 | BC031262 |
| MAPRE1 | NM_012325 |
| NIP30 | NM_024946 |

TABLE 2-continued

| Name | GenBank Accession No. |
|---|---|
| LRRC6 | NM_012472 |
| PAK1 | NM_002576 |
| C10orf91 | NM_173541 |
| STK25 | NM_006374 |
| C7orf50 | NM_032350 |
| ABL2 | NM_005158 |
| RAD51AP1 | NM_006479 |
| CCDC55 | NM_032141 |
| IRS1 | BC053895 |
| PDGFRB | NM_002609 |
| RBPJ | NM_203284 |
| STAC | BC020221 |
| MPG | BC014991 |
| SF3B4 | NM_005850 |
| FGFR3 | NM_000142 |
| ASPSCR1 | BC018722 |
| WIBG | NM_032345 |
| C3orf37 | BC009993 |
| IRAK4 | NM_016123.1 |

The present disclosure provides an isolated target antigen wherein the isolated target antigen comprises an amino acid sequence that is substantially similar to an antigenic sequence of an SLE-associated self-antigen. The present disclosure also provides antigenic fragments and variants of SLE-associated self antigens. In some embodiments, a subject isolated target antigen is synthetic, e.g., a subject synthetic target antigen is synthesized chemically in a laboratory.

A subject isolated target antigen can be from 6 amino acids in length up to the length of a naturally-occurring SLE-associated self-antigen, e.g., a subject isolated target antigen can be 6 amino acids (aa), 7 aa, 8 aa, 9 aa, 10 aa, 11 aa, 12-15 aa, 15-20 aa, 20-25 aa, 25-30 aa, 30-40) aa, 40-50 aa, 50-100 aa, or longer than 100 amino acids, e.g., 100 aa to 150 aa, or 150 aa to 200 aa. In some embodiments, a subject isolated target antigen has a length of from about 6 aa to about 150 aa, e.g., from about 6 aa to about 10 aa, from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 75 aa, from about 75 aa to about 100 aa, from about 100 aa to about 125 aa, or from about 125 aa to about 150 aa.

In Some embodiments, a subject isolated target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of the following GenBank Accession Numbers: NM_002752. BC026175. NM_000210, NM_024779, NM_001079, BC006769, BC032825, BC056415. BC047673, NM_00220, BC060319, NM_003141. NM_139162. NM_004596, NM_001004, BC004410, NM_003089, NM_003093, NM_004113, NM_018584, BC024289, BC012289, BC031262, NM_012325, NM_024946, NM_012472, NM_002576, NM_173541, NM_006374. NM_032350, NM_005158. NM_006479, NM_032141, BC053895, NM_002609, NM_203284. BC020221, BC014991, NM_005850, NM 000142, BC018722, NM_032345. BC009993, NM_016123.1, or XM_378350.2 (BC047417).

In some embodiments, a subject target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NOs:43-85, 148, and 149.

In some embodiments, a subject target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NOs:43-85; and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, or from 150 aa to 200 aa.

In some embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NO:s 43-85, 148, and 149.

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150 from 150 to 200, from 200 to 300, or from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:43 (NM_002752; MAPK9 (JNK2)).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150 from 150 to 200, from 200 to 300, or from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:43 (NM_002752); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 424 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:43 (NM_002752).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:44 (BC026175; ATF2).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or from 150 to 200, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:44 (BC026175); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 209 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:44 (BC026175).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 500, or from 500 to 1000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:45 (NM_000210; ITGA6; integrin-α6).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 500, or from 500 to 1000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:45 (NM_000210); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 500 aa, from 500 aa to 1000 aa, or from 1000 aa to 1073 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:45 (NM_000210).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:46 (NM_024779; phosphatidylinositol-5-phosphate 4-kinase, type 11, gamma; PIP5K2C).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:46 (NM_024779); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 400 aa, or from 400 aa to 421 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:46 (NM_024779).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, from 400 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:47 (NM_001079; zeta-chain (TCR) associated protein kinase 70 kDa; ZAP-70).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, from 400 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:47 (NM_001079); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 400 aa, from 400 aa to 600 aa, or from 600 aa to 619 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:47 (NM_001079).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:48 (BC006769; nucleolar and coiled-body phosphoprotein 1; NOLC1).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:48 (BC006769); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 400 aa, or from 400 aa to 418 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:48 (BC006769).

In some embodiments, a subject target antigen comprises f om about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 250, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:49 (BC032825; SH3-domain GRB2-like 2; SH3G12).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 250, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:49 (BC032825); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 250 aa, or from 250 aa to 279 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:49 (BC032825).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, from 400 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:50 (BC056415; RNA polymerase 11 associated protein 3; RPAP3).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 400, from 400 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:50 (BC056415); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 400 aa, from 400 aa to 600 aa, or from 600 aa to 631 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:50 (BC056415).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:51 (BC047673; N-terminal EF-hand calcium binding protein 3; NECAB3).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:51 (BC047673); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, or from 300 aa to 362 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:51 (BC047673).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence set forth in SEQ ID NO:52 (NM_002201; interferon stimulated exonuclease gene 20 kDa; ISG20).

In some embodiments, a subject target antigen comprises from about 6, 7, 8, 9, 10, 11, 12, 13-15, 15-17, 17-20, from 20 to 25, from 25 to 50, from 50 to 75, from 75 to 10, from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:52 (NM 002201); and has a length of 6 amino acids (an), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, or from 150 aa to 181 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:52 (NM 0.002201).

In some embodiments, a subject target antigen comprises from about 6, 7, 8, 9, 10, 11, 12, 13-15, 15-17, 17-20, from 20 to 25, from 25 to 50, from 50 to 75, from 75 to 80, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:53 (BC060319; chromosome 19 open reading frame 33; C19orf33).

In some embodiments, a subject target antigen comprises from about 6, 7, 8, 9, 10, 11, 12, 13-15, 15-17, 17-20, from 20 to 25, from 25 to 50, from 50 to 75, from 75 to 80, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:53 (BC060319); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 75 aa, or from 75 aa to 85 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:53 (BC060319).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:54 (NM_003141; *Homo sapiens* tripartite motif-containing 21; TRIM21).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:54 (NM_003141); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400, or from 400 aa to 475 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:54 (NM_003141).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:55 (NM_139162; *Homo sapiens* Smith-Magenis syndrome chromosome region, candidate 7 (SMCR7), transcript variant 1; SMCR7).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:55 (NM_139162); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 454 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:55 (NM_139162).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:56 (NM_0045%; small nuclear ribonucleoprotein polypeptide A; SNRPA).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:56 (NM_0045%); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 282 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:56 (NM_0045%).

In some embodiments, a subject target antigen comprises from about 6, 7, 8, 9, 10, 11, 12, 13-15, 15-17, 17-20, from 20 to 25, from 25 to 50, from 50 to 75, from 75 to 100, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:57 (NM_001004; ribosomal protein, large, P2; RPLP2).

In some embodiments, a subject target antigen comprises from about 6, 7, 8, 9, 10, 11, 12, 13-15, 15-17, 17-20, from 20 to 25, from 25 to 50, from 50 to 75, from 75 to 100, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:57 (NM_001004); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, or from 100 aa to 115 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:57 (NM_001004).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:58 (BC004410; castor zinc finger 1; CASZ1).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:58 (BC004410); and has a length of 6 amino acids (aa), 7 aa, 8 aa, 9 aa, 10 aa, 1 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 614 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:58 (BC004410).

In some embodiments, a subject target antigen comprises from about 6, 7, 8, 9, 10, 11, 12, 13-15, 15-17, 17-20, from 20 to 25, from 25 to 50, from 50 to 75, from 75 to 10, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:59 (NM_003089; small nuclear ribonucleoprotein 70 kDa polypeptide; SNRP70).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:59 (NM_003089); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 437 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:59 (NM_003089).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:60 (NM_003093; small nuclear ribonucleoprotein polypeptide C; SNRPC).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:60 (NM_003093); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, or from 150 aa to 159 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:60 (NM_003093).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:61 (NM_004113; fibroblast growth factor 12; FGF12).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:61 (NM_004113); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, or from 150 aa to 181 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:61 (NM_004113).

In some embodiments, a subject target antigen comprises from about 6, 7, 8, 9, 10, 11, 12, 13-15, 15-17, 17-20, from 20 to 25, from 25 to 50, from 50 to 75, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:62 (NM_018584; calcium/calmodulin-dependent protein kinase II inhibitor 1; CAMK2N1).

In some embodiments, a subject target antigen comprises from about 6, 7, 8, 9, 10, 11, 12, 13-15, 15-17, 17-20, from 20 to 25, from 25 to 50, from 50 to 75, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:62 (NM_018584); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, or from 50 aa to 78 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:62 (NM_018584).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:63 (BC024289; interferon, alpha-inducible protein 6; IFI6).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:63 (BC024289); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 471 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:63 (BC024289).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids (aa) of an amino acid sequence having at least about 50%, at least about 60%, at least about 70%, at least about 75%, at least about 80%, at least about 85%, at least about 0%, at least about 95%, at least about 98%, at least about 99%, or 100% amino acid sequence identity to the amino acid sequence set forth in SEQ ID NO:64 (BC012289; KIAA0515).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:64 (BC012289); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, or from 300 aa to 326 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:64 (BC012289).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:65 (BC031262; catenin (cadherin-associated protein), alpha 1; CTNNA1).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:65 (BC031262); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, 300 aa to 400 aa, 400 aa to 500 aa, or from 500 aa to 536 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:65 (BC031262).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:66 (NM_012325).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:66 (NM_012325; microtubule-associated protein, RP/EB family, member 1; MAPRE1); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 268 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:66 (NM_012325).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:67 (NM_024946; NEFA-interacting nuclear protein NIP30).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:67 (NM_024946); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 254 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:67 (NM_024946).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:68 (NM_012472; leucine rich repeat containing 6; LRRC6).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:68 (NM_012472); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 466 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:68 (NM_012472).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:69 (NM_002576).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:69 (NM_002576); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 545 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:69 (NM_002576).

In some embodiments, a subject target antigen comprises from about 6, 7, 8, 9, 10, 11, 12, 13-15, 15-17, 17-20, from 20 to 25, from 25 to 50, from 50 to 75, from 75 to 100, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:70 (NM_173541).

In some embodiments, a subject target antigen comprises from about 6, 7, 8, 9, 10, 11, 12, 13-15, 15-17, 17-20, from 20 to 25, from 25 to 50, from 50 to 75, from 75 to 100, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:70 (NM_173541); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 75 aa, from 75 aa to 100 aa, or from 100 aa to 145 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:70 (NM_173541).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:71 (NM_006374).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 30) to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:71 (NM_006374); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 426 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:71 (NM_006374).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:72 (NM_032350).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:72 (NM_032350); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 75 aa, from 75 aa to 100 aa, from 100 aa to 150 aa, or from 150 aa to 194 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:72 (NM_032350).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 750, from 750 to 1000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:73 (NM_005158).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 750, from 750 to 1000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:73 (NM_005158); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 750 aa, from 750 aa to 100 aa, or from 1000 aa to 1.146 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:73 (NM_005158).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 3M), or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:74 (NM_006479).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:74 (NM_006479); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa or from 300 aa to 335 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:74 (NM_006479).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:75 (NM_032141).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:75 (NM_032141); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 558 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:75 (NM_032141).

In some embodiments, a subject target antigen comprises from about 6, 7, 8, 9, 10, 11, 12, 13-15, 15-17, 17-20, from 20 to 25, from 25 to 50, from 50 to 75, from 75 to 10, from 100 to 150, from 150 to 200, from 200 to 300, from 300 to 400, from 400 to 500, from 500 to 750, from 750 to 1000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:76 (BC053895).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 750, from 750 to 1000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:76 (BC053895); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 10) aa, from 100 aa to 150 aa, from 150 aa to 200 aa, from 200 aa to 300 aa, from 300 aa to 400 aa, from 400 aa to 500 aa, from 500 aa to 750 aa, from 750 aa to 1000 aa, or from 1000 aa to 1,242 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:76 (BC053895).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 750, from 750 to 1000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:77 (NM_002609).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 30 aa to 400 aa, from 400 to 500, from 50M to 750, from 750 to 1000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:77 (NM_002609); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 750 aa, from 750 aa to 1000 aa, or from 1000 aa to 1.106 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:77 (NM_002609).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:78 (NM_203284).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:78 (NM_203284); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 486 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:78 (NM_203284).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:79 (BC020221).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at SEQ ID NO: about 99%, or 100% amino acid sequence identity to the amino acid sequence set forth in SEQ ID NO:79 (BC020221); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 402 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:79 (BC020221).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 9)%, or 100% amino acid sequence identity to the amino acid sequence set forth in SEQ ID NO:80 (BC014991).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:80 (BC014991); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 293 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:80 (BC014991).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:81 (NM_005850).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:81 (NM_005850); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 424 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:81 (NM_005850).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 3M), from 300 to 400, from 400 to 500, from 500 to 600, from 600 to 700, from 700 to 800, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:82 (NM_000142).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, from 600 to 700, from 700 to 800, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:82 (NM_000142); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, from 600 aa to 700 aa, from 700 aa to 800 aa, or from 800 aa to 806 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:82 (NM_000142).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:83 (BC018722).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:83 (BC018722); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 553 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:83 (BC018722).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:84 (NM_032345).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:84 (NM_032345); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 204 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:84 (NM_032345).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:85 (BC009993).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:85 (BC009993); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, or from 300 aa to 354 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:85 (BC009993).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, up to 460 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:148 (IRAK4; interleukin-1 receptor-associated kinase 4); and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 350 aa, from 350 aa to 400 aa, or from 400 aa to 460 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:148 (IRAK4).

In some embodiments, a subject target antigen comprises from about 6, 7, 8, 9, 10, 11, 12, 13-15, 15-17, 17-20, from 20 to 25, from 25 to 50, from 50 to 75, from 75 to 100, up to 120 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:149 (LOC400027); and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, or from 100 aa to 120 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:149 (LOC400027).

In some embodiments, a subject SLE-associated self-antigen differs in amino acid sequence by 1, 2, 3, 4, 5, 6, 7, 8, 9, 10, from 10 to 15, from 15 to 20, or from 20 to 25, amino acids compared to the amino acid sequence set forth in any one of SEQ ID NOs:43-85, 148, and 149.

Panel

The present disclosure provides a panel of 2, 3, 4, 5, 67, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 of the above-described SLE-associated self-antigens or isolated target antigens. A subject panel is useful for detecting in a biological sample the presence of antibody to the two or more antigens.

In some embodiments, two or more of the target antigens will be detectably labeled with distinguishable detectable labels, e.g., a first target antigen is labeled with a first detectable label, a second target antigen is labeled with a second detectable label, etc., where the first and the second (and any additional) detectable labels are distinguishable from one another.

In some embodiments, a subject panel comprises two or more SLE-associated self-antigen, where the antigens are immobilized on an insoluble support.

Type-1 Diabetes-Associated Self-Antigens

Self-antigens that are the target of an immune response generated in an individual who has type 1 insulin dependent diabetes mellitus (referred to herein as "type 1 diabetes-associated self-antigens") include, but are not limited to, those shown in Table 3, below.

TABLE 3

| Name | GenBank Accession No. |
|---|---|
| NUP50 | NM_007172 |
| ABL1 | NM_005157 |
| ATF2 | BC026175 |
| ATF2 | BC130335 |
| PAK1 | NM_002576 |
| CHEK2 | NM_001005735 |
| SPEG | NM_005876 |
| MAP2K (MEK1) | NM_002755 |
| PRKCB2 | NM_002738 |
| adducin 2 (beta) | BC065525 |

TABLE 3-continued

| Name | GenBank Accession No. |
| --- | --- |
| PLK1 | NM_005030 |
| NLK | NM_016231.2 |
| MGC2827 | NM_023940.1 |
| PRKCZ | NM_002744.2 |
| PDK1 | NM_002613 |
| NEK3 | NM_002498 |
| ZAP-70 | NM_001079 |
| transglutaminase 2 | BC003551 |
| coilin (COIL) | NM_004645 |
| MAPK9 (JNK2) | NM_002752 |
| PRKCG | NM_002739 |
| UBXN6 | NM_025241 |
| PRKCE | NM_005400 |
| UBE2H | NM_003344 |
| ABL2 | NM_005158 |
| PRKCB1 | NM_002738.5 |
| MGC2478 | BC002568.1 |
| C19orf57 | BC012945.1 |

The present disclosure provides an isolated target antigen wherein the isolated target antigen comprises an amino acid sequence that is substantially similar to an antigenic sequence of a type 1 diabetes-associated self-antigen. The present disclosure also provides antigenic fragments and variants of type 1 diabetes-associated self-antigens. In some embodiments, a subject isolated target antigen is synthetic, e.g., a subject synthetic target antigen is synthesized chemically in a laboratory.

A subject isolated target antigen can be from 6 amino acids in length up to the length of a naturally-occurring type 1 diabetes-associated self-antigen, e.g., a subject isolated target antigen can be 6 amino acids (aa), 7 aa, 8 aa, 9 aa, 10 aa, 11 aa, 12-15 aa, 15-20 aa, 20-25 aa, 25-30 aa, 30-40 aa, 40-50 aa, 50-100 aa, or longer than 100 amino acids, e.g., 100 aa to 150 aa, 150 aa to 200 aa. In some embodiments, a subject isolated target antigen has a length of from about 6 aa to about 150 aa, e.g., from about 6 aa to about 10 aa, from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 75 aa, from about 75 aa to about 100 aa, from about 100 aa to about 125 aa, or from about 125 aa to about 150 aa.

In some embodiments, a subject isolated target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of the following GenBank Accession Numbers: NM_007172, NM_005157, BC026175, BC130335, NM_002576, NM_001005735. NM_005876, NM_002755, NM_002738, BC065525, NM_005030. NM_002613, NM_002498, NM_001079, BC003551, NM_004645. NM_002752. NM_002739, NM_025241, NM_005400, NM_003344, NM_005158, NM_016231.2, NM_023940.1, NM_002744.2, NM_002738.5, BC002568.1, and BC012945.1.

In some embodiments, a subject target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NOs:86-107 and 150-155.

In some embodiments, a subject target antigen comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NOs: 86-107 and 150-155; and has a length of 6 amino acids (aa), 7 aa, 8 aa, 9 aa, 10 aa, 11 aa, from 12 aa to 15 aa, from 15 to 20 aa, from 20 to 25 aa, from 25 to 30 aa, from 30 to 40 aa, from 40 to 50 aa, from 50 to 100 aa, from 100 aa to 150 aa, or from 150 aa to 200 aa.

In some embodiments, a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one of SEQ ID NOs:86-107 and 150-155.

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:86 (NM_007172).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:86 (NM_007172); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 468 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:86 (NM_007172).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 1000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:87 (NM_005157).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 1000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:87 (NM_005157); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 1000 aa, or from 1000 aa to 1130 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:87 (NM_005157).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:88 (BC026175).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, or more, contiguous amino acids of an amino acid sequence having at least about 50%, at least about 60% u, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:88 (BC026175); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 209 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:88 (BC026175).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 50), or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:89 (BC130335).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:89 (BC130335); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 30) aa, from 300 aa to 400 aa, from 400 aa to 500 aa, or from 500 aa to 505 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:89 (BC130335).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:90 (NM_002576).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:90 (NM_002576); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 545 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:90 (NM_002576).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:91 (NM_001005735).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO: 91 (NM_001005735); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 586 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:91 (NM_001005735).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 1000, from 1000 to 1500, from 1500 to 2000, from 2000 to 2500, from 2500 to 3000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:92 (NM_005876).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 1000, from 1000 to 1500, from 1500 to 2000, from 2000 to 2500, from 2500 to 3000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:92 (NM_005876); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 1000 aa, from 1000 aa to 1500 aa, from 1500 aa to 2000 aa, from 2000 aa to 2500 aa, from 2500 aa to 3000 aa, or from 3000 aa to 3267 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:92 (NM_005876).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:93 (NM_002755).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100N % amino acid sequence identity to the amino acid sequence set forth in SEQ ID NO:93 (NM_002755); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, or from 300 aa to 393 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:93 (NM_002755).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:94 (NM_002738).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:94 (NM_002738); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 673 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:94 (NM_002738).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 50), from 500 to 600, from 600 to 700, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:95 (BC065525).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, from 600 to 700, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:95 (BC065525); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, from 600 aa to 700 aa, or from 700 aa to 726 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:95 (BC065525).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:% (NM_005030).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:% (NM_005030); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 603 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:% (NM_005030).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 30) to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:97 (NM_002613).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:97 (NM_002613); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 556 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:97 (NM_002613).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:98 (NM_002498).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, mm 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:98 (NM_002498); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 506 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:98 (NM_002498).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:99 (NM_001079).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:99 (NM_001079); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 619 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:9 (NM_001079).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 20, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:100 (BC003551).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 3M), from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:100 (BC003551); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 548 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:100 (BC003551).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:101 (NM_004645).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:101 (NM_004645); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 30) aa, from 300 aa to 400 aa, from 400 aa to 500 aa, or from 500 aa to 576 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO: 101 (NM_004645).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:102 (NM_002752).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:102 (NM_002752); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 424 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:102 (NM_002752).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:103 (NM_002739).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:103 (NM_002739); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 697 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:103 (NM_002739).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:104 (NM_025241).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:104 (NM_025241); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, or from 400 aa to 441 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:104 (NM_025241).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, from 600 to 700, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:105 (NM_005400).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 20, from 200 to 300, from 300 to 400, from 400 to 500, from 50) to 600, from 600 to 700, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:105 (NM_005400); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, from 600 aa to 700 aa, or from 700 aa to 737 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:105 (NM_005400).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:106 (NM_003344).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:106 (NM_003344); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, or from 150 aa to 183 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:106 (NM_003344).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 20, from 200 to 300, from 300 to 400, from 400 to 500, from 500 to 600, from 600 to 700, from 700 to 800, from 800 to 900, from 900 to 1000, or more, contiguous amino acids (aa) of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:107 (NM_005158).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 150, from 150 to 200, from 200 to 300, from 300 to 400, from 400 to 500, from 500 to 600, from 600 to 700, from 700 to 800, from 800 to 900, from 900 to 1000, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:107 (NM_005158); and has a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, from 600 aa to 700 aa, from 700 aa to 800 aa, from 800 aa to 900 aa, from 900 aa to 1,000 aa, or from 1,000 aa to 1,146 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:107 (NM_005158).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 200, from 200 to 300, from 300 to 400, from 400 up to 527 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:150 (nemo-like kinase (NLK)); and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 1 W aa, from 100 aa to 150 aa, from 150 aa to 200 aa, from 200 aa to 300 aa, from 300 aa to 400 aa, or from 400 aa to 527 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:150 (nemo-like kinase (NLK)).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 200, from 200 up to 248 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:151 (MGC2827; RASL11B); and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, or from 200 aa to 248 aa.

In some embodiments a subject target antigen comprises an amino acid sequence having at least about 50% u, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:151 (MGC2827; RASL11B).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 200, from 200 to 300, from 300 to 400, from 400 to 500, up to 592 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:152 (protein kinase C, zeta (PRKCA)); and may have a length of 6 amino acids (aa), 7 aa, 8 aa, 9 aa, 10 aa, 1 (aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, or from 500 aa to 592 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:152 (protein kinase C, zeta (PRKCZ)).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 200, from 200 to 300, from 300 to 400, from 400 to 500, from 500 to 600, up to 673 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:153 (protein kinase Cβ (PRKCB1)); and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 673 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:153 (protein kinase Cβ (PRKCB1)).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 20, from 200 to 300, up to 312 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:154 (MGC2478; cytokine induced apoptosis inhibitor 1); and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 3M) aa, or from 30) aa to 312 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:154 (MGC2478; cytokine induced apoptosis inhibitor 1).

In some embodiments, a subject target antigen comprises from about 6, 7, 8, 9, 10, 11, 12, 13-15, 15-17, 17-20, from 20 to 25, from 25 to 50, from 50 to 75, from 75 to 100, from 100 to 200, from 200 to 300, from 300 to 400, from 400 to 500, from 500 to 600, up to 637 or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:155 (C19orf57) and may have a length of 6 amino acids (aa), 7 aa, 8 aa, 9 aa, 10 aa, 11 aa, from 12 aa to 15 aa, from 15 aa to 20 aa, from 20 aa to 25 aa, from 25 aa to 30 aa, from 30 aa to 40 aa, from 40 aa to 50 aa, from 50 aa to 100 aa, from 100 aa to 150 aa, from 150 aa to 200 aa, from 200 aa to 300 aa, from 300 aa to 400 aa, from 400 aa to 500 aa, from 500 aa to 600 aa, or from 600 aa to 637 aa.

In some embodiments a subject target antigen comprises an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:155 (C9orf57).

In some embodiments, a subject type-1 diabetes-associated self-antigen differs in amino acid sequence by 1, 2, 3, 4, 5, 6, 7, 8, 9, 10, from 10 to 15, from 15 to 20, or from 20 to 25, amino acids compared to the amino acid sequence set forth in any one of SEQ ID NOs:86-107 and 150-155.

In some embodiments, one or more of the above type-1 diabetes-associated self-antigens are specifically excluded. For example, in one embodiment, transglutaminase 2 (BC003551) (SEQ ID NO:100) is specifically excluded.

Panel

The present disclosure provides a panel of 2, 3, 4, 5, 6, 7, 8, 9, 10, 11, 12, 13, 14, 15, 16, 17, 18, 19, 21, 22, 23, 24, 25, 26, 27, or 28 of the above-described type 1 diabetes-associated self-antigens or isolated target antigens. A subject panel is useful for detecting in a biological sample the presence of antibody to the two or more antigens.

In some embodiments, two or more of the target antigens will be detectably labeled with distinguishable detectable labels, e.g., a first target antigen is labeled with a first detectable label, a second target antigen is labeled with a second detectable label, etc., where the first and the second (and any additional) detectable labels are distinguishable from one another.

In some embodiments, a subject panel comprises two or more type 1 diabetes-associated self-antigens, where the antigens are immobilized on an insoluble support.

Diagnostic Methods

The present disclosure provides methods of diagnosing an autoimmune disorder and methods of identifying individuals at risk of developing an autoimmune disorder, the methods generally involving detecting an antibody response to a target antigen in an individual.

For example, the present disclosure provides methods of diagnosing whether an individual has Systemic Lupus Erythematosus (SLE) and methods of identifying individuals at risk of developing SLE. The present disclosure also provides methods of diagnosing whether an individual has type-1 insulin dependent diabetes mellitus and methods of identifying individuals at risk of developing type-1 insulin dependent diabetes mellitus. These methods are described in detail below.

In one embodiment, a method of diagnosing whether an individual has (or is at risk of developing) Systemic Lupus Erythematosus (SLE) is provided. The method generally involves contacting a biological sample, e.g., serum, from an individual with a subject target antigen and detecting the presence of an immune response specific for the subject target antigen.

In another embodiment, a method of diagnosing whether an individual has (or is at risk of developing) type-1 insulin dependent diabetes mellitus is provided. The method generally involves contacting a biological sample, e.g., serum, from an individual with a subject target antigen and detecting the presence of an immune response specific for the subject target antigen.

Various methods known in the art may be used to determine the presence of an immune response. The biological sample for analysis is typically blood, plasma, serum, mucous or cerebrospinal fluid from the patient. The sample is analyzed for indication of an immune response to any subject target antigen of the invention. The immune response can be determined from the presence of, e.g., antibodies or T-cells that specifically bind to the subject target antigen.

Where T cell responses are of interest, the sample is a sample comprising lymphocytes, e.g. the cellular portion of a blood sample, etc. T cells may be stained with a peptide/MHC complex, for example using detectably labeled MHC reagents (i•TAg™ MHC Tetramers, Beckman Coulter; BDU™ DimerX reagents; ProImmune Pro5® MHC class I Pentamers etc.) to determine the presence of T cells having specificity for a subject target antigen. Alternatively. T cells may be assayed in vitro for reactivity to a subject target antigen, using methods known in the art. For example, a sample comprising T cells may be contacted with a subject target antigen presented by an antigen presenting cell; or provided as a stable MHC complex; and the response of the cells quantitated, for example by proliferation, cytokine synthesis, cytotoxicity and the like. Measured values may thus include quantitation of antigen specific T cells, quantitation of T cell proliferation in response to the antigen, quantitation of cytokine release, e.g. IFN-γ, IL-2, etc. in response to presented antigen, percentage of specific cell lysis and the like.

In some embodiments, diagnostic methods involve detecting the number of subject target antigen-specific $CD8^+$ T cells in a biological sample obtained from an individual. The number of subject target antigen-specific $CD8^+$ T cells can be determined using, e.g., a $^{51}Cr$ release assay, where target cells pulsed with a subject target antigen and labeled with $^{51}Cr$ are contacted with a test sample that may contain subject target antigen-specific $CD8^+$ T cells. The number of subject target antigen-specific $CD8^+$ T cells is determined by measuring release of $^{51}Cr$ from the target cells.

Some methods may entail determining a baseline value of an immune response in a normal control, and comparing this with a value for the test immune response. A significant difference (i.e., greater than the typical margin of experimental error in repeat measurements of the same sample, expressed as one standard deviation from the mean of such measurements) in value of the immune response relative to a normal control signals the presence of an immune response against a subject target antigen in the sample. If the value for immune response does not change significantly, this signals the lack of an immune response against a subject target antigen in the sample. In other methods, a control value (i.e., a mean and standard deviation) of immune response is determined for a control population. Typically the individuals in the control population are free of the autoimmune disease of interest. Measured values of immune response in a patient may be compared with the control value.

In other methods, a control value of immune response (e.g., a mean and standard deviation) is determined from a control population of individuals who have undergone treatment with a therapeutic agent. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant can be indicated.

In other methods, a patient who is not presently receiving treatment but has undergone a previous course of treatment is monitored for immune response to determine whether a resumption of treatment is required. The measured value of immunize response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

Diagnostic Kits

The present disclosure further provides kits for use within any of the above diagnostic methods. Such kits typically comprise two or more components necessary for performing a diagnostic assay for the detection of immune responses specific to a subject target antigen. Components can be compounds, reagents, containers and/or equipment. Kits also typically contain labeling providing directions for use of the kit. For example, one container within a kit can contain a monoclonal antibody or fragment thereof or soluble T cell receptor that specifically binds to a subject target antigen, or to a subject target antigen/MHC complex. Alternatively, an MHC/subject target antigen peptide complex may be included. Such reagents can be provided attached to a support material. One or more additional containers can enclose elements, such as reagents or buffers, to be used in the assay. Such kits can also, or alternatively, contain a detection reagent that contains a reporter group suitable for direct or indirect detection of antibody binding. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

In one embodiment, a subject kit comprises a subject target antigen immobilized on a solid support and a labeled reagent capable of binding to an antibody specific for the subject target antigen.

Populations of Interest

The diagnostic methods discussed herein are not limited to use with a particular patient class or population of individuals. However, specific groups of patients/individuals may be of interest in connection with the methods disclosed herein. For example, the subject methods of diagnosing an individual for SLE may be of particular interest in connection with populations of individuals at high risk of developing SLE, e.g., populations of individuals having a family history of SLE, populations of individuals having specific HLA alleles associated with SLL, and populations of individuals having specific SNPs associated with SLE. It may also be of particular benefit to screen children for immune responses to SLE-associated self-antigens since much of the long term organ damage associated with SLE can be prevented with early diagnosis and treatment.

In the context of type-1 insulin dependent diabetes mellitus, it may be beneficial to screen individuals who have not yet been diagnosed on the basis of hyperglycemia since there is generally significant damage to beta islet cells by this point. Additional populations of interest include those with risk factors such as obesity, family history of diabetes and high-risk ethnicity (e.g., Hispanic, Native American, Afro-Caribbean and Pacific Islander).

The diagnostic methods discussed herein may also find use in the diagnosis and/or staging of additional autoimmune disorders including, but not limited to, rheumatoid arthritis, scleroderma, and mixed connective tissue disease.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); Ag, antigen(s); and the like.

Example 1: Identification of Target Antigens in Prostate Cancer Patients Treated with Anti-CTLA-4/GMCSF Combination Immunotherapy In order to identify immune responses unique to patients responsive to immunotherapy, protein arrays were screened with serum from prostate cancer patients characterized as responders or non-responders to anti-CTLA-4/GMCSF combination immunotherapy.

Materials and Methods

A protein array containing 8274 unique proteins was screened with serum from 3 responders and 3 non-responders, 8274 unique proteins were purified from baculovirus and printed on nc coated slides in duplicate+controls. Slides were blocked and then contacted with patient serum diluted 1:500. Following a wash step, anti-human IgG-Alexa Fluor® 647 secondary antibody was added to the slides. Slides were washed again and then imaged on an Axon microarray scanner. For responders and non-responders immune responses were measured both pre- and post treatment. Select target antigens were validated via western blot or immunoprecipitation.

Target antigens can be identified without normalization, as well as with Quantile Normalization and Robust linear Normalization. Where no normalization is utilized, an exemplary protocol is as follows: After scanning the slide with the axon scanner the data are analyzed using Invitrogen Prospector Software. This analysis software examines the fluorescence intensity of each spotted protein and determines if it is a significant hit by using a Z-score of >2.9 as the cutoff criteria. Certain candidates that do not satisfy the >2.9 cutoff because of low signal intensities but have at least a two fold increase in post versus pre-treatment sera and appear more frequently in responders compared to non-responders can also be considered.

Quantile Normalization forces the arrays to have identical intensity distribution so as to allow comparison between arrays that may have systematic measurement errors.

Robust Linear Normalization uses a statistical linear model and positive control proteins, e.g., IgG and V5 to fit the model and also removes systematic measurement errors.

Results

Target antigens exhibiting a greater immune response in responders relative to non-responders are listed in Table 1 above. FIG. 1 shows the results of a western blot assay designed to validate an exemplary target antigen. As indicated in FIG. 1, an immune response to the target antigen SYK is visible for a responder patient (24-8) post treatment. A similar response is not seen for non-responder (23-8) post treatment. (24-1) and (23-1) represent pre-treatment responses for responder and non-responder patients respectively.

FIGS. 2A-D show the results of an immunoprecipitation assay designed to validate exemplary target antigens. As shown in FIGS. 1 and 2A-D, the target antigens SYK. PAK6, and MITF each show increased immune response post-treatment in responders. An increase in immune response to SYK and MITF is observed only in patient 24. PAK6 shows an increase in immune response post-treatment for responders 19 and 20 and also one non-responder 22. In FIGS. 2A-D, pre-existing antibodies to the antigen CSAG1a are observed in responders 19 and 24, and not in any of the non-responders (21.22 and 23). 21-1 and 21-8 show results for a non-responder (21) pre-treatment (−1) and post-treatment (−8), 22-1 and 22-8 show results for a non-responder (22) pre-treatment (−1) and post-treatment (−8), 23-1 and 23-8 show results for a non-responder (23) pre-treatment (−4) and post-treatment (−8). 19-1 and 19-8 show results for a responder (19) pre-treatment (−1) and post-treatment (−8), 20-1 and 20-8 show results for a responder (20) pre-treatment (−4) and post-treatment (−8), 24-1 and 24-8 show results for a responder (24) pre-treatment (−1) and post-treatment (−8).

Example 2: Induction of Auto-Antibodies in SLE Patients

In order to identify new SLE-associated self-antigens, plasma from normal individuals or individuals with SLE was used to screen human protein arrays.

Materials and Methods

Plasma from 11 SLE and 5 Normal Individuals was used to screen protein arrays (Invitrogen Protoarrays). Each slide was spotted with 8000 different human proteins in duplicate.

Arrays were blocked and plasma was added. After washing 5×, arrays were contacted with Alexa647 labeled secondary antibody. The arrays were then scanned using an Axon scanner, and the data was analyzed using Invitrogen's Prospector Free Software. The Prospector analysis software examines the fluorescence intensity of each spotted protein and determines if it is a significant hit by using a Z-score of >3 as the cutoff criteria.

Results 38 different self-antigens were identified which showed significant fluorescence when exposed to scrum from individuals with SLE as compared to normal controls. Table 4 below represents some of the detected antibody responses to known SLE-associated nuclear antigens (Ags).

TABLE 4

| Known Auto-Ags | Description |
| --- | --- |
| Ro-52 | Associated with Ro-RNP complex; ubiquitin |
| SMITH | Associated with snRNA's to make up the snRNP complex |
| RNP complex ssDNA | Mediates the splicing of pre-mRNA |

In addition, several proteins not previously identified as SLE-associated self-antigens were identified. These proteins are set forth in Table 2 above.

Two of the proteins which exhibited high fluorescent values when contacted with serum from individuals with SLE were validated as discussed below in Example 3.

Example 3: Validation of Selected SLE-Associated Self-Antigens

Selected proteins identified via screening of the protoarrays were validated as SLE-associated self-antigens as follows.

Materials and Methods

The genes encoding the selected candidate SLE-associated self-antigens were cloned into a (ST-fusion expression vector and expressed in-vitro using a rabbit reticulolysate coupled transcription/translation system. The expressed protein was then incubated with SLE or normal plasma. The protein-antibody complex was then bound to protein A sepharose beads, washed, spun, and diluted in Lammelli buffer for SDS-PAGE.

Results

Figure 3:
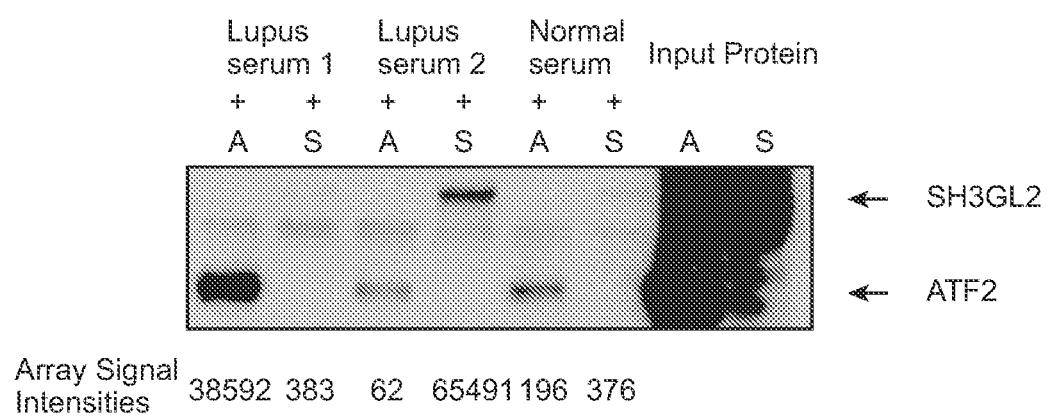
FIG. 3 shows the results of a western blot assay designed to validate two candidate SLE-associated self-antigens.
Figure 4A:
FIGS. 4A-L depict immunohistochemical analysis of patients' biopsies and prostate tumors.
Figure 4C:
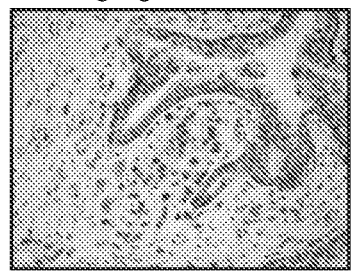
Figure 4E:
Figure 4B:
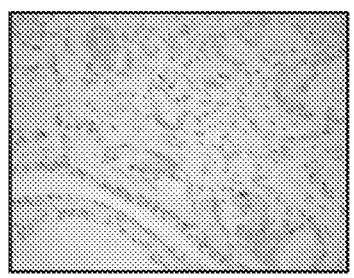
Figure 4D:
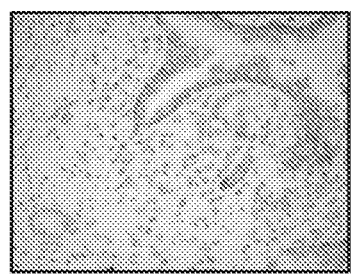
Figure 4F:
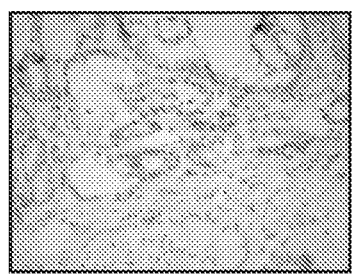
Figure 4G:
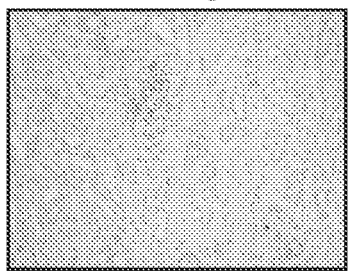
Figure 4H:
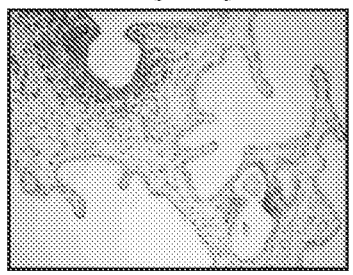
Figure 4I:
Figure 4J:
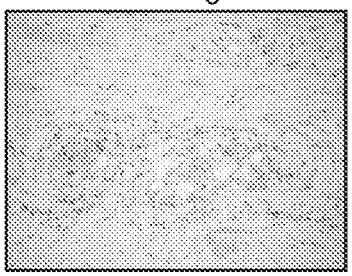
Figure 4K:
Figure 4L:
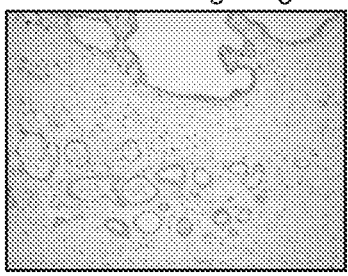

FIG. 3 shows western blot results for the above experiment. Candidates were considered validated if a stronger band was present for SLE serum with+protein as compared with normal serum+the same protein. ATF2 is expected to be around 63 kDa, and SII3GL2 is expected to be around 93 kDa. FIG. 3 shows stronger bands at about 63 kDa and 93 kDa (for ATF2 and SII3GL2 respectively) for SLE serum relative to normal serum. Based on these results, ATF2 and SH3GL2 were validated as SLE-associated self-antigens.

Example 4: Induction of Auto-antibodies in Type-1 Insulin Dependent Diabetes Mellitus Patients In order to identify new type 1 diabetes-associated self-antigens, plasma from normal individuals or individuals with type 1 diabetes was used to screen human protein arrays.

Materials and Methods

Plasma from type-1 diabetes and normal individuals was used to screen protein arrays (Invitrogen Protoarrays). Each slide was spotted with 8000 different human proteins in duplicate. Arrays were blocked and plasma was added. After washing 5×, arrays were contacted with Alexa647 labeled secondary antibody. The arrays were then scanned using an Axon scanner, and the data was analyzed using Invitrogen's Prospector Free Software. The Prospector analysis software examines the fluorescence intensity of each spotted protein and determines if it is a significant hit by using a Z-score of >3 as the cutoff criteria.

Results

Self-antigens were identified which showed significant fluorescence when exposed to serum from individuals with type-1 diabetes as compared to normal controls.

Several proteins, not previously identified as type 1 diabetes-associated self-antigens were identified. These proteins are set forth in Table 3 above.

Example 5: Immunohistochemical Analysis of Biopsies and Tumors

The results of immunohistochemical analysis of biopsies and tumors are shown in FIGS. 4A-L. Low grade tumor (a,d), high grade tumor (b, e), and patient 20's high grade tumor biopsy (c, f). Sections a, b and c were stained with anti-Pak6 antibodies (Novus Biologicals, NLS6942) and sections d, e and f were stained with normal rabbit IgG (Dako, X0903). Low grade tumor (g, h, and l), high grade tumor (j, k) and patient 24's high grade tumor biopsy (i), g and h shows the tumor and benign regions respectively of the same tumor section; and j and k shows the tumor and benign regions respectively of the same tumor section. There is no benign region in patent 24 tumor biopsy. Sections g to l were stained with anti-Syk antibodies (Sigma, HPAOO1384).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for inducing an immune response in an individual to a prostate cancer-associated antigen, the method comprising administering to the individual an effective amount of a composition comprising a polypeptide comprising an amino acid sequence having at least 95% amino acid sequence identity to the amino acid sequence set forth in SEQ ID NO: 23.

2. The method of claim 1, wherein the polypeptide comprises an amino acid sequence having at least 98% amino acid sequence identity to the amino acid sequence set forth in SEQ ID NO: 23.

3. The method of claim 1, wherein the polypeptide is multimerized.

4. The method of claim 1, wherein the polypeptide comprises an amino acid sequence having at least 99% amino acid sequence identity to the amino acid sequence set forth in SEQ ID NO: 23.

5. The method of claim 1, wherein the composition comprises an adjuvant.

6. The method of claim 5, wherein the adjuvant is alum, aluminum phosphate, aluminum hydroxide, or MF59.

7. The method of claim 1, wherein the polypeptide is linked to a carrier.

8. The method of claim 7, wherein the carrier is tetanus toxoid or diphtheria toxoid.

9. The method of claim 1, wherein the immune response is an antibody response, a CD4+ T cell response, or a cytotoxic T cell response.

10. The method of claim 1, wherein the polypeptide is administered in an amount of from 100 pg to 25 mg per dose.

11. The method of claim 1, wherein the polypeptide is administered in an amount of from 100 pg to 250 pg per dose.

12. The method of claim 1, wherein the individual is a human male.

13. The method of claim 12, wherein the human male has prostate cancer.

14. The method of claim 1, wherein the polypeptide comprises the amino acid sequence set forth in SEQ ID NO: 23.

* * * * *

SEQUENCE LISTING

```
<160> NUMBER OF SEQ ID NOS: 155

<210> SEQ ID NO 1
<211> LENGTH: 352
<212> TYPE: PRT
<213> ORGANISM: Homo sapiens
```

<400> SEQUENCE: 1

Met Ala Pro Lys Leu Ile Thr Val Leu Cys Leu Gly Phe Cys Leu Asn
1               5                   10                  15

Gln Lys Ile Cys Pro His Ala Gly Ala Gln Asp Lys Phe Ser Leu Ser
            20                  25                  30

Ala Trp Pro Ser Pro Val Val Pro Leu Gly Gly Arg Val Thr Leu Ser
        35                  40                  45

Cys His Ser His Leu Arg Phe Val Ile Trp Thr Ile Phe Gln Thr Thr
    50                  55                  60

Gly Thr Arg Ser His Glu Leu His Thr Gly Leu Ser Asn Asn Ile Thr
65                  70                  75                  80

Ile Ser Pro Val Thr Pro Glu His Ala Gly Thr Tyr Arg Cys Val Gly
                85                  90                  95

Ile Tyr Lys His Ala Ser Lys Trp Ser Ala Glu Ser Asn Ser Leu Lys
            100                 105                 110

Ile Ile Val Thr Gly Leu Phe Thr Lys Pro Ser Ile Ser Ala His Pro
        115                 120                 125

Ser Ser Leu Val His Ala Gly Ala Arg Val Ser Leu Arg Cys His Ser
    130                 135                 140

Glu Leu Ala Phe Asp Glu Phe Ile Leu Tyr Lys Glu Gly His Ile Gln
145                 150                 155                 160

His Ser Gln Gln Leu Asp Gln Gly Met Glu Ala Gly Ile His Tyr Val
                165                 170                 175

Glu Ala Val Phe Ser Met Gly Pro Val Thr Pro Ala His Ala Gly Ala
            180                 185                 190

Tyr Arg Cys Cys Gly Cys Phe His Ser Arg Tyr Glu Trp Ser Ala
        195                 200                 205

Pro Ser Asp Pro Leu Asp Ile Val Ile Thr Gly Lys Tyr Lys Lys Pro
    210                 215                 220

Ser Leu Ser Thr Gln Val Asp Pro Met Met Arg Leu Gly Glu Lys Leu
225                 230                 235                 240

Thr Leu Phe Cys Ser Ser Glu Ile Ser Phe Asp Gln Tyr His Leu Phe
                245                 250                 255

Arg His Gly Val Ala His Gly Gln Trp Leu Ser Gly Gln Arg His
            260                 265                 270

Arg Glu Ala Phe Gln Ala Asn Phe Ser Val Gly Arg Ala Thr Pro Val
    275                 280                 285

Pro Gly Gly Thr Tyr Arg Cys Tyr Gly Ser Phe Asn Asp Ser Pro Tyr
290                 295                 300

Lys Pro Pro Val Thr Arg Cys Asn Phe Thr Pro Gln Glu Thr Leu Arg
305                 310                 315                 320

Val Leu Leu Cys His Ser Gln Asn Pro Pro Leu Asn Leu Thr His Leu
                325                 330                 335

Ala Leu Lys Asp Ser Pro Ala Thr Cys Ile Cys Ser Leu Asp Ser Gln
            340                 345                 350

<210> SEQ ID NO 2
<211> LENGTH: 344
<212> TYPE: PRT
<213> ORGANISM: Homo sapiens

<400> SEQUENCE: 2

Met Ala Gln Lys Glu Asn Ser Tyr Pro Trp Pro Tyr Gly Arg Gln Thr
1               5                   10                  15

```
Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
                35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
    130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Met Gly Ala Gln Asp Leu Ile
    290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340

<210> SEQ ID NO 3
<211> LENGTH: 646
<212> TYPE: PRT
<213> ORGANISM: Homo sapiens

<400> SEQUENCE: 3

Met Glu Pro Ala Ala Gly Phe Leu Ser Pro Arg Pro Phe Gln Arg Ala
1               5                   10                  15

Ala Ala Ala Pro Ala Pro Pro Ala Gly Pro Gly Pro Pro Pro Ser Ala
            20                  25                  30

Leu Arg Gly Pro Glu Leu Glu Met Leu Ala Gly Leu Pro Thr Ser Asp
        35                  40                  45
```

```
Pro Gly Arg Leu Ile Thr Asp Pro Arg Ser Gly Arg Thr Tyr Leu Lys
    50                  55                  60

Gly Arg Leu Leu Gly Lys Gly Gly Phe Ala Arg Cys Tyr Glu Ala Thr
65                  70                  75                  80

Asp Thr Glu Thr Gly Ser Ala Tyr Ala Val Lys Val Ile Pro Gln Ser
                85                  90                  95

Arg Val Ala Lys Pro His Gln Arg Glu Lys Ile Leu Asn Glu Ile Glu
            100                 105                 110

Leu His Arg Asp Leu Gln His Arg His Ile Val Arg Phe Ser His His
        115                 120                 125

Phe Glu Asp Ala Asp Asn Ile Tyr Ile Phe Leu Glu Leu Cys Ser Arg
    130                 135                 140

Lys Ser Leu Ala His Ile Trp Lys Ala Arg His Thr Leu Leu Glu Pro
145                 150                 155                 160

Glu Val Arg Tyr Tyr Leu Arg Gln Ile Leu Ser Gly Leu Lys Tyr Leu
                165                 170                 175

His Gln Arg Gly Ile Leu His Arg Asp Leu Lys Leu Gly Asn Phe Phe
            180                 185                 190

Ile Thr Glu Asn Met Glu Leu Lys Val Gly Asp Phe Gly Leu Ala Ala
        195                 200                 205

Arg Leu Glu Pro Pro Glu Gln Arg Lys Lys Thr Ile Cys Gly Thr Pro
    210                 215                 220

Asn Tyr Val Ala Pro Glu Val Leu Leu Arg Gln Gly His Gly Pro Glu
225                 230                 235                 240

Ala Asp Val Trp Ser Leu Gly Cys Val Met Tyr Thr Leu Leu Cys Gly
                245                 250                 255

Ser Pro Pro Phe Glu Thr Ala Asp Leu Lys Glu Thr Tyr Arg Cys Ile
            260                 265                 270

Lys Gln Val His Tyr Thr Leu Pro Ala Ser Leu Ser Leu Pro Ala Arg
        275                 280                 285

Gln Leu Leu Ala Ala Ile Leu Arg Ala Ser Pro Arg Asp Arg Pro Ser
    290                 295                 300

Ile Asp Gln Ile Leu Arg His Asp Phe Phe Thr Lys Gly Tyr Thr Pro
305                 310                 315                 320

Asp Arg Leu Pro Ile Ser Ser Cys Val Thr Val Pro Asp Leu Thr Pro
                325                 330                 335

Pro Asn Pro Ala Arg Ser Leu Phe Ala Lys Val Thr Lys Ser Leu Phe
            340                 345                 350

Gly Arg Lys Lys Ser Lys Asn His Ala Gln Glu Arg Asp Glu Val
        355                 360                 365

Ser Gly Leu Val Ser Gly Leu Met Arg Thr Ser Val Gly His Gln Asp
    370                 375                 380

Ala Arg Pro Glu Ala Pro Ala Ser Gly Pro Ala Pro Val Ser Leu
385                 390                 395                 400

Val Glu Thr Ala Pro Glu Asp Ser Ser Pro Arg Gly Thr Leu Ala Ser
                405                 410                 415

Ser Gly Asp Gly Phe Glu Glu Gly Leu Thr Val Ala Thr Val Val Glu
            420                 425                 430

Ser Ala Leu Cys Ala Leu Arg Asn Cys Ile Ala Phe Met Pro Pro Ala
        435                 440                 445

Glu Gln Asn Pro Ala Pro Leu Ala Gln Pro Glu Pro Leu Val Trp Val
    450                 455                 460
```

```
Ser Lys Trp Val Asp Tyr Ser Asn Lys Phe Gly Phe Gly Tyr Gln Leu
465                 470                 475                 480

Ser Ser Arg Arg Val Ala Val Leu Phe Asn Asp Gly Thr His Met Ala
            485                 490                 495

Leu Ser Ala Asn Arg Lys Thr Val His Tyr Asn Pro Thr Ser Thr Lys
            500                 505                 510

His Phe Ser Phe Ser Val Gly Ala Val Pro Arg Ala Leu Gln Pro Gln
            515                 520                 525

Leu Gly Ile Leu Arg Tyr Phe Ala Ser Tyr Met Glu Gln His Leu Met
            530                 535                 540

Lys Gly Gly Asp Leu Pro Ser Val Glu Glu Val Glu Val Pro Ala Pro
545                 550                 555                 560

Pro Leu Leu Leu Gln Trp Val Lys Thr Asp Gln Ala Leu Leu Met Leu
                565                 570                 575

Phe Ser Asp Gly Thr Val Gln Val Asn Phe Tyr Gly Asp His Thr Lys
                580                 585                 590

Leu Ile Leu Ser Gly Trp Glu Pro Leu Leu Val Thr Phe Val Ala Arg
            595                 600                 605

Asn Arg Ser Ala Cys Thr Tyr Leu Ala Ser His Leu Arg Gln Leu Gly
610                 615                 620

Cys Ser Pro Asp Leu Arg Gln Arg Leu Arg Tyr Ala Leu Arg Leu Leu
625                 630                 635                 640

Arg Asp Arg Ser Pro Ala
                645

<210> SEQ ID NO 4
<211> LENGTH: 293
<212> TYPE: PRT
<213> ORGANISM: Homo sapiens

<400> SEQUENCE: 4

Met Pro Ala Arg Ser Gly Ala Gln Phe Cys Arg Arg Met Gly Gln Lys
1               5                   10                  15

Lys Gln Arg Pro Ala Arg Ala Gly Gln Pro His Ser Ser Ser Asp Ala
            20                  25                  30

Ala Gln Ala Pro Ala Glu Gln Pro His Ser Ser Ser Asp Ala Ala Gln
        35                  40                  45

Ala Pro Cys Pro Arg Glu Arg Cys Leu Gly Pro Thr Thr Pro Pro Gly
    50                  55                  60

Pro Tyr Arg Ser Ile Tyr Phe Ser Ser Pro Lys Gly His Leu Thr Arg
65              70                  75                  80

Leu Gly Leu Glu Phe Phe Asp Gln Pro Ala Val Pro Leu Ala Arg Ala
            85                  90                  95

Phe Leu Gly Gln Val Leu Val Arg Arg Leu Pro Asn Gly Thr Glu Leu
        100                 105                 110

Arg Gly Arg Ile Val Glu Thr Glu Ala Tyr Leu Gly Pro Glu Asp Glu
    115                 120                 125

Ala Ala His Ser Arg Gly Gly Arg Gln Thr Pro Arg Asn Arg Gly Met
130                 135                 140

Phe Met Lys Pro Gly Thr Leu Tyr Val Tyr Ile Ile Tyr Gly Met Tyr
145                 150                 155                 160

Phe Cys Met Asn Ile Ser Ser Gln Gly Asp Gly Ala Cys Val Leu Leu
                165                 170                 175

Arg Ala Leu Glu Pro Leu Glu Gly Leu Glu Thr Met Arg Gln Leu Arg
            180                 185                 190
```

```
Ser Thr Leu Arg Lys Gly Thr Ala Ser Arg Val Leu Lys Asp Arg Glu
        195                 200                 205

Leu Cys Ser Gly Pro Ser Lys Leu Cys Gln Ala Leu Ala Ile Asn Lys
    210                 215                 220

Ser Phe Asp Gln Arg Asp Leu Ala Gln Asp Glu Ala Val Trp Leu Glu
225                 230                 235                 240

Arg Gly Pro Leu Glu Pro Ser Glu Pro Ala Val Val Ala Ala Ala Arg
                245                 250                 255

Val Gly Val Gly His Ala Gly Glu Trp Ala Arg Lys Pro Leu Arg Phe
                260                 265                 270

Tyr Val Arg Gly Ser Pro Trp Val Ser Val Val Asp Arg Val Ala Glu
            275                 280                 285

Gln Asp Thr Gln Ala
        290

<210> SEQ ID NO 5
<211> LENGTH: 445
<212> TYPE: PRT
<213> ORGANISM: Homo sapiens

<400> SEQUENCE: 5

Met Pro Ser Arg Ala Glu Asp Tyr Glu Val Leu Tyr Thr Ile Gly Thr
1               5                   10                  15

Gly Ser Tyr Gly Arg Cys Gln Lys Ile Arg Arg Lys Ser Asp Gly Lys
            20                  25                  30

Ile Leu Val Trp Lys Glu Leu Asp Tyr Gly Ser Met Thr Glu Ala Glu
        35                  40                  45

Lys Gln Met Leu Val Ser Glu Val Asn Leu Leu Arg Glu Leu Lys His
    50                  55                  60

Pro Asn Ile Val Arg Tyr Tyr Asp Arg Ile Ile Asp Arg Thr Asn Thr
65                  70                  75                  80

Thr Leu Tyr Ile Val Met Glu Tyr Cys Glu Gly Gly Asp Leu Ala Ser
                85                  90                  95

Val Ile Thr Lys Gly Thr Lys Glu Arg Gln Tyr Leu Asp Glu Glu Phe
            100                 105                 110

Val Leu Arg Val Met Thr Gln Leu Thr Leu Ala Leu Lys Glu Cys His
        115                 120                 125

Arg Arg Ser Asp Gly Gly His Thr Val Leu His Arg Asp Leu Lys Pro
    130                 135                 140

Ala Asn Val Phe Leu Asp Gly Lys Gln Asn Val Lys Leu Gly Asp Phe
145                 150                 155                 160

Gly Leu Ala Arg Ile Leu Asn His Asp Thr Ser Phe Ala Lys Thr Phe
                165                 170                 175

Val Gly Thr Pro Tyr Tyr Met Ser Pro Glu Gln Met Asn Arg Met Ser
            180                 185                 190

Tyr Asn Glu Lys Ser Asp Ile Trp Ser Leu Gly Cys Leu Leu Tyr Glu
        195                 200                 205

Leu Cys Ala Leu Met Pro Pro Phe Thr Ala Phe Ser Gln Lys Glu Leu
    210                 215                 220

Ala Gly Lys Ile Arg Glu Gly Lys Phe Arg Arg Ile Pro Tyr Arg Tyr
225                 230                 235                 240

Ser Asp Glu Leu Asn Glu Ile Ile Thr Arg Met Leu Asn Leu Lys Asp
                245                 250                 255

Tyr His Arg Pro Ser Val Glu Glu Ile Leu Glu Asn Pro Leu Ile Ala
```

```
                    260                 265                 270
Asp Leu Val Ala Asp Glu Gln Arg Arg Asn Leu Glu Arg Arg Gly Arg
                275                 280                 285

Gln Leu Gly Glu Pro Glu Lys Ser Gln Asp Ser Ser Pro Val Leu Ser
            290                 295                 300

Glu Leu Lys Leu Lys Glu Ile Gln Leu Gln Glu Arg Glu Arg Ala Leu
305                 310                 315                 320

Lys Ala Arg Glu Glu Arg Leu Glu Gln Lys Glu Gln Glu Leu Cys Val
                325                 330                 335

Arg Glu Arg Leu Ala Glu Asp Lys Leu Ala Arg Ala Glu Asn Leu Leu
            340                 345                 350

Lys Asn Tyr Ser Leu Leu Lys Glu Arg Lys Phe Leu Ser Leu Ala Ser
        355                 360                 365

Asn Pro Glu Leu Leu Asn Leu Pro Ser Ser Val Ile Lys Lys Lys Val
        370                 375                 380

His Phe Ser Gly Glu Ser Lys Glu Asn Ile Met Arg Ser Glu Asn Ser
385                 390                 395                 400

Glu Ser Gln Leu Thr Ser Lys Ser Lys Cys Lys Asp Leu Lys Lys Arg
            405                 410                 415

Leu His Ala Ala Gln Leu Arg Ala Gln Ala Leu Ser Asp Ile Glu Lys
                420                 425                 430

Asn Tyr Gln Leu Lys Ser Arg Gln Ile Leu Gly Met Arg
            435                 440                 445

<210> SEQ ID NO 6
<211> LENGTH: 71
<212> TYPE: PRT
<213> ORGANISM: Homo sapiens

<400> SEQUENCE: 6

Met Glu Arg Ala Arg Asp Arg Leu His Leu Arg Arg Thr Thr Glu Gln
1               5                   10                  15

His Val Pro Glu Val Glu Val Gln Val Lys Arg Arg Arg Thr Ala Ser
            20                  25                  30

Leu Ser Asn Gln Glu Cys Gln Leu Tyr Pro Arg Arg Ser Gln Gln Gln
        35                  40                  45

Gln Val Pro Val Val Asp Phe Gln Ala Glu Leu Arg Gln Ala Phe Leu
    50                  55                  60

Ala Glu Thr Pro Arg Gly Gly
65                  70

<210> SEQ ID NO 7
<211> LENGTH: 1101
<212> TYPE: PRT
<213> ORGANISM: Homo sapiens

<400> SEQUENCE: 7

Met Ser Ala Lys Ala Ile Ser Glu Gln Thr Gly Lys Glu Leu Leu Tyr
1               5                   10                  15

Lys Phe Ile Cys Thr Thr Ser Ala Ile Gln Asn Arg Phe Lys Tyr Ala
            20                  25                  30

Arg Val Thr Pro Asp Thr Asp Trp Ala Arg Leu Leu Gln Asp His Pro
        35                  40                  45

Trp Leu Leu Ser Gln Asn Leu Val Val Lys Pro Asp Gln Leu Ile Lys
    50                  55                  60

Arg Arg Gly Lys Leu Gly Leu Val Gly Val Asn Leu Thr Leu Asp Gly
```

```
            65                  70                  75                  80
Val Lys Ser Trp Leu Lys Pro Arg Leu Gly Gln Glu Ala Thr Val Gly
                     85                  90                  95

Lys Ala Thr Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
            115                 120                 125

Gly Asp Tyr Val Leu Phe His His Glu Gly Val Asp Val Gly Asp
    130                 135                 140

Val Asp Ala Lys Ala Gln Lys Leu Leu Val Gly Val Asp Glu Lys Leu
145                 150                 155                 160

Asn Pro Glu Asp Ile Lys Lys His Leu Leu Val His Ala Pro Glu Asp
                165                 170                 175

Lys Lys Glu Ile Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
            195                 200                 205

Lys Asp Gly Val Tyr Val Leu Asp Leu Ala Ala Lys Val Asp Ala Thr
            210                 215                 220

Ala Asp Tyr Ile Cys Lys Val Lys Trp Gly Asp Ile Glu Phe Pro Pro
225                 230                 235                 240

Pro Phe Gly Arg Glu Ala Tyr Pro Glu Glu Ala Tyr Ile Ala Asp Leu
                245                 250                 255

Asp Ala Lys Ser Gly Ala Ser Leu Lys Leu Thr Leu Leu Asn Pro Lys
            260                 265                 270

Gly Arg Ile Trp Thr Met Val Ala Gly Gly Ala Ser Val Val Tyr
            275                 280                 285

Ser Asp Thr Ile Cys Asp Leu Gly Gly Val Asn Glu Leu Ala Asn Tyr
            290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Asp Gly Lys
                325                 330                 335

Ile Leu Ile Ile Gly Gly Ser Ile Ala Asn Phe Thr Asn Val Ala Ala
            340                 345                 350

Thr Phe Lys Gly Ile Val Arg Ala Ile Arg Asp Tyr Gln Gly Pro Leu
            355                 360                 365

Lys Glu His Glu Val Thr Ile Phe Val Arg Arg Gly Gly Pro Asn Tyr
            370                 375                 380

Gln Glu Gly Leu Arg Val Met Gly Glu Val Gly Lys Thr Thr Gly Ile
385                 390                 395                 400

Pro Ile His Val Phe Gly Thr Glu Thr His Met Thr Ala Ile Val Gly
                405                 410                 415

Met Ala Leu Gly His Arg Pro Ile Pro Asn Gln Pro Thr Ala Ala
            420                 425                 430

His Thr Ala Asn Phe Leu Leu Asn Ala Ser Gly Ser Thr Ser Thr Pro
            435                 440                 445

Ala Pro Ser Arg Thr Ala Ser Phe Ser Glu Ser Arg Ala Asp Glu Val
            450                 455                 460

Ala Pro Ala Lys Lys Ala Lys Pro Ala Met Pro Gln Asp Ser Val Pro
465                 470                 475                 480

Ser Pro Arg Ser Leu Gln Gly Lys Ser Thr Thr Leu Phe Ser Arg His
            485                 490                 495
```

```
Thr Lys Ala Ile Val Trp Gly Met Gln Thr Arg Ala Val Gln Gly Met
                500                 505                 510

Leu Asp Phe Asp Tyr Val Cys Ser Arg Asp Glu Pro Ser Val Ala Ala
                515                 520                 525

Met Val Tyr Pro Phe Thr Gly Asp His Lys Gln Lys Phe Tyr Trp Gly
                530                 535                 540

His Lys Glu Ile Leu Ile Pro Val Phe Lys Asn Met Ala Asp Ala Met
545                 550                 555                 560

Arg Lys His Pro Glu Val Asp Val Leu Ile Asn Phe Ala Ser Leu Arg
                565                 570                 575

Ser Ala Tyr Asp Ser Thr Met Glu Thr Met Asn Tyr Ala Gln Ile Arg
                580                 585                 590

Thr Ile Ala Ile Ile Ala Glu Gly Ile Pro Glu Ala Leu Thr Arg Lys
                595                 600                 605

Leu Ile Lys Lys Ala Asp Gln Lys Gly Val Thr Ile Ile Gly Pro Ala
                610                 615                 620

Thr Val Gly Gly Ile Lys Pro Gly Cys Phe Lys Ile Gly Asn Thr Gly
625                 630                 635                 640

Gly Met Leu Asp Asn Ile Leu Ala Ser Lys Leu Tyr Arg Pro Gly Ser
                645                 650                 655

Val Ala Tyr Val Ser Arg Ser Gly Gly Met Ser Asn Glu Leu Asn Asn
                660                 665                 670

Ile Ile Ser Arg Thr Thr Asp Gly Val Tyr Glu Gly Val Ala Ile Gly
                675                 680                 685

Gly Asp Arg Tyr Pro Gly Ser Thr Phe Met Asp His Val Leu Arg Tyr
690                 695                 700

Gln Asp Thr Pro Gly Val Lys Met Ile Val Val Leu Gly Glu Ile Gly
705                 710                 715                 720

Gly Thr Glu Glu Tyr Lys Ile Cys Arg Gly Ile Lys Glu Gly Arg Leu
                725                 730                 735

Thr Lys Pro Ile Val Cys Trp Cys Ile Gly Thr Cys Ala Thr Met Phe
                740                 745                 750

Ser Ser Glu Val Gln Phe Gly His Ala Gly Ala Cys Ala Asn Gln Ala
                755                 760                 765

Ser Glu Thr Ala Val Ala Lys Asn Gln Ala Leu Lys Glu Ala Gly Val
770                 775                 780

Phe Val Pro Arg Ser Phe Asp Glu Leu Gly Glu Ile Ile Gln Ser Val
785                 790                 795                 800

Tyr Glu Asp Leu Val Ala Asn Gly Val Ile Val Pro Ala Gln Glu Val
                805                 810                 815

Pro Pro Pro Thr Val Pro Met Asp Tyr Ser Trp Ala Arg Glu Leu Gly
                820                 825                 830

Leu Ile Arg Lys Pro Ala Ser Phe Met Thr Ser Ile Cys Asp Glu Arg
                835                 840                 845

Gly Gln Glu Leu Ile Tyr Ala Gly Met Pro Ile Thr Glu Val Phe Lys
                850                 855                 860

Glu Glu Met Gly Ile Gly Gly Val Leu Gly Leu Leu Trp Phe Gln Lys
865                 870                 875                 880

Arg Leu Pro Lys Tyr Ser Cys Gln Phe Ile Glu Met Cys Leu Met Val
                885                 890                 895

Thr Ala Asp His Gly Pro Ala Val Ser Gly Ala His Asn Thr Ile Ile
                900                 905                 910
```

```
Cys Ala Arg Ala Gly Lys Asp Leu Val Ser Ser Leu Thr Ser Gly Leu
            915                 920                 925

Leu Thr Ile Gly Asp Arg Phe Gly Gly Ala Leu Asp Ala Ala Ala Lys
        930                 935                 940

Met Phe Ser Lys Ala Phe Asp Ser Gly Ile Ile Pro Met Glu Phe Val
945                 950                 955                 960

Asn Lys Met Lys Lys Glu Gly Lys Leu Ile Met Gly Ile Gly His Arg
                965                 970                 975

Val Lys Ser Ile Asn Asn Pro Asp Met Arg Val Gln Ile Leu Lys Asp
            980                 985                 990

Tyr Val Arg Gln His Phe Pro Ala Thr Pro Leu Leu Asp Tyr Ala Leu
        995                 1000                1005

Glu Val Glu Lys Ile Thr Thr Ser Lys Lys Pro Asn Leu Ile Leu Asn
    1010                1015                1020

Val Asp Gly Leu Ile Gly Val Ala Phe Val Asp Met Leu Arg Asn Cys
1025                1030                1035                1040

Gly Ser Phe Thr Arg Glu Glu Ala Asp Glu Tyr Ile Asp Ile Gly Ala
                1045                1050                1055

Leu Asn Gly Ile Phe Val Leu Gly Arg Ser Met Gly Phe Ile Gly His
            1060                1065                1070

Tyr Leu Asp Gln Lys Arg Leu Lys Gln Gly Leu Tyr Arg His Pro Trp
        1075                1080                1085

Asp Asp Ile Ser Tyr Val Leu Pro Glu His Met Ser Met
        1090                1095                1100

<210> SEQ ID NO 8
<211> LENGTH: 499
<212> TYPE: PRT
<213> ORGANISM: Homo sapiens

<400> SEQUENCE: 8

Met Ala Ser Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
            20                  25                  30

Lys Ile Pro Thr Gly Gln Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile Gln Gln Ile Leu Glu Ser Val Asn His Cys His
        115                 120                 125

Leu Asn Gly Ile Val His Arg Asp Leu Lys Pro Glu Asn Leu Leu Leu
    130                 135                 140

Ala Ser Lys Ser Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190
```

-continued

```
Lys Pro Val Asp Met Trp Ala Cys Gly Val Ile Leu Tyr Ile Leu Leu
            195                 200                 205

Val Gly Tyr Pro Pro Phe Trp Asp Glu Asp Gln His Arg Leu Tyr Gln
        210                 215                 220

Gln Ile Lys Ala Gly Ala Tyr Asp Phe Pro Ser Pro Glu Trp Asp Thr
225                 230                 235                 240

Val Thr Pro Glu Ala Lys Asp Leu Ile Asn Lys Met Leu Thr Ile Asn
                245                 250                 255

Pro Ala Lys Arg Ile Thr Ala Ser Glu Ala Leu Lys His Pro Trp Ile
            260                 265                 270

Cys Gln Arg Ser Thr Val Ala Ser Met Met His Arg Gln Glu Thr Val
        275                 280                 285

Asp Cys Leu Lys Lys Phe Asn Ala Arg Arg Lys Leu Lys Gly Ala Ile
290                 295                 300

Leu Thr Thr Met Leu Ala Thr Arg Asn Phe Ser Ala Ala Lys Ser Leu
305                 310                 315                 320

Leu Lys Lys Pro Asp Gly Val Lys Glu Ser Thr Glu Ser Ser Asn Thr
                325                 330                 335

Thr Ile Glu Asp Glu Asp Val Lys Ala Arg Lys Gln Glu Ile Ile Lys
            340                 345                 350

Val Thr Glu Gln Leu Ile Glu Ala Ile Asn Asn Gly Asp Phe Glu Ala
        355                 360                 365

Tyr Thr Lys Ile Cys Asp Pro Gly Leu Thr Ala Phe Glu Pro Glu Ala
370                 375                 380

Leu Gly Asn Leu Val Glu Gly Met Asp Phe His Arg Phe Tyr Phe Glu
385                 390                 395                 400

Asn Ala Leu Ser Lys Ser Asn Lys Pro Ile His Thr Ile Ile Leu Asn
                405                 410                 415

Pro His Val His Leu Val Gly Asp Asp Ala Ala Cys Ile Ala Tyr Ile
            420                 425                 430

Arg Leu Thr Gln Tyr Met Asp Gly Ser Gly Met Pro Lys Thr Met Gln
        435                 440                 445

Ser Glu Glu Thr Arg Val Trp His Arg Arg Asp Gly Lys Trp Gln Asn
        450                 455                 460

Val His Phe His Arg Ser Gly Ser Pro Thr Val Pro Ile Lys Pro Pro
465                 470                 475                 480

Cys Ile Pro Asn Gly Lys Glu Asn Phe Ser Gly Gly Thr Ser Leu Trp
                485                 490                 495

Gln Asn Ile

<210> SEQ ID NO 9
<211> LENGTH: 681
<212> TYPE: PRT
<213> ORGANISM: Homo sapiens

<400> SEQUENCE: 9

Met Phe Arg Lys Lys Lys Lys Arg Pro Glu Ile Ser Ala Pro Gln
1               5                   10                  15

Asn Phe Gln His Arg Val His Thr Ser Phe Asp Pro Lys Glu Gly Lys
                20                  25                  30

Phe Val Gly Leu Pro Pro Gln Trp Gln Asn Ile Leu Asp Thr Leu Arg
            35                  40                  45

Arg Pro Lys Pro Val Val Asp Pro Ser Arg Ile Thr Arg Val Gln Leu
        50                  55                  60
```

-continued

```
Gln Pro Met Lys Thr Val Val Arg Gly Ser Ala Met Pro Val Asp Gly
 65                  70                  75                  80

Tyr Ile Ser Gly Leu Leu Asn Asp Ile Gln Lys Leu Ser Val Ile Ser
                 85                  90                  95

Ser Asn Thr Leu Arg Gly Arg Ser Pro Thr Ser Arg Arg Ala Gln
            100                 105                 110

Ser Leu Gly Leu Leu Gly Asp Glu His Trp Ala Thr Asp Pro Asp Met
            115                 120                 125

Tyr Leu Gln Ser Pro Gln Ser Glu Arg Thr Asp Pro His Gly Leu Tyr
130                 135                 140

Leu Ser Cys Asn Gly Gly Thr Pro Ala Gly His Lys Gln Met Pro Trp
145                 150                 155                 160

Pro Glu Pro Gln Ser Pro Arg Val Leu Pro Asn Gly Leu Ala Ala Lys
                165                 170                 175

Ala Gln Ser Leu Gly Pro Ala Glu Phe Gln Gly Ala Ser Gln Arg Cys
                180                 185                 190

Leu Gln Leu Gly Ala Cys Leu Gln Ser Ser Pro Gly Ala Ser Pro
                195                 200                 205

Pro Thr Gly Thr Asn Arg His Gly Met Lys Ala Ala Lys His Gly Ser
210                 215                 220

Glu Glu Ala Arg Pro Gln Ser Cys Leu Val Gly Ser Ala Thr Gly Arg
225                 230                 235                 240

Pro Gly Gly Glu Gly Ser Pro Ser Pro Lys Thr Arg Glu Ser Ser Leu
                245                 250                 255

Lys Arg Arg Leu Phe Arg Ser Met Phe Leu Ser Thr Ala Ala Thr Ala
                260                 265                 270

Pro Pro Ser Ser Ser Lys Pro Gly Pro Pro Gln Ser Lys Pro Asn
                275                 280                 285

Ser Ser Phe Arg Pro Pro Gln Lys Asp Asn Pro Pro Ser Leu Val Ala
            290                 295                 300

Lys Ala Gln Ser Leu Pro Ser Asp Gln Pro Val Gly Thr Phe Ser Pro
305                 310                 315                 320

Leu Thr Thr Ser Asp Thr Ser Ser Pro Gln Lys Ser Leu Arg Thr Ala
                325                 330                 335

Pro Ala Thr Gly Gln Leu Pro Gly Arg Ser Ser Pro Ala Gly Ser Pro
                340                 345                 350

Arg Thr Trp His Ala Gln Ile Ser Thr Ser Asn Leu Tyr Leu Pro Gln
                355                 360                 365

Asp Pro Thr Val Ala Lys Gly Ala Leu Ala Gly Glu Asp Thr Gly Val
370                 375                 380

Val Thr His Glu Gln Phe Lys Ala Ala Leu Arg Met Val Val Asp Gln
385                 390                 395                 400

Gly Asp Pro Arg Leu Leu Leu Asp Ser Tyr Val Lys Ile Gly Glu Gly
                405                 410                 415

Ser Thr Gly Ile Val Cys Leu Ala Arg Glu Lys His Ser Gly Arg Gln
                420                 425                 430

Val Ala Val Lys Met Met Asp Leu Arg Lys Gln Gln Arg Arg Glu Leu
                435                 440                 445

Leu Phe Asn Glu Val Val Ile Met Arg Asp Tyr Gln His Phe Asn Val
                450                 455                 460

Val Glu Met Tyr Lys Ser Tyr Leu Val Gly Glu Glu Leu Trp Val Leu
465                 470                 475                 480
```

```
Met Glu Phe Leu Gln Gly Gly Ala Leu Thr Asp Ile Val Ser Gln Val
                485                 490                 495

Arg Leu Asn Glu Glu Gln Ile Ala Thr Val Cys Glu Ala Val Leu Gln
            500                 505                 510

Ala Leu Ala Tyr Leu His Ala Gln Gly Val Ile His Arg Asp Ile Lys
        515                 520                 525

Ser Asp Ser Ile Leu Leu Thr Leu Asp Gly Arg Val Lys Leu Ser Asp
    530                 535                 540

Phe Gly Phe Cys Ala Gln Ile Ser Lys Asp Val Pro Lys Arg Lys Ser
545                 550                 555                 560

Leu Val Gly Thr Pro Tyr Trp Met Ala Pro Glu Val Ile Ser Arg Ser
                565                 570                 575

Leu Tyr Ala Thr Glu Val Asp Ile Trp Ser Leu Gly Ile Met Val Ile
            580                 585                 590

Glu Met Val Asp Gly Glu Pro Pro Tyr Phe Ser Asp Ser Pro Val Gln
        595                 600                 605

Ala Met Lys Arg Leu Arg Asp Ser Pro Pro Lys Leu Lys Asn Ser
    610                 615                 620

His Lys Val Ser Pro Val Leu Arg Asp Phe Leu Glu Arg Met Leu Val
625                 630                 635                 640

Arg Asp Pro Gln Glu Arg Ala Thr Ala Gln Glu Leu Leu Asp His Pro
                645                 650                 655

Phe Leu Leu Gln Thr Gly Leu Pro Glu Cys Leu Val Pro Leu Ile Gln
            660                 665                 670

Leu Tyr Arg Lys Gln Thr Ser Thr Cys
        675                 680

<210> SEQ ID NO 10
<211> LENGTH: 415
<212> TYPE: PRT
<213> ORGANISM: Homo sapiens

<400> SEQUENCE: 10

Met Glu Leu Arg Val Gly Asn Arg Tyr Arg Leu Gly Arg Lys Ile Gly
1               5                   10                  15

Ser Gly Ser Phe Gly Asp Ile Tyr Leu Gly Thr Asp Ile Ala Ala Gly
            20                  25                  30

Glu Glu Val Ala Ile Lys Leu Glu Cys Val Lys Thr Lys His Pro Gln
        35                  40                  45

Leu His Ile Glu Ser Lys Ile Tyr Lys Met Met Gln Gly Gly Val Gly
    50                  55                  60

Ile Pro Thr Ile Arg Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175
```

```
Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
            195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
            275                 280                 285

Asp Trp Asn Met Leu Lys Phe Gly Ala Ser Arg Ala Ala Asp Asp Ala
    290                 295                 300

Glu Arg Glu Arg Arg Asp Arg Glu Glu Arg Leu Arg His Ser Arg Asn
305                 310                 315                 320

Pro Ala Thr Arg Gly Leu Pro Ser Thr Ala Ser Gly Arg Leu Arg Gly
                325                 330                 335

Thr Gln Glu Val Ala Pro Pro Thr Pro Leu Thr Pro Thr Ser His Thr
            340                 345                 350

Ala Asn Thr Ser Pro Arg Pro Val Ser Gly Met Glu Arg Glu Arg Lys
            355                 360                 365

Val Ser Met Arg Leu His Arg Gly Ala Pro Val Asn Ile Ser Ser Ser
    370                 375                 380

Asp Leu Thr Gly Arg Gln Asp Thr Ser Arg Met Ser Thr Ser Gln Ile
385                 390                 395                 400

Pro Gly Arg Val Ala Ser Ser Gly Leu Gln Ser Val Val His Arg
                405                 410                 415

<210> SEQ ID NO 11
<211> LENGTH: 415
<212> TYPE: PRT
<213> ORGANISM: Homo sapiens

<400> SEQUENCE: 11

Met Asp Phe Asp Lys Lys Gly Gly Lys Gly Glu Thr Glu Glu Gly Arg
1               5                   10                  15

Arg Met Ser Lys Ala Gly Gly Gly Arg Ser Ser His Gly Ile Arg Ser
            20                  25                  30

Ser Gly Thr Ser Ser Gly Val Leu Met Val Gly Pro Asn Phe Arg Val
            35                  40                  45

Gly Lys Lys Ile Gly Cys Gly Asn Phe Gly Glu Leu Arg Leu Gly Lys
    50                  55                  60

Asn Leu Tyr Thr Asn Glu Tyr Val Ala Ile Lys Leu Glu Pro Ile Lys
65                  70                  75                  80

Ser Arg Ala Pro Gln Leu His Leu Glu Tyr Arg Phe Tyr Lys Gln Leu
                85                  90                  95

Ser Ala Thr Glu Gly Val Pro Gln Val Tyr Tyr Phe Gly Pro Cys Gly
            100                 105                 110

Lys Tyr Asn Ala Met Val Leu Glu Leu Leu Gly Pro Ser Leu Glu Asp
            115                 120                 125

Leu Phe Asp Leu Cys Asp Arg Thr Phe Thr Leu Lys Thr Val Leu Met
```

```
                130                 135                 140
Ile Ala Ile Gln Leu Ile Thr Arg Met Glu Tyr Val His Thr Lys Ser
145                 150                 155                 160

Leu Ile Tyr Arg Asp Val Lys Pro Glu Asn Phe Leu Val Gly Arg Pro
                165                 170                 175

Gly Thr Lys Arg Gln His Ala Ile His Ile Asp Phe Gly Leu Ala
                180                 185                 190

Lys Glu Tyr Ile Asp Pro Glu Thr Lys Lys His Ile Pro Tyr Arg Glu
                195                 200                 205

His Lys Ser Leu Thr Gly Thr Ala Arg Tyr Met Ser Ile Asn Thr His
                210                 215                 220

Leu Gly Lys Glu Gln Ser Arg Arg Asp Asp Leu Glu Ala Leu Gly His
225                 230                 235                 240

Met Phe Met Tyr Phe Leu Arg Gly Ser Leu Pro Trp Gln Gly Leu Lys
                245                 250                 255

Ala Asp Thr Leu Lys Glu Arg Tyr Gln Lys Ile Gly Asp Thr Lys Arg
                260                 265                 270

Ala Thr Pro Ile Glu Val Leu Cys Glu Asn Phe Pro Glu Glu Met Ala
                275                 280                 285

Thr Tyr Leu Arg Tyr Val Arg Arg Leu Asp Phe Phe Glu Lys Pro Asp
                290                 295                 300

Tyr Asp Tyr Leu Arg Lys Leu Phe Thr Asp Leu Phe Asp Arg Ser Gly
305                 310                 315                 320

Phe Val Phe Asp Tyr Glu Tyr Asp Trp Ala Gly Lys Pro Leu Pro Thr
                325                 330                 335

Pro Ile Gly Thr Val His Thr Asp Leu Pro Ser Gln Pro Gln Leu Arg
                340                 345                 350

Asp Lys Thr Gln Pro His Ser Lys Asn Gln Ala Leu Asn Ser Thr Asn
                355                 360                 365

Gly Glu Leu Asn Ala Asp Asp Pro Thr Ala Gly His Ser Asn Ala Pro
                370                 375                 380

Ile Thr Ala Pro Ala Glu Val Glu Val Ala Asp Glu Thr Lys Cys Cys
385                 390                 395                 400

Cys Phe Phe Lys Arg Arg Lys Arg Lys Ser Leu Gln Arg His Lys
                405                 410                 415

<210> SEQ ID NO 12
<211> LENGTH: 317
<212> TYPE: PRT
<213> ORGANISM: Homo sapiens

<400> SEQUENCE: 12

Met Arg Lys Thr Ser Asn Ser Cys Ile Met Glu Asn Gly His Gln Pro
1               5                   10                  15

Gly Thr Gly Pro Gly Asp Gly Pro Glu Ile Ala Gln Asn Phe Ser
                20                  25                  30

Ala Pro Asp Pro Pro Arg Pro Pro Val Ser Leu Ser Leu Arg Leu
                35                  40                  45

Pro His Gln Pro Val Thr Ala Ile Thr Arg Val Ser Asp Arg Phe Ser
                50                  55                  60

Gly Glu Thr Ser Ala Ala Ala Leu Ser Pro Met Ser Ala Ala Thr Leu
65                  70                  75                  80

Gly Gly Leu Asn Pro Ser Pro Ser Glu Val Ile Thr Pro Trp Thr Pro
                85                  90                  95
```

-continued

```
Ser Pro Ser Glu Lys Asn Ser Ser Phe Thr Trp Ser Val Pro Ser Ser
            100                 105                 110

Gly Tyr Gly Ala Val Thr Ala Ser Lys His Ser Asn Ser Pro Pro Leu
        115                 120                 125

Val Thr Pro Pro Gln Ser Pro Val Ser Pro Gln Pro Ala Ile Thr
    130                 135                 140

Gln Val His Arg Gln Gly Glu Arg Arg Arg Glu Leu Val Arg Ser Gln
145                 150                 155                 160

Thr Leu Pro Arg Thr Ser Glu Ala Gln Ala Arg Lys Ala Leu Phe Glu
                165                 170                 175

Lys Trp Glu Gln Glu Thr Ala Ala Gly Lys Gly Lys Gly Ala Arg
            180                 185                 190

Ala Arg Leu Lys Arg Ser Gln Ser Phe Gly Val Ala Ser Ala Ser Ser
        195                 200                 205

Ile Lys Gln Ile Leu Leu Glu Trp Cys Arg Ser Lys Thr Leu Gly Tyr
210                 215                 220

Gln His Val Asp Leu Gln Asn Phe Ser Ser Trp Ser Asp Gly Met
225                 230                 235                 240

Ala Phe Cys Ala Leu Val His Ser Phe Phe Pro Asp Ala Phe Asp Tyr
                245                 250                 255

Asn Ser Leu Ser Pro Thr Gln Arg Gln Lys Asn Phe Glu Leu Ala Phe
            260                 265                 270

Thr Met Ala Glu Asn Leu Ala Asn Cys Glu Arg Leu Ile Glu Val Glu
        275                 280                 285

Asp Met Met Val Met Gly Arg Lys Pro Asp Pro Met Cys Val Phe Thr
    290                 295                 300

Tyr Val Gln Ser Leu Tyr Asn His Leu Arg Arg Phe Glu
305                 310                 315

<210> SEQ ID NO 13
<211> LENGTH: 688
<212> TYPE: PRT
<213> ORGANISM: Homo sapiens

<400> SEQUENCE: 13

Met Ser Ser Arg Thr Val Leu Ala Pro Gly Asn Asp Arg Asn Ser Asp
1               5                   10                  15

Thr His Gly Thr Leu Gly Ser Gly Arg Ser Ser Asp Lys Gly Pro Ser
            20                  25                  30

Trp Ser Ser Arg Ser Leu Gly Ala Arg Cys Arg Asn Ser Ile Ala Ser
        35                  40                  45

Cys Pro Glu Glu Gln Pro His Val Gly Asn Tyr Arg Leu Leu Arg Thr
    50                  55                  60

Ile Gly Lys Gly Asn Phe Ala Lys Val Lys Leu Ala Arg His Ile Leu
65                  70                  75                  80

Thr Gly Arg Glu Val Ala Ile Lys Ile Ile Asp Lys Thr Gln Leu Asn
                85                  90                  95

Pro Ser Ser Leu Gln Lys Leu Phe Arg Glu Val Arg Ile Met Lys Gly
            100                 105                 110

Leu Asn His Pro Asn Ile Val Lys Leu Phe Glu Val Ile Glu Thr Glu
        115                 120                 125

Lys Thr Leu Tyr Leu Val Met Glu Tyr Ala Ser Ala Gly Glu Val Phe
    130                 135                 140

Asp Tyr Leu Val Ser His Gly Arg Met Lys Glu Lys Glu Ala Arg Ala
145                 150                 155                 160
```

-continued

Lys Phe Arg Gln Ile Val Ser Ala Val His Tyr Cys His Gln Lys Asn
                165                 170                 175

Ile Val His Arg Asp Leu Lys Ala Glu Asn Leu Leu Leu Asp Ala Glu
            180                 185                 190

Ala Asn Ile Lys Ile Ala Asp Phe Gly Phe Ser Asn Glu Phe Thr Leu
        195                 200                 205

Gly Ser Lys Leu Asp Thr Phe Cys Gly Ser Pro Pro Tyr Ala Ala Pro
    210                 215                 220

Glu Leu Phe Gln Gly Lys Lys Tyr Asp Gly Pro Glu Val Asp Ile Trp
225                 230                 235                 240

Ser Leu Gly Val Ile Leu Tyr Thr Leu Val Ser Gly Ser Leu Pro Phe
                245                 250                 255

Asp Gly His Asn Leu Lys Glu Leu Arg Glu Arg Val Leu Arg Gly Lys
            260                 265                 270

Tyr Arg Val Pro Phe Tyr Met Ser Thr Asp Cys Glu Ser Ile Leu Arg
        275                 280                 285

Arg Phe Leu Val Leu Asn Pro Ala Lys Arg Cys Thr Leu Glu Gln Ile
    290                 295                 300

Met Lys Asp Lys Trp Ile Asn Ile Gly Tyr Glu Gly Glu Glu Leu Lys
305                 310                 315                 320

Pro Tyr Thr Glu Pro Glu Glu Asp Phe Gly Asp Thr Lys Arg Ile Glu
                325                 330                 335

Val Met Val Gly Met Gly Tyr Thr Arg Glu Glu Ile Lys Glu Ser Leu
            340                 345                 350

Thr Ser Gln Lys Tyr Asn Glu Val Thr Ala Thr Tyr Leu Leu Leu Gly
        355                 360                 365

Arg Lys Thr Glu Glu Gly Gly Asp Arg Gly Ala Pro Gly Leu Ala Leu
    370                 375                 380

Ala Arg Val Arg Ala Pro Ser Asp Thr Thr Asn Gly Thr Ser Ser Ser
385                 390                 395                 400

Lys Gly Thr Ser His Ser Lys Gly Gln Arg Ser Ser Ser Thr Tyr
                405                 410                 415

His Arg Gln Arg Arg His Ser Asp Phe Cys Gly Pro Ser Pro Ala Pro
            420                 425                 430

Leu His Pro Lys Arg Ser Pro Thr Ser Thr Gly Glu Ala Glu Leu Lys
        435                 440                 445

Glu Glu Arg Leu Pro Gly Arg Lys Ala Ser Cys Ser Thr Ala Gly Ser
    450                 455                 460

Gly Ser Arg Gly Leu Pro Ser Ser Pro Met Val Ser Ser Ala His
465                 470                 475                 480

Asn Pro Asn Lys Ala Glu Ile Pro Glu Arg Arg Lys Asp Ser Thr Ser
                485                 490                 495

Thr Pro Asn Asn Leu Pro Pro Ser Met Met Thr Arg Arg Asn Thr Tyr
            500                 505                 510

Val Cys Thr Glu Arg Pro Gly Ala Glu Arg Pro Ser Leu Leu Pro Asn
        515                 520                 525

Gly Lys Glu Asn Ser Ser Gly Thr Pro Arg Val Pro Pro Ala Ser Pro
    530                 535                 540

Ser Ser His Ser Leu Ala Pro Pro Ser Gly Glu Arg Ser Arg Leu Ala
545                 550                 555                 560

Arg Gly Ser Thr Ile Arg Ser Thr Phe His Gly Gly Gln Val Arg Asp
                565                 570                 575

```
Arg Arg Ala Gly Gly Gly Gly Gly Val Gln Asn Gly Pro Pro
            580             585                 590

Ala Ser Pro Thr Leu Ala His Glu Ala Ala Pro Leu Pro Ala Gly Arg
        595                 600                 605

Pro Arg Pro Thr Thr Asn Leu Phe Thr Lys Leu Thr Ser Lys Leu Thr
        610                 615                 620

Arg Arg Val Thr Leu Asp Pro Ser Lys Arg Gln Asn Ser Asn Arg Cys
625                 630                 635                 640

Val Ser Gly Ala Ser Leu Pro Gln Gly Ser Lys Ile Arg Ser Gln Thr
            645                 650                 655

Asn Leu Arg Glu Ser Gly Asp Leu Arg Ser Gln Val Ala Ile Tyr Leu
        660                 665                 670

Gly Ile Lys Arg Lys Pro Pro Gly Cys Ser Asp Ser Pro Gly Val
        675                 680                 685

<210> SEQ ID NO 14
<211> LENGTH: 167
<212> TYPE: PRT
<213> ORGANISM: Homo sapiens

<400> SEQUENCE: 14

Met Glu Glu Thr Tyr Thr Asp Ser Leu Asp Pro Glu Lys Leu Leu Gln
1               5                   10                  15

Cys Pro Tyr Asp Lys Asn His Gln Ile Arg Ala Cys Arg Phe Pro Tyr
            20                  25                  30

His Leu Ile Lys Cys Arg Lys Asn His Pro Asp Val Ala Ser Lys Leu
        35                  40                  45

Ala Thr Cys Pro Phe Asn Ala Arg His Gln Val Pro Arg Ala Glu Ile
    50                  55                  60

Ser His His Ile Ser Ser Cys Asp Asp Arg Ser Cys Ile Glu Gln Asp
65                  70                  75                  80

Val Val Asn Gln Thr Arg Ser Leu Arg Gln Glu Thr Leu Ala Glu Ser
                85                  90                  95

Thr Trp Gln Cys Pro Pro Cys Asp Glu Asp Trp Asp Lys Asp Leu Trp
            100                 105                 110

Glu Gln Thr Ser Thr Pro Phe Val Trp Gly Thr Thr His Tyr Ser Asp
        115                 120                 125

Asn Asn Ser Pro Ala Ser Asn Ile Val Thr Glu His Lys Asn Asn Leu
    130                 135                 140

Ala Ser Gly Met Arg Val Pro Lys Ser Leu Pro Tyr Val Leu Pro Trp
145                 150                 155                 160

Lys Asn Asn Gly Asn Ala Gln
                165

<210> SEQ ID NO 15
<211> LENGTH: 325
<212> TYPE: PRT
<213> ORGANISM: Homo sapiens

<400> SEQUENCE: 15

Met Lys Glu Met Val Gly Gly Cys Cys Val Cys Ser Asp Glu Arg Gly
1               5                   10                  15

Trp Ala Glu Asn Pro Leu Val Tyr Cys Asp Gly His Ala Cys Ser Val
            20                  25                  30

Ala Val His Gln Ala Cys Tyr Gly Ile Val Gln Val Pro Thr Gly Pro
        35                  40                  45
```

```
Trp Phe Cys Arg Lys Cys Glu Ser Gln Glu Arg Ala Ala Arg Val Arg
 50                  55                  60
Cys Glu Leu Cys Pro His Lys Asp Gly Ala Leu Lys Arg Thr Asp Asn
 65                  70                  75                  80
Gly Gly Trp Ala His Val Val Cys Ala Leu Tyr Ile Pro Glu Val Gln
                 85                  90                  95
Phe Ala Asn Val Leu Thr Met Glu Pro Ile Val Leu Gln Tyr Val Pro
                100                 105                 110
His Asp Arg Phe Asn Lys Thr Cys Tyr Ile Cys Glu Glu Gln Gly Arg
                115                 120                 125
Glu Ser Lys Ala Ala Ser Gly Ala Cys Met Thr Cys Asn Arg His Gly
130                 135                 140
Cys Arg Gln Ala Phe His Val Thr Cys Ala Gln Met Ala Gly Leu Leu
145                 150                 155                 160
Cys Glu Glu Glu Val Leu Glu Val Asp Asn Val Lys Tyr Cys Gly Tyr
                165                 170                 175
Cys Lys Tyr His Phe Ser Lys Met Lys Thr Ser Arg His Ser Ser Gly
                180                 185                 190
Gly Gly Gly Gly Ala Gly Gly Gly Gly Ser Met Gly Gly Gly
                195                 200                 205
Gly Ser Gly Phe Ile Ser Gly Arg Arg Ser Arg Ser Ala Ser Pro Ser
210                 215                 220
Thr Gln Gln Glu Lys His Pro Thr His His Glu Arg Gly Gln Lys Lys
225                 230                 235                 240
Ser Arg Lys Asp Lys Glu Arg Leu Lys Gln Lys His Lys Lys Arg Pro
                245                 250                 255
Glu Ser Pro Pro Ser Ile Leu Thr Pro Pro Val Val Pro Thr Ala Asp
                260                 265                 270
Lys Pro Arg Arg Gly His Gln Ser Pro Thr Asn His Gly Ile Gly Ser
                275                 280                 285
Leu Gly Cys Cys Leu Pro Asp Thr Pro Ile Cys Leu Cys Pro Glu Gly
                290                 295                 300
Leu Ser Pro Gly Leu Leu Ser Ala Glu Ser Gly Gly Arg His Ser Gly
305                 310                 315                 320
Leu Leu Ser Lys Phe
                325

<210> SEQ ID NO 16
<211> LENGTH: 1072
<212> TYPE: PRT
<213> ORGANISM: Homo sapiens

<400> SEQUENCE: 16

Met Ala Lys Ala Thr Ser Gly Ala Ala Gly Leu Arg Leu Leu Leu Leu
 1                5                  10                  15
Leu Leu Leu Pro Leu Leu Gly Lys Val Ala Leu Gly Leu Tyr Phe Ser
                 20                  25                  30
Arg Asp Ala Tyr Trp Glu Lys Leu Tyr Val Asp Gln Ala Ala Gly Thr
                 35                  40                  45
Pro Leu Leu Tyr Val His Ala Leu Arg Asp Ala Pro Glu Glu Val Pro
                 50                  55                  60
Ser Phe Arg Leu Gly Gln His Leu Tyr Gly Thr Tyr Arg Thr Arg Leu
 65                  70                  75                  80
His Glu Asn Asn Trp Ile Cys Ile Gln Glu Asp Thr Gly Leu Leu Tyr
                 85                  90                  95
```

```
Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
            130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
            195                 200                 205

Gly Glu Gly Leu Pro Phe Arg Cys Ala Pro Asp Ser Leu Glu Val Ser
            210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
            275                 280                 285

Glu Asp Thr Val Val Ala Thr Leu Arg Val Phe Asp Ala Asp Val Val
            290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
            355                 360                 365

Thr Met Gln Leu Ala Val Leu Val Asn Asp Ser Asp Phe Gln Gly Pro
            370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
            450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510
```

-continued

```
Ala Gly Cys Pro Leu Ser Cys Ala Val Ser Lys Arg Arg Leu Glu Cys
            515                 520                 525
Glu Glu Cys Gly Gly Leu Gly Ser Pro Thr Gly Arg Cys Glu Trp Arg
        530                 535                 540
Gln Gly Asp Gly Lys Gly Ile Thr Arg Asn Phe Ser Thr Cys Ser Pro
545                 550                 555                 560
Ser Thr Lys Thr Cys Pro Asp Gly His Cys Asp Val Val Glu Thr Gln
                565                 570                 575
Asp Ile Asn Ile Cys Pro Gln Asp Cys Leu Arg Gly Ser Ile Val Gly
            580                 585                 590
Gly His Glu Pro Gly Glu Pro Arg Gly Ile Lys Ala Gly Tyr Gly Thr
        595                 600                 605
Cys Asn Cys Phe Pro Glu Glu Glu Lys Cys Phe Cys Glu Pro Glu Asp
    610                 615                 620
Ile Gln Asp Pro Leu Cys Asp Glu Leu Cys Arg Thr Val Ile Ala Ala
625                 630                 635                 640
Ala Val Leu Phe Ser Phe Ile Val Ser Val Leu Leu Ser Ala Phe Cys
                645                 650                 655
Ile His Cys Tyr His Lys Phe Ala His Lys Pro Pro Ile Ser Ser Ala
            660                 665                 670
Glu Met Thr Phe Arg Arg Pro Ala Gln Ala Phe Pro Val Ser Tyr Ser
        675                 680                 685
Ser Ser Gly Ala Arg Arg Pro Ser Leu Asp Ser Met Glu Asn Gln Val
    690                 695                 700
Ser Val Asp Ala Phe Lys Ile Leu Glu Asp Pro Lys Trp Glu Phe Pro
705                 710                 715                 720
Arg Lys Asn Leu Val Leu Gly Lys Thr Leu Gly Glu Gly Glu Phe Gly
                725                 730                 735
Lys Val Val Lys Ala Thr Ala Phe His Leu Lys Gly Arg Ala Gly Tyr
            740                 745                 750
Thr Thr Val Ala Val Lys Met Leu Lys Glu Asn Ala Ser Pro Ser Glu
        755                 760                 765
Leu Arg Asp Leu Leu Ser Glu Phe Asn Val Leu Lys Gln Val Asn His
    770                 775                 780
Pro His Val Ile Lys Leu Tyr Gly Ala Cys Ser Gln Asp Gly Pro Leu
785                 790                 795                 800
Leu Leu Ile Val Glu Tyr Ala Lys Tyr Gly Ser Leu Arg Gly Phe Leu
                805                 810                 815
Arg Glu Ser Arg Lys Val Gly Pro Gly Tyr Leu Gly Ser Gly Gly Ser
            820                 825                 830
Arg Asn Ser Ser Ser Leu Asp His Pro Asp Glu Arg Ala Leu Thr Met
        835                 840                 845
Gly Asp Leu Ile Ser Phe Ala Trp Gln Ile Ser Gln Gly Met Gln Tyr
    850                 855                 860
Leu Ala Glu Met Lys Leu Val His Arg Asp Leu Ala Ala Arg Asn Ile
865                 870                 875                 880
Leu Val Ala Glu Gly Arg Lys Met Lys Ile Ser Asp Phe Gly Leu Ser
                885                 890                 895
Arg Asp Val Tyr Glu Glu Asp Ser Tyr Val Lys Arg Ser Gln Gly Arg
            900                 905                 910
Ile Pro Val Lys Trp Met Ala Ile Glu Ser Leu Phe Asp His Ile Tyr
        915                 920                 925
Thr Thr Gln Ser Asp Val Trp Ser Phe Gly Val Leu Leu Trp Glu Ile
```

```
                930              935              940
Val Thr Leu Gly Gly Asn Pro Tyr Pro Gly Ile Pro Pro Glu Arg Leu
945                  950                  955                  960

Phe Asn Leu Leu Lys Thr Gly His Arg Met Glu Arg Pro Asp Asn Cys
                965                  970                  975

Ser Glu Glu Met Tyr Arg Leu Met Leu Gln Cys Trp Lys Gln Glu Pro
            980                  985                  990

Asp Lys Arg Pro Val Phe Ala Asp Ile Ser Lys Asp Leu Glu Lys Met
        995                 1000                 1005

Met Val Lys Arg Arg Asp Tyr Leu Asp Leu Ala Ala Ser Thr Pro Ser
       1010                 1015                 1020

Asp Ser Leu Ile Tyr Asp Asp Gly Leu Ser Glu Glu Glu Thr Pro Leu
1025                 1030                 1035                 1040

Val Asp Cys Asn Asn Ala Pro Leu Pro Arg Ala Leu Pro Ser Thr Trp
                1045                 1050                 1055

Ile Glu Asn Lys Leu Tyr Gly Arg Ile Ser His Ala Phe Thr Arg Phe
                1060                 1065                 1070

<210> SEQ ID NO 17
<211> LENGTH: 78
<212> TYPE: PRT
<213> ORGANISM: Homo sapiens

<400> SEQUENCE: 17

Met Ser Ala Thr Thr Ala Cys Trp Pro Ala Phe Thr Val Leu Gly Glu
1               5                   10                  15

Ala Arg Gly Asp Gln Val Asp Trp Ser Arg Leu Tyr Arg Asp Thr Gly
            20                  25                  30

Leu Val Lys Met Ser Arg Lys Pro Arg Ala Ser Ser Pro Phe Ser Asn
        35                  40                  45

Asn His Pro Ser Thr Pro Lys Arg Phe Pro Arg Gln Pro Arg Arg Glu
    50                  55                  60

Lys Gly Pro Val Lys Glu Val Pro Gly Thr Lys Gly Ser Pro
65                  70                  75

<210> SEQ ID NO 18
<211> LENGTH: 210
<212> TYPE: PRT
<213> ORGANISM: Homo sapiens

<400> SEQUENCE: 18

Met Ser Leu Thr Ser Asp Ala Ser Ser Pro Arg Ser Tyr Val Ser Pro
1               5                   10                  15

Arg Ile Ser Thr Pro Gln Thr Asn Thr Val Pro Ile Lys Pro Leu Ile
            20                  25                  30

Ser Thr Pro Pro Val Ser Ser Gln Pro Lys Val Ser Thr Pro Val Val
        35                  40                  45

Lys Gln Gly Pro Val Ser Gln Ser Ala Thr Gln Pro Val Thr Ala
    50                  55                  60

Asp Lys Gln Gln Gly His Glu Pro Val Ser Pro Arg Ser Leu Gln Arg
65                  70                  75                  80

Ser Ser Ser Gln Arg Ser Pro Ser Pro Gly Pro Asn His Thr Ser Asn
                85                  90                  95

Ser Ser Asn Ala Ser Asn Ala Thr Val Val Pro Gln Asn Ser Ser Ala
            100                 105                 110

Arg Ser Thr Cys Ser Leu Thr Pro Ala Leu Ala Ala His Phe Ser Glu
```

```
            115                 120                 125
Asn Leu Ile Lys His Val Gln Gly Trp Pro Ala Asp His Ala Glu Arg
            130                 135                 140
Gln Ala Ser Arg Leu Arg Glu Glu Ala His Asn Met Gly Thr Ile His
145                 150                 155                 160
Met Ser Glu Ile Cys Thr Glu Leu Lys Asn Leu Arg Ser Leu Val Arg
                165                 170                 175
Val Cys Glu Ile Gln Ala Thr Leu Arg Glu Gln Arg Ile Leu Phe Leu
                180                 185                 190
Arg Gln Gln Ile Lys Glu Leu Glu Lys Leu Lys Asn Gln Asn Ser Phe
                195                 200                 205
Met Val
    210

<210> SEQ ID NO 19
<211> LENGTH: 287
<212> TYPE: PRT
<213> ORGANISM: Homo sapiens

<400> SEQUENCE: 19

Met His Arg Leu Met Gly Val Asn Ser Thr Ala Ala Ala Ala Ala Gly
1               5                   10                  15
Gln Pro Asn Val Ser Cys Thr Cys Asn Cys Lys Arg Ser Leu Phe Gln
                20                  25                  30
Ser Met Glu Ile Thr Glu Leu Glu Phe Val Gln Ile Ile Ile Ile Val
                35                  40                  45
Val Val Met Met Val Met Val Val Ile Thr Cys Leu Leu Ser His
                50                  55                  60
Tyr Lys Leu Ser Ala Arg Ser Phe Ile Ser Arg His Ser Gln Gly Arg
65                  70                  75                  80
Arg Arg Glu Asp Ala Leu Ser Ser Glu Gly Cys Leu Trp Pro Ser Glu
                85                  90                  95
Ser Thr Val Ser Gly Asn Gly Ile Pro Glu Pro Gln Val Tyr Ala Pro
                100                 105                 110
Pro Arg Pro Thr Asp Arg Leu Ala Val Pro Pro Phe Ala Gln Arg Glu
                115                 120                 125
Arg Phe His Arg Phe Gln Pro Thr Tyr Pro Tyr Leu Gln His Glu Ile
                130                 135                 140
Asp Leu Pro Pro Thr Ile Ser Leu Ser Asp Gly Glu Glu Pro Pro Pro
145                 150                 155                 160
Tyr Gln Gly Pro Cys Thr Leu Gln Leu Arg Asp Pro Glu Gln Gln Leu
                165                 170                 175
Glu Leu Asn Arg Glu Ser Val Arg Ala Pro Pro Asn Arg Thr Ile Phe
                180                 185                 190
Asp Ser Asp Leu Met Asp Ser Ala Arg Leu Gly Gly Pro Cys Pro Pro
                195                 200                 205
Ser Ser Asn Ser Gly Ile Ser Ala Thr Cys Tyr Gly Ser Gly Gly Arg
                210                 215                 220
Met Glu Gly Pro Pro Thr Tyr Ser Glu Val Ile Gly His Tyr Pro
225                 230                 235                 240
Gly Ser Ser Phe Gln His Gln Gln Ser Gly Pro Ser Leu Leu
                245                 250                 255
Glu Gly Thr Arg Leu His His Thr His Ile Ala Pro Leu Glu Ser Ala
                260                 265                 270
```

```
Ala Ile Trp Ser Lys Glu Lys Asp Lys Gln Lys Gly His Pro Leu
            275                 280                 285

<210> SEQ ID NO 20
<211> LENGTH: 481
<212> TYPE: PRT
<213> ORGANISM: Homo sapiens

<400> SEQUENCE: 20

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365
```

```
Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu
```

```
<210> SEQ ID NO 21
<211> LENGTH: 147
<212> TYPE: PRT
<213> ORGANISM: Homo sapiens

<400> SEQUENCE: 21

Met Ser Gln Thr Arg Asp Leu Gln Gly Gly Lys Ala Phe Gly Leu Leu
1               5                   10                  15

Lys Ala Gln Gln Glu Glu Arg Leu Asp Glu Ile Asn Lys Gln Phe Leu
                20                  25                  30

Asp Asp Pro Lys Tyr Ser Ser Asp Glu Asp Leu Pro Ser Lys Leu Glu
            35                  40                  45

Gly Phe Lys Glu Lys Tyr Met Glu Phe Asp Leu Asn Gly Asn Gly Asp
        50                  55                  60

Ile Asp Ile Met Ser Leu Lys Arg Met Leu Glu Lys Leu Gly Val Pro
65                  70                  75                  80

Lys Thr His Leu Glu Leu Lys Lys Leu Ile Gly Glu Val Ser Ser Gly
                85                  90                  95

Ser Gly Glu Thr Phe Ser Tyr Pro Asp Phe Leu Arg Met Met Leu Gly
                100                 105                 110

Lys Arg Ser Ala Ile Leu Lys Met Ile Leu Met Tyr Glu Glu Lys Ala
            115                 120                 125

Arg Glu Lys Glu Lys Pro Thr Gly Pro Pro Ala Lys Lys Ala Ile Ser
        130                 135                 140

Glu Leu Pro
145
```

```
<210> SEQ ID NO 22
<211> LENGTH: 292
<212> TYPE: PRT
<213> ORGANISM: Homo sapiens

<400> SEQUENCE: 22

Met Ala Ala Cys Ile Ala Ala Gly His Trp Ala Met Gly Leu Gly
1               5                   10                  15

Arg Ser Phe Gln Ala Ala Arg Thr Leu Leu Pro Pro Ala Ser Ile
                20                  25                  30

Ala Cys Arg Val His Ala Gly Pro Val Arg Gln Gln Ser Thr Gly Pro
            35                  40                  45
```

-continued

Ser Glu Pro Gly Ala Phe Gln Pro Pro Lys Pro Val Ile Val Asp
    50                  55                  60

Lys His Arg Pro Val Glu Pro Glu Arg Phe Leu Ser Pro Glu Phe
65                  70                  75                  80

Ile Pro Arg Arg Gly Arg Thr Asp Pro Leu Lys Phe Gln Ile Glu Arg
                85                  90                  95

Lys Asp Met Leu Glu Arg Arg Lys Val Leu His Ile Pro Glu Phe Tyr
            100                 105                 110

Val Gly Ser Ile Leu Arg Val Thr Thr Ala Asp Pro Tyr Ala Ser Gly
            115                 120                 125

Lys Ile Ser Gln Phe Leu Gly Ile Cys Ile Gln Arg Ser Gly Arg Gly
130                 135                 140

Leu Gly Ala Thr Phe Ile Leu Arg Asn Val Ile Glu Gly Gln Gly Val
145                 150                 155                 160

Glu Ile Cys Phe Glu Leu Tyr Asn Pro Arg Val Gln Glu Ile Gln Val
                165                 170                 175

Val Lys Leu Glu Lys Arg Leu Asp Asp Ser Leu Leu Tyr Leu Arg Asp
            180                 185                 190

Ala Leu Pro Glu Tyr Ser Thr Phe Asp Val Asn Met Lys Pro Val Val
            195                 200                 205

Gln Glu Pro Asn Gln Lys Val Pro Val Asn Glu Leu Lys Val Lys Met
210                 215                 220

Lys Pro Lys Pro Trp Ser Lys Arg Trp Glu Arg Pro Asn Phe Asn Ile
225                 230                 235                 240

Lys Gly Ile Arg Phe Asp Leu Cys Leu Thr Glu Gln Gln Met Lys Glu
                245                 250                 255

Ala Gln Lys Trp Asn Gln Pro Trp Leu Glu Phe Asp Met Met Arg Glu
            260                 265                 270

Tyr Asp Thr Ser Lys Ile Glu Ala Ala Ile Trp Lys Glu Ile Glu Ala
            275                 280                 285

Ser Lys Arg Ser
    290

<210> SEQ ID NO 23
<211> LENGTH: 23
<212> TYPE: PRT
<213> ORGANISM: Homo sapiens

<400> SEQUENCE: 23

Met His Trp Glu Lys Val Asp Val Asn Asn Ser Ile Lys Gln Pro Tyr
1               5                   10                  15

Phe Leu Ile Lys Asn Asp Lys
            20

<210> SEQ ID NO 24
<211> LENGTH: 226
<212> TYPE: PRT
<213> ORGANISM: Homo sapiens

<400> SEQUENCE: 24

Met Ser Arg Ile Tyr His Asp Gly Ala Leu Arg Asn Lys Ala Val Gln
1               5                   10                  15

Ser Val Arg Leu Pro Gly Ala Trp Asp Pro Ala Ala His Gln Gly Gly
            20                  25                  30

Asn Gly Val Leu Leu Glu Gly Glu Leu Ile Asp Val Ser Arg His Ser
            35                  40                  45

```
Ile Leu Asp Thr His Gly Arg Lys Glu Arg Tyr Tyr Val Leu Tyr Ile
 50                  55                  60

Arg Pro Ser His Ile His Arg Arg Lys Phe Asp Ala Lys Gly Asn Glu
 65                  70                  75                  80

Ile Glu Pro Asn Phe Ser Ala Thr Arg Lys Val Asn Thr Gly Phe Leu
                 85                  90                  95

Met Ser Ser Tyr Lys Val Glu Ala Lys Gly Asp Thr Asp Arg Leu Thr
            100                 105                 110

Pro Glu Ala Leu Lys Gly Leu Val Asn Lys Pro Glu Leu Leu Ala Leu
            115                 120                 125

Thr Glu Ser Leu Thr Pro Asp His Thr Val Ala Phe Trp Met Pro Glu
130                 135                 140

Ser Glu Met Glu Val Met Glu Leu Glu Leu Gly Ala Gly Val Arg Leu
145                 150                 155                 160

Lys Thr Arg Gly Asp Gly Pro Phe Leu Asp Ser Leu Ala Lys Leu Glu
                165                 170                 175

Ala Gly Thr Val Thr Lys Cys Asn Phe Thr Gly Asp Gly Lys Thr Gly
            180                 185                 190

Ala Ser Trp Thr Asp Asn Ile Met Ala Gln Lys Cys Ser Lys Gly Ala
            195                 200                 205

Ala Ala Glu Ile Arg Glu Gln Gly Asp Gly Ala Glu Asp Glu Glu Trp
210                 215                 220

Asp Asp
225

<210> SEQ ID NO 25
<211> LENGTH: 154
<212> TYPE: PRT
<213> ORGANISM: Homo sapiens

<400> SEQUENCE: 25

Met Thr Thr Thr Thr Thr Phe Lys Gly Val Asp Pro Asn Ser Arg Asn
  1               5                  10                  15

Ser Ser Arg Val Leu Arg Pro Pro Gly Gly Gly Ser Asn Phe Ser Leu
                 20                  25                  30

Gly Phe Asp Glu Pro Thr Glu Gln Pro Val Arg Lys Asn Lys Met Ala
             35                  40                  45

Ser Asn Ile Phe Gly Thr Pro Glu Glu Asn Gln Ala Ser Trp Ala Lys
 50                  55                  60

Ser Ala Gly Ala Lys Ser Ser Gly Gly Arg Glu Asp Leu Glu Ser Ser
 65                  70                  75                  80

Gly Leu Gln Arg Arg Asn Ser Ser Glu Ala Ser Ser Gly Asp Phe Leu
                 85                  90                  95

Asp Leu Lys Gly Glu Gly Asp Ile His Glu Asn Val Asp Thr Asp Leu
            100                 105                 110

Pro Gly Ser Leu Gly Gln Ser Glu Glu Lys Pro Val Pro Ala Ala Pro
            115                 120                 125

Val Pro Ser Pro Val Ala Pro Ala Pro Val Pro Ser Arg Arg Asn Pro
130                 135                 140

Pro Gly Gly Lys Ser Ser Leu Val Leu Gly
145                 150

<210> SEQ ID NO 26
<211> LENGTH: 695
<212> TYPE: PRT
<213> ORGANISM: Homo sapiens
```

<400> SEQUENCE: 26

```
Met Ala Ser Thr Arg Ser Ile Glu Leu Glu His Phe Glu Glu Arg Asp
1               5                   10                  15

Lys Arg Pro Arg Pro Gly Ser Arg Arg Gly Ala Pro Ser Ser Ser Gly
            20                  25                  30

Gly Ser Ser Ser Ser Gly Pro Lys Gly Asn Gly Leu Ile Pro Ser Pro
                35                  40                  45

Ala His Ser Ala His Cys Ser Phe Tyr Arg Thr Arg Thr Leu Gln Ala
        50                  55                  60

Leu Ser Ser Glu Lys Lys Ala Lys Lys Ala Arg Phe Tyr Arg Asn Gly
65                  70                  75                  80

Asp Arg Tyr Phe Lys Gly Leu Val Phe Ala Ile Ser Ser Asp Arg Phe
                85                  90                  95

Arg Ser Phe Asp Ala Leu Leu Ile Glu Leu Thr Arg Ser Leu Ser Asp
                100                 105                 110

Asn Val Asn Leu Pro Gln Gly Val Arg Thr Ile Tyr Thr Ile Asp Gly
            115                 120                 125

Ser Arg Lys Val Thr Ser Leu Asp Glu Leu Leu Glu Gly Glu Ser Tyr
130                 135                 140

Val Cys Ala Ser Asn Glu Pro Phe Arg Lys Val Asp Tyr Thr Lys Asn
145                 150                 155                 160

Ile Asn Pro Asn Trp Ser Val Asn Ile Lys Gly Gly Thr Ser Arg Ala
                165                 170                 175

Leu Ala Ala Ala Ser Ser Val Lys Ser Glu Val Lys Glu Ser Lys Asp
            180                 185                 190

Phe Ile Lys Pro Lys Leu Val Thr Val Ile Arg Ser Gly Val Lys Pro
            195                 200                 205

Arg Lys Ala Val Arg Ile Leu Leu Asn Lys Lys Thr Ala His Ser Phe
210                 215                 220

Glu Gln Val Leu Thr Asp Ile Thr Glu Ala Ile Lys Leu Asp Ser Gly
225                 230                 235                 240

Val Val Lys Arg Leu Cys Thr Leu Asp Gly Lys Gln Val Thr Cys Leu
                245                 250                 255

Gln Asp Phe Phe Gly Asp Asp Asp Val Phe Ile Ala Cys Gly Pro Glu
            260                 265                 270

Lys Phe Arg Tyr Ala Gln Asp Asp Phe Val Leu Asp His Ser Glu Cys
            275                 280                 285

Arg Val Leu Lys Ser Ser Tyr Ser Arg Ser Ser Ala Val Lys Tyr Ser
290                 295                 300

Gly Ser Lys Ser Pro Gly Pro Ser Arg Arg Ser Lys Ser Pro Ala Ser
305                 310                 315                 320

Val Asn Gly Thr Pro Ser Ser Gln Leu Ser Thr Pro Lys Ser Thr Lys
                325                 330                 335

Ser Ser Ser Ser Ser Pro Thr Ser Pro Gly Ser Phe Arg Gly Leu Lys
            340                 345                 350

Ile Ser Ala His Gly Arg Ser Ser Asn Val Asn Gly Gly Pro Glu
            355                 360                 365

Leu Asp Arg Cys Ile Ser Pro Glu Gly Val Asn Gly Asn Arg Cys Ser
            370                 375                 380

Glu Ser Ser Thr Leu Leu Glu Lys Tyr Lys Ile Gly Lys Val Ile Gly
385                 390                 395                 400

Asp Gly Asn Phe Ala Val Val Lys Glu Cys Ile Asp Arg Ser Thr Gly
```

```
            405                 410                 415
Lys Glu Phe Ala Leu Lys Ile Ile Asp Lys Ala Lys Cys Cys Gly Lys
        420                 425                 430

Glu His Leu Ile Glu Asn Glu Val Ser Ile Leu Arg Arg Val Lys His
            435                 440                 445

Pro Asn Ile Ile Met Leu Val Glu Glu Met Glu Thr Ala Thr Glu Leu
        450                 455                 460

Phe Leu Val Met Glu Leu Val Lys Gly Gly Asp Leu Phe Asp Ala Ile
465                 470                 475                 480

Thr Ser Ser Thr Lys Tyr Thr Glu Arg Asp Gly Ser Ala Met Val Tyr
                485                 490                 495

Asn Leu Ala Asn Ala Leu Arg Tyr Leu His Gly Leu Ser Ile Val His
            500                 505                 510

Arg Asp Ile Lys Pro Glu Asn Leu Leu Val Cys Glu Tyr Pro Asp Gly
        515                 520                 525

Thr Lys Ser Leu Lys Leu Gly Asp Phe Gly Leu Ala Thr Val Val Glu
    530                 535                 540

Gly Pro Leu Tyr Thr Val Cys Gly Thr Pro Thr Tyr Val Ala Pro Glu
545                 550                 555                 560

Ile Ile Ala Glu Thr Gly Tyr Gly Leu Lys Val Asp Ile Trp Ala Ala
                565                 570                 575

Gly Val Ile Thr Tyr Ile Leu Leu Cys Gly Phe Pro Pro Phe Arg Ser
            580                 585                 590

Glu Asn Asn Leu Gln Glu Asp Leu Phe Asp Gln Ile Leu Ala Gly Lys
        595                 600                 605

Leu Glu Phe Pro Ala Pro Tyr Trp Asp Asn Ile Thr Asp Ser Ala Lys
    610                 615                 620

Glu Leu Ile Ser Gln Met Leu Gln Val Asn Val Glu Ala Arg Cys Thr
625                 630                 635                 640

Ala Gly Gln Ile Leu Ser His Pro Trp Val Ser Asp Asp Ala Ser Gln
                645                 650                 655

Glu Asn Asn Met Gln Ala Glu Val Thr Gly Lys Leu Lys Gln His Phe
            660                 665                 670

Asn Asn Ala Leu Pro Lys Gln Asn Ser Thr Thr Thr Gly Val Ser Val
        675                 680                 685

Ile Met Phe Asp Leu Thr Val
    690                 695

<210> SEQ ID NO 27
<211> LENGTH: 635
<212> TYPE: PRT
<213> ORGANISM: Homo sapiens

<400> SEQUENCE: 27

Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
            20                  25                  30

Gly Met Ser Asp Gly Leu Tyr Leu Leu Arg Gln Ser Arg Asn Tyr Leu
        35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Gly Arg
65                  70                  75                  80
```

-continued

```
Thr His Ala Ser Pro Ala Asp Leu Cys His Tyr His Ser Gln Glu Ser
                85                  90                  95
Asp Gly Leu Val Cys Leu Leu Lys Lys Pro Phe Asn Arg Pro Gln Gly
            100                 105                 110
Val Gln Pro Lys Thr Gly Pro Phe Glu Asp Leu Lys Glu Asn Leu Ile
        115                 120                 125
Arg Glu Tyr Val Lys Gln Thr Trp Asn Leu Gln Gly Gln Ala Leu Glu
    130                 135                 140
Gln Ala Ile Ile Ser Gln Lys Pro Gln Leu Glu Lys Leu Ile Ala Thr
145                 150                 155                 160
Thr Ala His Glu Lys Met Pro Trp Phe His Gly Lys Ile Ser Arg Glu
                165                 170                 175
Glu Ser Glu Gln Ile Val Leu Ile Gly Ser Lys Thr Asn Gly Lys Phe
            180                 185                 190
Leu Ile Arg Ala Arg Asp Asn Asn Gly Ser Tyr Ala Leu Cys Leu Leu
        195                 200                 205
His Glu Gly Lys Val Leu His Tyr Arg Ile Asp Lys Asp Lys Thr Gly
    210                 215                 220
Lys Leu Ser Ile Pro Glu Gly Lys Lys Phe Asp Thr Leu Trp Gln Leu
225                 230                 235                 240
Val Glu His Tyr Ser Tyr Lys Ala Asp Gly Leu Leu Arg Val Leu Thr
                245                 250                 255
Val Pro Cys Gln Lys Ile Gly Thr Gln Gly Asn Val Asn Phe Gly Gly
            260                 265                 270
Arg Pro Gln Leu Pro Gly Ser His Pro Ala Thr Trp Ser Ala Gly Gly
        275                 280                 285
Ile Ile Ser Arg Ile Lys Ser Tyr Ser Phe Pro Lys Pro Gly His Arg
    290                 295                 300
Lys Ser Ser Pro Ala Gln Gly Asn Arg Gln Glu Ser Thr Val Ser Phe
305                 310                 315                 320
Asn Pro Tyr Glu Pro Glu Leu Ala Pro Trp Ala Ala Asp Lys Gly Pro
                325                 330                 335
Gln Arg Glu Ala Leu Pro Met Asp Thr Glu Val Tyr Glu Ser Pro Tyr
            340                 345                 350
Ala Asp Pro Glu Glu Ile Arg Pro Lys Glu Val Tyr Leu Asp Arg Lys
        355                 360                 365
Leu Leu Thr Leu Glu Asp Lys Glu Leu Gly Ser Gly Asn Phe Gly Thr
    370                 375                 380
Val Lys Lys Gly Tyr Tyr Gln Met Lys Lys Val Val Lys Thr Val Ala
385                 390                 395                 400
Val Lys Ile Leu Lys Asn Glu Ala Asn Asp Pro Ala Leu Lys Asp Glu
                405                 410                 415
Leu Leu Ala Glu Ala Asn Val Met Gln Gln Leu Asp Asn Pro Tyr Ile
            420                 425                 430
Val Arg Met Ile Gly Ile Cys Glu Ala Glu Ser Trp Met Leu Val Met
        435                 440                 445
Glu Met Ala Glu Leu Gly Pro Leu Asn Lys Tyr Leu Gln Gln Asn Arg
    450                 455                 460
His Val Lys Asp Lys Asn Ile Ile Glu Leu Val His Gln Val Ser Met
465                 470                 475                 480
Gly Met Lys Tyr Leu Glu Glu Ser Asn Phe Val His Arg Asp Leu Ala
                485                 490                 495
Ala Arg Asn Val Leu Leu Val Thr Gln His Tyr Ala Lys Ile Ser Asp
```

```
                500                 505                 510
        Phe Gly Leu Ser Lys Ala Leu Arg Ala Asp Glu Asn Tyr Tyr Lys Ala
                        515                 520                 525

Gln Thr His Gly Lys Trp Pro Val Lys Trp Tyr Ala Pro Glu Cys Ile
                530                 535                 540

Asn Tyr Tyr Lys Phe Ser Ser Lys Ser Asp Val Trp Ser Phe Gly Val
        545                 550                 555                 560

Leu Met Trp Glu Ala Phe Ser Tyr Gly Gln Lys Pro Tyr Arg Gly Met
                        565                 570                 575

Lys Gly Ser Glu Val Thr Ala Met Leu Glu Lys Gly Glu Arg Met Gly
                    580                 585                 590

Cys Pro Ala Gly Cys Pro Arg Glu Met Tyr Asp Leu Met Asn Leu Cys
                        595                 600                 605

Trp Thr Tyr Asp Val Glu Asn Arg Pro Gly Phe Ala Ala Val Glu Leu
                    610                 615                 620

Arg Leu Arg Asn Tyr Tyr Tyr Asp Val Val Asn
        625                 630                 635

<210> SEQ ID NO 28
<211> LENGTH: 88
<212> TYPE: PRT
<213> ORGANISM: Homo sapiens

<400> SEQUENCE: 28

Met Asn Ala Ile His Thr Lys Glu Leu Leu Leu Thr Ser His Leu Gln
1               5                   10                  15

Ser Pro Pro Gly His Arg Gln Asp Pro Phe Asn Lys Ser Ser Ser Glu
                20                  25                  30

Thr Pro Ile Val Gln Asn Leu Gln Leu Ala Thr Gly Tyr His His Ser
            35                  40                  45

Leu Trp Leu Cys Lys Ile Lys Asp Leu Glu Glu Gly Trp Gly Gly Gly
        50                  55                  60

Ser Tyr Glu Lys Arg Gln Glu Lys Ser Ser Phe Asp Pro Met Leu Ser
65                  70                  75                  80

Glu Ser Val His Glu Glu Glu Ser
                85

<210> SEQ ID NO 29
<211> LENGTH: 79
<212> TYPE: PRT
<213> ORGANISM: Homo sapiens

<400> SEQUENCE: 29

Met Ser Glu Ile Leu Pro Tyr Ser Glu Asp Lys Met Gly Arg Phe Gly
1               5                   10                  15

Ala Asp Pro Glu Gly Ser Asp Leu Ser Phe Ser Cys Arg Leu Gln Asp
                20                  25                  30

Thr Asn Ser Phe Phe Ala Gly Asn Gln Ala Lys Arg Pro Pro Lys Leu
            35                  40                  45

Gly Gln Ile Gly Arg Ala Lys Arg Val Val Ile Glu Asp Asp Arg Ile
        50                  55                  60

Asp Asp Val Leu Lys Gly Met Gly Glu Lys Pro Pro Ser Gly Val
65                  70                  75

<210> SEQ ID NO 30
<211> LENGTH: 310
<212> TYPE: PRT
```

<213> ORGANISM: Homo sapiens

<400> SEQUENCE: 30

```
Met Gly Lys Arg Arg Cys Val Pro Pro Leu Glu Pro Lys Leu Ala Ala
1               5                   10                  15
Gly Cys Cys Gly Val Lys Lys Pro Lys Leu Ser Gly Ser Gly Thr His
                20                  25                  30
Ser His Gly Asn Gln Ser Thr Thr Val Pro Gly Ser Ser Ser Gly Pro
            35                  40                  45
Leu Gln Asn His Gln His Val Asp Ser Ser Gly Arg Glu Asn Val
    50                  55                  60
Ser Asp Leu Thr Leu Gly Pro Gly Asn Ser Pro Ile Thr Arg Met Asn
65                  70                  75                  80
Pro Ala Ser Gly Ala Leu Ser Pro Leu Pro Arg Pro Asn Gly Thr Ala
                85                  90                  95
Asn Thr Thr Lys Asn Leu Val Val Thr Ala Glu Met Cys Cys Tyr Cys
            100                 105                 110
Phe Asp Val Leu Tyr Cys His Leu Tyr Gly Phe Pro Gln Pro Arg Leu
        115                 120                 125
Pro Arg Phe Thr Asn Asp Pro Tyr Pro Leu Phe Val Thr Trp Lys Thr
130                 135                 140
Gly Arg Asp Lys Arg Leu Arg Gly Cys Ile Gly Thr Phe Ser Ala Met
145                 150                 155                 160
Asn Leu His Ser Gly Leu Arg Glu Tyr Thr Leu Thr Ser Ala Leu Lys
                165                 170                 175
Asp Ser Arg Phe Pro Pro Leu Thr Arg Glu Leu Pro Lys Leu Phe
        180                 185                 190
Cys Ser Val Ser Leu Leu Thr Asn Phe Glu Asp Ala Ser Asp Tyr Leu
        195                 200                 205
Asp Trp Glu Val Gly Val His Gly Ile Arg Ile Glu Phe Ile Asn Glu
        210                 215                 220
Lys Gly Val Lys Arg Thr Ala Thr Tyr Leu Pro Glu Val Ala Lys Glu
225                 230                 235                 240
Gln Asp Trp Asp Gln Ile Gln Thr Ile Asp Ser Leu Leu Arg Lys Gly
                245                 250                 255
Gly Phe Lys Ala Pro Ile Thr Ser Glu Phe Arg Lys Thr Ile Lys Leu
            260                 265                 270
Thr Arg Tyr Arg Ser Glu Lys Val Thr Ile Ser Tyr Ala Glu Tyr Ile
        275                 280                 285
Ala Ser Arg Gln His Cys Phe Gln Asn Gly Thr Leu His Ala Pro Pro
290                 295                 300
Leu Tyr Asn His Tyr Ser
305                 310
```

<210> SEQ ID NO 31
<211> LENGTH: 147
<212> TYPE: PRT
<213> ORGANISM: Homo sapiens

<400> SEQUENCE: 31

```
Met Ala Ala Thr Thr Gly Ser Gly Val Lys Val Pro Arg Asn Phe Arg
1               5                   10                  15
Leu Leu Glu Glu Leu Glu Glu Gly Gln Lys Gly Val Gly Asp Gly Thr
                20                  25                  30
Val Ser Trp Gly Leu Glu Asp Asp Glu Asp Met Thr Leu Thr Arg Trp
```

```
                35                  40                  45
Thr Gly Met Ile Ile Gly Pro Pro Arg Thr Ile Tyr Glu Asn Arg Ile
 50                  55                  60

Tyr Ser Leu Lys Ile Glu Cys Gly Pro Lys Tyr Pro Glu Ala Pro Pro
 65                  70                  75                  80

Phe Val Arg Phe Val Thr Lys Ile Asn Met Asn Gly Val Asn Ser Ser
                 85                  90                  95

Asn Gly Val Val Asp Pro Arg Ala Ile Ser Val Leu Ala Lys Trp Gln
                100                 105                 110

Asn Ser Tyr Ser Ile Lys Val Val Leu Gln Glu Leu Arg Arg Leu Met
                115                 120                 125

Met Ser Lys Glu Asn Met Lys Leu Pro Gln Pro Pro Glu Gly Gln Cys
130                 135                 140

Tyr Ser Asn
145

<210> SEQ ID NO 32
<211> LENGTH: 256
<212> TYPE: PRT
<213> ORGANISM: Homo sapiens

<400> SEQUENCE: 32

Met Ala Ala Val Lys Ser Thr Glu Ala His Pro Ser Ser Asn Lys Asp
 1               5                  10                  15

Pro Thr Gln Gly Gln Lys Ser Ala Leu Gln Gly Asn Ser Pro Asp Ser
                 20                  25                  30

Glu Ala Ser Arg Gln Arg Phe Arg Gln Phe Cys Tyr Gln Glu Val Thr
             35                  40                  45

Gly Pro His Glu Ala Phe Ser Lys Leu Trp Glu Leu Cys Cys Gln Trp
 50                  55                  60

Leu Arg Pro Lys Thr His Ser Lys Glu Ile Leu Glu Leu Leu Val
 65                  70                  75                  80

Leu Glu Gln Phe Leu Thr Ile Leu Pro Glu Glu Ile Gln Thr Trp Val
                 85                  90                  95

Arg Glu Gln His Pro Glu Asn Gly Glu Glu Ala Val Ala Leu Val Glu
                100                 105                 110

Asp Val Gln Arg Ala Pro Gly Gln Gln Val Leu Asp Ser Glu Lys Asp
                115                 120                 125

Leu Lys Val Leu Met Lys Glu Met Ala Pro Leu Gly Ala Thr Arg Glu
130                 135                 140

Ser Leu Arg Ser Gln Trp Lys Gln Glu Val Gln Pro Glu Glu Pro Thr
145                 150                 155                 160

Phe Lys Gly Ser Gln Ser Ser His Gln Arg Pro Gly Glu Gln Ser Glu
                165                 170                 175

Ala Trp Leu Ala Pro Gln Ala Pro Arg Asn Leu Pro Gln Asn Thr Gly
                180                 185                 190

Leu His Asp Gln Glu Thr Gly Ala Val Val Trp Thr Ala Gly Ser Gln
                195                 200                 205

Gly Pro Ala Met Arg Asp Asn Arg Ala Val Ser Leu Cys Gln Gln Glu
                210                 215                 220

Trp Met Cys Pro Gly Pro Ala Gln Arg Ala Leu Tyr Arg Gly Ala Thr
225                 230                 235                 240

Gln Arg Lys Asp Ser His Val Ser Leu Ala Thr Gly Ala Leu Gly Leu
                245                 250                 255
```

```
<210> SEQ ID NO 33
<211> LENGTH: 70
<212> TYPE: PRT
<213> ORGANISM: Homo sapiens

<400> SEQUENCE: 33

Met Ser Glu Val Lys Ser Arg Lys Lys Ser Gly Pro Lys Gly Ala Pro
1               5                   10                  15

Ala Ala Glu Pro Gly Lys Arg Ser Glu Gly Lys Thr Pro Val Ala
                20                  25                  30

Arg Ser Ser Gly Gly Gly Gly Trp Ala Asp Pro Arg Thr Cys Leu Ser
            35                  40                  45

Leu Leu Ser Leu Gly Thr Cys Leu Gly Leu Ala Cys Gly Arg Asn Leu
        50                  55                  60

Lys Leu Ser Trp Asn Asn
65                  70

<210> SEQ ID NO 34
<211> LENGTH: 480
<212> TYPE: PRT
<213> ORGANISM: Homo sapiens

<400> SEQUENCE: 34

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255
```

```
Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
    355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
    435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 35
<211> LENGTH: 78
<212> TYPE: PRT
<213> ORGANISM: Homo sapiens

<400> SEQUENCE: 35

Met Ser Glu Val Leu Pro Tyr Gly Asp Glu Lys Leu Ser Pro Tyr Gly
1               5                   10                  15

Asp Gly Gly Asp Val Gly Gln Ile Phe Ser Cys Arg Leu Gln Asp Thr
            20                  25                  30

Asn Asn Phe Phe Gly Ala Gly Gln Asn Lys Arg Pro Pro Lys Leu Gly
        35                  40                  45

Gln Ile Gly Arg Ser Lys Arg Val Val Ile Glu Asp Asp Arg Ile Asp
    50                  55                  60

Asp Val Leu Lys Asn Met Thr Asp Lys Ala Pro Pro Gly Val
65                  70                  75

<210> SEQ ID NO 36
<211> LENGTH: 885
<212> TYPE: PRT
<213> ORGANISM: Homo sapiens

<400> SEQUENCE: 36

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30
```

-continued

```
Glu Glu Ser Pro Phe Val Gly Asn Pro Gly Asn Ile Thr Gly Ala Arg
         35                  40                  45

Gly Leu Thr Gly Thr Leu Arg Cys Gln Leu Gln Val Gln Gly Glu Pro
 50                  55                  60

Pro Glu Val His Trp Leu Arg Asp Gly Gln Ile Leu Glu Leu Ala Asp
 65                  70                  75                  80

Ser Thr Gln Thr Gln Val Pro Leu Gly Glu Asp Gln Asp Asp Trp
                 85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
                115                 120                 125

Gln Pro Gly Tyr Val Gly Leu Glu Gly Leu Pro Tyr Phe Leu Glu Glu
130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
                180                 185                 190

His Val Pro Gly Leu Asn Lys Thr Ser Ser Phe Ser Cys Glu Ala His
                195                 200                 205

Asn Ala Lys Gly Val Thr Thr Ser Arg Thr Ala Thr Ile Thr Val Leu
                210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
                260                 265                 270

Ala Gly Glu Pro Asp Pro Pro Glu Glu Pro Leu Thr Ser Gln Ala Ser
                275                 280                 285

Val Pro Pro His Gln Leu Arg Leu Gly Ser Leu His Pro His Thr Pro
                290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
                355                 360                 365

Leu Ala Tyr Gln Gly Gln Asp Thr Pro Glu Val Leu Met Asp Ile Gly
                370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Val Lys Glu Pro
                420                 425                 430

Ser Thr Pro Ala Phe Ser Trp Pro Trp Trp Tyr Val Leu Leu Gly Ala
                435                 440                 445

Val Val Ala Ala Ala Cys Val Leu Ile Leu Ala Leu Phe Leu Val His
```

```
                450            455            460
Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
                485                 490                 495

Arg Arg Thr Thr Glu Ala Thr Leu Asn Ser Leu Gly Ile Ser Glu Glu
                500                 505                 510

Leu Lys Glu Lys Leu Arg Asp Val Met Val Asp Arg His Lys Val Ala
515                 520                 525

Leu Gly Lys Thr Leu Gly Glu Gly Glu Phe Gly Ala Val Met Glu Gly
        530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
                580                 585                 590

Gly Val Cys Phe Gln Gly Ser Glu Arg Glu Ser Phe Pro Ala Pro Val
            595                 600                 605

Val Ile Leu Pro Phe Met Lys His Gly Asp Leu His Ser Phe Leu Leu
610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
                660                 665                 670

Glu Asn Met Ser Val Cys Val Ala Asp Phe Gly Leu Ser Lys Lys Ile
            675                 680                 685

Tyr Asn Gly Asp Tyr Tyr Arg Gln Gly Arg Ile Ala Lys Met Pro Val
        690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735

Gly Gln Thr Pro Tyr Pro Gly Val Glu Asn Ser Glu Ile Tyr Asp Tyr
            740                 745                 750

Leu Arg Gln Gly Asn Arg Leu Lys Gln Pro Ala Asp Cys Leu Asp Gly
        755                 760                 765

Leu Tyr Ala Leu Met Ser Arg Cys Trp Glu Leu Asn Pro Gln Asp Arg
770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815

Glu Gly Gly Gly Tyr Pro Glu Pro Pro Gly Ala Ala Gly Gly Ala Asp
                820                 825                 830

Pro Pro Thr Gln Pro Asp Pro Lys Asp Ser Cys Ser Cys Leu Thr Ala
            835                 840                 845

Ala Glu Val His Pro Ala Gly Arg Tyr Val Leu Cys Pro Ser Thr Thr
        850                 855                 860

Pro Ser Pro Ala Gln Pro Ala Asp Arg Gly Ser Pro Ala Ala Pro Gly
865                 870                 875                 880
```

Gln Glu Asp Gly Ala
            885

<210> SEQ ID NO 37
<211> LENGTH: 403
<212> TYPE: PRT
<213> ORGANISM: Homo sapiens

<400> SEQUENCE: 37

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro

```
                    355                 360                 365
Ser Gln Arg Pro Met Leu Arg Glu Val Leu Glu His Pro Trp Ile Thr
370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 38
<211> LENGTH: 976
<212> TYPE: PRT
<213> ORGANISM: Homo sapiens

<400> SEQUENCE: 38

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
```

-continued

```
                325                 330                 335
Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
                355                 360                 365

Ser Asn Ile Arg Tyr Val Ser Glu Leu His Leu Thr Arg Leu Lys Gly
                370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
                420                 425                 430

Phe Pro Glu Pro Thr Ile Asp Trp Tyr Phe Cys Pro Gly Thr Glu Gln
                435                 440                 445

Arg Cys Ser Ala Ser Val Leu Pro Val Asp Val Gln Thr Leu Asn Ser
                450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
                500                 505                 510

Lys Glu Gln Ile His Pro His Thr Leu Phe Thr Pro Leu Leu Ile Gly
                515                 520                 525

Phe Val Ile Val Ala Gly Met Met Cys Ile Ile Val Met Ile Leu Thr
530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
                580                 585                 590

Lys Thr Leu Gly Ala Gly Ala Phe Gly Lys Val Val Glu Ala Thr Ala
                595                 600                 605

Tyr Gly Leu Ile Lys Ser Asp Ala Ala Met Thr Val Ala Val Lys Met
                610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
                660                 665                 670

Cys Cys Tyr Gly Asp Leu Leu Asn Phe Leu Arg Arg Lys Arg Asp Ser
                675                 680                 685

Phe Ile Cys Ser Lys Gln Glu Asp His Ala Glu Ala Ala Leu Tyr Lys
                690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
                740                 745                 750
```

Thr Pro Ala Ile Met Glu Asp Glu Leu Ala Leu Asp Leu Glu Asp
                755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
                820                 825                 830

Val Lys Trp Met Ala Pro Glu Ser Ile Phe Asn Cys Val Tyr Thr Phe
                835                 840                 845

Glu Ser Asp Val Trp Ser Tyr Gly Ile Phe Leu Trp Glu Leu Phe Ser
                850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
                900                 905                 910

Lys Arg Pro Thr Phe Lys Gln Ile Val Gln Leu Ile Glu Lys Gln Ile
                915                 920                 925

Ser Glu Ser Thr Asn His Ile Tyr Ser Asn Leu Ala Asn Cys Ser Pro
                930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 39
<211> LENGTH: 422
<212> TYPE: PRT
<213> ORGANISM: Homo sapiens

<400> SEQUENCE: 39

Met Asp His Pro Ser Arg Glu Lys Asp Glu Arg Gln Arg Thr Thr Lys
1               5                   10                  15

Pro Met Ala Gln Arg Ser Ala His Cys Ser Arg Pro Ser Gly Ser Ser
                20                  25                  30

Ser Ser Ser Gly Val Leu Met Val Gly Pro Asn Phe Arg Val Gly Lys
            35                  40                  45

Lys Ile Gly Cys Gly Asn Phe Gly Glu Leu Arg Leu Gly Lys Asn Leu
        50                  55                  60

Tyr Thr Asn Glu Tyr Val Ala Ile Lys Leu Glu Pro Ile Lys Ser Arg
65                  70                  75                  80

Ala Pro Gln Leu His Leu Glu Tyr Arg Phe Tyr Lys Gln Leu Gly Ser
                85                  90                  95

Ala Gly Glu Gly Leu Pro Gln Val Tyr Phe Gly Pro Cys Gly Lys
                100                 105                 110

Tyr Asn Ala Met Val Leu Glu Leu Leu Gly Pro Ser Leu Glu Asp Leu
                115                 120                 125

Phe Asp Leu Cys Asp Arg Thr Phe Thr Leu Lys Thr Val Leu Met Ile
            130                 135                 140

Ala Ile Gln Leu Leu Ser Arg Met Glu Tyr Val His Ser Lys Asn Leu

```
            145                 150                 155                 160
       Ile Tyr Arg Asp Val Lys Pro Glu Asn Phe Leu Ile Gly Arg Gln Gly
                       165                 170                 175

Asn Lys Lys Glu His Val Ile His Ile Ile Asp Phe Gly Leu Ala Lys
                       180                 185                 190

Glu Tyr Ile Asp Pro Glu Thr Lys Lys His Ile Pro Tyr Arg Glu His
                       195                 200                 205

Lys Ser Leu Thr Gly Thr Ala Arg Tyr Met Ser Ile Asn Thr His Leu
                       210                 215                 220

Gly Lys Glu Gln Ser Arg Arg Asp Asp Leu Glu Ala Leu Gly His Met
       225                 230                 235                 240

Phe Met Tyr Phe Leu Arg Gly Ser Leu Pro Trp Gln Gly Leu Lys Ala
                       245                 250                 255

Asp Thr Leu Lys Glu Arg Tyr Gln Lys Ile Gly Asp Thr Lys Arg Asn
                       260                 265                 270

Thr Pro Ile Glu Ala Leu Cys Glu Asn Phe Pro Glu Glu Met Ala Thr
                       275                 280                 285

Tyr Leu Arg Tyr Val Arg Arg Leu Asp Phe Phe Glu Lys Pro Asp Tyr
                       290                 295                 300

Glu Tyr Leu Arg Thr Leu Phe Thr Asp Leu Phe Glu Lys Lys Gly Tyr
       305                 310                 315                 320

Thr Phe Asp Tyr Ala Tyr Asp Trp Val Gly Arg Pro Ile Pro Thr Pro
                       325                 330                 335

Val Gly Ser Val His Val Asp Ser Gly Ala Ser Ala Ile Thr Arg Glu
                       340                 345                 350

Ser His Thr His Arg Asp Arg Pro Ser Gln Gln Pro Leu Arg Asn
                       355                 360                 365

Gln Val Val Ser Ser Thr Asn Gly Glu Leu Asn Val Asp Asp Pro Thr
       370                 375                 380

Gly Ala His Ser Asn Ala Pro Ile Thr Ala His Ala Glu Val Glu Val
       385                 390                 395                 400

Val Glu Glu Ala Lys Cys Cys Cys Phe Phe Lys Arg Lys Arg Lys Lys
                       405                 410                 415

Thr Ala Gln Arg His Lys
                       420

<210> SEQ ID NO 40
<211> LENGTH: 416
<212> TYPE: PRT
<213> ORGANISM: Homo sapiens

<400> SEQUENCE: 40

Met Glu Leu Arg Val Gly Asn Lys Tyr Arg Leu Gly Arg Lys Ile Gly
1               5                   10                  15

Ser Gly Ser Phe Gly Asp Ile Tyr Leu Gly Ala Asn Ile Ala Ser Gly
                20                  25                  30

Glu Glu Val Ala Ile Lys Leu Glu Cys Val Lys Thr Lys His Pro Gln
                35                  40                  45

Leu His Ile Glu Ser Lys Phe Tyr Lys Met Met Gln Gly Gly Val Gly
                50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95
```

```
Ser Arg Lys Phe Ser Leu Lys Thr Val Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ala Arg Asn Pro Glu Asp Val
    290                 295                 300

Asp Arg Glu Arg Arg Glu His Glu Arg Glu Glu Arg Met Gly Gln Leu
305                 310                 315                 320

Arg Gly Ser Ala Thr Arg Ala Leu Pro Pro Gly Pro Pro Thr Gly Ala
                325                 330                 335

Thr Ala Asn Arg Leu Arg Ser Ala Ala Glu Pro Val Ala Ser Thr Pro
            340                 345                 350

Ala Ser Arg Ile Gln Pro Ala Gly Asn Thr Ser Pro Arg Ala Ile Ser
        355                 360                 365

Arg Val Asp Arg Glu Lys Val Ser Met Arg Leu His Arg Gly Ala
    370                 375                 380

Pro Ala Asn Val Ser Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415

<210> SEQ ID NO 41
<211> LENGTH: 726
<212> TYPE: PRT
<213> ORGANISM: Homo sapiens

<400> SEQUENCE: 41

Met Glu Gly Glu Arg Lys Asn Asn Lys Arg Trp Tyr Phe Thr Arg
1               5                   10                  15

Glu Gln Leu Glu Asn Ser Pro Ser Arg Arg Phe Gly Val Asp Pro Asp
            20                  25                  30

Lys Glu Leu Ser Tyr Arg Gln Gln Ala Ala Asn Leu Leu Gln Asp Met
        35                  40                  45

Gly Gln Arg Leu Asn Val Ser Gln Leu Thr Ile Asn Thr Ala Ile Val
    50                  55                  60
```

```
Tyr Met His Arg Phe Tyr Met Ile Gln Ser Phe Thr Gln Phe Pro Gly
 65                  70                  75                  80

Asn Ser Val Ala Pro Ala Ala Leu Phe Leu Ala Ala Lys Val Glu Glu
                 85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
            115                 120                 125

Gln Val Gln Asp Leu Val Ile Leu Glu Ser Ile Ile Leu Gln Thr Leu
130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
            180                 185                 190

Pro Pro Val Val Ala Cys Val Cys Ile His Leu Ala Cys Lys Trp Ser
            195                 200                 205

Asn Trp Glu Ile Pro Val Ser Thr Asp Gly Lys His Trp Trp Glu Tyr
210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
            260                 265                 270

Gly Thr Asp Glu Lys Thr Ser Glu Gln Thr Ile Leu Asn Met Ile Ser
            275                 280                 285

Gln Ser Ser Ser Asp Thr Thr Ile Ala Gly Leu Met Ser Met Ser Thr
290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335

Ser Gln Pro Ser Phe Lys Leu Glu Pro Thr Gln Gly His Arg Thr Ser
            340                 345                 350

Glu Asn Leu Ala Leu Thr Gly Val Asp His Ser Leu Pro Gln Asp Gly
            355                 360                 365

Ser Asn Ala Phe Ile Ser Gln Lys Gln Asn Ser Lys Ser Val Pro Ser
370                 375                 380

Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
                405                 410                 415

Gln Tyr Ala Tyr Ala Ala Gln Asn Leu Leu Ser His His Asp Ser His
            420                 425                 430

Ser Ser Val Ile Leu Lys Met Pro Ile Glu Gly Ser Glu Asn Pro Glu
            435                 440                 445

Arg Pro Phe Leu Glu Lys Ala Asp Lys Thr Ala Leu Lys Met Arg Ile
            450                 455                 460

Pro Val Ala Gly Gly Asp Lys Ala Ala Ser Ser Lys Pro Glu Glu Ile
465                 470                 475                 480
```

```
Lys Met Arg Ile Lys Val His Ala Ala Asp Lys His Asn Ser Val
            485                 490                 495

Glu Asp Ser Val Thr Lys Ser Arg Glu His Lys Glu Lys His Lys Thr
        500                 505                 510

His Pro Ser Asn His His His His Asn His His Ser His Lys His
    515                 520                 525

Ser His Ser Gln Leu Pro Val Gly Thr Gly Asn Lys Arg Pro Gly Asp
    530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Thr Arg Lys Arg Gly Pro
                565                 570                 575

Ser Glu Glu Thr Gly Gly Ala Val Phe Asp His Pro Ala Lys Ile Ala
            580                 585                 590

Lys Ser Thr Lys Ser Ser Ser Leu Asn Phe Ser Phe Pro Ser Leu Pro
        595                 600                 605

Thr Met Gly Gln Met Pro Gly His Ser Ser Asp Thr Ser Gly Leu Ser
    610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
                645                 650                 655

Tyr Gln Asp Thr Val Asn Met Leu His Ser Leu Leu Ser Ala Gln Gly
            660                 665                 670

Val Gln Pro Thr Gln Pro Thr Ala Phe Glu Phe Val Arg Pro Tyr Ser
        675                 680                 685

Asp Tyr Leu Asn Pro Arg Ser Gly Gly Ile Ser Ser Arg Ser Gly Asn
    690                 695                 700

Thr Asp Lys Pro Arg Pro Pro Leu Pro Ser Glu Pro Pro Pro
705                 710                 715                 720

Leu Pro Pro Leu Pro Lys
            725

<210> SEQ ID NO 42
<211> LENGTH: 591
<212> TYPE: PRT
<213> ORGANISM: Homo sapiens

<400> SEQUENCE: 42

Met Phe Gly Lys Arg Lys Lys Arg Val Glu Ile Ser Ala Pro Ser Asn
1               5                   10                  15

Phe Glu His Arg Val His Thr Gly Phe Asp Gln His Glu Gln Lys Phe
            20                  25                  30

Thr Gly Leu Pro Arg Gln Trp Gln Ser Leu Ile Glu Glu Ser Ala Arg
        35                  40                  45

Arg Pro Lys Pro Leu Val Asp Pro Ala Cys Ile Thr Ser Ile Gln Pro
    50                  55                  60

Gly Ala Pro Lys Thr Ile Val Arg Gly Ser Lys Gly Ala Lys Asp Gly
65                  70                  75                  80

Ala Leu Thr Leu Leu Leu Asp Glu Phe Glu Asn Met Ser Val Thr Arg
                85                  90                  95

Ser Asn Ser Leu Arg Arg Asp Ser Pro Pro Pro Ala Arg Ala Arg
            100                 105                 110

Gln Glu Asn Gly Met Pro Glu Glu Pro Ala Thr Thr Ala Arg Gly Gly
        115                 120                 125
```

-continued

```
Pro Gly Lys Ala Gly Ser Arg Gly Arg Phe Ala Gly His Ser Glu Ala
    130                 135                 140
Gly Gly Gly Ser Gly Asp Arg Arg Ala Gly Pro Glu Lys Arg Pro
145                 150                 155                 160
Lys Ser Ser Arg Glu Gly Ser Gly Gly Pro Gln Glu Ser Ser Arg Asp
                    165                 170                 175
Lys Arg Pro Leu Ser Gly Pro Asp Val Gly Thr Pro Gln Pro Ala Gly
                180                 185                 190
Leu Ala Ser Gly Ala Lys Leu Ala Ala Gly Arg Pro Phe Asn Thr Tyr
                195                 200                 205
Pro Arg Ala Asp Thr Asp His Pro Ser Arg Gly Ala Gln Gly Glu Pro
            210                 215                 220
His Asp Val Ala Pro Asn Gly Pro Ser Ala Gly Gly Leu Ala Ile Pro
225                 230                 235                 240
Gln Ser Ser Ser Ser Ser Arg Pro Pro Thr Arg Ala Arg Gly Ala
                    245                 250                 255
Pro Ser Pro Gly Val Leu Gly Pro His Ala Ser Glu Pro Gln Leu Ala
                260                 265                 270
Pro Pro Ala Cys Thr Pro Ala Ala Pro Ala Val Pro Gly Pro Pro Gly
            275                 280                 285
Pro Arg Ser Pro Gln Arg Glu Pro Gln Arg Val Ser His Glu Gln Phe
290                 295                 300
Arg Ala Ala Leu Gln Leu Val Val Asp Pro Gly Asp Pro Arg Ser Tyr
305                 310                 315                 320
Leu Asp Asn Phe Ile Lys Ile Gly Glu Gly Ser Thr Gly Ile Val Cys
                    325                 330                 335
Ile Ala Thr Val Arg Ser Ser Gly Lys Leu Val Ala Val Lys Lys Met
                340                 345                 350
Asp Leu Arg Lys Gln Gln Arg Arg Glu Leu Leu Phe Asn Glu Val Val
                355                 360                 365
Ile Met Arg Asp Tyr Gln His Glu Asn Val Val Glu Met Tyr Asn Ser
            370                 375                 380
Tyr Leu Val Gly Asp Glu Leu Trp Val Val Met Glu Phe Leu Glu Gly
385                 390                 395                 400
Gly Ala Leu Thr Asp Ile Val Thr His Thr Arg Met Asn Glu Glu Gln
                    405                 410                 415
Ile Ala Ala Val Cys Leu Ala Val Leu Gln Ala Leu Ser Val Leu His
                420                 425                 430
Ala Gln Gly Val Ile His Arg Asp Ile Lys Ser Asp Ser Ile Leu Leu
            435                 440                 445
Thr His Asp Gly Arg Val Lys Leu Ser Asp Phe Gly Phe Cys Ala Gln
    450                 455                 460
Val Ser Lys Glu Val Pro Arg Arg Lys Ser Leu Val Gly Thr Pro Tyr
465                 470                 475                 480
Trp Met Ala Pro Glu Leu Ile Ser Arg Leu Pro Tyr Gly Pro Glu Val
                    485                 490                 495
Asp Ile Trp Ser Leu Gly Ile Met Val Ile Glu Met Val Asp Gly Glu
                500                 505                 510
Pro Pro Tyr Phe Asn Glu Pro Pro Leu Lys Ala Met Lys Met Ile Arg
            515                 520                 525
Asp Asn Leu Pro Pro Arg Leu Lys Asn Leu His Lys Val Ser Pro Ser
    530                 535                 540
```

```
Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
                580                 585                 590

<210> SEQ ID NO 43
<211> LENGTH: 424
<212> TYPE: PRT
<213> ORGANISM: Homo sapiens

<400> SEQUENCE: 43

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
                20                  25                  30

Gly Ser Gly Ala Gln Gly Ile Val Cys Ala Ala Phe Asp Thr Val Leu
            35                  40                  45

Gly Ile Asn Val Ala Val Lys Lys Leu Ser Arg Pro Phe Gln Asn Gln
50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Leu Val Lys Gly Cys Val Ile
210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335
```

```
Ile Tyr Asp Ala Gln Leu Glu Arg Glu His Ala Ile Glu Glu Trp
            340                 345                 350

Lys Glu Leu Ile Tyr Lys Glu Val Met Asp Trp Glu Arg Ser Lys
            355                 360                 365

Asn Gly Val Val Lys Asp Gln Pro Ser Asp Ala Ala Val Ser Ser Asn
370                 375                 380

Ala Thr Pro Ser Gln Ser Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
            405                 410                 415

Thr Gly Pro Leu Glu Gly Cys Arg
            420
```

<210> SEQ ID NO 44
<211> LENGTH: 209
<212> TYPE: PRT
<213> ORGANISM: Homo sapiens

<400> SEQUENCE: 44

```
Met Lys Phe Lys Leu His Val Asn Ser Ala Arg Gln Tyr Lys Asp Leu
1               5                   10                  15

Trp Asn Met Ser Asp Asp Lys Pro Phe Leu Cys Thr Ala Pro Gly Cys
            20                  25                  30

Gly Gln Arg Phe Thr Asn Glu Asp His Leu Ala Val His Lys His Lys
        35                  40                  45

His Glu Met Thr Leu Lys Phe Gly Pro Ala Arg Asn Asp Ser Val Ile
    50                  55                  60

Val Ala Asp Gln Thr Pro Thr Pro Thr Arg Phe Leu Lys Asn Cys Glu
65                  70                  75                  80

Glu Val Gly Leu Phe Asn Glu Leu Ala Ser Pro Phe Glu Asn Glu Phe
                85                  90                  95

Lys Lys Ala Ser Glu Asp Asp Ile Lys Lys Met Pro Leu Asp Leu Ser
            100                 105                 110

Pro Leu Ala Thr Pro Ile Ile Arg Ser Lys Ile Glu Glu Pro Ser Val
        115                 120                 125

Val Glu Thr Thr His Gln Asp Ser Pro Leu Pro His Pro Glu Ser Thr
    130                 135                 140

Thr Ser Asp Glu Lys Glu Val Pro Leu Ala Gln Thr Ala Gln Pro Thr
145                 150                 155                 160

Ser Ala Ile Val Arg Pro Ala Ser Leu Gln Val Pro Asn Val Leu Leu
                165                 170                 175

Thr Ser Ser Asp Ser Ser Val Ile Ile Gln Gln Ala Val Pro Ser Pro
            180                 185                 190

Thr Ser Ser Thr Val Ile Thr Gln Ala Pro Ser Ser Asn Arg Pro Ile
        195                 200                 205

Val
```

<210> SEQ ID NO 45
<211> LENGTH: 1073
<212> TYPE: PRT
<213> ORGANISM: Homo sapiens

<400> SEQUENCE: 45

```
Met Ala Ala Ala Gly Gln Leu Cys Leu Leu Tyr Leu Ser Ala Gly Leu
1               5                   10                  15
```

-continued

```
Leu Ser Arg Leu Gly Ala Ala Phe Asn Leu Asp Thr Arg Glu Asp Asn
         20                  25                  30

Val Ile Arg Lys Tyr Gly Asp Pro Gly Ser Leu Phe Gly Phe Ser Leu
             35                  40                  45

Ala Met His Trp Gln Leu Gln Pro Glu Asp Lys Arg Leu Leu Leu Val
         50                  55                  60

Gly Ala Pro Arg Ala Glu Ala Leu Pro Leu Gln Arg Ala Asn Arg Thr
 65                  70                  75                  80

Gly Gly Leu Tyr Ser Cys Asp Ile Thr Ala Arg Gly Pro Cys Thr Arg
                 85                  90                  95

Ile Glu Phe Asp Asn Asp Ala Asp Pro Thr Ser Glu Ser Lys Glu Asp
            100                 105                 110

Gln Trp Met Gly Val Thr Val Gln Ser Gln Gly Pro Gly Gly Lys Val
            115                 120                 125

Val Thr Cys Ala His Arg Tyr Glu Lys Arg Gln His Val Asn Thr Lys
130                 135                 140

Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Phe Ser Leu Asp Ser Gly Lys Gly Ile Val Ser Lys Asp
            260                 265                 270

Glu Ile Thr Phe Val Ser Gly Ala Pro Arg Ala Asn His Ser Gly Ala
        275                 280                 285

Val Val Leu Leu Lys Arg Asp Met Lys Ser Ala His Leu Leu Pro Glu
290                 295                 300

His Ile Phe Asp Gly Glu Gly Leu Ala Ser Ser Phe Gly Tyr Asp Val
305                 310                 315                 320

Ala Val Val Asp Leu Asn Lys Asp Gly Trp Gln Asp Ile Val Ile Gly
                325                 330                 335

Ala Pro Gln Tyr Phe Asp Arg Asp Gly Glu Val Gly Gly Ala Val Tyr
            340                 345                 350

Val Tyr Met Asn Gln Gln Gly Arg Trp Asn Asn Val Lys Pro Ile Arg
        355                 360                 365

Leu Asn Gly Thr Lys Asp Ser Met Phe Gly Ile Ala Val Lys Asn Ile
        370                 375                 380

Gly Asp Ile Asn Gln Asp Gly Tyr Pro Asp Ile Ala Val Gly Ala Pro
385                 390                 395                 400

Tyr Asp Asp Leu Gly Lys Val Phe Ile Tyr His Gly Ser Ala Asn Gly
                405                 410                 415

Ile Asn Thr Lys Pro Thr Gln Val Leu Lys Gly Ile Ser Pro Tyr Phe
            420                 425                 430

Gly Tyr Ser Ile Ala Gly Asn Met Asp Leu Asp Arg Asn Ser Tyr Pro
```

```
                435                 440                 445
Asp Val Ala Val Gly Ser Leu Ser Asp Ser Val Thr Ile Phe Arg Ser
450                 455                 460

Arg Pro Val Ile Asn Ile Gln Lys Thr Ile Thr Val Thr Pro Asn Arg
465                 470                 475                 480

Ile Asp Leu Arg Gln Lys Thr Ala Cys Gly Ala Pro Ser Gly Ile Cys
                485                 490                 495

Leu Gln Val Lys Ser Cys Phe Glu Tyr Thr Ala Asn Pro Ala Gly Tyr
                500                 505                 510

Asn Pro Ser Ile Ser Ile Val Gly Thr Leu Glu Ala Glu Lys Glu Arg
                515                 520                 525

Arg Lys Ser Gly Leu Ser Ser Arg Val Gln Phe Arg Asn Gln Gly Ser
530                 535                 540

Glu Pro Lys Tyr Thr Gln Glu Leu Thr Leu Lys Arg Gln Lys Gln Lys
545                 550                 555                 560

Val Cys Met Glu Glu Thr Leu Trp Leu Gln Asp Asn Ile Arg Asp Lys
                565                 570                 575

Leu Arg Pro Ile Pro Ile Thr Ala Ser Val Glu Ile Gln Glu Pro Ser
                580                 585                 590

Ser Arg Arg Arg Val Asn Ser Leu Pro Glu Val Leu Pro Ile Leu Asn
                595                 600                 605

Ser Asp Glu Pro Lys Thr Ala His Ile Asp Val His Phe Leu Lys Glu
610                 615                 620

Gly Cys Gly Asp Asp Asn Val Cys Asn Ser Asn Leu Lys Leu Glu Tyr
625                 630                 635                 640

Lys Phe Cys Thr Arg Glu Gly Asn Gln Asp Lys Phe Ser Tyr Leu Pro
                645                 650                 655

Ile Gln Lys Gly Val Pro Glu Leu Val Leu Lys Asp Gln Lys Asp Ile
                660                 665                 670

Ala Leu Glu Ile Thr Val Thr Asn Ser Pro Ser Asn Pro Arg Asn Pro
                675                 680                 685

Thr Lys Asp Gly Asp Asp Ala His Glu Ala Lys Leu Ile Ala Thr Phe
690                 695                 700

Pro Asp Thr Leu Thr Tyr Ser Ala Tyr Arg Glu Leu Arg Ala Phe Pro
705                 710                 715                 720

Glu Lys Gln Leu Ser Cys Val Ala Asn Gln Asn Gly Ser Gln Ala Asp
                725                 730                 735

Cys Glu Leu Gly Asn Pro Phe Lys Arg Asn Ser Asn Val Thr Phe Tyr
                740                 745                 750

Leu Val Leu Ser Thr Thr Glu Val Thr Phe Asp Thr Pro Asp Leu Asp
                755                 760                 765

Ile Asn Leu Lys Leu Glu Thr Thr Ser Asn Gln Asp Asn Leu Ala Pro
                770                 775                 780

Ile Thr Ala Lys Ala Lys Val Val Ile Glu Leu Leu Leu Ser Val Ser
785                 790                 795                 800

Gly Val Ala Lys Pro Ser Gln Val Tyr Phe Gly Gly Thr Val Val Gly
                805                 810                 815

Glu Gln Ala Met Lys Ser Glu Asp Glu Val Gly Ser Leu Ile Glu Tyr
                820                 825                 830

Glu Phe Arg Val Ile Asn Leu Gly Lys Pro Leu Thr Asn Leu Gly Thr
                835                 840                 845

Ala Thr Leu Asn Ile Gln Trp Pro Lys Glu Ile Ser Asn Gly Lys Trp
850                 855                 860
```

-continued

```
Leu Leu Tyr Leu Val Lys Val Glu Ser Lys Gly Leu Glu Lys Val Thr
865                 870                 875                 880

Cys Glu Pro Gln Lys Glu Ile Asn Ser Leu Asn Leu Thr Glu Ser His
                885                 890                 895

Asn Ser Arg Lys Lys Arg Glu Ile Thr Glu Lys Gln Ile Asp Asp Asn
            900                 905                 910

Arg Lys Phe Ser Leu Phe Ala Glu Arg Lys Tyr Gln Thr Leu Asn Cys
        915                 920                 925

Ser Val Asn Val Asn Cys Val Asn Ile Arg Cys Pro Leu Arg Gly Leu
    930                 935                 940

Asp Ser Lys Ala Ser Leu Ile Leu Arg Ser Arg Leu Trp Asn Ser Thr
945                 950                 955                 960

Phe Leu Glu Glu Tyr Ser Lys Leu Asn Tyr Leu Asp Ile Leu Met Arg
                965                 970                 975

Ala Phe Ile Asp Val Thr Ala Ala Glu Asn Ile Arg Leu Pro Asn
            980                 985                 990

Ala Gly Thr Gln Val Arg Val Thr Val Phe Pro Ser Lys Thr Val Ala
        995                 1000                1005

Gln Tyr Ser Gly Val Pro Trp Trp Ile Ile Leu Val Ala Ile Leu Ala
    1010                1015                1020

Gly Ile Leu Met Leu Ala Leu Leu Val Phe Ile Leu Trp Lys Cys Gly
1025                1030                1035                1040

Phe Phe Lys Arg Asn Lys Lys Asp His Tyr Asp Ala Thr Tyr His Lys
                1045                1050                1055

Ala Glu Ile His Ala Gln Pro Ser Asp Lys Glu Arg Leu Thr Ser Asp
            1060                1065                1070

Ala
```

<210> SEQ ID NO 46
<211> LENGTH: 421
<212> TYPE: PRT
<213> ORGANISM: Homo sapiens

<400> SEQUENCE: 46

```
Met Ala Ser Ser Val Pro Pro Ala Thr Val Ser Ala Ala Thr Ala
1               5                   10                  15

Gly Pro Gly Pro Gly Phe Gly Phe Ala Ser Lys Thr Lys Lys Lys His
                20                  25                  30

Phe Val Gln Gln Lys Val Lys Val Phe Arg Ala Ala Asp Pro Leu Val
            35                  40                  45

Gly Val Phe Leu Trp Gly Val Ala His Ser Ile Asn Glu Leu Ser Gln
        50                  55                  60

Val Pro Pro Val Met Leu Leu Pro Asp Asp Phe Lys Ala Ser Ser
65                  70                  75                  80

Lys Ile Lys Val Asn Asn His Leu Phe His Arg Glu Asn Leu Pro Ser
                85                  90                  95

His Phe Lys Phe Lys Glu Tyr Cys Pro Gln Val Phe Arg Asn Leu Arg
                100                 105                 110

Asp Arg Phe Gly Ile Asp Asp Gln Asp Tyr Leu Val Ser Leu Thr Arg
            115                 120                 125

Asn Pro Pro Ser Glu Ser Glu Gly Ser Asp Gly Arg Phe Leu Ile Ser
        130                 135                 140

Tyr Asp Arg Thr Leu Val Ile Lys Glu Val Ser Ser Glu Asp Ile Ala
145                 150                 155                 160
```

```
Asp Met His Ser Asn Leu Ser Asn Tyr His Gln Tyr Ile Val Lys Cys
                165                 170                 175

His Gly Asn Thr Leu Leu Pro Gln Phe Leu Gly Met Tyr Arg Val Ser
            180                 185                 190

Val Asp Asn Glu Asp Ser Tyr Met Leu Val Met Arg Asn Met Phe Ser
        195                 200                 205

His Arg Leu Pro Val His Arg Lys Tyr Asp Leu Lys Gly Ser Leu Val
    210                 215                 220

Ser Arg Glu Ala Ser Asp Lys Glu Lys Val Lys Glu Leu Pro Thr Leu
225                 230                 235                 240

Arg Asp Met Asp Phe Leu Asn Lys Asn Gln Lys Val Tyr Ile Gly Glu
                245                 250                 255

Glu Glu Lys Lys Ile Phe Leu Glu Lys Leu Lys Arg Asp Val Glu Phe
            260                 265                 270

Leu Val Gln Leu Lys Ile Met Asp Tyr Ser Leu Leu Leu Gly Ile His
        275                 280                 285

Asp Ile Ile Arg Gly Ser Glu Pro Glu Glu Ala Pro Val Arg Glu
    290                 295                 300

Asp Glu Ser Glu Val Asp Gly Asp Cys Ser Leu Thr Gly Pro Pro Ala
305                 310                 315                 320

Leu Val Gly Ser Tyr Gly Thr Ser Pro Glu Gly Ile Gly Gly Tyr Ile
                325                 330                 335

His Ser His Arg Pro Leu Gly Pro Gly Glu Phe Glu Ser Phe Ile Asp
            340                 345                 350

Val Tyr Ala Ile Arg Ser Ala Glu Gly Ala Pro Gln Lys Glu Val Tyr
        355                 360                 365

Phe Met Gly Leu Ile Asp Ile Leu Thr Gln Tyr Asp Ala Lys Lys Lys
    370                 375                 380

Ala Ala His Ala Ala Lys Thr Val Lys His Gly Ala Gly Ala Glu Ile
385                 390                 395                 400

Ser Thr Val His Pro Glu Gln Tyr Ala Lys Arg Phe Leu Asp Phe Ile
                405                 410                 415

Thr Asn Ile Phe Ala
            420

<210> SEQ ID NO 47
<211> LENGTH: 619
<212> TYPE: PRT
<213> ORGANISM: Homo sapiens

<400> SEQUENCE: 47

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
```

```
                 100                 105                 110
Gly Val Phe Asp Cys Leu Arg Asp Ala Met Val Arg Asp Tyr Val Arg
            115                 120                 125
Gln Thr Trp Lys Leu Glu Gly Glu Ala Leu Glu Gln Ala Ile Ile Ser
        130                 135                 140
Gln Ala Pro Gln Val Glu Lys Leu Ile Ala Thr Ala His Glu Arg
145                 150                 155                 160
Met Pro Trp Tyr His Ser Ser Leu Thr Arg Glu Glu Ala Glu Arg Lys
                165                 170                 175
Leu Tyr Ser Gly Ala Gln Thr Asp Gly Lys Phe Leu Leu Arg Pro Arg
            180                 185                 190
Lys Glu Gln Gly Thr Tyr Ala Leu Ser Leu Ile Tyr Gly Lys Thr Val
        195                 200                 205
Tyr His Tyr Leu Ile Ser Gln Asp Lys Ala Gly Lys Tyr Cys Ile Pro
    210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
Ser Ser Ala Ser Asn Ala Ser Gly Ala Ala Pro Thr Leu Pro Ala
            260                 265                 270
His Pro Ser Thr Leu Thr His Pro Gln Arg Arg Ile Asp Thr Leu Asn
        275                 280                 285
Ser Asp Gly Tyr Thr Pro Glu Pro Ala Arg Ile Thr Ser Pro Asp Lys
    290                 295                 300
Pro Arg Pro Met Pro Met Asp Thr Ser Val Tyr Glu Ser Pro Tyr Ser
305                 310                 315                 320
Asp Pro Glu Glu Leu Lys Asp Lys Lys Leu Phe Leu Lys Arg Asp Asn
                325                 330                 335
Leu Leu Ile Ala Asp Ile Glu Leu Gly Cys Gly Asn Phe Gly Ser Val
            340                 345                 350
Arg Gln Gly Val Tyr Arg Met Arg Lys Lys Gln Ile Asp Val Ala Ile
        355                 360                 365
Lys Val Leu Lys Gln Gly Thr Glu Lys Ala Asp Thr Glu Glu Met Met
    370                 375                 380
Arg Glu Ala Gln Ile Met His Gln Leu Asp Asn Pro Tyr Ile Val Arg
385                 390                 395                 400
Leu Ile Gly Val Cys Gln Ala Glu Ala Leu Met Leu Val Met Glu Met
                405                 410                 415
Ala Gly Gly Gly Pro Leu His Lys Phe Leu Val Gly Lys Arg Glu Glu
            420                 425                 430
Ile Pro Val Ser Asn Val Ala Glu Leu Leu His Gln Val Ser Met Gly
        435                 440                 445
Met Lys Tyr Leu Glu Glu Lys Asn Phe Val His Arg Asp Leu Ala Ala
    450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                485                 490                 495
Ser Ala Gly Lys Trp Pro Leu Lys Trp Tyr Ala Pro Glu Cys Ile Asn
            500                 505                 510
Phe Arg Lys Phe Ser Ser Arg Ser Asp Val Trp Ser Tyr Gly Val Thr
        515                 520                 525
```

Met Trp Glu Ala Leu Ser Tyr Gly Gln Lys Pro Tyr Lys Met Lys
            530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
                580                 585                 590

Met Arg Ala Cys Tyr Tyr Ser Leu Ala Ser Lys Val Glu Gly Pro Pro
                595                 600                 605

Gly Ser Thr Gln Lys Ala Glu Ala Ala Cys Ala
            610                 615

<210> SEQ ID NO 48
<211> LENGTH: 418
<212> TYPE: PRT
<213> ORGANISM: Homo sapiens

<400> SEQUENCE: 48

Met Lys Asn Lys Pro Gly Pro Tyr Ser Ser Val Pro Pro Ser Ala
1               5                   10                  15

Pro Pro Pro Lys Lys Ser Leu Gly Thr Gln Pro Pro Lys Lys Ala Val
                20                  25                  30

Glu Lys Gln Gln Pro Val Glu Ser Glu Asp Ser Asp Glu Ser
                35                  40                  45

Asp Ser Ser Ser Glu Glu Lys Lys Pro Pro Thr Lys Ala Val Val
    50                  55                  60

Ser Lys Ala Thr Thr Lys Pro Pro Ala Lys Lys Ala Ala Glu Ser
65                  70                  75                  80

Ser Ser Asp Ser Ser Asp Ser Asp Ser Glu Asp Asp Glu Ala Pro
                85                  90                  95

Ser Lys Pro Ala Gly Thr Thr Lys Asn Ser Ser Asn Lys Pro Ala Val
                100                 105                 110

Thr Thr Lys Ser Pro Ala Val Lys Pro Ala Ala Pro Lys Gln Pro
                115                 120                 125

Val Gly Gly Gly Gln Lys Leu Leu Thr Arg Lys Ala Asp Ser Ser Ser
    130                 135                 140

Ser Glu Glu Glu Ser Ser Ser Glu Glu Lys Thr Lys Lys Met
145                 150                 155                 160

Val Ala Thr Thr Lys Pro Lys Ala Thr Ala Lys Ala Ala Leu Ser Leu
                165                 170                 175

Pro Ala Lys Gln Ala Pro Gln Gly Ser Arg Asp Ser Ser Ser Asp Ser
                180                 185                 190

Asp Ser Ser Ser Glu Glu Glu Glu Lys Thr Ser Lys Ser Ala
    195                 200                 205

Val Lys Lys Lys Pro Gln Lys Val Ala Gly Ala Ala Pro Ser Lys
    210                 215                 220

Pro Ala Ser Ala Lys Lys Gly Lys Ala Glu Ser Ser Asn Ser Ser Ser
225                 230                 235                 240

Ser Asp Asp Ser Ser Glu Glu Glu Glu Lys Leu Lys Gly Lys Gly
                245                 250                 255

Ser Pro Arg Pro Gln Ala Pro Lys Ala Asn Gly Thr Ser Ala Leu Thr
                260                 265                 270

Ala Gln Asn Gly Lys Ala Ala Lys Asn Ser Glu Glu Glu Glu Glu

```
                275                 280                 285
Lys Lys Lys Ala Ala Val Val Ser Lys Ser Gly Ser Leu Lys Lys
    290                 295                 300

Arg Lys Gln Asn Glu Ala Ala Lys Glu Ala Glu Thr Pro Gln Ala Lys
305                 310                 315                 320

Lys Ile Lys Leu Gln Thr Pro Asn Thr Phe Pro Lys Arg Lys Lys Gly
                325                 330                 335

Glu Lys Arg Ala Ser Ser Pro Phe Arg Arg Val Arg Glu Glu Ile
            340                 345                 350

Glu Val Asp Ser Arg Val Ala Asp Asn Ser Phe Asp Ala Lys Arg Gly
        355                 360                 365

Ala Ala Gly Asp Trp Gly Glu Arg Ala Asn Gln Val Leu Lys Phe Thr
    370                 375                 380

Lys Gly Lys Ser Phe Arg His Glu Lys Thr Lys Lys Arg Gly Ser
385                 390                 395                 400

Tyr Arg Gly Gly Ser Ile Ser Val Gln Val Asn Ser Ile Lys Phe Asp
                405                 410                 415

Ser Glu

<210> SEQ ID NO 49
<211> LENGTH: 279
<212> TYPE: PRT
<213> ORGANISM: Homo sapiens

<400> SEQUENCE: 49

Met Ser Val Ala Gly Leu Lys Lys Gln Phe His Lys Ala Thr Gln Lys
1               5                   10                  15

Val Ser Glu Lys Val Gly Gly Ala Glu Gly Thr Lys Leu Asp Asp Asp
            20                  25                  30

Phe Lys Glu Met Glu Arg Lys Val Asp Val Thr Ser Arg Ala Val Met
        35                  40                  45

Glu Ile Met Thr Lys Thr Ile Glu Tyr Leu Gln Pro Asn Pro Ala Ser
    50                  55                  60

Arg Ala Lys Leu Ser Met Ile Asn Thr Met Ser Lys Ile Arg Gly Gln
65                  70                  75                  80

Glu Lys Gly Pro Gly Tyr Pro Gln Ala Glu Ala Leu Leu Ala Glu Ala
                85                  90                  95

Met Leu Lys Phe Gly Arg Glu Leu Gly Asp Asp Cys Asn Phe Gly Pro
            100                 105                 110

Ala Leu Gly Glu Val Gly Glu Ala Met Arg Glu Leu Ser Glu Val Lys
        115                 120                 125

Asp Ser Leu Asp Ile Glu Val Lys Gln Asn Phe Ile Asp Pro Leu Gln
    130                 135                 140

Asn Leu His Asp Lys Asp Leu Arg Glu Ile Gln His His Leu Lys Lys
145                 150                 155                 160

Leu Glu Gly Arg Arg Leu Asp Phe Asp Tyr Lys Lys Leu Arg Gln Gly
                165                 170                 175

Lys Ile Pro Asp Glu Glu Leu Arg Gln Ala Leu Glu Lys Phe Asp Glu
            180                 185                 190

Ser Lys Glu Ile Ala Glu Ser Ser Met Phe Asn Leu Leu Glu Met Asp
        195                 200                 205

Ile Glu Gln Val Ser Gln Leu Ser Ala Leu Val Gln Ala Gln Leu Glu
    210                 215                 220

Tyr His Lys Gln Ala Val Gln Ile Leu Gln Gln Val Thr Val Arg Leu
```

```
            225                 230                 235                 240
Glu Glu Arg Ile Arg Gln Ala Ser Ser Gln Pro Arg Arg Glu Tyr Gln
                245                 250                 255

Pro Lys Pro Arg Met Ser Leu Glu Phe Pro Thr Gly Asp Ser Thr Gln
                260                 265                 270

Pro Asn Gly Gly Leu Ser His
                275

<210> SEQ ID NO 50
<211> LENGTH: 631
<212> TYPE: PRT
<213> ORGANISM: Homo sapiens

<400> SEQUENCE: 50

Met Thr Ser Ala Asn Lys Ala Ile Glu Leu Gln Leu Gln Val Lys Gln
1               5                   10                  15

Asn Ala Glu Glu Leu Gln Asp Phe Met Arg Asp Leu Glu Asn Trp Glu
                20                  25                  30

Lys Asp Ile Lys Gln Lys Asp Met Glu Leu Arg Arg Gln Asn Gly Val
            35                  40                  45

Pro Glu Glu Asn Leu Pro Pro Ile Arg Asn Gly Asn Phe Arg Lys Lys
        50                  55                  60

Lys Lys Gly Lys Ala Lys Glu Ser Ser Lys Lys Thr Arg Glu Glu Asn
65                  70                  75                  80

Thr Lys Asn Arg Ile Lys Ser Tyr Asp Tyr Glu Ala Trp Ala Lys Leu
                85                  90                  95

Asp Val Asp Arg Ile Leu Asp Glu Leu Asp Lys Asp Ser Thr His
                100                 105                 110

Glu Ser Leu Ser Gln Glu Ser Glu Ser Glu Asp Gly Ile His Val
            115                 120                 125

Asp Ser Gln Lys Ala Leu Val Leu Lys Glu Lys Gly Asn Lys Tyr Phe
        130                 135                 140

Lys Gln Gly Lys Tyr Asp Glu Ala Ile Asp Cys Tyr Thr Lys Gly Met
145                 150                 155                 160

Asp Ala Asp Pro Tyr Asn Pro Val Leu Pro Thr Asn Arg Ala Ser Ala
                165                 170                 175

Tyr Phe Arg Leu Lys Lys Phe Ala Val Ala Glu Ser Asp Cys Asn Leu
                180                 185                 190

Ala Val Ala Leu Asn Arg Ser Tyr Thr Lys Ala Tyr Ser Arg Arg Gly
            195                 200                 205

Ala Ala Arg Phe Ala Leu Gln Lys Leu Glu Glu Ala Lys Lys Asp Tyr
        210                 215                 220

Glu Arg Val Leu Glu Leu Glu Pro Asn Asn Phe Glu Ala Thr Asn Glu
225                 230                 235                 240

Leu Arg Lys Ile Ser Gln Ala Leu Ala Ser Lys Glu Asn Ser Tyr Pro
                245                 250                 255

Lys Glu Ala Asp Ile Val Ile Lys Ser Thr Glu Gly Glu Arg Lys Gln
                260                 265                 270

Ile Glu Ala Gln Gln Asn Lys Gln Gln Ala Ile Ser Glu Lys Asp Arg
            275                 280                 285

Gly Asn Gly Phe Phe Lys Glu Gly Lys Tyr Glu Arg Ala Ile Glu Cys
        290                 295                 300

Tyr Thr Arg Gly Ile Ala Ala Asp Gly Ala Asn Ala Leu Leu Pro Ala
305                 310                 315                 320
```

-continued

```
Asn Arg Ala Met Ala Tyr Leu Lys Ile Gln Lys Tyr Glu Glu Ala Glu
            325                 330                 335

Lys Asp Cys Thr Gln Ala Ile Leu Leu Asp Gly Ser Tyr Ser Lys Ala
        340                 345                 350

Phe Ala Arg Arg Gly Thr Ala Arg Thr Phe Leu Gly Lys Leu Asn Glu
    355                 360                 365

Ala Lys Gln Asp Phe Glu Thr Val Leu Leu Glu Pro Gly Asn Lys
370                 375                 380

Gln Ala Val Thr Glu Leu Ser Lys Ile Lys Lys Pro Leu Lys Lys
385                 390                 395                 400

Val Ile Ile Glu Glu Thr Gly Asn Leu Ile Gln Thr Ile Asp Val Pro
                405                 410                 415

Asp Ser Thr Thr Ala Ala Ala Pro Glu Asn Asn Pro Ile Asn Leu Ala
            420                 425                 430

Asn Val Ile Ala Ala Thr Gly Thr Thr Ser Lys Lys Asn Ser Ser Gln
        435                 440                 445

Asp Asp Leu Phe Pro Thr Ser Asp Thr Pro Arg Ala Lys Val Leu Lys
    450                 455                 460

Ile Glu Glu Val Ser Asp Thr Ser Ser Leu Gln Pro Gln Ala Ser Leu
465                 470                 475                 480

Lys Gln Asp Val Cys Gln Ser Tyr Ser Glu Lys Met Pro Ile Glu Ile
                485                 490                 495

Glu Gln Lys Pro Ala Gln Phe Ala Thr Thr Val Leu Pro Pro Ile Pro
            500                 505                 510

Ala Asn Ser Phe Gln Leu Glu Ser Asp Phe Arg Gln Leu Lys Ser Ser
        515                 520                 525

Pro Asp Met Leu Tyr Gln Tyr Leu Lys Gln Ile Glu Pro Ser Leu Tyr
    530                 535                 540

Pro Lys Leu Phe Gln Lys Asn Leu Asp Pro Asp Val Phe Asn Gln Ile
545                 550                 555                 560

Val Lys Ile Leu His Asp Phe Tyr Ile Glu Lys Glu Lys Pro Leu Leu
                565                 570                 575

Ile Phe Glu Ile Leu Gln Arg Leu Ser Glu Leu Lys Arg Phe Asp Met
            580                 585                 590

Ala Val Met Phe Met Ser Glu Thr Glu Lys Lys Ile Ala Arg Ala Leu
        595                 600                 605

Phe Asn His Ile Asp Lys Ser Gly Leu Lys Asp Ser Ser Val Glu Glu
    610                 615                 620

Leu Lys Lys Arg Tyr Gly Gly
625                 630

<210> SEQ ID NO 51
<211> LENGTH: 362
<212> TYPE: PRT
<213> ORGANISM: Homo sapiens

<400> SEQUENCE: 51

Met Ala Cys Ala Gly Leu Leu Thr Val Cys Leu Leu Arg Pro Pro Ala
1               5                   10                  15

Pro Gln Pro Gln Pro Gln Thr Arg His Pro Gln Leu Ala Pro Asp
            20                  25                  30

Pro Gly Pro Ala Gly His Thr Leu Phe Gln Asp Val Phe Arg Arg Ala
        35                  40                  45

Asp Lys Asn Asp Asp Gly Lys Leu Ser Phe Glu Glu Phe Gln Asn Tyr
    50                  55                  60
```

Phe Ala Asp Gly Val Leu Ser Leu Gly Glu Leu Gln Glu Leu Phe Ser
65                  70                  75                  80

Gly Ile Asp Gly His Leu Thr Asp Asn Leu Glu Thr Glu Lys Leu Cys
                85                  90                  95

Asp Tyr Phe Ser Glu His Leu Gly Val Tyr Arg Pro Val Leu Ala Ala
            100                 105                 110

Leu Glu Ser Leu Asn Arg Ala Val Leu Ala Ala Met Asp Ala Thr Lys
        115                 120                 125

Leu Glu Tyr Glu Arg Ala Ser Lys Val Asp Gln Phe Val Thr Arg Phe
    130                 135                 140

Leu Leu Arg Glu Thr Val Ser Gln Leu Gln Ala Leu Gln Ser Ser Leu
145                 150                 155                 160

Glu Gly Ala Ser Asp Thr Leu Glu Ala Gln Ala His Gly Trp Arg Ser
                165                 170                 175

Asp Ala Glu Ser Val Glu Ala Gln Ser Arg Leu Cys Gly Ser Arg Arg
            180                 185                 190

Ala Gly Arg Arg Ala Leu Arg Ser Val Ser Arg Ser Ser Thr Trp Ser
        195                 200                 205

Pro Gly Ser Ser Asp Thr Gly Arg Ser Glu Ala Glu Met Gln Trp
    210                 215                 220

Arg Leu Gln Val Asn Arg Leu Gln Glu Leu Ile Asp Gln Leu Glu Cys
225                 230                 235                 240

Lys Ala Pro Arg Leu Glu Pro Leu Arg Glu Glu Asp Leu Ala Lys Gly
                245                 250                 255

Pro Asp Leu His Ile Leu Met Ala Gln Arg Val Gln Val Ala Glu
            260                 265                 270

Glu Gly Leu Gln Asp Phe His Arg Ala Leu Arg Cys Tyr Val Asp Phe
        275                 280                 285

Thr Gly Ala Gln Ser His Cys Leu His Val Ser Ala Gln Lys Met Leu
    290                 295                 300

Asp Gly Ala Ser Phe Thr Leu Tyr Glu Phe Trp Gln Asp Glu Ala Ser
305                 310                 315                 320

Trp Arg Arg His Gln Gln Ser Pro Gly Ser Lys Ala Phe Gln Arg Ile
                325                 330                 335

Leu Ile Asp His Leu Arg Ala Pro Asp Thr Leu Thr Thr Val Phe Phe
            340                 345                 350

Pro Ala Ser Trp Trp Ile Met Asn Asn Asn
        355                 360

<210> SEQ ID NO 52
<211> LENGTH: 181
<212> TYPE: PRT
<213> ORGANISM: Homo sapiens

<400> SEQUENCE: 52

Met Ala Gly Ser Arg Glu Val Val Ala Met Asp Cys Glu Met Val Gly
1               5                   10                  15

Leu Gly Pro His Arg Glu Ser Gly Leu Ala Arg Cys Ser Leu Val Asn
            20                  25                  30

Val His Gly Ala Val Leu Tyr Asp Lys Phe Ile Arg Pro Glu Gly Glu
        35                  40                  45

Ile Thr Asp Tyr Arg Thr Arg Val Ser Gly Val Thr Pro Gln His Met
    50                  55                  60

Val Gly Ala Thr Pro Phe Ala Val Ala Arg Leu Glu Ile Leu Gln Leu

```
            65                  70                  75                  80
Leu Lys Gly Lys Leu Val Val Gly His Asp Leu Lys His Asp Phe Gln
                85                  90                  95

Ala Leu Lys Glu Asp Met Ser Gly Tyr Thr Ile Tyr Asp Thr Ser Thr
            100                 105                 110

Asp Arg Leu Leu Trp Arg Glu Ala Lys Leu Asp His Cys Arg Arg Val
            115                 120                 125

Ser Leu Arg Val Leu Ser Glu Arg Leu Leu His Lys Ser Ile Gln Asn
        130                 135                 140

Ser Leu Leu Gly His Ser Ser Val Glu Asp Ala Arg Ala Thr Met Glu
145                 150                 155                 160

Leu Tyr Gln Ile Ser Gln Arg Ile Arg Ala Arg Arg Gly Leu Pro Arg
                165                 170                 175

Leu Ala Val Ser Asp
            180

<210> SEQ ID NO 53
<211> LENGTH: 85
<212> TYPE: PRT
<213> ORGANISM: Homo sapiens

<400> SEQUENCE: 53

Met Glu Phe Asp Leu Gly Ala Ala Leu Glu Pro Thr Ser Gln Lys Pro
1               5                   10                  15

Gly Val Gly Ala Gly His Gly Asp Pro Lys Leu Ser Pro His Lys
            20                  25                  30

Val Gln Gly Arg Ser Glu Ala Gly Ala Gly Pro Gly Pro Lys Ala Ser
            35                  40                  45

Asn Phe Arg Gly Leu Gly Lys Gly Arg Arg Leu Thr Ala Ala Pro Pro
        50                  55                  60

Ser Ser Lys Asp Thr Thr Ala Leu Pro Thr Pro Ala Ala Ala Pro Ala
65                  70                  75                  80

Ile Arg Thr Arg Met
                85

<210> SEQ ID NO 54
<211> LENGTH: 475
<212> TYPE: PRT
<213> ORGANISM: Homo sapiens

<400> SEQUENCE: 54

Met Ala Ser Ala Ala Arg Leu Thr Met Met Trp Glu Glu Val Thr Cys
1               5                   10                  15

Pro Ile Cys Leu Asp Pro Phe Val Glu Pro Val Ser Ile Glu Cys Gly
            20                  25                  30

His Ser Phe Cys Gln Glu Cys Ile Ser Gln Val Gly Lys Gly Gly Gly
            35                  40                  45

Ser Val Cys Pro Val Cys Arg Gln Arg Phe Leu Leu Lys Asn Leu Arg
        50                  55                  60

Pro Asn Arg Gln Leu Ala Asn Met Val Asn Asn Leu Lys Glu Ile Ser
65                  70                  75                  80

Gln Glu Ala Arg Glu Gly Thr Gln Gly Glu Arg Cys Ala Val His Gly
            85                  90                  95

Glu Arg Leu His Leu Phe Cys Glu Lys Asp Gly Lys Ala Leu Cys Trp
            100                 105                 110

Val Cys Ala Gln Ser Arg Lys His Arg Asp His Ala Met Val Pro Leu
```

-continued

```
            115                 120                 125

Glu Glu Ala Ala Gln Glu Tyr Gln Glu Lys Leu Gln Val Ala Leu Gly
            130                 135                 140

Glu Leu Arg Arg Lys Gln Glu Leu Ala Glu Lys Leu Glu Val Glu Ile
145                 150                 155                 160

Ala Ile Lys Arg Ala Asp Trp Lys Lys Thr Val Glu Thr Gln Lys Ser
                165                 170                 175

Arg Ile His Ala Glu Phe Val Gln Gln Lys Asn Phe Leu Val Glu Glu
                180                 185                 190

Glu Gln Arg Gln Leu Gln Glu Leu Lys Asp Glu Arg Glu Gln Leu
            195                 200                 205

Arg Ile Leu Gly Glu Lys Glu Ala Lys Leu Ala Gln Gln Ser Gln Ala
210                 215                 220

Leu Gln Glu Leu Ile Ser Glu Leu Asp Arg Arg Cys His Ser Ser Ala
225                 230                 235                 240

Leu Glu Leu Leu Gln Glu Val Ile Ile Val Leu Glu Arg Ser Glu Ser
                245                 250                 255

Trp Asn Leu Lys Asp Leu Asp Ile Thr Ser Pro Glu Leu Arg Ser Val
            260                 265                 270

Cys His Val Pro Gly Leu Lys Lys Met Leu Arg Thr Cys Ala Val His
            275                 280                 285

Ile Thr Leu Asp Pro Asp Thr Ala Asn Pro Trp Leu Ile Leu Ser Glu
290                 295                 300

Asp Arg Arg Gln Val Arg Leu Gly Asp Thr Gln Gln Ser Ile Pro Gly
305                 310                 315                 320

Asn Glu Glu Arg Phe Asp Ser Tyr Pro Met Val Leu Gly Ala Gln His
                325                 330                 335

Phe His Ser Gly Lys His Tyr Trp Glu Val Asp Val Thr Gly Lys Glu
                340                 345                 350

Ala Trp Asp Leu Gly Val Cys Arg Asp Ser Val Arg Arg Lys Gly His
            355                 360                 365

Phe Leu Leu Ser Ser Lys Ser Gly Phe Trp Thr Ile Trp Leu Trp Asn
            370                 375                 380

Lys Gln Lys Tyr Glu Ala Gly Thr Tyr Pro Gln Thr Pro Leu His Leu
385                 390                 395                 400

Gln Val Pro Pro Cys Gln Val Gly Ile Phe Leu Asp Tyr Glu Ala Gly
                405                 410                 415

Met Val Ser Phe Tyr Asn Ile Thr Asp His Gly Ser Leu Ile Tyr Ser
                420                 425                 430

Phe Ser Glu Cys Ala Phe Thr Gly Pro Leu Arg Pro Phe Phe Ser Pro
            435                 440                 445

Gly Phe Asn Asp Gly Gly Lys Asn Thr Ala Pro Leu Thr Leu Cys Pro
            450                 455                 460

Leu Asn Ile Gly Ser Gln Gly Ser Thr Asp Tyr
465                 470                 475

<210> SEQ ID NO 55
<211> LENGTH: 454
<212> TYPE: PRT
<213> ORGANISM: Homo sapiens

<400> SEQUENCE: 55

Met Ala Glu Phe Ser Gln Lys Arg Gly Lys Arg Ser Asp Glu Gly
1               5                   10                  15
```

```
Leu Gly Ser Met Val Asp Phe Leu Leu Ala Asn Ala Arg Val Leu
            20                  25                  30

Gly Val Gly Gly Ala Ala Val Leu Gly Ile Ala Thr Leu Ala Val Lys
        35                  40                  45

Arg Phe Ile Asp Arg Ala Thr Ser Pro Arg Asp Glu Asp Asp Thr Lys
50                  55                  60

Ala Asp Ser Trp Lys Glu Leu Ser Leu Leu Lys Ala Thr Pro His Leu
65                  70                  75                  80

Gln Pro Arg Pro Pro Ala Ala Leu Ser Gln Pro Val Leu Pro Leu
                85                  90                  95

Ala Pro Ser Ser Ser Ala Pro Glu Gly Pro Ala Glu Thr Asp Pro Glu
            100                 105                 110

Val Thr Pro Gln Leu Ser Ser Pro Ala Pro Leu Cys Leu Thr Leu Gln
        115                 120                 125

Glu Arg Leu Leu Ala Phe Glu Arg Asp Arg Val Thr Ile Pro Ala Ala
        130                 135                 140

Gln Val Ala Leu Ala Lys Gln Leu Ala Gly Asp Ile Ala Leu Glu Leu
145                 150                 155                 160

Gln Ala Tyr Phe Arg Ser Lys Phe Pro Glu Leu Pro Phe Gly Ala Phe
                165                 170                 175

Val Pro Gly Gly Pro Leu Tyr Asp Gly Leu Gln Ala Gly Ala Ala Asp
            180                 185                 190

His Val Arg Leu Leu Val Pro Leu Val Leu Glu Pro Gly Leu Trp Ser
        195                 200                 205

Leu Val Pro Gly Val Asp Thr Val Ala Arg Asp Pro Arg Cys Trp Ala
210                 215                 220

Val Arg Arg Thr Gln Leu Glu Phe Cys Pro Arg Gly Ser Ser Pro Trp
225                 230                 235                 240

Asp Arg Phe Leu Val Gly Gly Tyr Leu Ser Ser Arg Val Leu Leu Glu
                245                 250                 255

Leu Leu Arg Lys Ala Leu Ala Ala Ser Val Asn Trp Pro Ala Ile Gly
            260                 265                 270

Ser Leu Leu Gly Cys Leu Ile Arg Pro Ser Met Ala Ser Glu Glu Leu
        275                 280                 285

Leu Leu Glu Val Gln His Glu Arg Leu Glu Leu Thr Val Ala Val Leu
290                 295                 300

Val Ala Val Pro Gly Val Asp Ala Asp Asp Arg Leu Leu Leu Ala Trp
305                 310                 315                 320

Pro Leu Glu Gly Leu Ala Gly Asn Leu Trp Leu Gln Asp Leu Tyr Pro
                325                 330                 335

Val Glu Ala Ala Arg Leu Arg Ala Leu Asp Asp His Asp Ala Gly Thr
            340                 345                 350

Arg Arg Arg Leu Leu Leu Leu Cys Ala Val Cys Arg Gly Cys Ser
        355                 360                 365

Ala Leu Gly Gln Leu Gly Arg Gly His Leu Thr Gln Val Val Leu Arg
370                 375                 380

Leu Gly Glu Asp Asn Val Asp Trp Thr Glu Glu Ala Leu Gly Glu Arg
385                 390                 395                 400

Phe Leu Gln Ala Leu Glu Leu Leu Ile Gly Ser Leu Glu Gln Ala Ser
                405                 410                 415

Leu Pro Cys His Phe Asn Pro Ser Val Asn Leu Phe Ser Ser Leu Arg
            420                 425                 430

Glu Glu Glu Ile Asp Asp Ile Gly Tyr Ala Leu Tyr Ser Gly Leu Gln
```

-continued

```
            435                 440                 445
Glu Pro Glu Gly Leu Leu
    450

<210> SEQ ID NO 56
<211> LENGTH: 282
<212> TYPE: PRT
<213> ORGANISM: Homo sapiens

<400> SEQUENCE: 56

Met Ala Val Pro Glu Thr Arg Pro Asn His Thr Ile Tyr Ile Asn Asn
1               5                   10                  15

Leu Asn Glu Lys Ile Lys Lys Asp Glu Leu Lys Lys Ser Leu Tyr Ala
            20                  25                  30

Ile Phe Ser Gln Phe Gly Gln Ile Leu Asp Ile Leu Val Ser Arg Ser
        35                  40                  45

Leu Lys Met Arg Gly Gln Ala Phe Val Ile Phe Lys Glu Val Ser Ser
    50                  55                  60

Ala Thr Asn Ala Leu Arg Ser Met Gln Gly Phe Pro Phe Tyr Asp Lys
65                  70                  75                  80

Pro Met Arg Ile Gln Tyr Ala Lys Thr Asp Ser Asp Ile Ile Ala Lys
                85                  90                  95

Met Lys Gly Thr Phe Val Glu Arg Asp Arg Lys Arg Glu Lys Arg Lys
            100                 105                 110

Pro Lys Ser Gln Glu Thr Pro Ala Thr Lys Lys Ala Val Gln Gly Gly
        115                 120                 125

Gly Ala Thr Pro Val Val Gly Ala Val Gln Gly Pro Val Pro Gly Met
    130                 135                 140

Pro Pro Met Thr Gln Ala Pro Arg Ile Met His His Met Pro Gly Gln
145                 150                 155                 160

Pro Pro Tyr Met Pro Pro Gly Met Ile Pro Pro Gly Leu Ala
                165                 170                 175

Pro Gly Gln Ile Pro Pro Gly Ala Met Pro Pro Gln Gln Leu Met Pro
            180                 185                 190

Gly Gln Met Pro Pro Ala Gln Pro Leu Ser Glu Asn Pro Pro Asn His
        195                 200                 205

Ile Leu Phe Leu Thr Asn Leu Pro Glu Glu Thr Asn Glu Leu Met Leu
    210                 215                 220

Ser Met Leu Phe Asn Gln Phe Pro Gly Phe Lys Glu Val Arg Leu Val
225                 230                 235                 240

Pro Gly Arg His Asp Ile Ala Phe Val Glu Phe Asp Asn Glu Val Gln
                245                 250                 255

Ala Gly Ala Ala Arg Asp Ala Leu Gln Gly Phe Lys Ile Thr Gln Asn
            260                 265                 270

Asn Ala Met Lys Ile Ser Phe Ala Lys Lys
        275                 280

<210> SEQ ID NO 57
<211> LENGTH: 115
<212> TYPE: PRT
<213> ORGANISM: Homo sapiens

<400> SEQUENCE: 57

Met Arg Tyr Val Ala Ser Tyr Leu Leu Ala Ala Leu Gly Gly Asn Ser
1               5                   10                  15

Ser Pro Ser Ala Lys Asp Ile Lys Lys Ile Leu Asp Ser Val Gly Ile
```

```
                        20                  25                  30

Glu Ala Asp Asp Asp Arg Leu Asn Lys Val Ile Ser Glu Leu Asn Gly
                35                  40                  45

Lys Asn Ile Glu Asp Val Ile Ala Gln Gly Ile Gly Lys Leu Ala Ser
 50                  55                  60

Val Pro Ala Gly Gly Ala Val Ala Val Ser Ala Ala Pro Gly Ser Ala
 65                  70                  75                  80

Ala Pro Ala Ala Gly Ser Ala Pro Ala Ala Glu Glu Lys Lys Asp
                 85                  90                  95

Glu Lys Lys Glu Glu Ser Glu Glu Ser Asp Asp Asp Met Gly Phe Gly
                100                 105                 110

Leu Phe Asp
        115

<210> SEQ ID NO 58
<211> LENGTH: 614
<212> TYPE: PRT
<213> ORGANISM: Homo sapiens

<400> SEQUENCE: 58

Cys Met Gln Val Gly Cys Asn Lys Val Tyr Thr Ser Thr Ser Asp Val
 1               5                  10                  15

Met Thr His Glu Asn Phe His Lys Lys Asn Thr Gln Leu Ile Asn Asp
                20                  25                  30

Gly Phe Gln Arg Phe Arg Ala Thr Glu Asp Cys Gly Thr Ala Asp Cys
                35                  40                  45

Gln Phe Tyr Gly Gln Lys Thr Thr His Phe His Cys Arg Arg Pro Gly
 50                  55                  60

Cys Thr Phe Thr Phe Lys Asn Lys Cys Asp Ile Glu Lys His Lys Ser
 65                  70                  75                  80

Tyr His Ile Lys Asp Asp Ala Tyr Ala Lys Asp Gly Phe Lys Lys Phe
                85                  90                  95

Tyr Lys Tyr Glu Glu Cys Lys Tyr Glu Gly Cys Val Tyr Ser Lys Ala
                100                 105                 110

Thr Asn His Phe His Cys Ile Arg Ala Gly Cys Gly Phe Thr Phe Thr
                115                 120                 125

Ser Thr Ser Gln Met Thr Ser His Lys Arg Lys His Glu Arg His
130                 135                 140

Ile Arg Ser Ser Gly Ala Leu Gly Leu Pro Pro Ser Leu Leu Gly Ala
145                 150                 155                 160

Lys Asp Thr Glu His Glu Glu Ser Ser Asn Asp Asp Leu Val Asp Phe
                165                 170                 175

Ser Ala Leu Ser Ser Lys Asn Ser Ser Leu Ser Ala Ser Pro Thr Ser
                180                 185                 190

Gln Gln Ser Ser Ala Ser Leu Ala Ala Thr Ala Thr Glu Ala
                195                 200                 205

Gly Pro Ser Ala Thr Lys Pro Pro Asn Ser Lys Ile Ser Gly Leu Leu
210                 215                 220

Pro Gln Gly Leu Pro Gly Ser Ile Pro Leu Ala Leu Ala Leu Ser Asn
225                 230                 235                 240

Ser Gly Leu Pro Thr Pro Thr Pro Tyr Phe Pro Ile Leu Ala Gly Arg
                245                 250                 255

Gly Ser Thr Ser Leu Pro Val Gly Thr Pro Ser Leu Leu Gly Ala Val
                260                 265                 270
```

Ser Ser Gly Ser Ala Ala Ser Ala Thr Pro Asp Thr Pro Thr Leu Val
            275                 280                 285

Ala Ser Gly Ala Gly Asp Ser Ala Pro Val Ala Ala Ser Val Pro
        290                 295                 300

Ala Pro Pro Ala Ser Ile Met Glu Arg Ile Ser Ala Ser Lys Gly Leu
305                 310                 315                 320

Ile Ser Pro Met Met Ala Arg Leu Ala Ala Ala Leu Lys Pro Ser
                325                 330                 335

Ala Thr Phe Asp Pro Gly Ser Gly Gln Val Thr Pro Ala Arg Phe
            340                 345                 350

Pro Pro Ala Gln Val Lys Pro Glu Pro Gly Glu Ser Thr Gly Ala Pro
            355                 360                 365

Gly Pro His Glu Ala Ser Gln Asp Arg Ser Leu Asp Leu Thr Val Lys
    370                 375                 380

Glu Pro Ser Asn Glu Ser Asn Gly His Ala Val Pro Ala Asn Ser Ser
385                 390                 395                 400

Leu Leu Ser Ser Leu Met Asn Lys Met Ser Gln Gly Asn Pro Gly Leu
                405                 410                 415

Gly Ser Leu Leu Asn Ile Lys Ala Glu Ala Glu Gly Ser Pro Ala Ala
            420                 425                 430

Glu Pro Ser Pro Phe Leu Gly Lys Ala Val Lys Ala Leu Val Gln Glu
            435                 440                 445

Lys Leu Ala Glu Pro Trp Lys Val Tyr Leu Arg Arg Phe Gly Thr Lys
450                 455                 460

Asp Phe Cys Asp Gly Gln Cys Asp Phe Leu His Lys Ala His Phe His
465                 470                 475                 480

Cys Val Val Glu Glu Cys Gly Ala Leu Phe Ser Thr Leu Asp Gly Ala
                485                 490                 495

Ile Lys His Ala Asn Phe His Phe Arg Thr Glu Gly Gly Ala Ala Lys
            500                 505                 510

Gly Asn Thr Glu Ala Ala Phe Pro Ala Ser Ala Ala Glu Thr Lys Pro
            515                 520                 525

Pro Met Ala Pro Ser Ser Pro Val Pro Pro Val Thr Thr Ala Thr
            530                 535                 540

Val Ser Ser Leu Glu Gly Pro Ala Pro Ser Pro Ala Ser Val Pro Ser
545                 550                 555                 560

Thr Pro Thr Leu Leu Ala Trp Lys Gln Leu Ala Ser Thr Ile Pro Gln
                565                 570                 575

Met Pro Gln Ile Pro Ala Ser Val Pro His Leu Pro Ala Ser Pro Leu
            580                 585                 590

Ala Thr Thr Ser Leu Glu Asn Ala Lys Pro Gln Val Lys Pro Gly Phe
            595                 600                 605

Leu Gln Phe Gln Glu Lys
    610

<210> SEQ ID NO 59
<211> LENGTH: 437
<212> TYPE: PRT
<213> ORGANISM: Homo sapiens

<400> SEQUENCE: 59

Met Thr Gln Phe Leu Pro Pro Asn Leu Leu Ala Leu Phe Ala Pro Arg
1               5                   10                  15

Asp Pro Ile Pro Tyr Leu Pro Pro Leu Glu Lys Leu Pro His Glu Lys
            20                  25                  30

-continued

```
His His Asn Gln Pro Tyr Cys Gly Ile Ala Pro Tyr Ile Arg Glu Phe
         35                  40                  45

Glu Asp Pro Arg Asp Ala Pro Pro Thr Arg Ala Glu Thr Arg Glu
 50                  55                  60

Glu Arg Met Glu Arg Lys Arg Glu Lys Ile Glu Arg Arg Gln Gln
 65                  70                  75                  80

Glu Val Glu Thr Glu Leu Lys Met Trp Asp Pro His Asn Asp Pro Asn
                 85                  90                  95

Ala Gln Gly Asp Ala Phe Lys Thr Leu Phe Val Ala Arg Val Asn Tyr
                100                 105                 110

Asp Thr Thr Glu Ser Lys Leu Arg Arg Glu Phe Glu Val Tyr Gly Pro
                115                 120                 125

Ile Lys Arg Ile His Met Val Tyr Ser Lys Arg Ser Gly Lys Pro Arg
130                 135                 140

Gly Tyr Ala Phe Ile Glu Tyr Glu His Glu Arg Asp Met His Ser Ala
145                 150                 155                 160

Tyr Lys His Ala Asp Gly Lys Lys Ile Asp Gly Arg Arg Val Leu Val
                165                 170                 175

Asp Val Glu Arg Gly Arg Thr Val Lys Gly Trp Arg Pro Arg Arg Leu
                180                 185                 190

Gly Gly Gly Leu Gly Gly Thr Arg Arg Gly Ala Asp Val Asn Ile
            195                 200                 205

Arg His Ser Gly Arg Asp Asp Thr Ser Arg Tyr Asp Glu Arg Pro Gly
    210                 215                 220

Pro Ser Pro Leu Pro His Arg Asp Arg Asp Arg Glu Arg Glu
225                 230                 235                 240

Arg Arg Glu Arg Ser Arg Glu Arg Asp Lys Glu Arg Glu Arg Arg Arg
                245                 250                 255

Ser Arg Ser Arg Asp Arg Arg Arg Ser Arg Ser Arg Asp Lys Glu
                260                 265                 270

Glu Arg Arg Arg Ser Arg Glu Arg Ser Lys Asp Lys Asp Arg Asp Arg
                275                 280                 285

Lys Arg Arg Ser Ser Arg Ser Arg Glu Arg Ala Arg Arg Glu Arg Glu
290                 295                 300

Arg Lys Glu Glu Leu Arg Gly Gly Gly Asp Met Ala Glu Pro Ser
305                 310                 315                 320

Glu Ala Gly Asp Ala Pro Pro Asp Asp Gly Pro Gly Glu Leu Gly
                325                 330                 335

Pro Asp Gly Pro Asp Gly Pro Glu Glu Lys Gly Arg Asp Arg Asp Arg
                340                 345                 350

Glu Arg Arg Arg Ser His Arg Ser Glu Arg Glu Arg Arg Asp Arg
                355                 360                 365

Asp Arg Asp Arg Asp Arg Asp Arg Glu His Lys Arg Gly Glu Arg Gly
                370                 375                 380

Ser Glu Arg Gly Arg Asp Glu Ala Arg Gly Gly Gly Gly Gln Asp
385                 390                 395                 400

Asn Gly Leu Glu Gly Leu Gly Asn Asp Ser Arg Asp Met Tyr Met Glu
                405                 410                 415

Ser Glu Gly Gly Asp Gly Tyr Leu Ala Pro Glu Asn Gly Tyr Leu Met
                420                 425                 430

Glu Ala Ala Pro Glu
            435
```

<210> SEQ ID NO 60
<211> LENGTH: 159
<212> TYPE: PRT
<213> ORGANISM: Homo sapiens

<400> SEQUENCE: 60

Met Pro Lys Phe Tyr Cys Asp Tyr Cys Asp Thr Tyr Leu Thr His Asp
1               5                   10                  15

Ser Pro Ser Val Arg Lys Thr His Cys Ser Gly Arg Lys His Lys Glu
            20                  25                  30

Asn Val Lys Asp Tyr Tyr Gln Lys Trp Met Glu Glu Gln Ala Gln Ser
        35                  40                  45

Leu Ile Asp Lys Thr Thr Ala Ala Phe Gln Gln Gly Lys Ile Pro Pro
    50                  55                  60

Thr Pro Phe Ser Ala Pro Pro Ala Gly Ala Met Ile Pro Pro Pro Pro
65                  70                  75                  80

Pro Ser Leu Pro Gly Pro Pro Arg Pro Gly Met Met Pro Ala Pro His
                85                  90                  95

Met Gly Gly Pro Pro Met Met Pro Met Met Gly Pro Pro Pro Pro Gly
            100                 105                 110

Met Met Pro Val Gly Pro Ala Pro Gly Met Arg Pro Pro Met Gly Gly
        115                 120                 125

His Met Pro Met Met Pro Gly Pro Pro Met Met Arg Pro Pro Ala Arg
    130                 135                 140

Pro Met Met Val Pro Thr Arg Pro Gly Met Thr Arg Pro Asp Arg
145                 150                 155

<210> SEQ ID NO 61
<211> LENGTH: 181
<212> TYPE: PRT
<213> ORGANISM: Homo sapiens

<400> SEQUENCE: 61

Met Glu Ser Lys Glu Pro Gln Leu Lys Gly Ile Val Thr Arg Leu Phe
1               5                   10                  15

Ser Gln Gln Gly Tyr Phe Leu Gln Met His Pro Asp Gly Thr Ile Asp
            20                  25                  30

Gly Thr Lys Asp Glu Asn Ser Asp Tyr Thr Leu Phe Asn Leu Ile Pro
        35                  40                  45

Val Gly Leu Arg Val Val Ala Ile Gln Gly Val Lys Ala Ser Leu Tyr
    50                  55                  60

Val Ala Met Asn Gly Glu Gly Tyr Leu Tyr Ser Ser Asp Val Phe Thr
65                  70                  75                  80

Pro Glu Cys Lys Phe Lys Glu Ser Val Phe Glu Asn Tyr Tyr Val Ile
                85                  90                  95

Tyr Ser Ser Thr Leu Tyr Arg Gln Gln Glu Ser Gly Arg Ala Trp Phe
            100                 105                 110

Leu Gly Leu Asn Lys Glu Gly Gln Ile Met Lys Gly Asn Arg Val Lys
        115                 120                 125

Lys Thr Lys Pro Ser Ser His Phe Val Pro Lys Pro Ile Glu Val Cys
    130                 135                 140

Met Tyr Arg Glu Pro Ser Leu His Glu Ile Gly Glu Lys Gln Gly Arg
145                 150                 155                 160

Ser Arg Lys Ser Ser Gly Thr Pro Thr Met Asn Gly Gly Lys Val Val
                165                 170                 175

Asn Gln Asp Ser Thr
            180

<210> SEQ ID NO 62
<211> LENGTH: 78
<212> TYPE: PRT
<213> ORGANISM: Homo sapiens

<400> SEQUENCE: 62

Met Ser Glu Val Leu Pro Tyr Gly Asp Glu Lys Leu Ser Pro Tyr Gly
1               5                   10                  15

Asp Gly Gly Asp Val Gly Gln Ile Phe Ser Cys Arg Leu Gln Asp Thr
            20                  25                  30

Asn Asn Phe Phe Gly Ala Gly Gln Asn Lys Arg Pro Pro Lys Leu Gly
        35                  40                  45

Gln Ile Gly Arg Ser Lys Arg Val Val Ile Glu Asp Asp Arg Ile Asp
    50                  55                  60

Asp Val Leu Lys Asn Met Thr Asp Lys Ala Pro Pro Gly Val
65                  70                  75

<210> SEQ ID NO 63
<211> LENGTH: 471
<212> TYPE: PRT
<213> ORGANISM: Homo sapiens

<400> SEQUENCE: 63

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Ser Met Ser Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Leu Arg Gln Leu Thr Ser Tyr Trp Tyr Phe
        115                 120                 125

Asp Leu Trp Gly Arg Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

```
Pro Lys Ser Cys Asp Lys Thr His Thr Cys Pro Pro Cys Pro Ala Pro
                 245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 64
<211> LENGTH: 326
<212> TYPE: PRT
<213> ORGANISM: Homo sapiens

<400> SEQUENCE: 64

Met Pro Pro Met Pro Val Ala Ser Val Ala Pro Ser Ala Ser Met Pro
1               5                   10                  15

Gly Ser His Leu Pro Pro Leu Tyr Leu Asp Gly His Val Phe Ala Ser
            20                  25                  30

Gln Pro Arg Leu Val Pro Gln Thr Ile Pro Gln Gln Gln Ser Tyr Gln
        35                  40                  45

Gln Ala Ala Ala Gln Gln Ile Pro Ile Ser Leu His Thr Ser Leu
    50                  55                  60

Gln Ala Gln Ala Gln Leu Gly Leu Arg Gly Gly Leu Pro Val Ser Gln
65                  70                  75                  80

Ser Gln Glu Ile Phe Ser Ser Leu Gln Pro Phe Arg Ser Gln Val Tyr
                85                  90                  95

Met His Pro Ser Leu Ser Pro Ser Thr Met Ile Leu Ser Gly Gly
            100                 105                 110

Thr Ala Leu Lys Pro Pro Tyr Ser Ala Phe Pro Gly Met Gln Pro Leu
        115                 120                 125

Glu Met Val Lys Pro Gln Ser Gly Ser Pro Tyr Gln Pro Met Ser Gly
    130                 135                 140
```

```
Asn Gln Ala Leu Val Tyr Glu Gly Gln Leu Ser Gln Ala Ala Gly Leu
145                 150                 155                 160

Gly Ala Ser Gln Met Leu Asp Ser Gln Leu Pro Gln Leu Thr Met Pro
                165                 170                 175

Leu Pro Arg Tyr Gly Ser Gly Gln Gln Pro Leu Ile Leu Pro Gln Ser
            180                 185                 190

Ile Gln Leu Pro Pro Gly Gln Ser Leu Ser Val Gly Ala Pro Arg Arg
        195                 200                 205

Ile Pro Pro Pro Gly Ser Gln Pro Pro Val Leu Asn Thr Ser Arg Glu
    210                 215                 220

Pro Ser Gln Met Glu Met Lys Gly Phe His Phe Ala Asp Ser Lys Gln
225                 230                 235                 240

Asn Val Pro Ser Gly Gly Pro Val Pro Ser Pro Gln Thr Tyr Arg Pro
                245                 250                 255

Ser Ser Ala Ser Pro Ser Gly Lys Pro Ser Gly Ser Ala Val Asn Met
            260                 265                 270

Gly Ser Val Gln Gly His Tyr Val Gln Gln Ala Lys Gln Arg Val Asp
        275                 280                 285

Glu Lys Pro Ser Leu Gly Ala Val Lys Leu Gln Glu Ala Pro Ser Ala
    290                 295                 300

Ala Ser Gln Met Lys Arg Thr Gly Ala Ile Lys Pro Arg Ala Val Lys
305                 310                 315                 320

Val Glu Glu Ser Lys Ala
                325

<210> SEQ ID NO 65
<211> LENGTH: 536
<212> TYPE: PRT
<213> ORGANISM: Homo sapiens

<400> SEQUENCE: 65

Met Thr Lys Lys Thr Arg Asp Leu Arg Arg Gln Leu Arg Lys Ala Val
1               5                   10                  15

Met Asp His Val Ser Asp Ser Phe Leu Glu Thr Asn Val Pro Leu Leu
                20                  25                  30

Val Leu Ile Glu Ala Ala Lys Asn Gly Asn Glu Lys Glu Val Lys Glu
            35                  40                  45

Tyr Ala Gln Val Phe Arg Glu His Ala Asn Lys Leu Ile Glu Val Ala
        50                  55                  60

Asn Leu Ala Cys Ser Ile Ser Asn Asn Glu Glu Gly Val Lys Leu Val
65                  70                  75                  80

Arg Met Ser Ala Ser Gln Leu Glu Ala Leu Cys Pro Gln Val Ile Asn
                85                  90                  95

Ala Ala Leu Ala Leu Ala Ala Lys Pro Gln Ser Lys Leu Ala Gln Glu
            100                 105                 110

Asn Met Asp Leu Phe Lys Glu Gln Trp Glu Lys Gln Val Arg Val Leu
        115                 120                 125

Thr Asp Ala Val Asp Asp Ile Thr Ser Ile Asp Asp Phe Leu Ala Val
    130                 135                 140

Ser Glu Asn His Ile Leu Glu Asp Val Asn Lys Cys Val Ile Ala Leu
145                 150                 155                 160

Gln Glu Lys Asp Val Asp Gly Leu Asp Arg Thr Ala Gly Ala Ile Arg
                165                 170                 175

Gly Arg Ala Ala Arg Val Ile His Val Val Thr Ser Glu Met Asp Asn
```

```
              180                 185                 190

Tyr Glu Pro Gly Val Tyr Thr Glu Lys Val Leu Glu Ala Thr Lys Leu
            195                 200                 205

Leu Ser Asn Thr Val Met Pro Arg Phe Thr Glu Gln Val Glu Ala Ala
        210                 215                 220

Val Glu Ala Leu Ser Ser Asp Pro Ala Gln Pro Met Asp Glu Asn Glu
225                 230                 235                 240

Phe Ile Asp Ala Ser Arg Leu Val Tyr Asp Gly Ile Arg Asp Ile Arg
                245                 250                 255

Lys Ala Val Leu Met Ile Arg Thr Pro Glu Glu Leu Asp Asp Ser Asp
            260                 265                 270

Phe Glu Thr Glu Asp Phe Asp Val Arg Ser Arg Thr Ser Val Gln Thr
        275                 280                 285

Glu Asp Asp Gln Leu Ile Ala Gly Gln Ser Ala Arg Ala Ile Met Ala
290                 295                 300

Gln Leu Pro Gln Glu Gln Lys Ala Lys Ile Ala Glu Gln Val Ala Ser
305                 310                 315                 320

Phe Gln Glu Glu Lys Ser Lys Leu Asp Ala Glu Val Ser Lys Trp Asp
                325                 330                 335

Asp Ser Gly Asn Asp Ile Ile Val Leu Ala Lys Gln Met Cys Met Ile
            340                 345                 350

Met Met Glu Met Thr Asp Phe Thr Arg Gly Lys Gly Pro Leu Lys Asn
        355                 360                 365

Thr Ser Asp Val Ile Ser Ala Ala Lys Lys Ile Ala Glu Ala Gly Ser
370                 375                 380

Arg Met Asp Lys Leu Gly Arg Thr Ile Ala Asp His Cys Pro Asp Ser
385                 390                 395                 400

Ala Cys Lys Gln Asp Leu Leu Ala Tyr Leu Gln Arg Ile Ala Leu Tyr
                405                 410                 415

Cys His Gln Leu Asn Ile Cys Ser Lys Val Lys Ala Glu Val Gln Asn
            420                 425                 430

Leu Gly Gly Glu Leu Val Val Ser Gly Val Asp Ser Ala Met Ser Leu
        435                 440                 445

Ile Gln Ala Ala Lys Asn Leu Met Asn Ala Val Val Gln Thr Val Lys
450                 455                 460

Ala Ser Tyr Val Ala Ser Thr Lys Tyr Gln Lys Ser Gln Gly Met Ala
465                 470                 475                 480

Ser Leu Asn Leu Pro Ala Val Ser Trp Lys Met Lys Ala Pro Glu Lys
                485                 490                 495

Lys Pro Leu Val Lys Arg Glu Lys Gln Asp Glu Thr Gln Thr Lys Ile
            500                 505                 510

Lys Arg Ala Ser Gln Lys Lys His Val Asn Pro Val Gln Ala Leu Ser
        515                 520                 525

Glu Phe Lys Ala Met Asp Ser Ile
530                 535

<210> SEQ ID NO 66
<211> LENGTH: 268
<212> TYPE: PRT
<213> ORGANISM: Homo sapiens

<400> SEQUENCE: 66

Met Ala Val Asn Val Tyr Ser Thr Ser Val Thr Ser Asp Asn Leu Ser
1               5                   10                  15
```

Arg His Asp Met Leu Ala Trp Ile Asn Glu Ser Leu Gln Leu Asn Leu
            20                  25                  30

Thr Lys Ile Glu Gln Leu Cys Ser Gly Ala Ala Tyr Cys Gln Phe Met
        35                  40                  45

Asp Met Leu Phe Pro Gly Ser Ile Ala Leu Lys Lys Val Lys Phe Gln
    50                  55                  60

Ala Lys Leu Glu His Glu Tyr Ile Gln Asn Phe Lys Ile Leu Gln Ala
65                  70                  75                  80

Gly Phe Lys Arg Met Gly Val Asp Lys Ile Pro Val Asp Lys Leu
                85                  90                  95

Val Lys Gly Lys Phe Gln Asp Asn Phe Glu Phe Val Gln Trp Phe Lys
            100                 105                 110

Lys Phe Phe Asp Ala Asn Tyr Asp Gly Lys Asp Tyr Asp Pro Val Ala
        115                 120                 125

Ala Arg Gln Gly Gln Glu Thr Ala Val Ala Pro Ser Leu Val Ala Pro
    130                 135                 140

Ala Leu Asn Lys Pro Lys Lys Pro Leu Thr Ser Ser Ala Ala Pro
145                 150                 155                 160

Gln Arg Pro Ile Ser Thr Gln Arg Thr Ala Ala Pro Lys Ala Gly
            165                 170                 175

Pro Gly Val Val Arg Lys Asn Pro Gly Val Gly Asn Gly Asp Asp Glu
        180                 185                 190

Ala Ala Glu Leu Met Gln Gln Val Asn Val Leu Lys Leu Thr Val Glu
    195                 200                 205

Asp Leu Glu Lys Glu Arg Asp Phe Tyr Phe Gly Lys Leu Arg Asn Ile
210                 215                 220

Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
            245                 250                 255

Asp Glu Gly Gly Pro Gln Glu Glu Gln Glu Tyr
            260                 265

<210> SEQ ID NO 67
<211> LENGTH: 254
<212> TYPE: PRT
<213> ORGANISM: Homo sapiens

<400> SEQUENCE: 67

Met Asp Gly Gly Asp Gly Asn Leu Ile Ile Lys Lys Arg Phe Val
1               5                   10                  15

Ser Glu Ala Glu Leu Asp Glu Arg Arg Lys Arg Arg Gln Glu Glu Trp
            20                  25                  30

Glu Lys Val Arg Lys Pro Glu Asp Pro Glu Glu Cys Pro Glu Glu Val
        35                  40                  45

Tyr Asp Pro Arg Ser Leu Tyr Glu Arg Leu Gln Glu Gln Lys Asp Arg
    50                  55                  60

Lys Gln Gln Glu Tyr Glu Gln Phe Lys Phe Lys Asn Met Val Arg
65                  70                  75                  80

Gly Leu Asp Glu Asp Glu Thr Asn Phe Leu Asp Glu Val Ser Arg Gln
            85                  90                  95

Gln Glu Leu Ile Glu Lys Gln Arg Arg Glu Glu Glu Leu Lys Glu Leu
        100                 105                 110

Lys Glu Tyr Arg Asn Asn Leu Lys Lys Val Gly Ile Ser Gln Glu Asn
    115                 120                 125

```
Lys Lys Glu Val Glu Lys Leu Thr Val Lys Pro Ile Glu Thr Lys
130                 135                 140

Asn Lys Phe Ser Gln Ala Lys Leu Leu Ala Gly Ala Val Lys His Lys
145                 150                 155                 160

Ser Ser Glu Ser Gly Asn Ser Val Lys Arg Leu Lys Pro Asp Pro Glu
            165                 170                 175

Pro Asp Asp Lys Asn Gln Glu Pro Ser Ser Cys Lys Ser Leu Gly Asn
            180                 185                 190

Thr Ser Leu Ser Gly Pro Ser Ile His Cys Pro Ser Ala Ala Val Cys
        195                 200                 205

Ile Gly Ile Leu Pro Gly Leu Gly Ala Tyr Ser Gly Ser Ser Asp Ser
210                 215                 220

Glu Ser Ser Ser Asp Ser Glu Gly Thr Ile Asn Ala Thr Gly Lys Ile
225                 230                 235                 240

Val Ser Ser Ile Phe Arg Thr Asn Thr Phe Leu Glu Ala Pro
                245                 250

<210> SEQ ID NO 68
<211> LENGTH: 466
<212> TYPE: PRT
<213> ORGANISM: Homo sapiens

<400> SEQUENCE: 68

Met Gly Trp Ile Thr Glu Asp Leu Ile Arg Arg Asn Ala Glu His Asn
1               5                   10                  15

Asp Cys Val Ile Phe Ser Leu Glu Glu Leu Ser Leu His Gln Gln Glu
            20                  25                  30

Ile Glu Arg Leu Glu His Ile Asp Lys Trp Cys Arg Asp Leu Lys Ile
        35                  40                  45

Leu Tyr Leu Gln Asn Asn Leu Ile Gly Lys Ile Glu Asn Val Ser Lys
50                  55                  60

Leu Lys Lys Leu Glu Tyr Leu Asn Leu Ala Leu Asn Asn Ile Glu Lys
65                  70                  75                  80

Ile Glu Asn Leu Glu Gly Cys Glu Glu Leu Ala Lys Leu Asp Leu Thr
                85                  90                  95

Val Asn Phe Ile Gly Glu Leu Ser Ser Ile Lys Asn Leu Gln His Asn
            100                 105                 110

Ile His Leu Lys Glu Leu Phe Leu Met Gly Asn Pro Cys Ala Ser Phe
        115                 120                 125

Asp His Tyr Arg Glu Phe Val Val Ala Thr Leu Pro Gln Leu Lys Trp
130                 135                 140

Leu Asp Gly Lys Glu Ile Glu Pro Ser Glu Arg Ile Lys Ala Leu Gln
145                 150                 155                 160

Asp Tyr Ser Val Ile Glu Pro Gln Ile Arg Glu Gln Glu Lys Asp His
                165                 170                 175

Cys Leu Lys Arg Ala Lys Leu Lys Glu Glu Ala Gln Arg Lys His Gln
            180                 185                 190

Glu Glu Asp Lys Asn Glu Asp Lys Arg Ser Asn Ala Gly Phe Asp Gly
        195                 200                 205

Arg Trp Tyr Thr Asp Ile Asn Ala Thr Leu Ser Ser Leu Glu Ser Lys
210                 215                 220

Asp His Leu Gln Ala Pro Asp Thr Glu Glu His Asn Thr Lys Lys Leu
225                 230                 235                 240

Asp Asn Ser Glu Asp Asp Leu Glu Phe Trp Asn Lys Pro Cys Leu Phe
```

```
                        245                 250                 255
Thr Pro Glu Ser Arg Leu Glu Thr Leu Arg His Met Glu Lys Gln Arg
                260                 265                 270

Lys Lys Gln Glu Lys Leu Ser Glu Lys Lys Lys Val Lys Pro Pro
            275                 280                 285

Arg Thr Leu Ile Thr Glu Asp Gly Lys Ala Leu Asn Val Asn Glu Pro
        290                 295                 300

Lys Ile Asp Phe Ser Leu Lys Asp Asn Glu Lys Gln Ile Ile Leu Asp
305                 310                 315                 320

Leu Ala Val Tyr Arg Tyr Met Asp Thr Ser Leu Ile Asp Val Asp Val
                325                 330                 335

Gln Pro Thr Tyr Val Arg Val Met Ile Lys Gly Lys Pro Phe Gln Leu
            340                 345                 350

Val Leu Pro Ala Glu Val Lys Pro Asp Ser Ser Ala Lys Arg Ser
        355                 360                 365

Gln Thr Thr Gly His Leu Val Ile Cys Met Pro Lys Val Gly Glu Val
        370                 375                 380

Ile Thr Gly Gly Gln Arg Ala Phe Lys Ser Met Lys Thr Thr Ser Asp
385                 390                 395                 400

Arg Ser Arg Glu Gln Thr Asn Thr Arg Ser Lys His Met Glu Lys Leu
                405                 410                 415

Glu Val Asp Pro Ser Lys His Ser Phe Pro Asp Val Thr Asn Ile Val
            420                 425                 430

Gln Glu Lys Lys His Thr Pro Arg Arg Pro Glu Pro Lys Ile Ile
        435                 440                 445

Pro Ser Glu Glu Asp Pro Thr Phe Glu Asp Asn Pro Glu Val Pro Pro
    450                 455                 460

Leu Ile
465

<210> SEQ ID NO 69
<211> LENGTH: 545
<212> TYPE: PRT
<213> ORGANISM: Homo sapiens

<400> SEQUENCE: 69

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140
```

```
Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
            180                 185                 190

Arg Pro Glu His Thr Lys Ser Val Tyr Thr Arg Ser Val Ile Glu Pro
                195                 200                 205

Leu Pro Val Thr Pro Thr Arg Asp Val Ala Thr Ser Pro Ile Ser Pro
            210                 215                 220

Thr Glu Asn Asn Thr Thr Pro Pro Asp Ala Leu Thr Arg Asn Thr Glu
225                 230                 235                 240

Lys Gln Lys Lys Pro Lys Met Ser Asp Glu Ile Leu Glu Lys
                245                 250                 255

Leu Arg Ser Ile Val Ser Val Gly Asp Pro Lys Lys Tyr Thr Arg
                260                 265                 270

Phe Glu Lys Ile Gly Gln Gly Ala Ser Gly Thr Val Tyr Thr Ala Met
                275                 280                 285

Asp Val Ala Thr Gly Gln Glu Val Ala Ile Lys Gln Met Asn Leu Gln
290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
            355                 360                 365

Val Cys Arg Glu Cys Leu Gln Ala Leu Glu Phe Leu His Ser Asn Gln
            370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
                420                 425                 430

Pro Glu Val Val Thr Arg Lys Ala Tyr Gly Pro Lys Val Asp Ile Trp
            435                 440                 445

Ser Leu Gly Ile Met Ala Ile Glu Met Ile Gly Glu Pro Pro Tyr
            450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
                485                 490                 495

Phe Leu Asn Arg Cys Leu Glu Met Asp Val Glu Lys Arg Gly Ser Ala
                500                 505                 510

Lys Glu Leu Leu Gln His Gln Phe Leu Lys Ile Ala Lys Pro Leu Ser
                515                 520                 525

Ser Leu Thr Pro Leu Ile Ala Ala Ala Lys Glu Ala Thr Lys Asn Asn
                530                 535                 540

His
545
```

<210> SEQ ID NO 70
<211> LENGTH: 145
<212> TYPE: PRT
<213> ORGANISM: Homo sapiens

<400> SEQUENCE: 70

```
Met Trp Ser Phe Leu Pro Gly Ala Glu Ser Val Ser Met Gly Pro Val
1               5                   10                  15

Pro Gly Val Ser Ser Leu Gly Ala Cys Trp Thr His Asp Gln Asp Ser
            20                  25                  30

Gly Arg Ala Glu Asp Arg Pro Gln Ala Pro Arg Ile Thr Gln Tyr Thr
        35                  40                  45

Trp Val Leu Ser Phe Leu Phe Thr Glu Lys Pro Gln Thr Arg Ser Thr
    50                  55                  60

Ser Pro Ile Ser His Gln Gly Gln Pro Gln Thr Thr Arg Ala Leu Ser
65                  70                  75                  80

Leu Arg Gln Pro Gln His Pro Ser Ala Pro Ala Ser Gly Arg Pro Arg
                85                  90                  95

Pro Pro His Ser Ser Gly Pro Asp Leu Ala Glu Ala Ala Pro Val Val
            100                 105                 110

Asp Gln Ala Ser Gln Ala Ala Gly Arg Ala Ser Ser Gly Leu Gly Leu
        115                 120                 125

Trp Glu Gln Ala Ser Val Ser Gln Gly Phe Arg Asn Ala Ala Phe Glu
    130                 135                 140

Ala
145
```

<210> SEQ ID NO 71
<211> LENGTH: 426
<212> TYPE: PRT
<213> ORGANISM: Homo sapiens

<400> SEQUENCE: 71

```
Met Ala His Leu Arg Gly Phe Ala Asn Gln His Ser Arg Val Asp Pro
1               5                   10                  15

Glu Glu Leu Phe Thr Lys Leu Asp Arg Ile Gly Lys Gly Ser Phe Gly
            20                  25                  30

Glu Val Tyr Lys Gly Ile Asp Asn His Thr Lys Glu Val Val Ala Ile
        35                  40                  45

Lys Ile Ile Asp Leu Glu Glu Ala Glu Asp Glu Ile Glu Asp Ile Gln
    50                  55                  60

Gln Glu Ile Thr Val Leu Ser Gln Cys Asp Ser Pro Tyr Ile Thr Arg
65                  70                  75                  80

Tyr Phe Gly Ser Tyr Leu Lys Ser Thr Lys Leu Trp Ile Ile Met Glu
                85                  90                  95

Tyr Leu Gly Gly Gly Ser Ala Leu Asp Leu Leu Lys Pro Gly Pro Leu
            100                 105                 110

Glu Glu Thr Tyr Ile Ala Thr Ile Leu Arg Glu Ile Leu Lys Gly Leu
        115                 120                 125

Asp Tyr Leu His Ser Glu Arg Lys Ile His Arg Asp Ile Lys Ala Ala
    130                 135                 140

Asn Val Leu Leu Ser Glu Gln Gly Asp Val Lys Leu Ala Asp Phe Gly
145                 150                 155                 160

Val Ala Gly Gln Leu Thr Asp Thr Gln Ile Lys Arg Asn Thr Phe Val
                165                 170                 175

Gly Thr Pro Phe Trp Met Ala Pro Glu Val Ile Lys Gln Ser Ala Tyr
```

```
                180                 185                 190
Asp Phe Lys Ala Asp Ile Trp Ser Leu Gly Ile Thr Ala Ile Glu Leu
            195                 200                 205

Ala Lys Gly Glu Pro Pro Asn Ser Asp Leu His Pro Met Arg Val Leu
        210                 215                 220

Phe Leu Ile Pro Lys Asn Ser Pro Pro Thr Leu Glu Gly Gln His Ser
225                 230                 235                 240

Lys Pro Phe Lys Glu Phe Val Glu Ala Cys Leu Asn Lys Asp Pro Arg
                245                 250                 255

Phe Arg Pro Thr Ala Lys Glu Leu Leu Lys His Lys Phe Ile Thr Arg
            260                 265                 270

Tyr Thr Lys Lys Thr Ser Phe Leu Thr Glu Leu Ile Asp Arg Tyr Lys
        275                 280                 285

Arg Trp Lys Ser Glu Gly His Gly Glu Glu Ser Ser Glu Asp Ser
    290                 295                 300

Asp Ile Asp Gly Glu Ala Glu Asp Gly Glu Gln Gly Pro Ile Trp Thr
305                 310                 315                 320

Phe Pro Pro Thr Ile Arg Pro Ser Pro His Ser Lys Leu His Lys Gly
                325                 330                 335

Thr Ala Leu His Ser Ser Gln Lys Pro Ala Glu Pro Val Lys Arg Gln
            340                 345                 350

Pro Arg Ser Gln Cys Leu Ser Thr Leu Val Arg Pro Val Phe Gly Glu
        355                 360                 365

Leu Lys Glu Lys His Lys Gln Ser Gly Gly Ser Val Gly Ala Leu Glu
    370                 375                 380

Glu Leu Glu Asn Ala Phe Ser Leu Ala Glu Glu Ser Cys Pro Gly Ile
385                 390                 395                 400

Ser Asp Lys Leu Met Val His Leu Val Glu Arg Val Gln Arg Phe Ser
                405                 410                 415

His Asn Arg Asn His Leu Thr Ser Thr Arg
            420                 425

<210> SEQ ID NO 72
<211> LENGTH: 194
<212> TYPE: PRT
<213> ORGANISM: Homo sapiens

<400> SEQUENCE: 72

Met Ala Lys Gln Lys Arg Lys Val Pro Glu Val Thr Glu Lys Lys Asn
1               5                   10                  15

Lys Lys Leu Lys Lys Ala Ser Ala Glu Gly Pro Leu Leu Gly Pro Glu
            20                  25                  30

Ala Ala Pro Ser Gly Glu Gly Ala Gly Ser Lys Gly Glu Ala Val Leu
        35                  40                  45

Arg Pro Gly Leu Asp Ala Glu Pro Glu Leu Ser Pro Glu Glu Gln Arg
    50                  55                  60

Val Leu Glu Arg Lys Leu Lys Lys Arg Lys Glu Glu Arg Gln
65                  70                  75                  80

Arg Leu Arg Glu Ala Gly Leu Val Ala Gln His Pro Pro Ala Arg Arg
                85                  90                  95

Ser Gly Ala Glu Leu Ala Leu Asp Tyr Leu Cys Arg Trp Ala Gln Lys
            100                 105                 110

His Lys Asn Trp Arg Phe Gln Lys Thr Arg Gln Thr Trp Leu Leu Leu
        115                 120                 125
```

His Met Tyr Asp Ser Asp Lys Val Pro Asp Glu His Phe Ser Thr Leu
    130                 135                 140

Leu Ala Tyr Leu Glu Gly Leu Gln Gly Arg Ala Arg Glu Leu Thr Val
145                 150                 155                 160

Gln Lys Ala Glu Ala Leu Met Arg Glu Leu Asp Glu Glu Gly Ser Asp
                165                 170                 175

Pro Pro Leu Pro Gly Arg Ala Gln Arg Ile Arg Gln Val Leu Gln Leu
                180                 185                 190

Leu Ser

<210> SEQ ID NO 73
<211> LENGTH: 1146
<212> TYPE: PRT
<213> ORGANISM: Homo sapiens

<400> SEQUENCE: 73

Met Val Leu Gly Thr Val Leu Leu Pro Pro Asn Ser Tyr Gly Arg Asp
1               5                   10                  15

Gln Asp Thr Ser Leu Cys Cys Leu Cys Thr Glu Ala Ser Glu Ser Ala
                20                  25                  30

Leu Pro Asp Leu Thr Glu Ala Leu His Arg Pro Tyr Gly Cys Asp Val
            35                  40                  45

Glu Pro Gln Ala Leu Asn Glu Ala Ile Arg Trp Ser Ser Lys Glu Asn
50                  55                  60

Leu Leu Gly Ala Thr Glu Ser Asp Pro Asn Leu Phe Val Ala Leu Tyr
65                  70                  75                  80

Asp Phe Val Ala Ser Gly Asp Asn Thr Leu Ser Ile Thr Lys Gly Glu
                85                  90                  95

Lys Leu Arg Val Leu Gly Tyr Asn Gln Asn Gly Glu Trp Ser Glu Val
            100                 105                 110

Arg Ser Lys Asn Gly Gln Gly Trp Val Pro Ser Asn Tyr Ile Thr Pro
    115                 120                 125

Val Asn Ser Leu Glu Lys His Ser Trp Tyr His Gly Pro Val Ser Arg
130                 135                 140

Ser Ala Ala Glu Tyr Leu Leu Ser Ser Leu Ile Asn Gly Ser Phe Leu
145                 150                 155                 160

Val Arg Glu Ser Glu Ser Ser Pro Gly Gln Leu Ser Ile Ser Leu Arg
                165                 170                 175

Tyr Glu Gly Arg Val Tyr His Tyr Arg Ile Asn Thr Ala Asp Gly
            180                 185                 190

Lys Val Tyr Val Thr Ala Glu Ser Arg Phe Ser Thr Leu Ala Glu Leu
    195                 200                 205

Val His His His Ser Thr Val Ala Asp Gly Leu Val Thr Thr Leu His
210                 215                 220

Tyr Pro Ala Pro Lys Cys Asn Lys Pro Thr Val Tyr Gly Val Ser Pro
225                 230                 235                 240

Ile His Asp Lys Trp Glu Met Glu Arg Thr Asp Ile Thr Met Lys His
                245                 250                 255

Lys Leu Gly Gly Gly Gln Tyr Gly Glu Val Tyr Val Gly Val Trp Lys
            260                 265                 270

Lys Tyr Ser Leu Thr Val Ala Val Lys Thr Leu Lys Glu Asp Thr Met
    275                 280                 285

Glu Val Glu Glu Phe Leu Lys Glu Ala Ala Val Met Lys Glu Ile Lys
290                 295                 300

```
His Pro Asn Leu Val Gln Leu Leu Gly Val Cys Thr Leu Glu Pro Pro
305                 310                 315                 320

Phe Tyr Ile Val Thr Glu Tyr Met Pro Tyr Gly Asn Leu Leu Asp Tyr
                325                 330                 335

Leu Arg Glu Cys Asn Arg Glu Glu Val Thr Ala Val Val Leu Leu Tyr
                340                 345                 350

Met Ala Thr Gln Ile Ser Ser Ala Met Glu Tyr Leu Glu Lys Lys Asn
                355                 360                 365

Phe Ile His Arg Asp Leu Ala Ala Arg Asn Cys Leu Val Gly Glu Asn
            370                 375                 380

His Val Val Lys Val Ala Asp Phe Gly Leu Ser Arg Leu Met Thr Gly
385                 390                 395                 400

Asp Thr Tyr Thr Ala His Ala Gly Ala Lys Phe Pro Ile Lys Trp Thr
                    405                 410                 415

Ala Pro Glu Ser Leu Ala Tyr Asn Thr Phe Ser Ile Lys Ser Asp Val
                420                 425                 430

Trp Ala Phe Gly Val Leu Leu Trp Glu Ile Ala Thr Tyr Gly Met Ser
                435                 440                 445

Pro Tyr Pro Gly Ile Asp Leu Ser Gln Val Tyr Asp Leu Leu Glu Lys
450                 455                 460

Gly Tyr Arg Met Glu Gln Pro Glu Gly Cys Pro Pro Lys Val Tyr Glu
465                 470                 475                 480

Leu Met Arg Ala Cys Trp Lys Trp Ser Pro Ala Asp Arg Pro Ser Phe
                485                 490                 495

Ala Glu Thr His Gln Ala Phe Glu Thr Met Phe His Asp Ser Ser Ile
                500                 505                 510

Ser Glu Glu Val Ala Glu Glu Leu Gly Arg Ala Ala Ser Ser Ser Ser
                515                 520                 525

Val Val Pro Tyr Leu Pro Arg Leu Pro Ile Leu Pro Ser Lys Thr Arg
                530                 535                 540

Thr Leu Lys Lys Gln Val Glu Asn Lys Glu Asn Ile Glu Gly Ala Gln
545                 550                 555                 560

Asp Ala Thr Glu Asn Ser Ala Ser Ser Leu Ala Pro Gly Phe Ile Arg
                565                 570                 575

Gly Ala Gln Ala Ser Ser Gly Ser Pro Ala Leu Pro Arg Lys Gln Arg
                580                 585                 590

Asp Lys Ser Pro Ser Ser Leu Leu Glu Asp Ala Lys Glu Thr Cys Phe
                595                 600                 605

Thr Arg Asp Arg Lys Gly Gly Phe Phe Ser Ser Phe Met Lys Lys Arg
                610                 615                 620

Asn Ala Pro Thr Pro Lys Arg Ser Ser Ser Phe Arg Glu Met Glu
625                 630                 635                 640

Asn Gln Pro His Lys Lys Tyr Glu Leu Thr Gly Asn Phe Ser Ser Val
                645                 650                 655

Ala Ser Leu Gln His Ala Asp Gly Phe Ser Phe Thr Pro Ala Gln Gln
                660                 665                 670

Glu Ala Asn Leu Val Pro Pro Lys Cys Tyr Gly Gly Ser Phe Ala Gln
                675                 680                 685

Arg Asn Leu Cys Asn Asp Asp Gly Gly Gly Gly Ser Gly Thr
                690                 695                 700

Ala Gly Gly Gly Trp Ser Gly Ile Thr Gly Phe Phe Thr Pro Arg Leu
705                 710                 715                 720

Ile Lys Lys Thr Leu Gly Leu Arg Ala Gly Lys Pro Thr Ala Ser Asp
```

```
                    725                 730                 735
Asp Thr Ser Lys Pro Phe Pro Arg Ser Asn Ser Thr Ser Ser Met Ser
                740                 745                 750
Ser Gly Leu Pro Glu Gln Asp Arg Met Ala Met Thr Leu Pro Arg Asn
            755                 760                 765
Cys Gln Arg Ser Lys Leu Gln Leu Glu Arg Thr Val Ser Thr Ser Ser
        770                 775                 780
Gln Pro Glu Glu Asn Val Asp Arg Ala Asn Asp Met Leu Pro Lys Lys
785                 790                 795                 800
Ser Glu Glu Ser Ala Ala Pro Ser Arg Glu Arg Pro Lys Ala Lys Leu
                805                 810                 815
Leu Pro Arg Gly Ala Thr Ala Leu Pro Leu Arg Thr Pro Ser Gly Asp
                820                 825                 830
Leu Ala Ile Thr Glu Lys Asp Pro Pro Gly Val Gly Val Ala Gly Val
                835                 840                 845
Ala Ala Ala Pro Lys Gly Lys Glu Lys Asn Gly Gly Ala Arg Leu Gly
            850                 855                 860
Met Ala Gly Val Pro Glu Asp Gly Glu Gln Pro Gly Trp Pro Ser Pro
865                 870                 875                 880
Ala Lys Ala Ala Pro Val Leu Pro Thr Thr His Asn His Lys Val Pro
                885                 890                 895
Val Leu Ile Ser Pro Thr Leu Lys His Thr Pro Ala Asp Val Gln Leu
                900                 905                 910
Ile Gly Thr Asp Ser Gln Gly Asn Lys Phe Lys Leu Leu Ser Glu His
            915                 920                 925
Gln Val Thr Ser Ser Gly Asp Lys Asp Arg Pro Arg Arg Val Lys Pro
        930                 935                 940
Lys Cys Ala Pro Pro Pro Pro Val Met Arg Leu Leu Gln His Pro
945                 950                 955                 960
Ser Ile Cys Ser Asp Pro Thr Glu Glu Pro Thr Ala Leu Thr Ala Gly
                965                 970                 975
Gln Ser Thr Ser Glu Thr Gln Glu Gly Gly Lys Lys Ala Ala Leu Gly
            980                 985                 990
Ala Val Pro Ile Ser Gly Lys Ala Gly Arg Pro Val Met Pro Pro Pro
        995                 1000                1005
Gln Val Pro Leu Pro Thr Ser Ser Ile Ser Pro Ala Lys Met Ala Asn
    1010                1015                1020
Gly Thr Ala Gly Thr Lys Val Ala Leu Arg Lys Thr Lys Gln Ala Ala
1025                1030                1035                1040
Glu Lys Ile Ser Ala Asp Lys Ile Ser Lys Glu Ala Leu Leu Glu Cys
                1045                1050                1055
Ala Asp Leu Leu Ser Ser Ala Leu Thr Glu Pro Val Pro Asn Ser Gln
            1060                1065                1070
Leu Val Asp Thr Gly His Gln Leu Leu Asp Tyr Cys Ser Gly Tyr Val
        1075                1080                1085
Asp Cys Ile Pro Gln Thr Arg Asn Lys Phe Ala Phe Arg Glu Ala Val
    1090                1095                1100
Ser Lys Leu Glu Leu Ser Leu Gln Glu Leu Gln Val Ser Ala Ala
1105                1110                1115                1120
Ala Gly Val Pro Gly Thr Asn Pro Val Leu Asn Asn Leu Leu Ser Cys
            1125                1130                1135
Val Gln Glu Ile Ser Asp Val Val Gln Arg
        1140                1145
```

<210> SEQ ID NO 74
<211> LENGTH: 335
<212> TYPE: PRT
<213> ORGANISM: Homo sapiens

<400> SEQUENCE: 74

Met Val Arg Pro Val Arg His Lys Lys Pro Val Asn Tyr Ser Gln Phe
1               5                   10                  15

Asp His Ser Asp Ser Asp Asp Phe Val Ser Ala Thr Val Pro Leu
            20                  25                  30

Asn Lys Lys Ser Arg Thr Ala Pro Lys Glu Leu Lys Gln Asp Lys Pro
        35                  40                  45

Lys Pro Asn Leu Asn Asn Leu Arg Lys Glu Glu Ile Pro Val Gln Glu
    50                  55                  60

Lys Thr Pro Lys Lys Arg Met Ala Leu Asp Asp Lys Leu Tyr Gln Arg
65                  70                  75                  80

Asp Leu Glu Val Ala Leu Ala Leu Ser Val Lys Glu Leu Pro Thr Val
                85                  90                  95

Thr Thr Asn Val Gln Asn Ser Gln Asp Lys Ser Ile Glu Lys His Gly
            100                 105                 110

Ser Ser Lys Ile Glu Thr Met Asn Lys Ser Pro His Ile Ser Asn Cys
        115                 120                 125

Ser Val Ala Ser Asp Tyr Leu Asp Leu Asp Lys Ile Thr Val Glu Asp
    130                 135                 140

Asp Val Gly Gly Val Gln Gly Lys Arg Lys Ala Ala Ser Lys Ala Ala
145                 150                 155                 160

Ala Gln Gln Arg Lys Ile Leu Leu Glu Gly Ser Asp Gly Asp Ser Ala
                165                 170                 175

Asn Asp Thr Glu Pro Asp Phe Ala Pro Gly Glu Asp Ser Glu Asp Asp
            180                 185                 190

Ser Asp Phe Cys Glu Ser Glu Asp Asn Asp Glu Asp Phe Ser Met Arg
        195                 200                 205

Lys Ser Lys Val Lys Glu Ile Lys Lys Glu Val Lys Val Lys Ser
    210                 215                 220

Pro Val Glu Lys Lys Glu Lys Lys Ser Lys Ser Lys Cys Asn Ala Leu
225                 230                 235                 240

Val Thr Ser Val Asp Ser Ala Pro Ala Val Lys Ser Glu Ser Gln
                245                 250                 255

Ser Leu Pro Lys Lys Val Ser Leu Ser Ser Asp Thr Thr Arg Lys Pro
            260                 265                 270

Leu Glu Ile Arg Ser Pro Ser Ala Glu Ser Lys Lys Pro Lys Trp Val
        275                 280                 285

Pro Pro Ala Ala Ser Gly Gly Ser Arg Ser Ser Ser Pro Leu Val
290                 295                 300

Val Val Ser Val Lys Ser Pro Asn Gln Ser Leu Arg Leu Gly Leu Ser
305                 310                 315                 320

Arg Leu Ala Arg Val Lys Pro Leu His Pro Asn Ala Thr Ser Thr
                325                 330                 335

<210> SEQ ID NO 75
<211> LENGTH: 558
<212> TYPE: PRT
<213> ORGANISM: Homo sapiens

<400> SEQUENCE: 75

-continued

```
Met Ala Ile Pro Gly Arg Gln Tyr Gly Leu Ile Leu Pro Lys Lys Thr
1               5                   10                  15

Gln Gln Leu His Pro Val Leu Gln Lys Pro Ser Val Phe Gly Asn Asp
            20                  25                  30

Ser Asp Asp Asp Asp Glu Thr Ser Val Ser Glu Ser Leu Gln Arg Glu
        35                  40                  45

Ala Ala Lys Lys Gln Ala Met Lys Gln Thr Lys Leu Glu Ile Gln Lys
    50                  55                  60

Ala Leu Ala Glu Asp Ala Thr Val Tyr Glu Tyr Asp Ser Ile Tyr Asp
65                  70                  75                  80

Glu Met Gln Lys Lys Lys Glu Glu Asn Asn Pro Lys Leu Leu Leu Gly
                85                  90                  95

Lys Asp Arg Lys Pro Lys Tyr Ile His Asn Leu Leu Lys Ala Val Glu
            100                 105                 110

Ile Arg Lys Lys Glu Gln Glu Lys Arg Met Glu Lys Lys Ile Gln Arg
        115                 120                 125

Glu Arg Glu Met Glu Lys Gly Glu Phe Asp Asp Lys Glu Ala Phe Val
    130                 135                 140

Thr Ser Ala Tyr Lys Lys Lys Leu Gln Glu Arg Ala Glu Glu Glu Glu
145                 150                 155                 160

Arg Glu Lys Arg Ala Ala Ala Leu Glu Ala Cys Leu Asp Val Thr Lys
                165                 170                 175

Gln Lys Asp Leu Ser Gly Phe Tyr Arg His Leu Leu Asn Gln Ala Val
            180                 185                 190

Gly Glu Glu Glu Val Pro Lys Cys Ser Phe Arg Glu Ala Arg Ser Gly
        195                 200                 205

Ile Lys Glu Glu Lys Ser Arg Gly Phe Ser Asn Glu Val Ser Ser Lys
    210                 215                 220

Asn Arg Ile Pro Gln Glu Lys Cys Ile Leu Gln Thr Asp Val Lys Val
225                 230                 235                 240

Glu Glu Asn Pro Asp Ala Asp Ser Asp Phe Asp Ala Lys Ser Ser Ala
                245                 250                 255

Asp Asp Glu Ile Glu Glu Thr Arg Val Asn Cys Arg Arg Glu Lys Val
            260                 265                 270

Ile Glu Thr Pro Glu Asn Asp Phe Lys His His Arg Ser Gln Asn His
        275                 280                 285

Ser Arg Ser Pro Ser Glu Glu Arg Gly His Ser Thr Arg His His Thr
    290                 295                 300

Lys Gly Ser Arg Thr Ser Arg Gly His Glu Lys Arg Glu Asp Gln His
305                 310                 315                 320

Gln Gln Lys Gln Ser Arg Asp Gln Glu Asn His Tyr Thr Asp Arg Asp
                325                 330                 335

Tyr Arg Lys Glu Arg Asp Ser His Arg His Arg Glu Ala Ser His Arg
            340                 345                 350

Asp Ser His Trp Lys Arg His Glu Gln Glu Asp Lys Pro Arg Ala Arg
        355                 360                 365

Asp Gln Arg Glu Arg Ser Asp Arg Val Trp Lys Arg Glu Lys Asp Arg
    370                 375                 380

Glu Lys Tyr Ser Gln Arg Glu Gln Arg Asp Arg Gln Asn Asp
385                 390                 395                 400

Gln Asn Arg Pro Ser Glu Lys Gly Glu Lys Glu Lys Ser Lys Ala
                405                 410                 415
```

Lys Glu Glu His Met Lys Val Arg Lys Glu Arg Tyr Glu Asn Asn Asp
                420                 425                 430

Lys Tyr Arg Asp Arg Glu Lys Arg Glu Val Gly Val Gln Ser Ser Glu
            435                 440                 445

Arg Asn Gln Asp Arg Lys Glu Ser Ser Pro Asn Ser Arg Ala Lys Asp
450                 455                 460

Lys Phe Leu Asp Gln Glu Arg Ser Asn Lys Met Arg Asn Met Ala Lys
465                 470                 475                 480

Asp Lys Glu Arg Asn Gln Glu Lys Pro Ser Asn Ser Glu Ser Ser Leu
                485                 490                 495

Gly Ala Lys His Arg Leu Thr Glu Glu Gly Gln Glu Lys Gly Lys Glu
            500                 505                 510

Gln Glu Arg Pro Pro Glu Ala Val Ser Lys Phe Ala Lys Arg Asn Asn
        515                 520                 525

Glu Glu Thr Val Met Ser Ala Arg Asp Arg Tyr Leu Ala Arg Gln Met
530                 535                 540

Ala Arg Val Asn Ala Lys Thr Tyr Ile Glu Lys Glu Asp Asp
545                 550                 555

<210> SEQ ID NO 76
<211> LENGTH: 1242
<212> TYPE: PRT
<213> ORGANISM: Homo sapiens

<400> SEQUENCE: 76

Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Phe Ile Glu
    210                 215                 220

Val Gly Arg Ser Ala Val Thr Gly Pro Gly Glu Phe Trp Met Gln Val
225                 230                 235                 240

```
Asp Asp Ser Val Val Ala Gln Asn Met His Glu Thr Ile Leu Glu Ala
            245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
            275                 280                 285

Leu Asn Asn Pro Pro Pro Ser Gln Val Gly Leu Thr Arg Arg Ser Arg
            290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Asn
            340                 345                 350

Arg Thr His Ala His Arg His Arg Gly Ser Ala Arg Leu His Pro Pro
                355                 360                 365

Leu Asn His Ser Arg Ser Ile Pro Met Pro Ala Ser Arg Cys Ser Pro
    370                 375                 380

Ser Ala Thr Ser Pro Val Ser Leu Ser Ser Ser Ser Thr Ser Gly His
385                 390                 395                 400

Gly Ser Thr Ser Asp Cys Leu Phe Pro Arg Arg Ser Ala Ser Val
                405                 410                 415

Ser Gly Ser Pro Ser Asp Gly Gly Phe Ile Ser Ser Asp Glu Tyr Gly
                420                 425                 430

Ser Ser Pro Cys Asp Phe Arg Ser Phe Arg Ser Val Thr Pro Asp
                435                 440                 445

Ser Leu Gly His Thr Pro Pro Ala Arg Gly Glu Glu Leu Ser Asn
            450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
            500                 505                 510

Ser Ala Ala Asp Leu Asp Asn Arg Phe Arg Lys Arg Thr His Ser Ala
            515                 520                 525

Gly Thr Ser Pro Thr Ile Thr His Gln Lys Thr Pro Ser Gln Ser Ser
    530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
            580                 585                 590

Glu Arg Arg Gly Gly His His Arg Pro Asp Ser Ser Thr Leu His Thr
                595                 600                 605

Asp Asp Gly Tyr Met Pro Met Ser Pro Gly Val Ala Pro Val Pro Ser
            610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655
```

-continued

Val Asp Pro Asn Gly Tyr Met Met Met Ser Pro Ser Gly Gly Cys Ser
            660                 665                 670

Pro Asp Ile Gly Gly Gly Pro Ser Ser Ser Ser Ser Ser Asn Ala
            675                 680                 685

Val Pro Ser Gly Thr Ser Tyr Gly Lys Leu Trp Thr Asn Gly Val Gly
            690                 695                 700

Gly His His Ser His Val Leu Pro His Pro Lys Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Ser Pro Ser Asp Cys Tyr Tyr Gly
            740                 745                 750

Pro Glu Asp Pro Gln His Lys Pro Val Leu Ser Tyr Tyr Ser Leu Pro
            755                 760                 765

Arg Ser Phe Lys His Thr Gln Arg Pro Gly Glu Pro Glu Glu Gly Ala
            770                 775                 780

Arg His Gln His Leu Arg Leu Ser Thr Ser Ser Gly Arg Leu Leu Tyr
785                 790                 795                 800

Ala Ala Thr Ala Asp Asp Ser Ser Ser Thr Ser Ser Asp Ser Leu
            805                 810                 815

Gly Gly Gly Tyr Cys Gly Ala Arg Leu Glu Pro Ser Leu Pro His Pro
            820                 825                 830

His His Gln Val Leu Gln Pro His Leu Pro Arg Lys Val Asp Thr Ala
            835                 840                 845

Ala Gln Thr Asn Ser Arg Leu Ala Arg Pro Thr Arg Leu Ser Leu Gly
850                 855                 860

Asp Pro Lys Ala Ser Thr Leu Pro Arg Ala Arg Glu Gln Gln Gln Gln
865                 870                 875                 880

Gln Gln Pro Leu Leu His Pro Pro Glu Pro Lys Ser Pro Gly Glu Tyr
            885                 890                 895

Val Asn Ile Glu Phe Gly Ser Asp Gln Ser Gly Tyr Leu Ser Gly Pro
            900                 905                 910

Val Ala Phe His Ser Ser Pro Ser Val Arg Cys Pro Ser Gln Leu Gln
            915                 920                 925

Pro Ala Pro Arg Glu Glu Glu Thr Gly Thr Glu Glu Tyr Met Lys Met
            930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Pro Gly Ala Ala Ser Ile Cys
                965                 970                 975

Arg Pro Thr Arg Ala Val Pro Ser Ser Arg Gly Asp Tyr Met Thr Met
            980                 985                 990

Gln Met Ser Cys Pro Arg Gln Ser Tyr Val Asp Thr Ser Pro Ala Ala
            995                 1000                1005

Pro Val Ser Tyr Ala Asp Met Arg Thr Gly Ile Ala Ala Glu Glu Val
            1010                1015                1020

Ser Leu Pro Arg Ala Thr Met Ala Ala Ala Ser Ser Ser Ser Ala Ala
1025                1030                1035                1040

Ser Ala Ser Pro Thr Gly Pro Gln Gly Ala Ala Glu Leu Ala Ala His
                1045                1050                1055

Ser Ser Leu Leu Gly Gly Pro Gln Gly Pro Gly Gly Met Ser Ala Phe
                1060                1065                1070

Thr Arg Val Asn Leu Ser Pro Asn Arg Asn Gln Ser Ala Lys Val Ile

```
                1075                1080                1085

Arg Ala Asp Pro Gln Gly Cys Arg Arg His Ser Ser Glu Thr Phe
    1090                1095                1100

Ser Ser Thr Pro Ser Ala Thr Arg Val Gly Asn Thr Val Pro Phe Gly
1105                1110                1115                1120

Ala Gly Ala Ala Val Gly Gly Gly Gly Ser Ser Ser Ser Ser Glu
                1125                1130                1135

Asp Val Lys Arg His Ser Ser Ala Ser Phe Glu Asn Val Trp Leu Arg
                1140                1145                1150

Pro Gly Glu Leu Gly Gly Ala Pro Lys Glu Pro Ala Lys Leu Cys Gly
                1155                1160                1165

Ala Ala Gly Gly Leu Glu Asn Gly Leu Asn Tyr Ile Asp Leu Asp Leu
    1170                1175                1180

Val Lys Asp Phe Lys Gln Cys Pro Gln Glu Cys Thr Pro Glu Pro Gln
1185                1190                1195                1200

Pro Pro Pro Pro Pro Pro His Gln Pro Leu Gly Ser Gly Glu Ser
                1205                1210                1215

Ser Ser Thr Arg Arg Ser Ser Glu Asp Leu Ser Ala Tyr Ala Ser Ile
                1220                1225                1230

Ser Phe Gln Lys Gln Pro Glu Asp Arg Gln
                1235                1240

<210> SEQ ID NO 77
<211> LENGTH: 1106
<212> TYPE: PRT
<213> ORGANISM: Homo sapiens

<400> SEQUENCE: 77

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
                35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
                115                 120                 125

Pro Asn Asp Ala Glu Glu Leu Phe Ile Phe Leu Thr Glu Ile Thr Glu
                130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
                195                 200                 205
```

```
Leu Gln Val Ser Ser Ile Asn Val Ser Val Asn Ala Val Gln Thr Val
210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
                260                 265                 270
Arg Ser Ile Leu His Ile Pro Ser Ala Glu Leu Glu Asp Ser Gly Thr
                275                 280                 285
Tyr Thr Cys Asn Val Thr Glu Ser Val Asn Asp His Gln Asp Glu Lys
290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
                340                 345                 350
Asp Asn Arg Thr Leu Gly Asp Ser Ser Ala Gly Glu Ile Ala Leu Ser
                355                 360                 365
Thr Arg Asn Val Ser Glu Thr Arg Tyr Val Ser Glu Leu Thr Leu Val
370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
                420                 425                 430
Thr Val Arg Cys Arg Gly Arg Gly Met Pro Gln Pro Asn Ile Ile Trp
                435                 440                 445
Ser Ala Cys Arg Asp Leu Lys Arg Cys Pro Arg Glu Leu Pro Pro Thr
450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
                485                 490                 495
Leu Gln His Val Asp Arg Pro Leu Ser Val Arg Cys Thr Leu Arg Asn
                500                 505                 510
Ala Val Gly Gln Asp Thr Gln Glu Val Ile Val Val Pro His Ser Leu
                515                 520                 525
Pro Phe Lys Val Val Ile Ser Ala Ile Leu Ala Leu Val Val Leu
530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                565                 570                 575
His Glu Tyr Ile Tyr Val Asp Pro Met Gln Leu Pro Tyr Asp Ser Thr
                580                 585                 590
Trp Glu Leu Pro Arg Asp Gln Leu Val Leu Gly Arg Thr Leu Gly Ser
                595                 600                 605
Gly Ala Phe Gly Gln Val Val Glu Ala Thr Ala His Gly Leu Ser His
                610                 615                 620
Ser Gln Ala Thr Met Lys Val Ala Val Lys Met Leu Lys Ser Thr Ala
```

```
            625                 630                 635                 640
Arg Ser Ser Glu Lys Gln Ala Leu Met Ser Glu Leu Lys Ile Met Ser
                    645                 650                 655

His Leu Gly Pro His Leu Asn Val Val Asn Leu Leu Gly Ala Cys Thr
                660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
        690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                    725                 730                 735

Asp Gly Gly Tyr Met Asp Met Ser Lys Asp Glu Ser Val Asp Tyr Val
                740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
        770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                    805                 810                 815

Leu Ala Ser Lys Asn Cys Val His Arg Asp Leu Ala Ala Arg Asn Val
                820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
        850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                    885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
            915                 920                 925

Ala Ser Asp Glu Ile Tyr Glu Ile Met Gln Lys Cys Trp Glu Glu Lys
        930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                    965                 970                 975

Phe Leu Arg Ser Asp His Pro Ala Ile Leu Arg Ser Gln Ala Arg Leu
                980                 985                 990

Pro Gly Phe His Gly Leu Arg Ser Pro Leu Asp Thr Ser Ser Val Leu
            995                 1000                1005

Tyr Thr Ala Val Gln Pro Asn Glu Gly Asp Asn Asp Tyr Ile Ile Pro
        1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
                    1045                1050                1055
```

```
Thr Ile Ser Cys Asp Ser Pro Leu Glu Pro Gln Asp Glu Pro Glu Pro
                1060                1065                1070

Glu Pro Gln Leu Glu Leu Gln Val Glu Pro Glu Pro Glu Leu Glu Gln
            1075                1080                1085

Leu Pro Asp Ser Gly Cys Pro Ala Pro Arg Ala Glu Ala Glu Asp Ser
        1090                1095                1100

Phe Leu
1105

<210> SEQ ID NO 78
<211> LENGTH: 486
<212> TYPE: PRT
<213> ORGANISM: Homo sapiens

<400> SEQUENCE: 78

Met Ala Trp Ile Lys Arg Lys Phe Gly Glu Arg Pro Pro Lys Arg
1               5                   10                  15

Leu Thr Arg Glu Ala Met Arg Asn Tyr Leu Lys Glu Arg Gly Asp Gln
            20                  25                  30

Thr Val Leu Ile Leu His Ala Lys Val Ala Gln Lys Ser Tyr Gly Asn
        35                  40                  45

Glu Lys Arg Phe Phe Cys Pro Pro Pro Cys Val Tyr Leu Met Gly Ser
    50                  55                  60

Gly Trp Lys Lys Lys Lys Glu Gln Met Glu Arg Asp Gly Cys Ser Glu
65                  70                  75                  80

Gln Glu Ser Gln Pro Cys Ala Phe Ile Gly Ile Gly Asn Ser Asp Gln
                85                  90                  95

Glu Met Gln Gln Leu Asn Leu Glu Gly Lys Asn Tyr Cys Thr Ala Lys
            100                 105                 110

Thr Leu Tyr Ile Ser Asp Ser Asp Lys Arg Lys His Phe Met Leu Ser
        115                 120                 125

Val Lys Met Phe Tyr Gly Asn Ser Asp Asp Ile Gly Val Phe Leu Ser
    130                 135                 140

Lys Arg Ile Lys Val Ile Ser Lys Pro Ser Lys Lys Lys Gln Ser Leu
145                 150                 155                 160

Lys Asn Ala Asp Leu Cys Ile Ala Ser Gly Thr Lys Val Ala Leu Phe
                165                 170                 175

Asn Arg Leu Arg Ser Gln Thr Val Ser Thr Arg Tyr Leu His Val Glu
            180                 185                 190

Gly Gly Asn Phe His Ala Ser Ser Gln Gln Trp Gly Ala Phe Phe Ile
        195                 200                 205

His Leu Leu Asp Asp Asp Glu Ser Glu Gly Glu Glu Phe Thr Val Arg
    210                 215                 220

Asp Gly Tyr Ile His Tyr Gly Gln Thr Val Lys Leu Val Cys Ser Val
225                 230                 235                 240

Thr Gly Met Ala Leu Pro Arg Leu Ile Ile Arg Lys Val Asp Lys Gln
                245                 250                 255

Thr Ala Leu Leu Asp Ala Asp Asp Pro Val Ser Gln Leu His Lys Cys
            260                 265                 270

Ala Phe Tyr Leu Lys Asp Thr Glu Arg Met Tyr Leu Cys Leu Ser Gln
        275                 280                 285

Glu Arg Ile Ile Gln Phe Gln Ala Thr Pro Cys Pro Lys Glu Pro Asn
    290                 295                 300

Lys Glu Met Ile Asn Asp Gly Ala Ser Trp Thr Ile Ile Ser Thr Asp
```

```
                305                 310                 315                 320
Lys Ala Glu Tyr Thr Phe Tyr Glu Gly Met Gly Pro Val Leu Ala Pro
                    325                 330                 335

Val Thr Pro Val Pro Val Val Glu Ser Leu Gln Leu Asn Gly Gly
                340                 345                 350

Asp Val Ala Met Leu Glu Leu Thr Gly Gln Asn Phe Thr Pro Asn Leu
                    355                 360                 365

Arg Val Trp Phe Gly Asp Val Glu Ala Glu Thr Met Tyr Arg Cys Gly
                370                 375                 380

Glu Ser Met Leu Cys Val Val Pro Asp Ile Ser Ala Phe Arg Glu Gly
385                 390                 395                 400

Trp Arg Trp Val Arg Gln Pro Val Gln Val Pro Val Thr Leu Val Arg
                    405                 410                 415

Asn Asp Gly Ile Ile Tyr Ser Thr Ser Leu Thr Phe Thr Tyr Thr Pro
                420                 425                 430

Glu Pro Gly Pro Arg Pro His Cys Ser Ala Ala Gly Ala Ile Leu Arg
                435                 440                 445

Ala Asn Ser Ser Gln Val Pro Pro Asn Glu Ser Asn Thr Asn Ser Glu
                450                 455                 460

Gly Ser Tyr Thr Asn Ala Ser Thr Asn Ser Thr Ser Val Thr Ser Ser
465                 470                 475                 480

Thr Ala Thr Val Val Ser
                485

<210> SEQ ID NO 79
<211> LENGTH: 402
<212> TYPE: PRT
<213> ORGANISM: Homo sapiens

<400> SEQUENCE: 79

Met Ile Pro Pro Ser Ser Pro Arg Glu Asp Gly Val Asp Gly Leu Pro
1               5                   10                  15

Lys Glu Ala Val Gly Ala Glu Gln Pro Pro Ser Pro Ala Ser Thr Ser
                20                  25                  30

Ser Gln Glu Ser Lys Leu Gln Lys Leu Lys Arg Ser Leu Ser Phe Lys
            35                  40                  45

Thr Lys Ser Leu Arg Ser Lys Ser Ala Asp Asn Phe Phe Gln Arg Thr
        50                  55                  60

Asn Ser Glu Asp Met Lys Leu Gln Ala His Met Val Ala Glu Ile Ser
65                  70                  75                  80

Pro Ser Ser Ser Pro Leu Pro Ala Pro Gly Ser Leu Thr Ser Thr Pro
                85                  90                  95

Ala Arg Ala Gly Leu His Pro Gly Gly Lys Ala His Ala Phe His Glu
            100                 105                 110

Tyr Ile Phe Lys Lys Pro Thr Phe Cys Asp Val Cys Asn His Met Ile
        115                 120                 125

Val Gly Thr Asn Ala Lys His Gly Leu Arg Cys Lys Ala Cys Lys Met
    130                 135                 140

Ser Ile His His Lys Cys Thr Asp Gly Leu Ala Pro Gln Arg Cys Met
145                 150                 155                 160

Gly Lys Leu Pro Lys Gly Phe Arg Arg Tyr Tyr Ser Ser Pro Leu Leu
                165                 170                 175

Ile His Glu Gln Phe Gly Cys Ile Lys Glu Val Met Pro Ile Ala Cys
            180                 185                 190
```

```
Gly Asn Lys Val Asp Pro Val Tyr Glu Thr Leu Arg Phe Gly Thr Ser
            195                 200                 205

Leu Ala Gln Arg Thr Lys Lys Gly Ser Ser Gly Ser Gly Ser Asp Ser
    210                 215                 220

Pro His Arg Thr Ser Thr Ser Asp Leu Val Glu Val Pro Glu Glu Ala
225                 230                 235                 240

Asn Gly Pro Gly Gly Gly Tyr Asp Leu Arg Lys Arg Ser Asn Ser Val
                245                 250                 255

Phe Thr Tyr Pro Glu Asn Gly Thr Asp Asp Phe Arg Asp Pro Ala Lys
            260                 265                 270

Asn Ile Asn His Gln Gly Ser Leu Ser Lys Asp Pro Leu Gln Met Asn
        275                 280                 285

Thr Tyr Val Ala Leu Tyr Lys Phe Val Pro Gln Glu Asn Glu Asp Leu
    290                 295                 300

Glu Met Arg Pro Gly Asp Ile Ile Thr Leu Leu Glu Asp Ser Asn Glu
305                 310                 315                 320

Asp Trp Trp Lys Gly Lys Ile Gln Asp Arg Ile Gly Phe Phe Pro Ala
                325                 330                 335

Asn Phe Val Gln Arg Leu Gln Gln Asn Glu Lys Ile Phe Arg Cys Val
            340                 345                 350

Arg Thr Phe Ile Gly Cys Lys Glu Gln Gly Gln Ile Thr Leu Lys Glu
        355                 360                 365

Asn Gln Ile Cys Val Ser Ser Glu Glu Gln Asp Gly Phe Ile Arg
    370                 375                 380

Val Leu Ser Gly Lys Lys Lys Gly Leu Ile Pro Leu Asp Val Leu Glu
385                 390                 395                 400

Asn Ile

<210> SEQ ID NO 80
<211> LENGTH: 293
<212> TYPE: PRT
<213> ORGANISM: Homo sapiens

<400> SEQUENCE: 80

Met Pro Ala Arg Ser Gly Ala Gln Phe Cys Arg Met Gly Gln Lys
1               5                   10                  15

Lys Gln Arg Pro Ala Arg Ala Gly Gln Pro His Ser Ser Ser Asp Ala
            20                  25                  30

Ala Gln Ala Pro Ala Glu Gln Pro His Ser Ser Ser Asp Ala Ala Gln
        35                  40                  45

Ala Pro Cys Pro Arg Glu Arg Cys Leu Gly Pro Thr Thr Pro Gly
    50                  55                  60

Pro Tyr Arg Ser Ile Tyr Phe Ser Ser Pro Lys Gly His Leu Thr Arg
65                  70                  75                  80

Leu Gly Leu Glu Phe Phe Asp Gln Pro Ala Val Pro Leu Ala Arg Ala
                85                  90                  95

Phe Leu Gly Gln Val Leu Val Arg Arg Leu Pro Asn Gly Thr Glu Leu
            100                 105                 110

Arg Gly Arg Ile Val Glu Thr Glu Ala Tyr Leu Gly Pro Glu Asp Glu
        115                 120                 125

Ala Ala His Ser Arg Gly Gly Arg Gln Thr Pro Arg Asn Arg Gly Met
    130                 135                 140

Phe Met Lys Pro Gly Thr Leu Tyr Val Tyr Ile Ile Tyr Gly Met Tyr
145                 150                 155                 160
```

```
Phe Cys Met Asn Ile Ser Ser Gln Gly Asp Gly Ala Cys Val Leu Leu
                165                 170                 175

Arg Ala Leu Glu Pro Leu Glu Gly Leu Glu Thr Met Arg Gln Leu Arg
            180                 185                 190

Ser Thr Leu Arg Lys Gly Thr Ala Ser Arg Val Leu Lys Asp Arg Glu
        195                 200                 205

Leu Cys Ser Gly Pro Ser Lys Leu Cys Gln Ala Leu Ala Ile Asn Lys
    210                 215                 220

Ser Phe Asp Gln Arg Asp Leu Ala Gln Asp Glu Ala Val Trp Leu Glu
225                 230                 235                 240

Arg Gly Pro Leu Glu Pro Ser Glu Pro Ala Val Val Ala Ala Ala Arg
                245                 250                 255

Val Gly Val Gly His Ala Gly Glu Trp Ala Arg Lys Pro Leu Arg Phe
            260                 265                 270

Tyr Val Arg Gly Ser Pro Trp Val Ser Val Val Asp Arg Val Ala Glu
        275                 280                 285

Gln Asp Thr Gln Ala
    290

<210> SEQ ID NO 81
<211> LENGTH: 424
<212> TYPE: PRT
<213> ORGANISM: Homo sapiens

<400> SEQUENCE: 81

Met Ala Ala Gly Pro Ile Ser Glu Arg Asn Gln Asp Ala Thr Val Tyr
1               5                   10                  15

Val Gly Gly Leu Asp Glu Lys Val Ser Glu Pro Leu Leu Trp Glu Leu
            20                  25                  30

Phe Leu Gln Ala Gly Pro Val Val Asn Thr His Met Pro Lys Asp Arg
        35                  40                  45

Val Thr Gly Gln His Gln Gly Tyr Gly Phe Val Glu Phe Leu Ser Glu
    50                  55                  60

Glu Asp Ala Asp Tyr Ala Ile Lys Ile Met Asn Met Ile Lys Leu Tyr
65                  70                  75                  80

Gly Lys Pro Ile Arg Val Asn Lys Ala Ser Ala His Asn Lys Asn Leu
                85                  90                  95

Asp Val Gly Ala Asn Ile Phe Ile Gly Asn Leu Asp Pro Glu Ile Asp
            100                 105                 110

Glu Lys Leu Leu Tyr Asp Thr Phe Ser Ala Phe Gly Val Ile Leu Gln
        115                 120                 125

Thr Pro Lys Ile Met Arg Asp Pro Asp Thr Gly Asn Ser Lys Gly Tyr
    130                 135                 140

Ala Phe Ile Asn Phe Ala Ser Phe Asp Ala Ser Asp Ala Ala Ile Glu
145                 150                 155                 160

Ala Met Asn Gly Gln Tyr Leu Cys Asn Arg Pro Ile Thr Val Ser Tyr
                165                 170                 175

Ala Phe Lys Lys Asp Ser Lys Gly Glu Arg His Gly Ser Ala Ala Glu
            180                 185                 190

Arg Leu Leu Ala Ala Gln Asn Pro Leu Ser Gln Ala Asp Arg Pro His
        195                 200                 205

Gln Leu Phe Ala Asp Ala Pro Pro Pro Ser Ala Pro Asn Pro Val
    210                 215                 220

Val Ser Ser Leu Gly Ser Gly Leu Pro Pro Pro Gly Met Pro Pro Pro
225                 230                 235                 240
```

Gly Ser Phe Pro Pro Pro Val Pro Pro Gly Ala Leu Pro Pro Gly
                245                 250                 255

Ile Pro Pro Ala Met Pro Pro Pro Met Pro Gly Ala Ala Gly
            260                 265                 270

His Gly Pro Pro Ser Ala Gly Thr Pro Ala Gly His Pro Gly His
            275                 280                 285

Gly His Ser His Pro His Pro Phe Pro Pro Gly Gly Met Pro His Pro
            290                 295                 300

Gly Met Ser Gln Met Gln Leu Ala His His Gly Pro His Gly Leu Gly
305                 310                 315                 320

His Pro His Ala Gly Pro Pro Gly Ser Gly Gln Pro Pro Arg
            325                 330                 335

Pro Pro Pro Gly Met Pro His Pro Gly Pro Pro Met Gly Met Pro
            340                 345                 350

Pro Arg Gly Pro Pro Phe Gly Ser Pro Met Gly His Pro Gly Pro Met
            355                 360                 365

Pro Pro His Gly Met Arg Gly Pro Pro Leu Met Pro Pro His Gly
            370                 375                 380

Tyr Thr Gly Pro Pro Arg Pro Pro Tyr Gly Tyr Gln Arg Gly Pro
385                 390                 395                 400

Leu Pro Pro Pro Arg Pro Thr Pro Arg Pro Pro Val Pro Pro Arg Gly
            405                 410                 415

Pro Leu Arg Gly Pro Leu Pro Gln
            420

<210> SEQ ID NO 82
<211> LENGTH: 806
<212> TYPE: PRT
<213> ORGANISM: Homo sapiens

<400> SEQUENCE: 82

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly

```
                180             185             190
Arg Glu Phe Arg Gly Glu His Arg Ile Gly Ile Lys Leu Arg His
            195                 200                 205
Gln Gln Trp Ser Leu Val Met Glu Ser Val Val Pro Ser Asp Arg Gly
            210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
            290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Leu Val Glu Ala Asp Glu
            355                 360                 365
Ala Gly Ser Val Tyr Ala Gly Ile Leu Ser Tyr Gly Val Gly Phe Phe
            370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
            435                 440                 445
Pro Thr Leu Ala Asn Val Ser Glu Leu Glu Leu Pro Ala Asp Pro Lys
            450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
            530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
            595                 600                 605
```

```
Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 83
<211> LENGTH: 553
<212> TYPE: PRT
<213> ORGANISM: Homo sapiens

<400> SEQUENCE: 83

Met Ala Ala Pro Ala Gly Gly Gly Ser Ala Val Ser Val Leu Ala
1                   5                   10                  15

Pro Asn Gly Arg Arg His Thr Val Lys Val Thr Pro Ser Thr Val Leu
                20                  25                  30

Leu Gln Val Leu Glu Asp Thr Cys Arg Arg Gln Asp Phe Asn Pro Cys
            35                  40                  45

Glu Tyr Asp Leu Lys Phe Gln Arg Ser Val Leu Asp Leu Ser Leu Gln
        50                  55                  60

Trp Arg Phe Ala Asn Leu Pro Asn Asn Ala Lys Leu Glu Met Val Pro
65                  70                  75                  80

Ala Ser Arg Ser Arg Glu Gly Pro Glu Asn Met Val Arg Ile Ala Leu
                85                  90                  95

Gln Leu Asp Asp Gly Ser Arg Leu Gln Asp Ser Phe Cys Ser Gly Gln
            100                 105                 110

Thr Leu Trp Glu Leu Leu Ser His Phe Pro Gln Ile Arg Glu Cys Leu
        115                 120                 125

Gln His Pro Gly Gly Ala Thr Pro Val Cys Val Tyr Thr Arg Asp Glu
    130                 135                 140

Val Thr Gly Glu Ala Ala Leu Arg Gly Thr Thr Leu Gln Ser Leu Gly
145                 150                 155                 160

Leu Thr Gly Gly Ser Ala Thr Ile Arg Phe Val Met Lys Cys Tyr Asp
```

```
                165                 170                 175
Pro Val Gly Lys Thr Pro Gly Ser Leu Gly Ser Ser Ala Ser Ala Gly
            180                 185                 190

Gln Ala Ala Ala Ser Ala Pro Leu Pro Leu Glu Ser Gly Glu Leu Ser
            195                 200                 205

Arg Gly Asp Leu Ser Arg Pro Glu Asp Ala Asp Thr Ser Gly Pro Cys
            210                 215                 220

Cys Glu His Thr Gln Glu Lys Gln Ser Thr Arg Ala Pro Ala Ala Ala
225                 230                 235                 240

Pro Phe Val Pro Phe Ser Gly Gly Gln Arg Gln Gly Gly Pro Pro
            245                 250                 255

Gly Pro Thr Arg Pro Leu Thr Ser Ser Ala Lys Leu Pro Lys Ser
            260                 265                 270

Leu Ser Ser Pro Gly Gly Pro Ser Lys Pro Lys Ser Lys Ser Gly
            275                 280                 285

Gln Asp Pro Gln Gln Glu Gln Glu Arg Glu Arg Asp Pro Gln
            290                 295                 300

Gln Glu Gln Glu Arg Glu Arg Pro Val Asp Arg Glu Pro Val Asp Arg
305                 310                 315                 320

Glu Pro Val Val Cys His Pro Asp Leu Glu Glu Arg Leu Gln Ala Trp
                325                 330                 335

Pro Ala Glu Leu Pro Asp Glu Phe Phe Glu Leu Thr Val Asp Asp Val
            340                 345                 350

Arg Arg Arg Leu Ala Gln Leu Lys Ser Glu Arg Lys Arg Leu Glu Glu
            355                 360                 365

Ala Pro Leu Val Thr Lys Ala Phe Arg Glu Ala Gln Ile Lys Glu Lys
            370                 375                 380

Leu Glu Arg Tyr Pro Lys Val Ala Leu Arg Val Leu Phe Pro Asp Arg
385                 390                 395                 400

Tyr Val Leu Gln Gly Phe Phe Arg Pro Ser Glu Thr Val Gly Asp Leu
                405                 410                 415

Arg Asp Phe Val Arg Ser His Leu Gly Asn Pro Glu Leu Ser Phe Tyr
            420                 425                 430

Leu Phe Ile Thr Pro Pro Lys Thr Val Leu Asp Asp His Thr Gln Thr
            435                 440                 445

Leu Phe Gln Ala Asn Leu Phe Pro Ala Ala Leu Val His Leu Gly Ala
            450                 455                 460

Glu Glu Pro Ala Gly Val Tyr Leu Glu Pro Gly Leu Leu Glu His Ala
465                 470                 475                 480

Ile Ser Pro Ser Ala Ala Asp Val Leu Val Ala Arg Tyr Met Ser Arg
                485                 490                 495

Ala Ala Gly Ser Pro Ser Pro Leu Pro Ala Pro Asp Pro Ala Pro Lys
            500                 505                 510

Ser Glu Pro Ala Ala Glu Glu Gly Ala Leu Val Pro Pro Glu Pro Ile
            515                 520                 525

Pro Gly Thr Ala Gln Pro Val Lys Arg Ser Leu Gly Lys Val Pro Lys
            530                 535                 540

Trp Leu Lys Leu Pro Ala Ser Lys Arg
545                 550

<210> SEQ ID NO 84
<211> LENGTH: 204
<212> TYPE: PRT
<213> ORGANISM: Homo sapiens
```

<400> SEQUENCE: 84

Met Glu Ala Ala Gly Ser Pro Ala Ala Thr Glu Thr Gly Lys Tyr Ile
1               5                   10                  15

Ala Ser Thr Gln Arg Pro Asp Gly Thr Trp Arg Lys Gln Arg Arg Val
            20                  25                  30

Lys Glu Gly Tyr Val Pro Gln Glu Glu Val Pro Val Tyr Glu Asn Lys
        35                  40                  45

Tyr Val Lys Phe Phe Lys Ser Lys Pro Glu Leu Pro Pro Gly Leu Ser
    50                  55                  60

Pro Glu Ala Thr Ala Pro Val Thr Pro Ser Arg Pro Glu Gly Gly Glu
65                  70                  75                  80

Pro Gly Leu Ser Lys Thr Ala Lys Arg Asn Leu Lys Arg Lys Glu Lys
                85                  90                  95

Arg Arg Gln Gln Gln Glu Lys Gly Glu Ala Glu Ala Leu Ser Arg Thr
            100                 105                 110

Leu Asp Lys Val Ser Leu Glu Glu Thr Ala Gln Leu Pro Ser Ala Pro
        115                 120                 125

Gln Gly Ser Arg Ala Ala Pro Thr Ala Ala Ser Asp Gln Pro Asp Ser
    130                 135                 140

Ala Ala Thr Thr Glu Lys Ala Lys Lys Ile Lys Asn Leu Lys Lys Lys
145                 150                 155                 160

Leu Arg Gln Val Glu Glu Leu Gln Arg Ile Gln Ala Gly Glu Val
            165                 170                 175

Ser Gln Pro Ser Lys Glu Gln Leu Glu Lys Leu Ala Arg Arg Arg Ala
            180                 185                 190

Leu Glu Glu Glu Leu Glu Asp Leu Glu Leu Gly Leu
            195                 200

<210> SEQ ID NO 85
<211> LENGTH: 354
<212> TYPE: PRT
<213> ORGANISM: Homo sapiens

<400> SEQUENCE: 85

Met Cys Gly Arg Thr Ser Cys His Leu Pro Arg Asp Val Leu Thr Arg
1               5                   10                  15

Ala Cys Ala Tyr Gln Asp Arg Gly Gln Gln Arg Leu Pro Glu Trp
            20                  25                  30

Arg Asp Pro Asp Lys Tyr Cys Pro Ser Tyr Asn Lys Ser Pro Gln Ser
        35                  40                  45

Asn Ser Pro Val Leu Leu Ser Arg Leu His Phe Asp Lys Asp Ala Asp
    50                  55                  60

Ser Ser Glu Arg Ile Ile Ala Pro Met Arg Trp Gly Leu Val Pro Ser
65                  70                  75                  80

Trp Phe Lys Glu Ser Asp Pro Ser Lys Leu Gln Phe Asn Thr Thr Asn
                85                  90                  95

Cys Arg Ser Asp Thr Val Met Glu Lys Arg Ser Phe Lys Val Pro Leu
            100                 105                 110

Gly Lys Gly Arg Arg Cys Val Val Leu Ala Asp Gly Phe Tyr Glu Trp
        115                 120                 125

Gln Arg Cys Gln Gly Thr Asn Gln Arg Gln Pro Tyr Phe Ile Tyr Phe
    130                 135                 140

Pro Gln Ile Lys Thr Glu Lys Ser Gly Ser Ile Gly Ala Ala Asp Ser
145                 150                 155                 160

-continued

Pro Glu Asn Trp Glu Lys Val Trp Asp Asn Trp Arg Leu Leu Thr Met
                165                 170                 175

Ala Gly Ile Phe Asp Cys Trp Glu Pro Pro Glu Gly Gly Asp Val Leu
            180                 185                 190

Tyr Ser Tyr Thr Ile Ile Thr Val Asp Ser Cys Lys Gly Leu Ser Asp
        195                 200                 205

Ile His His Arg Met Pro Ala Ile Leu Asp Gly Glu Glu Ala Val Ser
    210                 215                 220

Lys Trp Leu Asp Phe Gly Glu Val Ser Thr Gln Ala Leu Lys Leu
225                 230                 235                 240

Ile His Pro Thr Glu Asn Ile Thr Phe His Ala Val Ser Ser Val Val
                245                 250                 255

Asn Asn Ser Arg Asn Asn Thr Pro Glu Cys Leu Ala Pro Val Asp Leu
            260                 265                 270

Val Val Lys Lys Glu Leu Arg Ala Ser Gly Ser Ser Gln Arg Met Leu
        275                 280                 285

Gln Trp Leu Ala Thr Lys Ser Pro Lys Lys Glu Asp Ser Lys Thr Pro
    290                 295                 300

Gln Lys Glu Glu Ser Asp Val Pro Gln Trp Ser Ser Gln Phe Leu Gln
305                 310                 315                 320

Lys Ser Pro Leu Pro Thr Lys Arg Gly Thr Ala Gly Leu Leu Glu Gln
                325                 330                 335

Trp Leu Lys Arg Glu Lys Glu Glu Pro Val Ala Lys Arg Pro Tyr
            340                 345                 350

Ser Gln

<210> SEQ ID NO 86
<211> LENGTH: 468
<212> TYPE: PRT
<213> ORGANISM: Homo sapiens

<400> SEQUENCE: 86

Met Ala Lys Arg Asn Ala Glu Lys Glu Leu Thr Asp Arg Asn Trp Asp
1               5                   10                  15

Gln Glu Asp Glu Ala Glu Glu Val Gly Thr Phe Ser Met Ala Ser Glu
                20                  25                  30

Glu Val Leu Lys Asn Arg Ala Ile Lys Lys Ala Lys Arg Arg Asn Val
            35                  40                  45

Gly Phe Glu Ser Asp Thr Gly Gly Ala Phe Lys Gly Phe Lys Gly Leu
        50                  55                  60

Val Val Pro Ser Gly Gly Arg Phe Ser Gly Phe Gly Ser Gly Ala
65                  70                  75                  80

Gly Gly Lys Pro Leu Glu Gly Leu Ser Asn Gly Asn Asn Ile Thr Ser
                85                  90                  95

Ala Pro Pro Phe Ala Ser Ala Lys Ala Ala Asp Pro Lys Val Ala
            100                 105                 110

Phe Gly Ser Leu Ala Ala Asn Gly Pro Thr Thr Leu Val Asp Lys Val
        115                 120                 125

Ser Asn Pro Lys Thr Asn Gly Asp Ser Gln Gln Pro Ser Ser Ser Gly
    130                 135                 140

Leu Ala Ser Ser Lys Ala Cys Val Gly Asn Ala Tyr His Lys Gln Leu
145                 150                 155                 160

Ala Ala Leu Asn Cys Ser Val Arg Asp Trp Ile Val Lys His Val Asn
                165                 170                 175

```
Thr Asn Pro Leu Cys Asp Leu Thr Pro Ile Phe Lys Asp Tyr Glu Lys
            180                 185                 190

Tyr Leu Ala Asn Ile Glu Gln Gln His Gly Asn Ser Gly Arg Asn Ser
            195                 200                 205

Glu Ser Glu Ser Asn Lys Val Ala Ala Glu Thr Gln Ser Pro Ser Leu
            210                 215                 220

Phe Gly Ser Thr Lys Leu Gln Gln Glu Ser Thr Phe Leu Phe His Gly
225                 230                 235                 240

Asn Lys Thr Glu Asp Thr Pro Asp Lys Lys Met Glu Val Ala Ser Glu
            245                 250                 255

Lys Lys Thr Asp Pro Ser Ser Leu Gly Ala Thr Ser Ala Ser Phe Asn
            260                 265                 270

Phe Gly Lys Lys Val Asp Ser Ser Val Leu Gly Ser Leu Ser Ser Val
            275                 280                 285

Pro Leu Thr Gly Phe Ser Phe Ser Pro Gly Asn Ser Ser Leu Phe Gly
            290                 295                 300

Lys Asp Thr Thr Gln Ser Lys Pro Val Ser Ser Pro Phe Pro Thr Lys
305                 310                 315                 320

Pro Leu Glu Gly Gln Ala Glu Gly Asp Ser Gly Glu Cys Lys Gly Gly
            325                 330                 335

Asp Glu Glu Asn Asp Glu Pro Pro Lys Val Val Thr Glu Val
            340                 345                 350

Lys Glu Glu Asp Ala Phe Tyr Ser Lys Lys Cys Lys Leu Phe Tyr Lys
            355                 360                 365

Lys Asp Asn Glu Phe Lys Glu Lys Gly Ile Gly Thr Leu His Leu Lys
            370                 375                 380

Pro Thr Ala Asn Gln Lys Thr Gln Leu Leu Val Arg Ala Asp Thr Asn
385                 390                 395                 400

Leu Gly Asn Ile Leu Leu Asn Val Leu Ile Pro Pro Asn Met Pro Cys
            405                 410                 415

Thr Arg Thr Gly Lys Asn Asn Val Leu Ile Val Cys Val Pro Asn Pro
            420                 425                 430

Pro Ile Asp Glu Lys Asn Ala Thr Met Pro Val Thr Met Leu Ile Arg
            435                 440                 445

Val Lys Thr Ser Glu Asp Ala Asp Glu Leu His Lys Ile Leu Leu Glu
            450                 455                 460

Lys Lys Asp Ala
465

<210> SEQ ID NO 87
<211> LENGTH: 1130
<212> TYPE: PRT
<213> ORGANISM: Homo sapiens

<400> SEQUENCE: 87

Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
            35                  40                  45

Asn Ser Lys Glu Asn Leu Leu Ala Gly Pro Ser Glu Asn Asp Pro Asn
            50                  55                  60

Leu Phe Val Ala Leu Tyr Asp Phe Val Ala Ser Gly Asp Asn Thr Leu
```

```
                65                  70                  75                  80
Ser Ile Thr Lys Gly Glu Lys Leu Arg Val Leu Gly Tyr Asn His Asn
                    85                  90                  95

Gly Glu Trp Cys Glu Ala Gln Thr Lys Asn Gly Gln Gly Trp Val Pro
                    100                 105                 110

Ser Asn Tyr Ile Thr Pro Val Asn Ser Leu Glu Lys His Ser Trp Tyr
                    115                 120                 125

His Gly Pro Val Ser Arg Asn Ala Ala Glu Tyr Leu Leu Ser Ser Gly
        130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                    165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gln Tyr Gly Glu Val
            245                 250                 255

Tyr Glu Gly Val Trp Lys Lys Tyr Ser Leu Thr Val Ala Val Lys Thr
                260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
        290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
            420                 425                 430

Ala Thr Tyr Gly Met Ser Pro Tyr Pro Gly Ile Asp Leu Ser Gln Val
        435                 440                 445

Tyr Glu Leu Leu Glu Lys Asp Tyr Arg Met Glu Arg Pro Glu Gly Cys
        450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495
```

```
Phe Gln Glu Ser Ser Ile Ser Asp Glu Val Glu Lys Glu Leu Gly Lys
            500                 505                 510

Gln Gly Val Arg Gly Ala Val Ser Thr Leu Leu Gln Ala Pro Glu Leu
            515                 520                 525

Pro Thr Lys Thr Arg Thr Ser Arg Arg Ala Ala Glu His Arg Asp Thr
            530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
            595                 600                 605

Lys Thr Ala Pro Thr Pro Pro Lys Arg Ser Ser Ser Phe Arg Glu Met
            610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
            675                 680                 685

Lys Ser Ser Thr Leu Thr Ser Ser Arg Leu Ala Thr Gly Glu Glu Glu
            690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
            755                 760                 765

Glu Asn Arg Ser Asp Gln Val Thr Arg Gly Thr Val Thr Pro Pro
            770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Gly Lys Gly Ser Ala Leu Gly Thr Pro Ala Ala Ala
            835                 840                 845

Glu Pro Val Thr Pro Thr Ser Lys Ala Gly Ser Gly Ala Pro Gly Gly
            850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Pro Ala Ser Ala Gly Lys Ala Gly Gly
            900                 905                 910
```

```
Lys Pro Ser Gln Ser Pro Ser Gln Glu Ala Ala Gly Glu Ala Val Leu
            915                 920                 925

Gly Ala Lys Thr Lys Ala Thr Ser Leu Val Asp Ala Val Asn Ser Asp
    930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ala Leu
                980                 985                 990

Ala Gly Asp Gln Pro Ser Ser Thr Ala Phe Ile Pro Leu Ile Ser Thr
    995                 1000                1005

Arg Val Ser Leu Arg Lys Thr Arg Gln Pro Pro Glu Arg Ile Ala Ser
    1010                1015                1020

Gly Ala Ile Thr Lys Gly Val Val Leu Asp Ser Thr Glu Ala Leu Cys
1025                1030                1035                1040

Leu Ala Ile Ser Arg Asn Ser Glu Gln Met Ala Ser His Ser Ala Val
                1045                1050                1055

Leu Glu Ala Gly Lys Asn Leu Tyr Thr Phe Cys Val Ser Tyr Val Asp
    1060                1065                1070

Ser Ile Gln Gln Met Arg Asn Lys Phe Ala Phe Arg Glu Ala Ile Asn
    1075                1080                1085

Lys Leu Glu Asn Asn Leu Arg Glu Leu Gln Ile Cys Pro Ala Thr Ala
    1090                1095                1100

Gly Ser Gly Pro Ala Ala Thr Gln Asp Phe Ser Lys Leu Leu Ser Ser
1105                1110                1115                1120

Val Lys Glu Ile Ser Asp Ile Val Gln Arg
                1125                1130

<210> SEQ ID NO 88
<211> LENGTH: 209
<212> TYPE: PRT
<213> ORGANISM: Homo sapiens

<400> SEQUENCE: 88

Met Lys Phe Lys Leu His Val Asn Ser Ala Arg Gln Tyr Lys Asp Leu
1               5                   10                  15

Trp Asn Met Ser Asp Asp Lys Pro Phe Leu Cys Thr Ala Pro Gly Cys
            20                  25                  30

Gly Gln Arg Phe Thr Asn Glu Asp His Leu Ala Val His Lys His Lys
        35                  40                  45

His Glu Met Thr Leu Lys Phe Gly Pro Ala Arg Asn Asp Ser Val Ile
    50                  55                  60

Val Ala Asp Gln Thr Pro Thr Pro Thr Arg Phe Leu Lys Asn Cys Glu
65                  70                  75                  80

Glu Val Gly Leu Phe Asn Glu Leu Ala Ser Pro Phe Glu Asn Glu Phe
                85                  90                  95

Lys Lys Ala Ser Glu Asp Asp Ile Lys Lys Met Pro Leu Asp Leu Ser
            100                 105                 110

Pro Leu Ala Thr Pro Ile Ile Arg Ser Lys Ile Glu Glu Pro Ser Val
        115                 120                 125

Val Glu Thr Thr His Gln Asp Ser Pro Leu Pro His Pro Glu Ser Thr
    130                 135                 140

Thr Ser Asp Glu Lys Glu Val Pro Leu Ala Gln Thr Ala Gln Pro Thr
145                 150                 155                 160
```

```
Ser Ala Ile Val Arg Pro Ala Ser Leu Gln Val Pro Asn Val Leu Leu
            165                 170                 175

Thr Ser Ser Asp Ser Ser Val Ile Ile Gln Gln Ala Val Pro Ser Pro
            180                 185                 190

Thr Ser Ser Thr Val Ile Thr Gln Ala Pro Ser Ser Asn Arg Pro Ile
            195                 200                 205

Val

<210> SEQ ID NO 89
<211> LENGTH: 505
<212> TYPE: PRT
<213> ORGANISM: Homo sapiens

<400> SEQUENCE: 89

Met Lys Phe Lys Leu His Val Asn Ser Ala Arg Gln Tyr Lys Asp Leu
1               5                   10                  15

Trp Asn Met Ser Asp Asp Lys Pro Phe Leu Cys Thr Ala Pro Gly Cys
            20                  25                  30

Gly Gln Arg Phe Thr Asn Glu Asp His Leu Ala Val His Lys His Lys
            35                  40                  45

His Glu Met Thr Leu Lys Phe Gly Pro Ala Arg Asn Asp Ser Val Ile
    50                  55                  60

Val Ala Asp Gln Thr Pro Thr Pro Thr Arg Phe Leu Lys Asn Cys Glu
65                  70                  75                  80

Glu Val Gly Leu Phe Asn Glu Leu Ala Ser Pro Phe Glu Asn Glu Phe
                85                  90                  95

Lys Lys Ala Ser Glu Asp Asp Ile Lys Lys Met Pro Leu Asp Leu Ser
            100                 105                 110

Pro Leu Ala Thr Pro Ile Ile Arg Ser Lys Ile Glu Pro Ser Val
            115                 120                 125

Val Glu Thr Thr His Gln Asp Ser Pro Leu Pro His Pro Glu Ser Thr
    130                 135                 140

Thr Ser Asp Glu Lys Glu Val Pro Leu Ala Gln Thr Ala Gln Pro Thr
145                 150                 155                 160

Ser Ala Ile Val Arg Pro Ala Ser Leu Gln Val Pro Asn Val Leu Leu
            165                 170                 175

Thr Ser Ser Asp Ser Ser Val Ile Ile Gln Gln Ala Val Pro Ser Pro
            180                 185                 190

Thr Ser Ser Thr Val Ile Thr Gln Ala Pro Ser Ser Asn Arg Pro Ile
            195                 200                 205

Val Pro Val Pro Gly Pro Phe Pro Leu Leu Leu His Leu Pro Asn Gly
            210                 215                 220

Gln Thr Met Pro Val Ala Ile Pro Ala Ser Ile Thr Ser Ser Asn Val
225                 230                 235                 240

His Val Pro Ala Ala Val Pro Leu Val Arg Pro Val Thr Met Val Pro
            245                 250                 255

Ser Val Pro Gly Ile Pro Gly Pro Ser Ser Pro Gln Pro Val Gln Ser
            260                 265                 270

Glu Ala Lys Met Arg Leu Lys Ala Ala Leu Thr Gln Gln His Pro Pro
            275                 280                 285

Val Thr Asn Gly Asp Thr Val Lys Gly His Gly Ser Gly Leu Val Arg
            290                 295                 300

Thr Gln Ser Glu Glu Ser Arg Pro Gln Ser Leu Gln Gln Pro Ala Thr
305                 310                 315                 320
```

```
Ser Thr Thr Glu Thr Pro Ala Ser Pro Ala His Thr Pro Gln Thr
            325                 330                 335

Gln Ser Thr Ser Gly Arg Arg Arg Ala Ala Asn Glu Asp Pro Asp
            340                 345                 350

Glu Lys Arg Arg Lys Phe Leu Glu Arg Asn Arg Ala Ala Ala Ser Arg
            355                 360                 365

Cys Arg Gln Lys Arg Lys Val Trp Val Gln Ser Leu Glu Lys Lys Ala
370                 375                 380

Glu Asp Leu Ser Ser Leu Asn Gly Gln Leu Gln Ser Glu Val Thr Leu
385                 390                 395                 400

Leu Arg Asn Glu Val Ala Gln Leu Lys Gln Leu Leu Leu Ala His Lys
            405                 410                 415

Asp Cys Pro Val Thr Ala Met Gln Lys Lys Ser Gly Tyr His Thr Ala
            420                 425                 430

Asp Lys Asp Asp Ser Ser Glu Asp Ile Ser Val Pro Ser Ser Pro His
            435                 440                 445

Thr Glu Ala Ile Gln His Ser Ser Val Ser Thr Ser Asn Gly Val Ser
            450                 455                 460

Ser Thr Ser Lys Ala Glu Ala Val Ala Thr Ser Val Leu Thr Gln Met
465                 470                 475                 480

Ala Asp Gln Ser Thr Glu Pro Ala Leu Ser Gln Ile Val Met Ala Pro
            485                 490                 495

Ser Ser Gln Ser Gln Pro Ser Gly Ser
            500                 505

<210> SEQ ID NO 90
<211> LENGTH: 545
<212> TYPE: PRT
<213> ORGANISM: Homo sapiens

<400> SEQUENCE: 90

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Asp Ala Thr Pro Pro Pro Val Ile Ala Pro
```

```
                180             185             190
Arg Pro Glu His Thr Lys Ser Val Tyr Thr Arg Ser Val Ile Glu Pro
            195                 200                 205
Leu Pro Val Thr Pro Thr Arg Asp Val Ala Thr Ser Pro Ile Ser Pro
            210                 215                 220
Thr Glu Asn Asn Thr Thr Pro Pro Asp Ala Leu Thr Arg Asn Thr Glu
225                 230                 235                 240
Lys Gln Lys Lys Pro Lys Met Ser Asp Glu Glu Ile Leu Glu Lys
                245                 250                 255
Leu Arg Ser Ile Val Ser Val Gly Asp Pro Lys Lys Tyr Thr Arg
            260                 265                 270
Phe Glu Lys Ile Gly Gln Gly Ala Ser Gly Thr Val Tyr Thr Ala Met
            275                 280                 285
Asp Val Ala Thr Gly Gln Glu Val Ala Ile Lys Gln Met Asn Leu Gln
            290                 295                 300
Gln Gln Pro Lys Lys Glu Leu Ile Ile Asn Glu Ile Leu Val Met Arg
305                 310                 315                 320
Glu Asn Lys Asn Pro Asn Ile Val Asn Tyr Leu Asp Ser Tyr Leu Val
                325                 330                 335
Gly Asp Glu Leu Trp Val Val Met Glu Tyr Leu Ala Gly Gly Ser Leu
            340                 345                 350
Thr Asp Val Val Thr Glu Thr Cys Met Asp Glu Gly Gln Ile Ala Ala
            355                 360                 365
Val Cys Arg Glu Cys Leu Gln Ala Leu Glu Phe Leu His Ser Asn Gln
370                 375                 380
Val Ile His Arg Asp Ile Lys Ser Asp Asn Ile Leu Leu Gly Met Asp
385                 390                 395                 400
Gly Ser Val Lys Leu Thr Asp Phe Gly Phe Cys Ala Gln Ile Thr Pro
            405                 410                 415
Glu Gln Ser Lys Arg Ser Thr Met Val Gly Thr Pro Tyr Trp Met Ala
            420                 425                 430
Pro Glu Val Val Thr Arg Lys Ala Tyr Gly Pro Lys Val Asp Ile Trp
            435                 440                 445
Ser Leu Gly Ile Met Ala Ile Glu Met Ile Glu Gly Glu Pro Pro Tyr
            450                 455                 460
Leu Asn Glu Asn Pro Leu Arg Ala Leu Tyr Leu Ile Ala Thr Asn Gly
465                 470                 475                 480
Thr Pro Glu Leu Gln Asn Pro Glu Lys Leu Ser Ala Ile Phe Arg Asp
                485                 490                 495
Phe Leu Asn Arg Cys Leu Glu Met Asp Val Glu Lys Arg Gly Ser Ala
            500                 505                 510
Lys Glu Leu Leu Gln His Gln Phe Leu Lys Ile Ala Lys Pro Leu Ser
            515                 520                 525
Ser Leu Thr Pro Leu Ile Ala Ala Ala Lys Glu Ala Thr Lys Asn Asn
            530                 535                 540
His
545

<210> SEQ ID NO 91
<211> LENGTH: 586
<212> TYPE: PRT
<213> ORGANISM: Homo sapiens

<400> SEQUENCE: 91
```

```
Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
            20                  25                  30

Ser Gln Ser Gln Gly Ile Ser Ser Ser Thr Ser Thr Met Pro Asn
        35                  40                  45

Ser Ser Gln Ser Ser His Ser Ser Ser Gly Thr Leu Ser Ser Leu Glu
    50                  55                  60

Thr Val Ser Thr Gln Glu Leu Tyr Ser Ile Pro Glu Asp Gln Glu Pro
65                  70                  75                  80

Glu Asp Gln Glu Pro Glu Glu Pro Thr Pro Ala Pro Trp Ala Arg Leu
                85                  90                  95

Trp Ala Leu Gln Asp Gly Phe Ala Asn Leu Glu Thr Glu Ser Gly His
            100                 105                 110

Val Thr Gln Ser Asp Leu Glu Leu Leu Leu Ser Ser Asp Pro Pro Ala
            115                 120                 125

Ser Ala Ser Gln Ser Ala Gly Ile Arg Gly Val Arg His His Pro Arg
    130                 135                 140

Pro Val Cys Ser Leu Lys Cys Val Asn Asp Asn Tyr Trp Phe Gly Arg
145                 150                 155                 160

Asp Lys Ser Cys Glu Tyr Cys Phe Asp Glu Pro Leu Leu Lys Arg Thr
                165                 170                 175

Asp Lys Tyr Arg Thr Tyr Ser Lys Lys His Phe Arg Ile Phe Arg Glu
            180                 185                 190

Val Gly Pro Lys Asn Ser Tyr Ile Ala Tyr Ile Glu Asp His Ser Gly
            195                 200                 205

Asn Gly Thr Phe Val Asn Thr Glu Leu Val Gly Lys Gly Lys Arg Arg
210                 215                 220

Pro Leu Asn Asn Asn Ser Glu Ile Ala Leu Ser Leu Ser Arg Asn Lys
225                 230                 235                 240

Val Phe Val Phe Phe Asp Leu Thr Val Asp Asp Gln Ser Val Tyr Pro
                245                 250                 255

Lys Ala Leu Arg Asp Glu Tyr Ile Met Ser Lys Thr Leu Gly Ser Gly
            260                 265                 270

Ala Cys Gly Glu Val Lys Leu Ala Phe Glu Arg Lys Thr Cys Lys Lys
            275                 280                 285

Val Ala Ile Lys Ile Ile Ser Lys Arg Lys Phe Ala Ile Gly Ser Ala
            290                 295                 300

Arg Glu Ala Asp Pro Ala Leu Asn Val Glu Thr Glu Ile Glu Ile Leu
305                 310                 315                 320

Lys Lys Leu Asn His Pro Cys Ile Ile Lys Ile Lys Asn Phe Phe Asp
                325                 330                 335

Ala Glu Asp Tyr Tyr Ile Val Leu Glu Leu Met Glu Gly Gly Glu Leu
            340                 345                 350

Phe Asp Lys Val Val Gly Asn Lys Arg Leu Lys Glu Ala Thr Cys Lys
            355                 360                 365

Leu Tyr Phe Tyr Gln Met Leu Leu Ala Val Gln Tyr Leu His Glu Asn
    370                 375                 380

Gly Ile Ile His Arg Asp Leu Lys Pro Glu Asn Val Leu Leu Ser Ser
385                 390                 395                 400

Gln Glu Glu Asp Cys Leu Ile Lys Ile Thr Asp Phe Gly His Ser Lys
                405                 410                 415

Ile Leu Gly Glu Thr Ser Leu Met Arg Thr Leu Cys Gly Thr Pro Thr
```

```
            420                 425                 430
Tyr Leu Ala Pro Glu Val Leu Val Ser Val Gly Thr Ala Gly Tyr Asn
            435                 440                 445
Arg Ala Val Asp Cys Trp Ser Leu Gly Val Ile Leu Phe Ile Cys Leu
            450                 455                 460
Ser Gly Tyr Pro Pro Phe Ser Glu His Arg Thr Gln Val Ser Leu Lys
465                 470                 475                 480
Asp Gln Ile Thr Ser Gly Lys Tyr Asn Phe Ile Pro Glu Val Trp Ala
            485                 490                 495
Glu Val Ser Glu Lys Ala Leu Asp Leu Val Lys Lys Leu Leu Val Val
            500                 505                 510
Asp Pro Lys Ala Arg Phe Thr Thr Glu Glu Ala Leu Arg His Pro Trp
            515                 520                 525
Leu Gln Asp Glu Asp Met Lys Arg Lys Phe Gln Asp Leu Leu Ser Glu
            530                 535                 540
Glu Asn Glu Ser Thr Ala Leu Pro Gln Val Leu Ala Gln Pro Ser Thr
545                 550                 555                 560
Ser Arg Lys Arg Pro Arg Glu Gly Glu Ala Glu Gly Ala Glu Thr Thr
            565                 570                 575
Lys Arg Pro Ala Val Cys Ala Ala Val Leu
            580                 585
```

<210> SEQ ID NO 92
<211> LENGTH: 3267
<212> TYPE: PRT
<213> ORGANISM: Homo sapiens

<400> SEQUENCE: 92

```
Met Gln Lys Ala Arg Gly Thr Arg Gly Glu Asp Ala Gly Thr Arg Ala
1               5                   10                  15
Pro Pro Ser Pro Gly Val Pro Pro Lys Arg Ala Lys Val Gly Ala Gly
            20                  25                  30
Gly Gly Ala Pro Val Ala Val Ala Gly Ala Pro Val Phe Leu Arg Pro
            35                  40                  45
Leu Lys Asn Ala Ala Val Cys Ala Gly Ser Asp Val Arg Leu Arg Val
            50                  55                  60
Val Val Ser Gly Thr Pro Gln Pro Ser Leu Arg Trp Phe Arg Asp Gly
65              70                  75                  80
Gln Leu Leu Pro Ala Pro Ala Pro Glu Pro Ser Cys Leu Trp Leu Arg
            85                  90                  95
Arg Cys Gly Ala Gln Asp Ala Gly Val Tyr Ser Cys Met Ala Gln Asn
            100                 105                 110
Glu Arg Gly Arg Ala Ser Cys Glu Ala Val Leu Thr Val Leu Glu Val
            115                 120                 125
Gly Asp Ser Glu Thr Ala Glu Asp Asp Ile Ser Asp Val Gln Gly Thr
            130                 135                 140
Gln Arg Leu Glu Leu Arg Asp Asp Gly Ala Phe Ser Thr Pro Thr Gly
145                 150                 155                 160
Gly Ser Asp Thr Leu Val Gly Thr Ser Leu Asp Thr Pro Pro Thr Ser
            165                 170                 175
Val Thr Gly Thr Ser Glu Glu Val Ser Trp Trp Gly Ser Gly Gln
            180                 185                 190
Thr Val Leu Glu Gln Glu Ala Gly Ser Gly Gly Thr Arg Arg Leu
            195                 200                 205
```

```
Pro Gly Ser Pro Arg Gln Ala Gln Ala Thr Gly Ala Gly Pro Arg His
    210                 215                 220

Leu Gly Val Glu Pro Leu Val Arg Ala Ser Arg Ala Asn Leu Val Gly
225                 230                 235                 240

Ala Ser Trp Gly Ser Glu Asp Ser Leu Ser Val Ala Ser Asp Leu Tyr
                245                 250                 255

Gly Ser Ala Phe Ser Leu Tyr Arg Gly Arg Ala Leu Ser Ile His Val
            260                 265                 270

Ser Val Pro Gln Ser Gly Leu Arg Glu Glu Pro Asp Leu Gln Pro
        275                 280                 285

Gln Leu Ala Ser Glu Ala Pro Arg Arg Pro Ala Gln Pro Pro Ser
290                 295                 300

Lys Ser Ala Leu Leu Pro Pro Ser Pro Arg Val Gly Lys Arg Ser
305                 310                 315                 320

Pro Pro Gly Pro Pro Ala Gln Pro Ala Ala Thr Pro Thr Ser Pro His
                325                 330                 335

Arg Arg Thr Gln Glu Pro Val Leu Pro Glu Asp Thr Thr Thr Glu Glu
            340                 345                 350

Lys Arg Gly Lys Lys Ser Lys Ser Ser Gly Pro Ser Leu Ala Gly Thr
            355                 360                 365

Ala Glu Ser Arg Pro Gln Thr Pro Leu Ser Glu Ala Ser Gly Arg Leu
370                 375                 380

Ser Ala Leu Gly Arg Ser Pro Arg Leu Val Arg Ala Gly Ser Arg Ile
385                 390                 395                 400

Leu Asp Lys Leu Gln Phe Phe Glu Glu Arg Arg Arg Ser Leu Glu Arg
                405                 410                 415

Ser Asp Ser Pro Pro Ala Pro Leu Arg Pro Trp Val Pro Leu Arg Lys
            420                 425                 430

Ala Arg Ser Leu Glu Gln Pro Lys Ser Glu Arg Gly Ala Pro Trp Gly
            435                 440                 445

Thr Pro Gly Ala Ser Gln Glu Glu Leu Arg Ala Pro Gly Ser Val Ala
    450                 455                 460

Glu Arg Arg Arg Leu Phe Gln Gln Lys Ala Ala Ser Leu Asp Glu Arg
465                 470                 475                 480

Thr Arg Gln Arg Ser Pro Ala Ser Asp Leu Glu Leu Arg Phe Ala Gln
                485                 490                 495

Glu Leu Gly Arg Ile Arg Arg Ser Thr Ser Arg Glu Glu Leu Val Arg
                500                 505                 510

Ser His Glu Ser Leu Arg Ala Thr Leu Gln Arg Ala Pro Ser Pro Arg
            515                 520                 525

Glu Pro Gly Glu Pro Pro Leu Phe Ser Arg Pro Ser Thr Pro Lys Thr
    530                 535                 540

Ser Arg Ala Val Ser Pro Ala Ala Gln Pro Ser Pro Ser Ser
545                 550                 555                 560

Ala Glu Lys Pro Gly Asp Glu Pro Gly Arg Pro Arg Ser Arg Gly Pro
                565                 570                 575

Ala Gly Arg Thr Glu Pro Gly Glu Gly Pro Gln Gln Glu Val Arg Arg
            580                 585                 590

Arg Asp Gln Phe Pro Leu Thr Arg Ser Arg Ala Ile Gln Glu Cys Arg
            595                 600                 605

Ser Pro Val Pro Pro Pro Ala Ala Asp Pro Glu Ala Arg Thr Lys
610                 615                 620

Ala Pro Pro Gly Arg Lys Arg Glu Pro Pro Ala Gln Ala Val Arg Phe
```

-continued

```
            625                 630                 635                 640
        Leu Pro Trp Ala Thr Pro Gly Leu Glu Gly Ala Ala Val Pro Gln Thr
                        645                 650                 655
        Leu Glu Lys Asn Arg Ala Gly Pro Glu Ala Glu Lys Arg Leu Arg Arg
                        660                 665                 670
        Gly Pro Glu Glu Asp Gly Pro Trp Gly Pro Trp Asp Arg Gly Ala
                        675                 680                 685
        Arg Ser Gln Gly Lys Gly Arg Arg Ala Arg Pro Thr Ser Pro Glu Leu
                        690                 695                 700
        Glu Ser Ser Asp Asp Ser Tyr Val Ser Ala Gly Glu Glu Pro Leu Glu
        705                 710                 715                 720
        Ala Pro Val Phe Glu Ile Pro Leu Gln Asn Val Val Ala Pro Gly
                        725                 730                 735
        Ala Asp Val Leu Leu Lys Cys Ile Ile Thr Ala Asn Pro Pro Pro Gln
                        740                 745                 750
        Val Ser Trp His Lys Asp Gly Ser Ala Leu Arg Ser Glu Gly Arg Leu
                        755                 760                 765
        Leu Leu Arg Ala Glu Gly Glu Arg His Thr Leu Leu Leu Arg Glu Ala
                        770                 775                 780
        Arg Ala Ala Asp Ala Gly Ser Tyr Met Ala Thr Ala Thr Asn Glu Leu
        785                 790                 795                 800
        Gly Gln Ala Thr Cys Ala Ala Ser Leu Thr Val Arg Pro Gly Gly Ser
                        805                 810                 815
        Thr Ser Pro Phe Ser Ser Pro Ile Thr Ser Asp Glu Glu Tyr Leu Ser
                        820                 825                 830
        Pro Pro Glu Glu Phe Pro Glu Pro Gly Glu Thr Trp Pro Arg Thr Pro
                        835                 840                 845
        Thr Met Lys Pro Ser Pro Ser Gln Asn Arg Arg Ser Ser Asp Thr Gly
                        850                 855                 860
        Ser Lys Ala Pro Pro Thr Phe Lys Val Ser Leu Met Asp Gln Ser Val
        865                 870                 875                 880
        Arg Glu Gly Gln Asp Val Ile Met Ser Ile Arg Val Gln Gly Glu Pro
                        885                 890                 895
        Lys Pro Val Val Ser Trp Leu Arg Asn Arg Gln Pro Val Arg Pro Asp
                        900                 905                 910
        Gln Arg Arg Phe Ala Glu Glu Ala Glu Gly Gly Leu Cys Arg Leu Arg
                        915                 920                 925
        Ile Leu Ala Ala Glu Arg Gly Asp Ala Gly Phe Tyr Thr Cys Lys Ala
                        930                 935                 940
        Val Asn Glu Tyr Gly Ala Arg Gln Cys Glu Ala Arg Leu Glu Val Arg
        945                 950                 955                 960
        Ala His Pro Glu Ser Arg Ser Leu Ala Val Leu Ala Pro Leu Gln Asp
                        965                 970                 975
        Val Asp Val Gly Ala Gly Glu Met Ala Leu Phe Glu Cys Leu Val Ala
                        980                 985                 990
        Gly Pro Thr Asp Val Glu Val Asp Trp Leu Cys Arg Gly Arg Leu Leu
                        995                 1000                1005
        Gln Pro Ala Leu Leu Lys Cys Lys Met His Phe Asp Gly Arg Lys Cys
                        1010                1015                1020
        Lys Leu Leu Leu Thr Ser Val His Glu Asp Asp Ser Gly Val Tyr Thr
        1025                1030                1035                1040
        Cys Lys Leu Ser Thr Ala Lys Asp Glu Leu Thr Cys Ser Ala Arg Leu
                        1045                1050                1055
```

```
Thr Val Arg Pro Ser Leu Ala Pro Leu Phe Thr Arg Leu Leu Glu Asp
            1060                1065                1070

Val Glu Val Leu Glu Gly Arg Ala Ala Arg Phe Asp Cys Lys Ile Ser
        1075                1080                1085

Gly Thr Pro Pro Val Val Thr Trp Thr His Phe Gly Cys Pro Met
    1090                1095                1100

Glu Glu Ser Glu Asn Leu Arg Leu Arg Gln Asp Gly Gly Leu His Ser
1105                1110                1115                1120

Leu His Ile Ala His Val Gly Ser Glu Asp Glu Gly Leu Tyr Ala Val
            1125                1130                1135

Ser Ala Val Asn Thr His Gly Gln Ala His Cys Ser Ala Gln Leu Tyr
            1140                1145                1150

Val Glu Glu Pro Arg Thr Ala Ala Ser Gly Pro Ser Ser Lys Leu Glu
        1155                1160                1165

Lys Met Pro Ser Ile Pro Glu Glu Pro Glu Gln Gly Glu Leu Glu Arg
    1170                1175                1180

Leu Ser Ile Pro Asp Phe Leu Arg Pro Leu Gln Asp Leu Glu Val Gly
1185                1190                1195                1200

Leu Ala Lys Glu Ala Met Leu Glu Cys Gln Val Thr Gly Leu Pro Tyr
            1205                1210                1215

Pro Thr Ile Ser Trp Phe His Asn Gly His Arg Ile Gln Ser Ser Asp
            1220                1225                1230

Asp Arg Arg Met Thr Gln Tyr Arg Asp Val His Arg Leu Val Phe Pro
            1235                1240                1245

Ala Val Gly Pro Gln His Ala Gly Val Tyr Lys Ser Val Ile Ala Asn
            1250                1255                1260

Lys Leu Gly Lys Ala Ala Cys Tyr Ala His Leu Tyr Val Thr Asp Val
1265                1270                1275                1280

Val Pro Gly Pro Pro Asp Gly Ala Pro Gln Val Val Ala Val Thr Gly
            1285                1290                1295

Arg Met Val Thr Leu Thr Trp Asn Pro Pro Arg Ser Leu Asp Met Ala
            1300                1305                1310

Ile Asp Pro Asp Ser Leu Thr Tyr Thr Val Gln His Gln Val Leu Gly
            1315                1320                1325

Ser Asp Gln Trp Thr Ala Leu Val Thr Gly Leu Arg Glu Pro Gly Trp
            1330                1335                1340

Ala Ala Thr Gly Leu Arg Lys Gly Val Gln His Ile Phe Arg Val Leu
1345                1350                1355                1360

Ser Thr Thr Val Lys Ser Ser Lys Pro Ser Pro Ser Glu Pro
            1365                1370                1375

Val Gln Leu Leu Glu His Gly Pro Thr Leu Glu Glu Ala Pro Ala Met
            1380                1385                1390

Leu Asp Lys Pro Asp Ile Val Tyr Val Val Glu Gly Gln Pro Ala Ser
        1395                1400                1405

Val Thr Val Thr Phe Asn His Val Glu Ala Gln Val Val Trp Arg Ser
    1410                1415                1420

Cys Arg Gly Ala Leu Leu Glu Ala Arg Ala Gly Val Tyr Glu Leu Ser
1425                1430                1435                1440

Gln Pro Asp Asp Gln Tyr Cys Leu Arg Ile Cys Arg Val Ser Arg
            1445                1450                1455

Arg Asp Met Gly Ala Leu Thr Cys Thr Ala Arg Asn Arg His Gly Thr
            1460                1465                1470
```

```
Gln Thr Cys Ser Val Thr Leu Glu Leu Ala Glu Ala Pro Arg Phe Glu
        1475                1480                1485

Ser Ile Met Glu Asp Val Glu Val Gly Ala Gly Glu Thr Ala Arg Phe
        1490                1495                1500

Ala Val Val Glu Gly Lys Pro Leu Pro Asp Ile Met Trp Tyr Lys
1505                1510                1515                1520

Asp Glu Val Leu Leu Thr Glu Ser Ser His Val Ser Phe Val Tyr Glu
            1525                1530                1535

Glu Asn Glu Cys Ser Leu Val Val Leu Ser Thr Gly Ala Gln Asp Gly
            1540                1545                1550

Gly Val Tyr Thr Cys Thr Ala Gln Asn Leu Ala Gly Glu Val Ser Cys
        1555                1560                1565

Lys Ala Glu Leu Ala Val His Ser Ala Gln Thr Ala Met Glu Val Glu
        1570                1575                1580

Gly Val Gly Glu Asp Glu Asp His Arg Gly Arg Arg Leu Ser Asp Phe
1585                1590                1595                1600

Tyr Asp Ile His Gln Glu Ile Gly Arg Gly Ala Phe Ser Tyr Leu Arg
            1605                1610                1615

Arg Ile Val Glu Arg Ser Ser Gly Leu Glu Phe Ala Ala Lys Phe Ile
        1620                1625                1630

Pro Ser Gln Ala Lys Pro Lys Ala Ser Ala Arg Arg Glu Ala Arg Leu
        1635                1640                1645

Leu Ala Arg Leu Gln His Asp Cys Val Leu Tyr Phe His Glu Ala Phe
        1650                1655                1660

Glu Arg Arg Arg Gly Leu Val Ile Val Thr Glu Leu Cys Thr Glu Glu
1665                1670                1675                1680

Leu Leu Glu Arg Ile Ala Arg Lys Pro Thr Val Cys Glu Ser Glu Ile
            1685                1690                1695

Arg Ala Tyr Met Arg Gln Val Leu Glu Gly Ile His Tyr Leu His Gln
        1700                1705                1710

Ser His Val Leu His Leu Asp Val Lys Pro Glu Asn Leu Leu Val Trp
        1715                1720                1725

Asp Gly Ala Ala Gly Glu Gln Gln Val Arg Ile Cys Asp Phe Gly Asn
        1730                1735                1740

Ala Gln Glu Leu Thr Pro Gly Glu Pro Gln Tyr Cys Gln Tyr Gly Thr
1745                1750                1755                1760

Pro Glu Phe Val Ala Pro Glu Ile Val Asn Gln Ser Pro Val Ser Gly
            1765                1770                1775

Val Thr Asp Ile Trp Pro Val Gly Val Val Ala Phe Leu Cys Leu Thr
        1780                1785                1790

Gly Ile Ser Pro Phe Val Gly Glu Asn Asp Arg Thr Thr Leu Met Asn
        1795                1800                1805

Ile Arg Asn Tyr Asn Val Ala Phe Glu Glu Thr Thr Phe Leu Ser Leu
        1810                1815                1820

Ser Arg Glu Ala Arg Gly Phe Leu Ile Lys Val Leu Val Gln Asp Arg
1825                1830                1835                1840

Leu Arg Pro Thr Ala Glu Glu Thr Leu Glu His Pro Trp Phe Lys Thr
            1845                1850                1855

Gln Ala Lys Gly Ala Glu Val Ser Thr Asp His Leu Lys Leu Phe Leu
        1860                1865                1870

Ser Arg Arg Arg Trp Gln Arg Ser Gln Ile Ser Tyr Lys Cys His Leu
        1875                1880                1885

Val Leu Arg Pro Ile Pro Glu Leu Leu Arg Ala Pro Pro Glu Arg Val
```

```
            1890            1895            1900
Trp Val Thr Met Pro Arg Arg Pro Pro Ser Gly Gly Leu Ser Ser
1905            1910            1915            1920

Ser Ser Asp Ser Glu Glu Glu Leu Glu Glu Leu Pro Ser Val Pro
        1925            1930            1935

Arg Pro Leu Gln Pro Glu Phe Ser Gly Ser Arg Val Ser Leu Thr Asp
        1940            1945            1950

Ile Pro Thr Glu Asp Glu Ala Leu Gly Thr Pro Glu Thr Gly Ala Ala
        1955            1960            1965

Thr Pro Met Asp Trp Gln Glu Gln Gly Arg Ala Pro Ser Gln Asp Gln
        1970            1975            1980

Glu Ala Pro Ser Pro Glu Ala Leu Pro Ser Pro Gly Gln Glu Pro Ala
1985            1990            1995            2000

Ala Gly Ala Ser Pro Arg Arg Gly Glu Leu Arg Arg Gly Ser Ser Ala
        2005            2010            2015

Glu Ser Ala Leu Pro Arg Ala Gly Pro Arg Glu Leu Gly Arg Gly Leu
        2020            2025            2030

His Lys Ala Ala Ser Val Glu Leu Pro Gln Arg Arg Ser Pro Ser Pro
        2035            2040            2045

Gly Ala Thr Arg Leu Ala Arg Gly Gly Leu Gly Glu Gly Glu Tyr Ala
        2050            2055            2060

Gln Arg Leu Gln Ala Leu Arg Gln Arg Leu Leu Arg Gly Gly Pro Glu
2065            2070            2075            2080

Asp Gly Lys Val Ser Gly Leu Arg Gly Pro Leu Leu Glu Ser Leu Gly
        2085            2090            2095

Gly Arg Ala Arg Asp Pro Arg Met Ala Arg Ala Ala Ser Ser Glu Ala
        2100            2105            2110

Ala Pro His His Gln Pro Pro Leu Glu Asn Arg Gly Leu Gln Lys Ser
        2115            2120            2125

Ser Ser Phe Ser Gln Gly Glu Ala Glu Pro Arg Gly Arg His Arg Arg
        2130            2135            2140

Ala Gly Ala Pro Leu Glu Ile Pro Val Ala Arg Leu Gly Ala Arg Arg
2145            2150            2155            2160

Leu Gln Glu Ser Pro Ser Leu Ser Ala Leu Ser Glu Ala Gln Pro Ser
        2165            2170            2175

Ser Pro Ala Arg Pro Ser Ala Pro Lys Pro Ser Thr Pro Lys Ser Ala
        2180            2185            2190

Glu Pro Ser Ala Thr Thr Pro Ser Asp Ala Pro Gln Pro Pro Ala Pro
        2195            2200            2205

Gln Pro Ala Gln Asp Lys Ala Pro Glu Pro Arg Pro Glu Pro Val Arg
        2210            2215            2220

Ala Ser Lys Pro Ala Pro Pro Gln Ala Leu Gln Thr Leu Ala Leu
2225            2230            2235            2240

Pro Leu Thr Pro Tyr Ala Gln Ile Ile Gln Ser Leu Gln Leu Ser Gly
        2245            2250            2255

His Ala Gln Gly Pro Ser Gln Gly Pro Ala Ala Pro Ser Glu Pro
        2260            2265            2270

Lys Pro His Ala Ala Val Phe Ala Arg Val Ala Ser Pro Pro Gly
        2275            2280            2285

Ala Pro Glu Lys Arg Val Pro Ser Ala Gly Gly Pro Pro Val Leu Ala
        2290            2295            2300

Glu Lys Ala Arg Val Pro Thr Val Pro Pro Arg Pro Gly Ser Ser Leu
2305            2310            2315            2320
```

```
Ser Ser Ser Ile Glu Asn Leu Glu Ser Glu Ala Val Phe Glu Ala Lys
            2325                2330                2335

Phe Lys Arg Ser Arg Glu Ser Pro Leu Ser Leu Gly Leu Arg Leu Leu
            2340                2345                2350

Ser Arg Ser Arg Ser Glu Glu Arg Gly Pro Phe Arg Gly Ala Glu Glu
            2355                2360                2365

Glu Asp Gly Ile Tyr Arg Pro Ser Pro Ala Gly Thr Pro Leu Glu Leu
            2370                2375                2380

Val Arg Arg Pro Glu Arg Ser Arg Ser Val Gln Asp Leu Arg Ala Val
2385                2390                2395                2400

Gly Glu Pro Gly Leu Val Arg Arg Leu Ser Leu Ser Leu Ser Gln Arg
            2405                2410                2415

Leu Arg Arg Thr Pro Pro Ala Gln Arg His Pro Ala Trp Glu Ala Arg
            2420                2425                2430

Gly Gly Asp Gly Glu Ser Ser Glu Gly Gly Ser Ser Ala Arg Gly Ser
            2435                2440                2445

Pro Val Leu Ala Met Arg Arg Arg Leu Ser Phe Thr Leu Glu Arg Leu
            2450                2455                2460

Ser Ser Arg Leu Gln Arg Ser Gly Ser Ser Glu Asp Ser Gly Gly Ala
2465                2470                2475                2480

Ser Gly Arg Ser Thr Pro Leu Phe Gly Arg Leu Arg Arg Ala Thr Ser
            2485                2490                2495

Glu Gly Glu Ser Leu Arg Arg Leu Gly Leu Pro His Asn Gln Leu Ala
            2500                2505                2510

Ala Gln Ala Gly Ala Thr Thr Pro Ser Ala Glu Ser Leu Gly Ser Glu
            2515                2520                2525

Ala Ser Ala Thr Ser Gly Ser Ser Ala Pro Gly Glu Ser Arg Ser Arg
            2530                2535                2540

Leu Arg Trp Gly Phe Ser Arg Pro Arg Lys Asp Lys Gly Leu Ser Pro
2545                2550                2555                2560

Pro Asn Leu Ser Ala Ser Val Gln Glu Glu Leu Gly His Gln Tyr Val
            2565                2570                2575

Arg Ser Glu Ser Asp Phe Pro Pro Val Phe His Ile Lys Leu Lys Asp
            2580                2585                2590

Gln Val Leu Leu Glu Gly Glu Ala Ala Thr Leu Leu Cys Leu Pro Ala
            2595                2600                2605

Ala Cys Pro Ala Pro His Ile Ser Trp Met Lys Asp Lys Lys Ser Leu
            2610                2615                2620

Arg Ser Glu Pro Ser Val Ile Ile Val Ser Cys Lys Asp Gly Arg Gln
2625                2630                2635                2640

Leu Leu Ser Ile Pro Arg Ala Gly Lys Arg His Ala Gly Leu Tyr Glu
            2645                2650                2655

Cys Ser Ala Thr Asn Val Leu Gly Ser Ile Thr Ser Ser Cys Thr Val
            2660                2665                2670

Ala Val Ala Arg Val Pro Gly Lys Leu Ala Pro Glu Val Pro Gln
            2675                2680                2685

Thr Tyr Gln Asp Thr Ala Leu Val Leu Trp Lys Pro Gly Asp Ser Arg
            2690                2695                2700

Ala Pro Cys Thr Tyr Thr Leu Glu Arg Arg Val Asp Gly Glu Ser Val
2705                2710                2715                2720

Trp His Pro Val Ser Ser Gly Ile Pro Asp Cys Tyr Tyr Asn Val Thr
            2725                2730                2735
```

-continued

His Leu Pro Val Gly Val Thr Val Arg Phe Arg Val Ala Cys Ala Asn
        2740                2745                2750

Arg Ala Gly Gln Gly Pro Phe Ser Asn Ser Ser Glu Lys Val Phe Val
        2755                2760                2765

Arg Gly Thr Gln Asp Ser Ser Ala Val Pro Ser Ala Ala His Gln Glu
        2770                2775                2780

Ala Pro Val Thr Ser Arg Pro Ala Arg Ala Arg Pro Asp Ser Pro
2785                2790                2795                2800

Thr Ser Leu Ala Pro Pro Leu Ala Pro Ala Ala Pro Thr Pro Pro Ser
        2805                2810                2815

Val Thr Val Ser Pro Ser Ser Pro Pro Thr Pro Pro Ser Gln Ala Leu
        2820                2825                2830

Ser Ser Leu Lys Ala Val Gly Pro Pro Gln Thr Pro Pro Arg Arg
        2835                2840                2845

His Arg Gly Leu Gln Ala Ala Arg Pro Ala Glu Pro Thr Leu Pro Ser
        2850                2855                2860

Thr His Val Thr Pro Ser Glu Pro Lys Pro Phe Val Leu Asp Thr Gly
2865                2870                2875                2880

Thr Pro Ile Pro Ala Ser Thr Pro Gln Gly Val Lys Pro Val Ser Ser
        2885                2890                2895

Ser Thr Pro Val Tyr Val Val Thr Ser Phe Val Ser Ala Pro Pro Ala
        2900                2905                2910

Pro Glu Pro Pro Ala Pro Glu Pro Pro Pro Glu Pro Thr Lys Val Thr
        2915                2920                2925

Val Gln Ser Leu Ser Pro Ala Lys Glu Val Val Ser Ser Pro Gly Ser
        2930                2935                2940

Ser Pro Arg Ser Ser Pro Arg Pro Glu Gly Thr Thr Leu Arg Gln Gly
2945                2950                2955                2960

Pro Pro Gln Lys Pro Tyr Thr Phe Leu Glu Glu Lys Ala Arg Gly Arg
        2965                2970                2975

Phe Gly Val Val Arg Ala Cys Arg Glu Asn Ala Thr Gly Arg Thr Phe
        2980                2985                2990

Val Ala Lys Ile Val Pro Tyr Ala Ala Glu Gly Lys Arg Arg Val Leu
        2995                3000                3005

Gln Glu Tyr Glu Val Leu Arg Thr Leu His His Glu Arg Ile Met Ser
        3010                3015                3020

Leu His Glu Ala Tyr Ile Thr Pro Arg Tyr Leu Val Leu Ile Ala Glu
3025                3030                3035                3040

Ser Cys Gly Asn Arg Glu Leu Leu Cys Gly Leu Ser Asp Arg Phe Arg
        3045                3050                3055

Tyr Ser Glu Asp Asp Val Ala Thr Tyr Met Val Gln Leu Leu Gln Gly
        3060                3065                3070

Leu Asp Tyr Leu His Gly His His Val Leu His Leu Asp Ile Lys Pro
        3075                3080                3085

Asp Asn Leu Leu Leu Ala Pro Asp Asn Ala Leu Lys Ile Val Asp Phe
3090                3095                3100

Gly Ser Ala Gln Pro Tyr Asn Pro Gln Ala Leu Arg Pro Leu Gly His
3105                3110                3115                3120

Arg Thr Gly Thr Leu Glu Phe Met Ala Pro Glu Met Val Lys Gly Glu
        3125                3130                3135

Pro Ile Gly Ser Ala Thr Asp Ile Trp Gly Ala Gly Val Leu Thr Tyr
        3140                3145                3150

Ile Met Leu Ser Gly Arg Ser Pro Phe Tyr Glu Pro Asp Pro Gln Glu

```
                    3155                3160                3165
Thr Glu Ala Arg Ile Val Gly Gly Arg Phe Asp Ala Phe Gln Leu Tyr
        3170                3175                3180

Pro Asn Thr Ser Gln Ser Ala Thr Leu Phe Leu Arg Lys Val Leu Ser
3185                3190                3195                3200

Val His Pro Trp Ser Arg Pro Ser Leu Gln Asp Cys Leu Ala His Pro
                3205                3210                3215

Trp Leu Gln Asp Ala Tyr Leu Met Lys Leu Arg Arg Gln Thr Leu Thr
            3220                3225                3230

Phe Thr Thr Asn Arg Leu Lys Glu Phe Leu Gly Glu Gln Arg Arg Arg
        3235                3240                3245

Arg Ala Glu Ala Ala Thr Arg His Lys Val Leu Leu Arg Ser Tyr Pro
    3250                3255                3260

Gly Gly Pro
3265

<210> SEQ ID NO 93
<211> LENGTH: 393
<212> TYPE: PRT
<213> ORGANISM: Homo sapiens

<400> SEQUENCE: 93

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255
```

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
            275                 280                 285

Arg Pro Arg Thr Pro Gly Arg Pro Leu Ser Ser Tyr Gly Met Asp Ser
            290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
            370                 375                 380

Ser Thr Pro Thr His Ala Ala Gly Val
385                 390

<210> SEQ ID NO 94
<211> LENGTH: 673
<212> TYPE: PRT
<213> ORGANISM: Homo sapiens

<400> SEQUENCE: 94

Met Ala Asp Pro Ala Gly Pro Pro Ser Glu Gly Glu Ser
1               5                   10              15

Thr Val Arg Phe Ala Arg Lys Gly Ala Leu Arg Gln Lys Asn Val His
            20                  25                  30

Glu Val Lys Asn His Lys Phe Thr Ala Arg Phe Phe Lys Gln Pro Thr
            35                  40                  45

Phe Cys Ser His Cys Thr Asp Phe Ile Trp Gly Phe Gly Lys Gln Gly
        50                  55                  60

Phe Gln Cys Gln Val Cys Cys Phe Val Val His Lys Arg Cys His Glu
65              70                  75                  80

Phe Val Thr Phe Ser Cys Pro Gly Ala Asp Lys Gly Pro Ala Ser Asp
            85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
            115                 120                 125

Gly Met Lys Cys Asp Thr Cys Met Met Asn Val His Lys Arg Cys Val
        130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
            165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
            195                 200                 205

Lys Gln Lys Thr Lys Thr Ile Lys Cys Ser Leu Asn Pro Glu Trp Asn
        210                 215                 220

Glu Thr Phe Arg Phe Gln Leu Lys Glu Ser Asp Lys Asp Arg Arg Leu
225                 230                 235                 240

-continued

```
Ser Val Glu Ile Trp Asp Trp Asp Leu Thr Ser Arg Asn Asp Phe Met
            245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
            275                 280                 285

Pro Val Pro Pro Glu Gly Ser Glu Ala Asn Glu Glu Leu Arg Gln Lys
            290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Gly Asn Arg Asp Arg
            325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
            355                 360                 365

Ala Val Lys Ile Leu Lys Lys Asp Val Val Ile Gln Asp Asp Asp Val
            370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
            405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
            435                 440                 445

Glu Ile Ala Ile Gly Leu Phe Phe Leu Gln Ser Lys Gly Ile Ile Tyr
            450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
            485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
            515                 520                 525

Val Leu Leu Tyr Glu Met Leu Ala Gly Gln Ala Pro Phe Glu Gly Glu
            530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
            565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
            595                 600                 605

Glu Arg Lys Glu Ile Gln Pro Pro Tyr Lys Pro Lys Ala Cys Gly Arg
            610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
            645                 650                 655
```

-continued

Glu Gly Phe Ser Phe Val Asn Ser Glu Phe Leu Lys Pro Glu Val Lys
            660                 665                 670

Ser

<210> SEQ ID NO 95
<211> LENGTH: 726
<212> TYPE: PRT
<213> ORGANISM: Homo sapiens

<400> SEQUENCE: 95

Met Ser Glu Glu Thr Val Pro Glu Ala Ala Ser Pro Pro Pro Pro Gln
1               5                   10                  15

Gly Gln Pro Tyr Phe Asp Arg Phe Ser Glu Asp Pro Glu Tyr Met
            20                  25                  30

Arg Leu Arg Asn Arg Ala Ala Asp Leu Arg Gln Asp Phe Asn Leu Met
        35                  40                  45

Glu Gln Lys Lys Arg Val Thr Met Ile Leu Gln Ser Pro Ser Phe Arg
    50                  55                  60

Glu Glu Leu Glu Gly Leu Ile Gln Glu Gln Met Lys Lys Gly Asn Asn
65                  70                  75                  80

Ser Ser Asn Ile Trp Ala Leu Arg Gln Ile Ala Asp Phe Met Ala Ser
                85                  90                  95

Thr Ser His Ala Val Phe Pro Thr Ser Ser Met Asn Val Ser Met Met
            100                 105                 110

Thr Pro Ile Asn Asp Leu His Thr Ala Asp Ser Leu Asn Leu Ala Lys
        115                 120                 125

Gly Glu Arg Leu Met Arg Cys Lys Ile Ser Ser Val Tyr Arg Leu Leu
    130                 135                 140

Asp Leu Tyr Gly Trp Ala Gln Leu Ser Asp Thr Tyr Val Thr Leu Arg
145                 150                 155                 160

Val Ser Lys Glu Gln Asp His Phe Leu Ile Ser Pro Lys Gly Val Ser
                165                 170                 175

Cys Ser Glu Val Thr Ala Ser Ser Leu Ile Lys Val Asn Ile Leu Gly
            180                 185                 190

Glu Val Val Glu Lys Gly Ser Ser Cys Phe Pro Val Asp Thr Thr Gly
        195                 200                 205

Phe Cys Leu His Ser Ala Ile Tyr Ala Ala Arg Pro Asp Val Arg Cys
    210                 215                 220

Ile Ile His Leu His Thr Pro Ala Thr Ala Ala Val Ser Ala Met Lys
225                 230                 235                 240

Trp Gly Leu Leu Pro Val Ser His Asn Ala Leu Leu Val Gly Asp Met
                245                 250                 255

Ala Tyr Tyr Asp Phe Asn Gly Glu Met Glu Gln Glu Ala Asp Arg Ile
            260                 265                 270

Asn Leu Gln Lys Cys Leu Gly Pro Thr Cys Lys Ile Leu Val Leu Arg
        275                 280                 285

Asn His Gly Val Val Ala Leu Gly Asp Thr Val Glu Glu Ala Phe Tyr
    290                 295                 300

Lys Ile Phe His Leu Gln Ala Ala Cys Glu Ile Gln Val Ser Ala Leu
305                 310                 315                 320

Ser Ser Ala Gly Gly Val Glu Asn Leu Ile Leu Leu Glu Gln Glu Lys
                325                 330                 335

His Arg Pro His Glu Val Gly Ser Val Gln Trp Ala Gly Ser Thr Phe
            340                 345                 350

Gly Pro Met Gln Lys Ser Arg Leu Gly Glu His Glu Phe Glu Ala Leu
            355                 360                 365

Met Arg Met Leu Asp Asn Leu Gly Tyr Arg Thr Gly Tyr Thr Tyr Arg
370                 375                 380

His Pro Phe Val Gln Glu Lys Thr Lys His Lys Ser Glu Val Glu Ile
385                 390                 395                 400

Pro Ala Thr Val Thr Ala Phe Val Phe Glu Glu Asp Gly Ala Pro Val
            405                 410                 415

Pro Ala Leu Arg Gln His Ala Gln Gln Gln Lys Glu Lys Thr Arg
            420                 425                 430

Trp Leu Asn Thr Pro Asn Ala Tyr Leu Arg Val Asn Val Ala Asp Glu
            435                 440                 445

Val Gln Arg Ser Met Gly Ser Pro Arg Pro Lys Thr Thr Trp Met Lys
            450                 455                 460

Ala Asp Glu Val Glu Lys Ser Ser Gly Met Pro Ile Arg Ile Glu
465                 470                 475                 480

Asn Pro Asn Gln Phe Val Pro Leu Tyr Thr Asp Pro Gln Glu Val Leu
            485                 490                 495

Glu Met Arg Asn Lys Ile Arg Glu Gln Asn Arg Gln Asp Val Lys Ser
            500                 505                 510

Ala Gly Pro Gln Ser Gln Leu Leu Ala Ser Val Ile Ala Glu Lys Ser
            515                 520                 525

Arg Ser Pro Ser Thr Glu Ser Gln Leu Met Ser Lys Gly Asp Glu Asp
            530                 535                 540

Thr Lys Asp Asp Ser Glu Glu Thr Val Pro Asn Pro Phe Ser Gln Leu
545                 550                 555                 560

Thr Asp Gln Glu Leu Glu Glu Tyr Lys Lys Glu Val Glu Arg Lys Lys
            565                 570                 575

Leu Glu Leu Asp Gly Glu Lys Glu Thr Ala Pro Glu Pro Gly Ser
            580                 585                 590

Pro Ala Lys Ser Ala Pro Ala Ser Pro Val Gln Ser Pro Ala Lys Glu
            595                 600                 605

Ala Glu Thr Lys Ser Pro Leu Val Ser Pro Ser Lys Ser Leu Glu Glu
            610                 615                 620

Gly Thr Lys Lys Thr Glu Thr Ser Lys Ala Ala Thr Thr Glu Pro Glu
625                 630                 635                 640

Thr Thr Gln Pro Glu Gly Val Val Asn Gly Arg Glu Glu Gln
            645                 650                 655

Thr Ala Glu Glu Ile Leu Ser Lys Gly Leu Ser Gln Met Thr Thr Ser
            660                 665                 670

Ala Asp Thr Asp Val Asp Thr Ser Lys Asp Lys Thr Glu Ser Val Thr
            675                 680                 685

Ser Gly Pro Met Ser Pro Glu Gly Ser Pro Lys Ser Pro Ser Lys
690                 695                 700

Lys Lys Lys Lys Phe Arg Thr Pro Ser Phe Leu Lys Lys Ser Lys Lys
705                 710                 715                 720

Lys Glu Lys Val Glu Ser
            725

<210> SEQ ID NO 96
<211> LENGTH: 603
<212> TYPE: PRT
<213> ORGANISM: Homo sapiens

<400> SEQUENCE: 96

-continued

```
Met Ser Ala Ala Val Thr Ala Gly Lys Leu Ala Arg Ala Pro Ala Asp
1               5                   10                  15

Pro Gly Lys Ala Gly Val Pro Gly Val Ala Ala Pro Gly Ala Pro Ala
            20                  25                  30

Ala Ala Pro Pro Ala Lys Glu Ile Pro Glu Val Leu Val Asp Pro Arg
        35                  40                  45

Ser Arg Arg Arg Tyr Val Arg Gly Arg Phe Leu Gly Lys Gly Gly Phe
    50                  55                  60

Ala Lys Cys Phe Glu Ile Ser Asp Ala Asp Thr Lys Glu Val Phe Ala
65                  70                  75                  80

Gly Lys Ile Val Pro Lys Ser Leu Leu Leu Lys Pro His Gln Arg Glu
                85                  90                  95

Lys Met Ser Met Glu Ile Ser Ile His Arg Ser Leu Ala His Gln His
                100                 105                 110

Val Val Gly Phe His Gly Phe Phe Glu Asp Asn Asp Phe Val Phe Val
            115                 120                 125

Val Leu Glu Leu Cys Arg Arg Arg Ser Leu Leu Glu Leu His Lys Arg
130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Arg Val Ile His Arg Asp
                165                 170                 175

Leu Lys Leu Gly Asn Leu Phe Leu Asn Glu Asp Leu Glu Val Lys Ile
                180                 185                 190

Gly Asp Phe Gly Leu Ala Thr Lys Val Glu Tyr Asp Gly Glu Arg Lys
            195                 200                 205

Lys Thr Leu Cys Gly Thr Pro Asn Tyr Ile Ala Pro Glu Val Leu Ser
210                 215                 220

Lys Lys Gly His Ser Phe Glu Val Asp Val Trp Ser Ile Gly Cys Ile
225                 230                 235                 240

Met Tyr Thr Leu Leu Val Gly Lys Pro Pro Phe Glu Thr Ser Cys Leu
                245                 250                 255

Lys Glu Thr Tyr Leu Arg Ile Lys Lys Asn Glu Tyr Ser Ile Pro Lys
                260                 265                 270

His Ile Asn Pro Val Ala Ala Ser Leu Ile Gln Lys Met Leu Gln Thr
                275                 280                 285

Asp Pro Thr Ala Arg Pro Thr Ile Asn Glu Leu Leu Asn Asp Glu Phe
            290                 295                 300

Phe Thr Ser Gly Tyr Ile Pro Ala Arg Leu Pro Ile Thr Cys Leu Thr
305                 310                 315                 320

Ile Pro Pro Arg Phe Ser Ile Ala Pro Ser Ser Leu Asp Pro Ser Asn
                325                 330                 335

Arg Lys Pro Leu Thr Val Leu Asn Lys Gly Leu Glu Asn Pro Leu Pro
                340                 345                 350

Glu Arg Pro Arg Glu Lys Glu Pro Val Val Arg Glu Thr Gly Glu
            355                 360                 365

Val Val Asp Cys His Leu Ser Asp Met Leu Gln Gln Leu His Ser Val
            370                 375                 380

Asn Ala Ser Lys Pro Ser Glu Arg Gly Leu Val Arg Gln Glu Glu Ala
385                 390                 395                 400

Glu Asp Pro Ala Cys Ile Pro Ile Phe Trp Val Ser Lys Trp Val Asp
                405                 410                 415
```

```
Tyr Ser Asp Lys Tyr Gly Leu Gly Tyr Gln Leu Cys Asp Asn Ser Val
            420                 425                 430

Gly Val Leu Phe Asn Asp Ser Thr Arg Leu Ile Leu Tyr Asn Asp Gly
        435                 440                 445

Asp Ser Leu Gln Tyr Ile Glu Arg Asp Gly Thr Glu Ser Tyr Leu Thr
        450                 455                 460

Val Ser Ser His Pro Asn Ser Leu Met Lys Lys Ile Thr Leu Leu Lys
465                 470                 475                 480

Tyr Phe Arg Asn Tyr Met Ser Glu His Leu Leu Lys Ala Gly Ala Asn
                485                 490                 495

Ile Thr Pro Arg Glu Gly Asp Glu Leu Ala Arg Leu Pro Tyr Leu Arg
            500                 505                 510

Thr Trp Phe Arg Thr Arg Ser Ala Ile Ile Leu His Leu Ser Asn Gly
            515                 520                 525

Ser Val Gln Ile Asn Phe Phe Gln Asp His Thr Lys Leu Ile Leu Cys
            530                 535                 540

Pro Leu Met Ala Ala Val Thr Tyr Ile Asp Glu Lys Arg Asp Phe Arg
545                 550                 555                 560

Thr Tyr Arg Leu Ser Leu Leu Glu Glu Tyr Gly Cys Cys Lys Glu Leu
                565                 570                 575

Ala Ser Arg Leu Arg Tyr Ala Arg Thr Met Val Asp Lys Leu Leu Ser
            580                 585                 590

Ser Arg Ser Ala Ser Asn Arg Leu Lys Ala Ser
            595                 600
```

<210> SEQ ID NO 97
<211> LENGTH: 556
<212> TYPE: PRT
<213> ORGANISM: Homo sapiens

<400> SEQUENCE: 97

```
Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
        130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190
```

```
Leu Glu Tyr Leu His Gly Lys Gly Ile Ile His Arg Asp Leu Lys Pro
            195                 200                 205
Glu Asn Ile Leu Leu Asn Glu Asp Met His Ile Gln Ile Thr Asp Phe
        210                 215                 220
Gly Thr Ala Lys Val Leu Ser Pro Glu Ser Lys Gln Ala Arg Ala Asn
225                 230                 235                 240
Ser Phe Val Gly Thr Ala Gln Tyr Val Ser Pro Glu Leu Leu Thr Glu
                245                 250                 255
Lys Ser Ala Cys Lys Ser Ser Asp Leu Trp Ala Leu Gly Cys Ile Ile
            260                 265                 270
Tyr Gln Leu Val Ala Gly Leu Pro Pro Phe Arg Ala Gly Asn Glu Tyr
        275                 280                 285
Leu Ile Phe Gln Lys Ile Ile Lys Leu Glu Tyr Asp Phe Pro Glu Lys
        290                 295                 300
Phe Phe Pro Lys Ala Arg Asp Leu Val Glu Lys Leu Leu Val Leu Asp
305                 310                 315                 320
Ala Thr Lys Arg Leu Gly Cys Glu Glu Met Glu Gly Tyr Gly Pro Leu
                325                 330                 335
Lys Ala His Pro Phe Phe Glu Ser Val Thr Trp Glu Asn Leu His Gln
            340                 345                 350
Gln Thr Pro Pro Lys Leu Thr Ala Tyr Leu Pro Ala Met Ser Glu Asp
        355                 360                 365
Asp Glu Asp Cys Tyr Gly Asn Tyr Asp Asn Leu Leu Ser Gln Phe Gly
        370                 375                 380
Cys Met Gln Val Ser Ser Ser Ser Ser His Ser Leu Ser Ala Ser
385                 390                 395                 400
Asp Thr Gly Leu Pro Gln Arg Ser Gly Ser Asn Ile Glu Gln Tyr Ile
                405                 410                 415
His Asp Leu Asp Ser Asn Ser Phe Glu Leu Asp Leu Gln Phe Ser Glu
            420                 425                 430
Asp Glu Lys Arg Leu Leu Leu Glu Lys Gln Ala Gly Gly Asn Pro Trp
        435                 440                 445
His Gln Phe Val Glu Asn Asn Leu Ile Leu Lys Met Gly Pro Val Asp
        450                 455                 460
Lys Arg Lys Gly Leu Phe Ala Arg Arg Arg Gln Leu Leu Leu Thr Glu
465                 470                 475                 480
Gly Pro His Leu Tyr Tyr Val Asp Pro Val Asn Lys Val Leu Lys Gly
                485                 490                 495
Glu Ile Pro Trp Ser Gln Glu Leu Arg Pro Glu Ala Lys Asn Phe Lys
            500                 505                 510
Thr Phe Phe Val His Thr Pro Asn Arg Thr Tyr Tyr Leu Met Asp Pro
        515                 520                 525
Ser Gly Asn Ala His Lys Trp Cys Arg Lys Ile Gln Glu Val Trp Arg
        530                 535                 540
Gln Arg Tyr Gln Ser His Pro Asp Ala Ala Val Gln
545                 550                 555

<210> SEQ ID NO 98
<211> LENGTH: 506
<212> TYPE: PRT
<213> ORGANISM: Homo sapiens

<400> SEQUENCE: 98

Met Asp Asp Tyr Met Val Leu Arg Met Ile Gly Glu Gly Ser Phe Gly
```

-continued

```
1               5                    10                    15
Arg Ala Leu Leu Val Gln His Glu Ser Ser Asn Gln Met Phe Ala Met
                20                  25                  30

Lys Glu Ile Arg Leu Pro Lys Ser Phe Ser Asn Thr Gln Asn Ser Arg
                35                  40                  45

Lys Glu Ala Val Leu Leu Ala Lys Met Lys His Pro Asn Ile Val Ala
    50                  55                  60

Phe Lys Glu Ser Phe Glu Ala Glu Gly His Leu Tyr Ile Val Met Glu
65                  70                  75                  80

Tyr Cys Asp Gly Gly Asp Leu Met Gln Lys Ile Lys Gln Gln Lys Gly
                85                  90                  95

Lys Leu Phe Pro Glu Asp Met Ile Leu Asn Trp Phe Thr Gln Met Cys
                100                 105                 110

Leu Gly Val Asn His Ile His Lys Lys Arg Val Leu His Arg Asp Ile
                115                 120                 125

Lys Ser Lys Asn Ile Phe Leu Thr Gln Asn Gly Lys Val Lys Leu Gly
    130                 135                 140

Asp Phe Gly Ser Ala Arg Leu Leu Ser Asn Pro Met Ala Phe Ala Cys
145                 150                 155                 160

Thr Tyr Val Gly Thr Pro Tyr Tyr Val Pro Pro Glu Ile Trp Glu Asn
                165                 170                 175

Leu Pro Tyr Asn Asn Lys Ser Asp Ile Trp Ser Leu Gly Cys Ile Leu
                180                 185                 190

Tyr Glu Leu Cys Thr Leu Lys His Pro Phe Gln Ala Asn Ser Trp Lys
                195                 200                 205

Asn Leu Ile Leu Lys Val Cys Gln Gly Cys Ile Ser Pro Leu Pro Ser
    210                 215                 220

His Tyr Ser Tyr Glu Leu Gln Phe Leu Val Lys Gln Met Phe Lys Arg
225                 230                 235                 240

Asn Pro Ser His Arg Pro Ser Ala Thr Thr Leu Leu Ser Arg Gly Ile
                245                 250                 255

Val Ala Arg Leu Val Gln Lys Cys Leu Pro Pro Glu Ile Ile Met Glu
                260                 265                 270

Tyr Gly Glu Glu Val Leu Glu Glu Ile Lys Asn Ser Lys His Asn Thr
                275                 280                 285

Pro Arg Lys Lys Thr Asn Pro Ser Arg Ile Arg Ile Ala Leu Gly Asn
    290                 295                 300

Glu Ala Ser Thr Val Gln Glu Glu Gln Asp Arg Lys Gly Ser His
305                 310                 315                 320

Thr Asp Leu Glu Ser Ile Asn Glu Asn Leu Val Glu Ser Ala Leu Arg
                325                 330                 335

Arg Val Asn Arg Glu Glu Lys Gly Asn Lys Ser Val His Leu Arg Lys
                340                 345                 350

Ala Ser Ser Pro Asn Leu His Arg Arg Gln Trp Glu Lys Asn Val Pro
                355                 360                 365

Asn Thr Ala Leu Thr Ala Leu Glu Asn Ala Ser Ile Leu Thr Ser Ser
    370                 375                 380

Leu Thr Ala Glu Asp Asp Arg Gly Gly Ser Val Ile Lys Tyr Ser Lys
385                 390                 395                 400

Asn Thr Thr Arg Lys Gln Trp Leu Lys Glu Thr Pro Asp Thr Leu Leu
                405                 410                 415

Asn Ile Leu Lys Asn Ala Asp Leu Ser Leu Ala Phe Gln Thr Tyr Thr
                420                 425                 430
```

-continued

Ile Tyr Arg Pro Gly Ser Glu Gly Phe Leu Lys Gly Pro Leu Ser Glu
            435                 440                 445

Glu Thr Glu Ala Ser Asp Ser Val Asp Gly Gly His Asp Ser Val Ile
    450                 455                 460

Leu Asp Pro Glu Arg Leu Glu Pro Gly Leu Asp Glu Asp Thr Asp
465                 470                 475                 480

Phe Glu Glu Glu Asp Asp Asn Pro Asp Trp Val Ser Glu Leu Lys Lys
                485                 490                 495

Arg Ala Gly Trp Gln Gly Leu Cys Asp Arg
            500                 505

<210> SEQ ID NO 99
<211> LENGTH: 619
<212> TYPE: PRT
<213> ORGANISM: Homo sapiens

<400> SEQUENCE: 99

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys

| | | 290 | | | 295 | | | 300 | | | |
|---|---|---|---|---|---|---|---|---|---|---|---|

Pro Arg Pro Met Pro Met Asp Thr Ser Val Tyr Glu Ser Pro Tyr Ser
305              310              315              320

Asp Pro Glu Glu Leu Lys Asp Lys Lys Leu Phe Leu Lys Arg Asp Asn
              325              330              335

Leu Leu Ile Ala Asp Ile Glu Leu Gly Cys Gly Asn Phe Gly Ser Val
              340              345              350

Arg Gln Gly Val Tyr Arg Met Arg Lys Lys Gln Ile Asp Val Ala Ile
              355              360              365

Lys Val Leu Lys Gln Gly Thr Glu Lys Ala Asp Thr Glu Glu Met Met
              370              375              380

Arg Glu Ala Gln Ile Met His Gln Leu Asp Asn Pro Tyr Ile Val Arg
385              390              395              400

Leu Ile Gly Val Cys Gln Ala Glu Ala Leu Met Leu Val Met Glu Met
                   405              410              415

Ala Gly Gly Gly Pro Leu His Lys Phe Leu Val Gly Lys Arg Glu Glu
              420              425              430

Ile Pro Val Ser Asn Val Ala Glu Leu Leu His Gln Val Ser Met Gly
              435              440              445

Met Lys Tyr Leu Glu Glu Lys Asn Phe Val His Arg Asp Leu Ala Ala
450              455              460

Arg Asn Val Leu Leu Val Asn Arg His Tyr Ala Lys Ile Ser Asp Phe
465              470              475              480

Gly Leu Ser Lys Ala Leu Gly Ala Asp Asp Ser Tyr Tyr Thr Ala Arg
              485              490              495

Ser Ala Gly Lys Trp Pro Leu Lys Trp Tyr Ala Pro Glu Cys Ile Asn
              500              505              510

Phe Arg Lys Phe Ser Ser Arg Ser Asp Val Trp Ser Tyr Gly Val Thr
              515              520              525

Met Trp Glu Ala Leu Ser Tyr Gly Gln Lys Pro Tyr Lys Lys Met Lys
530              535              540

Gly Pro Glu Val Met Ala Phe Ile Glu Gln Gly Lys Arg Met Glu Cys
545              550              555              560

Pro Pro Glu Cys Pro Pro Glu Leu Tyr Ala Leu Met Ser Asp Cys Trp
              565              570              575

Ile Tyr Lys Trp Glu Asp Arg Pro Asp Phe Leu Thr Val Glu Gln Arg
              580              585              590

Met Arg Ala Cys Tyr Tyr Ser Leu Ala Ser Lys Val Glu Gly Pro Pro
              595              600              605

Gly Ser Thr Gln Lys Ala Glu Ala Ala Cys Ala
              610              615

<210> SEQ ID NO 100
<211> LENGTH: 548
<212> TYPE: PRT
<213> ORGANISM: Homo sapiens

<400> SEQUENCE: 100

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
              20               25                  30

Val Arg Arg Gly Gln Pro Phe Trp Leu Thr Leu His Phe Glu Gly Arg
              35               40                  45

```
Asn Tyr Glu Ala Ser Val Asp Ser Leu Thr Phe Ser Val Val Thr Gly
 50                  55                  60

Pro Ala Pro Ser Gln Glu Ala Gly Thr Lys Ala Arg Phe Pro Leu Arg
 65                  70                  75                  80

Asp Ala Val Glu Glu Gly Asp Trp Thr Ala Thr Val Val Asp Gln Gln
                 85                  90                  95

Asp Cys Thr Leu Ser Leu Gln Leu Thr Thr Pro Ala Asn Ala Pro Ile
                100                 105                 110

Gly Leu Tyr Arg Leu Ser Leu Glu Ala Ser Thr Gly Tyr Gln Gly Ser
                115                 120                 125

Ser Phe Val Leu Gly His Phe Ile Leu Leu Phe Asn Ala Trp Cys Pro
130                 135                 140

Ala Asp Ala Val Tyr Leu Asp Ser Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
                180                 185                 190

Cys Leu Ile Leu Leu Asp Val Asn Pro Lys Phe Leu Lys Asn Ala Gly
                195                 200                 205

Arg Asp Cys Ser Arg Arg Ser Ser Pro Val Tyr Val Gly Arg Val Val
210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
                260                 265                 270

Lys Tyr Gly Gln Cys Trp Val Phe Ala Ala Val Ala Cys Thr Val Leu
                275                 280                 285

Arg Cys Leu Gly Ile Pro Thr Arg Val Val Thr Asn Tyr Asn Ser Ala
290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
                340                 345                 350

Gly Trp Gln Ala Leu Asp Pro Thr Pro Gln Glu Lys Ser Glu Gly Thr
                355                 360                 365

Tyr Cys Cys Gly Pro Val Pro Val Arg Ala Ile Lys Glu Gly Asp Leu
370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Gly Ser Val His Lys Ser Ile
                405                 410                 415

Asn Arg Ser Leu Ile Val Gly Leu Lys Ile Ser Thr Lys Ser Val Gly
                420                 425                 430

Arg Asp Glu Arg Glu Asp Ile Thr His Thr Tyr Lys Tyr Pro Glu Gly
                435                 440                 445

Ser Ser Glu Glu Arg Glu Ala Phe Thr Arg Ala Asn His Leu Asn Lys
450                 455                 460

Leu Ala Glu Lys Glu Glu Thr Gly Met Ala Met Arg Ile Arg Val Gly
```

-continued

```
            465                 470                 475                 480
        Gln Ser Met Asn Met Gly Ser Asp Phe Asp Val Phe Ala His Ile Thr
                        485                 490                 495

Asn Asn Thr Ala Glu Glu Tyr Val Cys Arg Leu Leu Leu Cys Ala Arg
                    500                 505                 510

Thr Val Ser Tyr Asn Gly Ile Leu Gly Pro Glu Cys Gly Thr Lys Tyr
                    515                 520                 525

Leu Leu Asn Leu Asn Leu Glu Pro Phe Ser Gly Lys Ala Leu Cys Ser
                530                 535                 540

Trp Ser Ile Cys
        545

<210> SEQ ID NO 101
<211> LENGTH: 576
<212> TYPE: PRT
<213> ORGANISM: Homo sapiens

<400> SEQUENCE: 101

Met Ala Ala Ser Glu Thr Val Arg Leu Arg Leu Gln Phe Asp Tyr Pro
1               5                   10                  15

Pro Pro Ala Thr Pro His Cys Thr Ala Phe Trp Leu Leu Val Asp Leu
                20                  25                  30

Asn Arg Cys Arg Val Val Thr Asp Leu Ile Ser Leu Ile Arg Gln Arg
            35                  40                  45

Phe Gly Phe Ser Ser Gly Ala Phe Leu Gly Leu Tyr Leu Glu Gly Gly
        50                  55                  60

Leu Leu Pro Pro Ala Glu Ser Ala Arg Leu Val Arg Asp Asn Asp Cys
65                  70                  75                  80

Leu Arg Val Lys Leu Glu Glu Arg Gly Val Ala Glu Asn Ser Val Val
                85                  90                  95

Ile Ser Asn Gly Asp Ile Asn Leu Ser Leu Arg Lys Ala Lys Lys Arg
                100                 105                 110

Ala Phe Gln Leu Glu Glu Gly Glu Glu Thr Glu Pro Asp Cys Lys Tyr
            115                 120                 125

Ser Lys Lys His Trp Lys Ser Arg Glu Asn Asn Asn Asn Asn Glu Lys
        130                 135                 140

Val Leu Asp Leu Glu Pro Lys Ala Val Thr Asp Gln Thr Val Ser Lys
145                 150                 155                 160

Lys Asn Lys Arg Lys Asn Lys Ala Thr Cys Gly Thr Val Gly Asp Asp
                165                 170                 175

Asn Glu Glu Ala Lys Arg Lys Ser Pro Lys Lys Glu Lys Cys Glu
            180                 185                 190

Tyr Lys Lys Lys Ala Lys Asn Pro Lys Ser Pro Lys Val Gln Ala Val
        195                 200                 205

Lys Asp Trp Ala Asn Gln Arg Cys Ser Ser Pro Lys Gly Ser Ala Arg
    210                 215                 220

Asn Ser Leu Val Lys Ala Lys Arg Lys Gly Ser Val Ser Val Cys Ser
225                 230                 235                 240

Lys Glu Ser Pro Ser Ser Ser Glu Ser Glu Ser Cys Asp Glu Ser
                245                 250                 255

Ile Ser Asp Gly Pro Ser Lys Val Thr Leu Glu Ala Arg Asn Ser Ser
            260                 265                 270

Glu Lys Leu Pro Thr Glu Leu Ser Lys Glu Glu Pro Ser Thr Lys Asn
        275                 280                 285
```

-continued

Thr Thr Ala Asp Lys Leu Ala Ile Lys Leu Gly Phe Ser Leu Thr Pro
290                 295                 300

Ser Lys Gly Lys Thr Ser Gly Thr Thr Ser Ser Ser Asp Ser Ser
305                 310                 315                 320

Ala Glu Ser Asp Gln Cys Leu Met Ser Ser Thr Pro Glu Cys
                325                 330                 335

Ala Ala Gly Phe Leu Lys Thr Val Gly Leu Phe Ala Gly Arg Gly Arg
                340                 345                 350

Pro Gly Pro Gly Leu Ser Ser Gln Thr Ala Gly Ala Gly Trp Arg
                355                 360                 365

Arg Ser Gly Ser Asn Gly Gly Gly Gln Ala Pro Gly Ala Ser Pro Ser
370                 375                 380

Val Ser Leu Pro Ala Ser Leu Gly Arg Gly Trp Gly Arg Glu Glu Asn
385                 390                 395                 400

Leu Phe Ser Trp Lys Gly Ala Lys Gly Arg Gly Met Arg Gly Arg Gly
                405                 410                 415

Arg Gly Arg Gly His Pro Val Ser Cys Val Val Asn Arg Ser Thr Asp
                420                 425                 430

Asn Gln Arg Gln Gln Leu Asn Asp Val Val Lys Asn Ser Ser Thr
435                 440                 445

Ile Ile Gln Asn Pro Val Glu Thr Pro Lys Lys Asp Tyr Ser Leu Leu
450                 455                 460

Pro Leu Leu Ala Ala Ala Pro Gln Val Gly Glu Lys Ile Ala Phe Lys
465                 470                 475                 480

Leu Leu Glu Leu Thr Ser Ser Tyr Ser Pro Asp Val Ser Asp Tyr Lys
                485                 490                 495

Glu Gly Arg Ile Leu Ser His Asn Pro Glu Thr Gln Gln Val Asp Ile
                500                 505                 510

Glu Ile Leu Ser Ser Leu Pro Ala Leu Arg Glu Pro Gly Lys Phe Asp
                515                 520                 525

Leu Val Tyr His Asn Glu Asn Gly Ala Glu Val Glu Tyr Ala Val
                530                 535                 540

Thr Gln Glu Ser Lys Ile Thr Val Phe Trp Lys Glu Leu Ile Asp Pro
545                 550                 555                 560

Arg Leu Ile Ile Glu Ser Pro Ser Asn Thr Ser Ser Thr Glu Pro Ala
                565                 570                 575

<210> SEQ ID NO 102
<211> LENGTH: 424
<212> TYPE: PRT
<213> ORGANISM: Homo sapiens

<400> SEQUENCE: 102

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
                20                  25                  30

Gly Ser Gly Ala Gln Gly Ile Val Cys Ala Ala Phe Asp Thr Val Leu
            35                  40                  45

Gly Ile Asn Val Ala Val Lys Lys Leu Ser Arg Pro Phe Gln Asn Gln
        50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Leu Val Lys Gly Cys Val Ile
    210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
        355                 360                 365

Asn Gly Val Val Lys Asp Gln Pro Ser Asp Ala Ala Val Ser Ser Asn
    370                 375                 380

Ala Thr Pro Ser Gln Ser Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420

<210> SEQ ID NO 103
<211> LENGTH: 697
<212> TYPE: PRT
<213> ORGANISM: Homo sapiens

<400> SEQUENCE: 103

Met Ala Gly Leu Gly Pro Gly Val Gly Asp Ser Glu Gly Gly Pro Arg
1               5                   10                  15

Pro Leu Phe Cys Arg Lys Gly Ala Leu Arg Gln Lys Val Val His Glu
            20                  25                  30

Val Lys Ser His Lys Phe Thr Ala Arg Phe Phe Lys Gln Pro Thr Phe

-continued

```
            35                  40                  45
Cys Ser His Cys Thr Asp Phe Ile Trp Gly Ile Gly Lys Gln Gly Leu
 50                  55                  60
Gln Cys Gln Val Cys Ser Phe Val Val His Arg Arg Cys His Glu Phe
 65                  70                  75                  80
Val Thr Phe Glu Cys Pro Gly Ala Gly Lys Gly Pro Gln Thr Asp Asp
                 85                  90                  95
Pro Arg Asn Lys His Lys Phe Arg Leu His Ser Tyr Ser Ser Pro Thr
            100                 105                 110
Phe Cys Asp His Cys Gly Ser Leu Leu Tyr Gly Leu Val His Gln Gly
            115                 120                 125
Met Lys Cys Ser Cys Cys Glu Met Asn Val His Arg Arg Cys Val Arg
    130                 135                 140
Ser Val Pro Ser Leu Cys Gly Val Asp His Thr Glu Arg Arg Gly Arg
145                 150                 155                 160
Leu Gln Leu Glu Ile Arg Ala Pro Thr Ala Asp Glu Ile His Val Thr
                165                 170                 175
Val Gly Glu Ala Arg Asn Leu Ile Pro Met Asp Pro Asn Gly Leu Ser
            180                 185                 190
Asp Pro Tyr Val Lys Leu Lys Leu Ile Pro Asp Pro Arg Asn Leu Thr
            195                 200                 205
Lys Gln Lys Thr Arg Thr Val Lys Ala Thr Leu Asn Pro Val Trp Asn
    210                 215                 220
Glu Thr Phe Val Phe Asn Leu Lys Pro Gly Asp Val Glu Arg Arg Leu
225                 230                 235                 240
Ser Val Glu Val Trp Asp Trp Asp Arg Thr Ser Arg Asn Asp Phe Met
                245                 250                 255
Gly Ala Met Ser Phe Gly Val Ser Glu Leu Leu Lys Ala Pro Val Asp
            260                 265                 270
Gly Trp Tyr Lys Leu Leu Asn Gln Glu Glu Gly Glu Tyr Tyr Asn Val
            275                 280                 285
Pro Val Ala Asp Ala Asp Asn Cys Ser Leu Leu Gln Lys Phe Glu Ala
    290                 295                 300
Cys Asn Tyr Pro Leu Glu Leu Tyr Glu Arg Val Arg Met Gly Pro Ser
305                 310                 315                 320
Ser Ser Pro Ile Pro Ser Pro Ser Pro Thr Asp Pro Lys Arg
                325                 330                 335
Cys Phe Phe Gly Ala Ser Pro Gly Arg Leu His Ile Ser Asp Phe Ser
            340                 345                 350
Phe Leu Met Val Leu Gly Lys Gly Ser Phe Gly Lys Val Met Leu Ala
            355                 360                 365
Glu Arg Arg Gly Ser Asp Glu Leu Tyr Ala Ile Lys Ile Leu Lys Lys
    370                 375                 380
Asp Val Ile Val Gln Asp Asp Val Asp Cys Thr Leu Val Glu Lys
385                 390                 395                 400
Arg Val Leu Ala Leu Gly Gly Arg Gly Pro Gly Gly Arg Pro His Phe
                405                 410                 415
Leu Thr Gln Leu His Ser Thr Phe Gln Thr Pro Asp Arg Leu Tyr Phe
            420                 425                 430
Val Met Glu Tyr Val Thr Gly Gly Asp Leu Met Tyr His Ile Gln Gln
            435                 440                 445
Leu Gly Lys Phe Lys Glu Pro His Ala Ala Phe Tyr Ala Ala Glu Ile
    450                 455                 460
```

```
Ala Ile Gly Leu Phe Phe Leu His Asn Gln Gly Ile Tyr Arg Asp
465                 470                 475                 480

Leu Lys Leu Asp Asn Val Met Leu Asp Ala Glu Gly His Ile Lys Ile
                485                 490                 495

Thr Asp Phe Gly Met Cys Lys Glu Asn Val Phe Pro Gly Thr Thr Thr
            500                 505                 510

Arg Thr Phe Cys Gly Thr Pro Asp Tyr Ile Ala Pro Glu Ile Ile Ala
        515                 520                 525

Tyr Gln Pro Tyr Gly Lys Ser Val Asp Trp Trp Ser Phe Gly Val Leu
    530                 535                 540

Leu Tyr Glu Met Leu Ala Gly Gln Pro Pro Phe Asp Gly Glu Asp Glu
545                 550                 555                 560

Glu Glu Leu Phe Gln Ala Ile Met Glu Gln Thr Val Thr Tyr Pro Lys
                565                 570                 575

Ser Leu Ser Arg Glu Ala Val Ala Ile Cys Lys Gly Phe Leu Thr Lys
            580                 585                 590

His Pro Gly Lys Arg Leu Gly Ser Gly Pro Asp Gly Glu Pro Thr Ile
        595                 600                 605

Arg Ala His Gly Phe Phe Arg Trp Ile Asp Trp Glu Arg Leu Glu Arg
610                 615                 620

Leu Glu Ile Pro Pro Pro Phe Arg Pro Arg Pro Cys Gly Arg Ser Gly
625                 630                 635                 640

Glu Asn Phe Asp Lys Phe Phe Thr Arg Ala Ala Pro Ala Leu Thr Pro
                645                 650                 655

Pro Asp Arg Leu Val Leu Ala Ser Ile Asp Gln Ala Asp Phe Gln Gly
            660                 665                 670

Phe Thr Tyr Val Asn Pro Asp Phe Val His Pro Asp Ala Arg Ser Pro
        675                 680                 685

Thr Ser Pro Val Pro Val Pro Val Met
    690                 695

<210> SEQ ID NO 104
<211> LENGTH: 441
<212> TYPE: PRT
<213> ORGANISM: Homo sapiens

<400> SEQUENCE: 104

Met Lys Lys Phe Phe Gln Glu Phe Lys Ala Asp Ile Lys Phe Lys Ser
1               5                   10                  15

Ala Gly Pro Gly Gln Lys Leu Lys Glu Ser Val Gly Glu Lys Ala His
                20                  25                  30

Lys Glu Lys Pro Asn Gln Pro Ala Pro Arg Pro Pro Arg Gln Gly Pro
            35                  40                  45

Thr Asn Glu Ala Gln Met Ala Ala Ala Ala Leu Ala Arg Leu Glu
50                  55                  60

Gln Lys Gln Ser Arg Ala Trp Gly Pro Thr Ser Gln Asp Thr Ile Arg
65                  70                  75                  80

Asn Gln Val Arg Lys Glu Leu Gln Ala Glu Ala Thr Val Ser Gly Ser
                85                  90                  95

Pro Glu Ala Pro Gly Thr Asn Val Val Ser Glu Pro Arg Glu Glu Gly
            100                 105                 110

Ser Ala His Leu Ala Val Pro Gly Val Tyr Phe Thr Cys Pro Leu Thr
        115                 120                 125

Gly Ala Thr Leu Arg Lys Asp Gln Arg Asp Ala Cys Ile Lys Glu Ala
```

```
                130             135             140
Ile Leu Leu His Phe Ser Thr Asp Pro Val Ala Ala Ser Ile Met Lys
145                 150                 155                 160

Ile Tyr Thr Phe Asn Lys Asp Gln Asp Arg Val Lys Leu Gly Val Asp
                165                 170                 175

Thr Ile Ala Lys Tyr Leu Asp Asn Ile His Leu His Pro Glu Glu
            180                 185                 190

Lys Tyr Arg Lys Ile Lys Leu Gln Asn Lys Val Phe Gln Glu Arg Ile
                195                 200                 205

Asn Cys Leu Glu Gly Thr His Glu Phe Phe Glu Ala Ile Gly Phe Gln
            210                 215                 220

Lys Val Leu Leu Pro Ala Gln Asp Gln Glu Asp Pro Glu Glu Phe Tyr
225                 230                 235                 240

Val Leu Ser Glu Thr Thr Leu Ala Gln Pro Gln Ser Leu Glu Arg His
                245                 250                 255

Lys Glu Gln Leu Leu Ala Ala Glu Pro Val Arg Ala Lys Leu Asp Arg
            260                 265                 270

Gln Arg Arg Val Phe Gln Pro Ser Pro Leu Ala Ser Gln Phe Glu Leu
            275                 280                 285

Pro Gly Asp Phe Phe Asn Leu Thr Ala Glu Glu Ile Lys Arg Glu Gln
290                 295                 300

Arg Leu Arg Ser Glu Ala Val Glu Arg Leu Ser Val Leu Arg Thr Lys
305                 310                 315                 320

Ala Met Arg Glu Lys Glu Glu Gln Arg Gly Leu Arg Lys Tyr Asn Tyr
                325                 330                 335

Thr Leu Leu Arg Val Arg Leu Pro Asp Gly Cys Leu Leu Gln Gly Thr
            340                 345                 350

Phe Tyr Ala Arg Glu Arg Leu Gly Ala Val Tyr Gly Phe Val Arg Glu
            355                 360                 365

Ala Leu Gln Ser Asp Trp Leu Pro Phe Glu Leu Leu Ala Ser Gly Gly
            370                 375                 380

Gln Lys Leu Ser Glu Asp Glu Asn Leu Ala Leu Asn Glu Cys Gly Leu
385                 390                 395                 400

Val Pro Ser Ala Leu Leu Thr Phe Ser Trp Asp Met Ala Val Leu Glu
            405                 410                 415

Asp Ile Lys Ala Ala Gly Ala Glu Pro Asp Ser Ile Leu Lys Pro Glu
            420                 425                 430

Leu Leu Ser Ala Ile Glu Lys Leu Leu
            435                 440

<210> SEQ ID NO 105
<211> LENGTH: 737
<212> TYPE: PRT
<213> ORGANISM: Homo sapiens

<400> SEQUENCE: 105

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
            35                  40                  45

Ser Arg Ile Gly Gln Thr Ala Thr Lys Gln Lys Thr Asn Ser Pro Ala
50                  55                  60
```

-continued

```
Trp His Asp Glu Phe Val Thr Asp Val Cys Asn Gly Arg Lys Ile Glu
 65                  70                  75                  80

Leu Ala Val Phe His Asp Ala Pro Ile Gly Tyr Asp Asp Phe Val Ala
                 85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Arg Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Gln Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285

Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ile Ala Gly Ala Glu Ser Pro Gln Pro Ala Ser Gly Ser
                325                 330                 335

Ser Pro Ser Glu Glu Asp Arg Ser Lys Ser Ala Pro Thr Ser Pro Cys
            340                 345                 350

Asp Gln Glu Ile Lys Glu Leu Glu Asn Asn Ile Arg Lys Ala Leu Ser
        355                 360                 365

Phe Asp Asn Arg Gly Glu Glu His Arg Ala Ala Ser Ser Pro Asp Gly
    370                 375                 380

Gln Leu Met Ser Pro Gly Glu Asn Gly Glu Val Arg Gln Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
        435                 440                 445

Asp Val Asp Cys Thr Met Thr Glu Lys Arg Ile Leu Ala Leu Ala Arg
    450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
```

```
            485                 490                 495
Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
            515                 520                 525

Ile Tyr Arg Asp Leu Lys Leu Asp Asn Ile Leu Leu Asp Ala Glu Gly
            530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
            595                 600                 605

Ala Asp Asn Glu Asp Asp Leu Phe Glu Ser Ile Leu His Asp Asp Val
            610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
                645                 650                 655

Asn Gly Glu Asp Ala Ile Lys Gln His Pro Phe Phe Lys Glu Ile Asp
                660                 665                 670

Trp Val Leu Leu Glu Gln Lys Lys Ile Lys Pro Pro Phe Lys Pro Arg
                675                 680                 685

Ile Lys Thr Lys Arg Asp Val Asn Asn Phe Asp Gln Asp Phe Thr Arg
            690                 695                 700

Glu Glu Pro Val Leu Thr Leu Val Asp Glu Ala Ile Val Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 106
<211> LENGTH: 183
<212> TYPE: PRT
<213> ORGANISM: Homo sapiens

<400> SEQUENCE: 106

Met Ser Ser Pro Ser Pro Gly Lys Arg Arg Met Asp Thr Asp Val Val
1               5                   10                  15

Lys Leu Ile Glu Ser Lys His Glu Val Thr Ile Leu Gly Gly Leu Asn
            20                  25                  30

Glu Phe Val Val Lys Phe Tyr Gly Pro Gln Gly Thr Pro Tyr Glu Gly
            35                  40                  45

Gly Val Trp Lys Val Arg Val Asp Leu Pro Asp Lys Tyr Pro Phe Lys
            50                  55                  60

Ser Pro Ser Ile Gly Phe Met Asn Lys Ile Phe His Pro Asn Ile Asp
65                  70                  75                  80

Glu Ala Ser Gly Thr Val Cys Leu Asp Val Ile Asn Gln Thr Trp Thr
                85                  90                  95

Ala Leu Tyr Asp Leu Thr Asn Ile Phe Glu Ser Phe Leu Pro Gln Leu
            100                 105                 110

Leu Ala Tyr Pro Asn Pro Ile Asp Pro Leu Asn Gly Asp Ala Ala Ala
```

|  |  | 115 |  |  | 120 |  |  | 125 |  |  |  |

Met Tyr Leu His Arg Pro Glu Glu Tyr Lys Gln Lys Ile Lys Glu Tyr
    130                 135                 140

Ile Gln Lys Tyr Ala Thr Glu Ala Leu Lys Glu Gln Glu Glu Gly
145                 150                 155                 160

Thr Gly Asp Ser Ser Glu Ser Ser Met Ser Asp Phe Ser Glu Asp
                165                 170                 175

Glu Ala Gln Asp Met Glu Leu
                180

<210> SEQ ID NO 107
<211> LENGTH: 1146
<212> TYPE: PRT
<213> ORGANISM: Homo sapiens

<400> SEQUENCE: 107

Met Val Leu Gly Thr Val Leu Leu Pro Pro Asn Ser Tyr Gly Arg Asp
1               5                   10                  15

Gln Asp Thr Ser Leu Cys Cys Leu Cys Thr Glu Ala Ser Glu Ser Ala
                20                  25                  30

Leu Pro Asp Leu Thr Glu Ala Leu His Arg Pro Tyr Gly Cys Asp Val
            35                  40                  45

Glu Pro Gln Ala Leu Asn Glu Ala Ile Arg Trp Ser Ser Lys Glu Asn
50                  55                  60

Leu Leu Gly Ala Thr Glu Ser Asp Pro Asn Leu Phe Val Ala Leu Tyr
65                  70                  75                  80

Asp Phe Val Ala Ser Gly Asp Asn Thr Leu Ser Ile Thr Lys Gly Glu
                85                  90                  95

Lys Leu Arg Val Leu Gly Tyr Asn Gln Asn Gly Glu Trp Ser Glu Val
            100                 105                 110

Arg Ser Lys Asn Gly Gln Gly Trp Val Pro Ser Asn Tyr Ile Thr Pro
        115                 120                 125

Val Asn Ser Leu Glu Lys His Ser Trp Tyr His Gly Pro Val Ser Arg
130                 135                 140

Ser Ala Ala Glu Tyr Leu Leu Ser Ser Leu Ile Asn Gly Ser Phe Leu
145                 150                 155                 160

Val Arg Glu Ser Glu Ser Ser Pro Gly Gln Leu Ser Ile Ser Leu Arg
                165                 170                 175

Tyr Glu Gly Arg Val Tyr His Tyr Arg Ile Asn Thr Ala Asp Gly
            180                 185                 190

Lys Val Tyr Val Thr Ala Glu Ser Arg Phe Ser Thr Leu Ala Glu Leu
        195                 200                 205

Val His His Ser Thr Val Ala Asp Gly Leu Val Thr Thr Leu His
210                 215                 220

Tyr Pro Ala Pro Lys Cys Asn Lys Pro Thr Val Tyr Gly Val Ser Pro
225                 230                 235                 240

Ile His Asp Lys Trp Glu Met Glu Arg Thr Asp Ile Thr Met Lys His
                245                 250                 255

Lys Leu Gly Gly Gly Gln Tyr Gly Glu Val Tyr Val Gly Val Trp Lys
            260                 265                 270

Lys Tyr Ser Leu Thr Val Ala Val Lys Thr Leu Lys Glu Asp Thr Met
        275                 280                 285

Glu Val Glu Glu Phe Leu Lys Glu Ala Ala Val Met Lys Glu Ile Lys
    290                 295                 300

-continued

```
His Pro Asn Leu Val Gln Leu Leu Gly Val Cys Thr Leu Glu Pro Pro
305                 310                 315                 320

Phe Tyr Ile Val Thr Glu Tyr Met Pro Tyr Gly Asn Leu Leu Asp Tyr
                325                 330                 335

Leu Arg Glu Cys Asn Arg Glu Val Thr Ala Val Val Leu Leu Tyr
            340                 345                 350

Met Ala Thr Gln Ile Ser Ser Ala Met Glu Tyr Leu Glu Lys Lys Asn
                355                 360                 365

Phe Ile His Arg Asp Leu Ala Ala Arg Asn Cys Leu Val Gly Glu Asn
        370                 375                 380

His Val Val Lys Val Ala Asp Phe Gly Leu Ser Arg Leu Met Thr Gly
385                 390                 395                 400

Asp Thr Tyr Thr Ala His Ala Gly Ala Lys Phe Pro Ile Lys Trp Thr
                405                 410                 415

Ala Pro Glu Ser Leu Ala Tyr Asn Thr Phe Ser Ile Lys Ser Asp Val
            420                 425                 430

Trp Ala Phe Gly Val Leu Leu Trp Glu Ile Ala Thr Tyr Gly Met Ser
                435                 440                 445

Pro Tyr Pro Gly Ile Asp Leu Ser Gln Val Tyr Asp Leu Leu Glu Lys
450                 455                 460

Gly Tyr Arg Met Glu Gln Pro Glu Gly Cys Pro Pro Lys Val Tyr Glu
465                 470                 475                 480

Leu Met Arg Ala Cys Trp Lys Trp Ser Pro Ala Asp Arg Pro Ser Phe
                485                 490                 495

Ala Glu Thr His Gln Ala Phe Glu Thr Met Phe His Asp Ser Ser Ile
            500                 505                 510

Ser Glu Glu Val Ala Glu Glu Leu Gly Arg Ala Ala Ser Ser Ser Ser
            515                 520                 525

Val Val Pro Tyr Leu Pro Arg Leu Pro Ile Leu Pro Ser Lys Thr Arg
530                 535                 540

Thr Leu Lys Lys Gln Val Glu Asn Lys Glu Asn Ile Glu Gly Ala Gln
545                 550                 555                 560

Asp Ala Thr Glu Asn Ser Ala Ser Ser Leu Ala Pro Gly Phe Ile Arg
                565                 570                 575

Gly Ala Gln Ala Ser Ser Gly Ser Pro Ala Leu Pro Arg Lys Gln Arg
            580                 585                 590

Asp Lys Ser Pro Ser Ser Leu Leu Glu Asp Ala Lys Glu Thr Cys Phe
        595                 600                 605

Thr Arg Asp Arg Lys Gly Gly Phe Phe Ser Ser Phe Met Lys Lys Arg
610                 615                 620

Asn Ala Pro Thr Pro Lys Arg Ser Ser Ser Phe Arg Glu Met Glu
625                 630                 635                 640

Asn Gln Pro His Lys Lys Tyr Glu Leu Thr Gly Asn Phe Ser Ser Val
                645                 650                 655

Ala Ser Leu Gln His Ala Asp Gly Phe Ser Phe Thr Pro Ala Gln Gln
            660                 665                 670

Glu Ala Asn Leu Val Pro Pro Lys Cys Tyr Gly Gly Ser Phe Ala Gln
                675                 680                 685

Arg Asn Leu Cys Asn Asp Asp Gly Gly Gly Gly Gly Ser Gly Thr
            690                 695                 700

Ala Gly Gly Gly Trp Ser Gly Ile Thr Gly Phe Phe Thr Pro Arg Leu
705                 710                 715                 720

Ile Lys Lys Thr Leu Gly Leu Arg Ala Gly Lys Pro Thr Ala Ser Asp
```

```
                    725                 730                 735
Asp Thr Ser Lys Pro Phe Pro Arg Ser Asn Ser Thr Ser Ser Met Ser
                740                 745                 750

Ser Gly Leu Pro Glu Gln Asp Arg Met Ala Met Thr Leu Pro Arg Asn
            755                 760                 765

Cys Gln Arg Ser Lys Leu Gln Leu Glu Arg Thr Val Ser Thr Ser Ser
        770                 775                 780

Gln Pro Glu Glu Asn Val Asp Arg Ala Asn Asp Met Leu Pro Lys Lys
785                 790                 795                 800

Ser Glu Glu Ser Ala Ala Pro Ser Arg Glu Arg Pro Lys Ala Lys Leu
                805                 810                 815

Leu Pro Arg Gly Ala Thr Ala Leu Pro Leu Arg Thr Pro Ser Gly Asp
            820                 825                 830

Leu Ala Ile Thr Glu Lys Asp Pro Pro Gly Val Gly Val Ala Gly Val
        835                 840                 845

Ala Ala Ala Pro Lys Gly Lys Glu Lys Asn Gly Gly Ala Arg Leu Gly
    850                 855                 860

Met Ala Gly Val Pro Glu Asp Gly Glu Gln Pro Gly Trp Pro Ser Pro
865                 870                 875                 880

Ala Lys Ala Ala Pro Val Leu Pro Thr Thr His Asn His Lys Val Pro
                885                 890                 895

Val Leu Ile Ser Pro Thr Leu Lys His Thr Pro Ala Asp Val Gln Leu
            900                 905                 910

Ile Gly Thr Asp Ser Gln Gly Asn Lys Phe Lys Leu Leu Ser Glu His
        915                 920                 925

Gln Val Thr Ser Ser Gly Asp Lys Asp Arg Pro Arg Arg Val Lys Pro
    930                 935                 940

Lys Cys Ala Pro Pro Pro Pro Val Met Arg Leu Leu Gln His Pro
945                 950                 955                 960

Ser Ile Cys Ser Asp Pro Thr Glu Glu Pro Thr Ala Leu Thr Ala Gly
                965                 970                 975

Gln Ser Thr Ser Glu Thr Gln Glu Gly Gly Lys Lys Ala Ala Leu Gly
            980                 985                 990

Ala Val Pro Ile Ser Gly Lys Ala Gly Arg Pro Val Met Pro Pro Pro
        995                1000                1005

Gln Val Pro Leu Pro Thr Ser Ser Ile Ser Pro Ala Lys Met Ala Asn
    1010                1015                1020

Gly Thr Ala Gly Thr Lys Val Ala Leu Arg Lys Thr Lys Gln Ala Ala
1025                1030                1035                1040

Glu Lys Ile Ser Ala Asp Lys Ile Ser Lys Glu Ala Leu Leu Glu Cys
                1045                1050                1055

Ala Asp Leu Leu Ser Ser Ala Leu Thr Glu Pro Val Pro Asn Ser Gln
            1060                1065                1070

Leu Val Asp Thr Gly His Gln Leu Leu Asp Tyr Cys Ser Gly Tyr Val
        1075                1080                1085

Asp Cys Ile Pro Gln Thr Arg Asn Lys Phe Ala Phe Arg Glu Ala Val
    1090                1095                1100

Ser Lys Leu Glu Leu Ser Leu Gln Glu Leu Gln Val Ser Ala Ala
1105                1110                1115                1120

Ala Gly Val Pro Gly Thr Asn Pro Val Leu Asn Asn Leu Leu Ser Cys
                1125                1130                1135

Val Gln Glu Ile Ser Asp Val Val Gln Arg
            1140                1145
```

<210> SEQ ID NO 108
<211> LENGTH: 365
<212> TYPE: PRT
<213> ORGANISM: Homo sapiens

<400> SEQUENCE: 108

```
Met Asn Arg Glu Asp Arg Asn Val Leu Arg Met Lys Glu Arg Glu Arg
1               5                   10                  15

Arg Asn Gln Glu Ile Gln Gln Gly Glu Asp Ala Phe Pro Pro Ser Ser
            20                  25                  30

Pro Leu Phe Ala Glu Pro Tyr Lys Val Thr Ser Lys Glu Asp Lys Leu
        35                  40                  45

Ser Ser Arg Ile Gln Ser Met Leu Gly Asn Tyr Asp Glu Met Lys Asp
    50                  55                  60

Phe Ile Gly Asp Arg Ser Ile Pro Lys Leu Val Ala Ile Pro Lys Pro
65                  70                  75                  80

Thr Val Pro Pro Ser Ala Asp Glu Lys Ser Asn Pro Asn Phe Phe Glu
                85                  90                  95

Gln Arg His Gly Gly Ser His Gln Ser Ser Lys Trp Thr Pro Val Gly
            100                 105                 110

Pro Ala Pro Ser Thr Ser Gln Ser Gln Lys Arg Ser Ser Gly Leu Gln
        115                 120                 125

Ser Gly His Ser Ser Gln Arg Thr Ser Ala Gly Ser Ser Ser Gly Thr
    130                 135                 140

Asn Ser Ser Gly Gln Arg His Asp Arg Glu Ser Tyr Asn Asn Ser Gly
145                 150                 155                 160

Ser Ser Ser Arg Lys Lys Gly Gln His Gly Ser Glu His Ser Lys Ser
                165                 170                 175

Arg Ser Ser Pro Gly Lys Pro Gln Ala Val Ser Ser Leu Asn Ser
            180                 185                 190

Ser His Ser Arg Ser His Gly Asn Asp His His Ser Lys Glu His Gln
    195                 200                 205

Arg Ser Lys Ser Pro Arg Asp Pro Asp Ala Asn Trp Asp Ser Pro Ser
210                 215                 220

Arg Val Pro Phe Ser Ser Gly Gln His Ser Thr Gln Ser Phe Pro Pro
225                 230                 235                 240

Ser Leu Met Ser Lys Ser Asn Ser Met Leu Gln Lys Pro Thr Ala Tyr
                245                 250                 255

Val Arg Pro Met Asp Gly Gln Glu Ser Met Glu Pro Lys Leu Ser Ser
            260                 265                 270

Glu His Tyr Ser Ser Gln Ser His Gly Asn Ser Met Thr Glu Leu Lys
        275                 280                 285

Pro Ser Ser Lys Ala His Leu Thr Lys Leu Lys Ile Pro Ser Gln Pro
    290                 295                 300

Leu Asp Ala Ser Ala Ser Gly Asp Val Ser Cys Val Asp Glu Ile Leu
305                 310                 315                 320

Lys Glu Met Thr His Ser Trp Pro Pro Leu Thr Ala Ile His Thr
                325                 330                 335

Pro Cys Lys Thr Glu Pro Ser Lys Phe Pro Phe Pro Thr Lys Glu Ser
            340                 345                 350

Gln Gln Ser Asn Phe Gly Thr Gly Glu Gln Arg Leu Lys
        355                 360                 365
```

<210> SEQ ID NO 109
<211> LENGTH: 726
<212> TYPE: PRT
<213> ORGANISM: Homo sapiens

<400> SEQUENCE: 109

```
Met Glu Gly Glu Arg Lys Asn Asn Lys Arg Trp Tyr Phe Thr Arg
1               5                   10                  15

Glu Gln Leu Glu Asn Ser Pro Ser Arg Arg Phe Gly Val Asp Pro Asp
            20                  25                  30

Lys Glu Leu Ser Tyr Arg Gln Gln Ala Ala Asn Leu Leu Gln Asp Met
                35                  40                  45

Gly Gln Arg Leu Asn Val Ser Gln Leu Thr Ile Asn Thr Ala Ile Val
50                  55                  60

Tyr Met His Arg Phe Tyr Met Ile Gln Ser Phe Thr Gln Phe Pro Gly
65                  70                  75                  80

Asn Ser Val Ala Pro Ala Ala Leu Phe Leu Ala Ala Lys Val Glu Glu
                85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
        115                 120                 125

Gln Val Gln Asp Leu Val Ile Leu Glu Ser Ile Ile Leu Gln Thr Leu
130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
            180                 185                 190

Pro Pro Val Val Ala Cys Val Cys Ile His Leu Ala Cys Lys Trp Ser
        195                 200                 205

Asn Trp Glu Ile Pro Val Ser Thr Asp Gly Lys His Trp Trp Glu Tyr
210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
            260                 265                 270

Gly Thr Asp Glu Lys Thr Ser Glu Gln Thr Ile Leu Asn Met Ile Ser
        275                 280                 285

Gln Ser Ser Ser Asp Thr Thr Ile Ala Gly Leu Met Ser Met Ser Thr
290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335

Ser Gln Pro Ser Phe Lys Leu Glu Pro Thr Gln Gly His Arg Thr Ser
            340                 345                 350

Glu Asn Leu Ala Leu Thr Gly Val Asp His Ser Leu Pro Gln Asp Gly
        355                 360                 365

Ser Asn Ala Phe Ile Ser Gln Lys Gln Asn Ser Lys Val Pro Ser
370                 375                 380
```

```
Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
            405                 410                 415

Gln Tyr Ala Tyr Ala Ala Gln Asn Leu Leu Ser His His Asp Ser His
            420                 425                 430

Ser Ser Val Ile Leu Lys Met Pro Ile Glu Gly Ser Glu Asn Pro Glu
            435                 440                 445

Arg Pro Phe Leu Glu Lys Ala Asp Lys Thr Ala Leu Lys Met Arg Ile
            450                 455                 460

Pro Val Ala Gly Gly Asp Lys Ala Ala Ser Ser Lys Pro Glu Glu Ile
465                 470                 475                 480

Lys Met Arg Ile Lys Val His Ala Ala Ala Asp Lys His Asn Ser Val
                485                 490                 495

Glu Asp Ser Val Thr Lys Ser Arg Glu His Lys Glu Lys His Lys Thr
                500                 505                 510

His Pro Ser Asn His His His His Asn His Ser His Lys His
515                 520                 525

Ser His Ser Gln Leu Pro Val Gly Thr Gly Asn Lys Arg Pro Gly Asp
530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Thr Arg Lys Arg Gly Pro
            565                 570                 575

Ser Glu Glu Thr Gly Gly Ala Val Phe Asp His Pro Ala Lys Ile Ala
            580                 585                 590

Lys Ser Thr Lys Ser Ser Ser Leu Asn Phe Ser Phe Pro Ser Leu Pro
            595                 600                 605

Thr Met Gly Gln Met Pro Gly His Ser Ser Asp Thr Ser Gly Leu Ser
610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
            645                 650                 655

Tyr Gln Asp Thr Val Asn Met Leu His Ser Leu Leu Ser Ala Gln Gly
            660                 665                 670

Val Gln Pro Thr Gln Pro Thr Ala Phe Glu Phe Val Arg Pro Tyr Ser
            675                 680                 685

Asp Tyr Leu Asn Pro Arg Ser Gly Gly Ile Ser Ser Arg Ser Gly Asn
690                 695                 700

Thr Asp Lys Pro Arg Pro Pro Leu Pro Ser Glu Pro Pro Pro
705                 710                 715                 720

Leu Pro Pro Leu Pro Lys
                725

<210> SEQ ID NO 110
<211> LENGTH: 258
<212> TYPE: PRT
<213> ORGANISM: Homo sapiens

<400> SEQUENCE: 110

Met Thr His Asp Lys Ser Trp Arg Arg Cys Ser Ile Ser Gly Ser Thr
1               5                   10                  15

Lys Cys Arg Cys Gly Ser Arg Ile Ala Gly Pro Asn Ala Leu Gly Ser
            20                  25                  30
```

Gly Gly Ser Arg Ser Ser Ser Ser Ser Arg Ser Ile Leu Ser Ser
            35                  40                  45

Ser Ile Leu Ser Ser Ser Ile Pro Ser Ser Ser Ser Ser Ser Ser
 50                  55                  60

Pro Ser Ser Ser His Ser Ser Ser Pro Ser Ser His Ser Ser Ser
 65                  70                  75                  80

Ser Ser Pro Ser Ser Ser Ser Thr Ser Ser Pro Ser Ser Ser Ser
                85                  90                  95

Ser Ser Ser Ser Ser Ser Ser Pro Ser Ser Asn Ser Ser Ser Ser
            100                 105                 110

Ser Ser Ser Ser Ser Pro Ser Ser Ser Ser Ser Ser Ser Ser Ser
            115                 120                 125

Pro Ser Ser Ser Ser Ser Ser Pro Ser Ser Ser Ser Ser Ser Ser
 130                 135                 140

Ser Ser Pro Ser Ser Ser Ser Ser Pro Ser Ser Ser Ser Ser Ser
145                 150                 155                 160

Ser Ser Ser Ser Ser Ser Pro Ser Ser Ser Ser Pro Ser Ser Ser
                165                 170                 175

Gly Ser Ser Pro Ser Ser Ser Asn Ser Ser Pro Ser Ser Ser Ser
            180                 185                 190

Ser Pro Ser Ser Ser Ser Ser Pro Ser Pro Arg Ser Ser Ser Pro
     195                 200                 205

Ser Ser Ser Ser Ser Ser Thr Ser Ser Pro Ser Thr Ser Ser Pro Ser
210                 215                 220

Ser Ser Ser Pro Ser Ser Ser Ser Pro Ser Ser Ser Cys Pro Ser Ala
225                 230                 235                 240

Ala Leu Gly Arg Arg Pro Gln Ser Pro Gln Ser Ser His Cys Ala Pro
                245                 250                 255

Phe Pro

<210> SEQ ID NO 111
<211> LENGTH: 358
<212> TYPE: PRT
<213> ORGANISM: Homo sapiens

<400> SEQUENCE: 111

Met Asp Asp Ala Thr Val Leu Arg Lys Lys Gly Tyr Ile Val Gly Ile
 1               5                   10                  15

Asn Leu Gly Lys Gly Ser Tyr Ala Lys Val Lys Ser Ala Tyr Ser Glu
                20                  25                  30

Arg Leu Lys Phe Asn Val Ala Val Lys Ile Ile Asp Arg Lys Lys Thr
            35                  40                  45

Pro Thr Asp Phe Val Glu Arg Phe Leu Pro Arg Glu Met Asp Ile Leu
 50                  55                  60

Ala Thr Val Asn His Gly Ser Ile Ile Lys Thr Tyr Glu Ile Phe Glu
 65                  70                  75                  80

Thr Ser Asp Gly Arg Ile Tyr Ile Ile Met Glu Leu Gly Val Gln Gly
                85                  90                  95

Asp Leu Leu Glu Phe Ile Lys Cys Gln Gly Ala Leu His Glu Asp Val
            100                 105                 110

Ala Arg Lys Met Phe Arg Gln Leu Ser Ser Ala Val Lys Tyr Cys His
            115                 120                 125

Asp Leu Asp Ile Val His Arg Asp Leu Lys Cys Glu Asn Leu Leu Leu
            130                 135                 140

```
Asp Lys Asp Phe Asn Ile Lys Leu Ser Asp Phe Gly Phe Ser Lys Arg
145                 150                 155                 160

Cys Leu Arg Asp Ser Asn Gly Arg Ile Ile Leu Ser Lys Thr Phe Cys
            165                 170                 175

Gly Ser Ala Ala Tyr Ala Ala Pro Glu Val Leu Gln Ser Ile Pro Tyr
            180                 185                 190

Gln Pro Lys Val Tyr Asp Ile Trp Ser Leu Gly Val Ile Leu Tyr Ile
            195                 200                 205

Met Val Cys Gly Ser Met Pro Tyr Asp Asp Ser Asp Ile Arg Lys Met
210                 215                 220

Leu Arg Ile Gln Lys Glu His Arg Val Asp Phe Pro Arg Ser Lys Asn
225                 230                 235                 240

Leu Thr Cys Glu Cys Lys Asp Leu Ile Tyr Arg Met Leu Gln Pro Asp
            245                 250                 255

Val Ser Gln Arg Leu His Ile Asp Glu Ile Leu Ser His Ser Trp Leu
            260                 265                 270

Gln Pro Pro Lys Pro Lys Ala Thr Ser Ser Ala Ser Phe Lys Arg Glu
            275                 280                 285

Gly Glu Gly Lys Tyr Arg Ala Glu Cys Lys Leu Asp Thr Lys Thr Gly
290                 295                 300

Leu Arg Pro Asp His Arg Pro Asp His Lys Leu Gly Ala Lys Thr Gln
305                 310                 315                 320

His Arg Leu Leu Val Val Pro Glu Asn Glu Asn Arg Met Glu Asp Arg
            325                 330                 335

Leu Ala Glu Thr Ser Arg Ala Lys Asp His His Ile Ser Gly Ala Glu
            340                 345                 350

Val Gly Lys Ala Ser Thr
            355

<210> SEQ ID NO 112
<211> LENGTH: 661
<212> TYPE: PRT
<213> ORGANISM: Homo sapiens

<400> SEQUENCE: 112

Met Glu Gly Ala Ala Ala Pro Val Ala Gly Asp Arg Pro Asp Leu Gly
1               5                   10                  15

Leu Gly Ala Pro Gly Ser Pro Arg Glu Ala Val Ala Gly Ala Thr Ala
            20                  25                  30

Ala Leu Glu Pro Arg Lys Pro His Gly Val Lys Arg His His His Lys
            35                  40                  45

His Asn Leu Lys His Arg Tyr Glu Leu Gln Glu Thr Leu Gly Lys Gly
            50                  55                  60

Thr Tyr Gly Lys Val Lys Arg Ala Thr Glu Arg Phe Ser Gly Arg Val
65                  70                  75                  80

Val Ala Ile Lys Ser Ile Arg Lys Asp Lys Ile Lys Asp Glu Gln Asp
            85                  90                  95

Met Val His Ile Arg Arg Glu Ile Glu Ile Met Ser Ser Leu Asn His
            100                 105                 110

Pro His Ile Ile Ser Ile Tyr Glu Val Phe Glu Asn Lys Asp Lys Ile
            115                 120                 125

Val Ile Ile Met Glu Tyr Ala Ser Lys Gly Glu Leu Tyr Asp Tyr Ile
            130                 135                 140

Ser Glu Arg Arg Arg Leu Ser Glu Arg Glu Thr Arg His Phe Phe Arg
```

```
145                 150                 155                 160
Gln Ile Val Ser Ala Val His Tyr Cys His Lys Asn Gly Val His
                165                 170                 175

Arg Asp Leu Lys Leu Glu Asn Ile Leu Leu Asp Asp Asn Cys Asn Ile
                180                 185                 190

Lys Ile Ala Asp Phe Gly Leu Ser Asn Leu Tyr Gln Lys Asp Lys Phe
                195                 200                 205

Leu Gln Thr Phe Cys Gly Ser Pro Leu Tyr Ala Ser Pro Glu Ile Val
                210                 215                 220

Asn Gly Arg Pro Tyr Arg Gly Pro Glu Val Asp Ser Trp Ala Leu Gly
225                 230                 235                 240

Val Leu Leu Tyr Thr Leu Val Tyr Gly Thr Met Pro Phe Asp Gly Phe
                245                 250                 255

Asp His Lys Asn Leu Ile Arg Gln Ile Ser Ser Gly Glu Tyr Arg Glu
                260                 265                 270

Pro Thr Gln Pro Ser Asp Ala Arg Gly Leu Ile Arg Trp Met Leu Met
                275                 280                 285

Val Asn Pro Asp Arg Arg Ala Thr Ile Glu Asp Ile Ala Asn His Trp
                290                 295                 300

Trp Val Asn Trp Gly Tyr Lys Ser Ser Val Cys Asp Cys Asp Ala Leu
305                 310                 315                 320

His Asp Ser Glu Ser Pro Leu Leu Ala Arg Ile Ile Asp Trp His His
                325                 330                 335

Arg Ser Thr Gly Leu Gln Ala Asp Thr Glu Ala Lys Met Lys Gly Leu
                340                 345                 350

Ala Lys Pro Thr Thr Ser Glu Val Met Leu Glu Arg Gln Arg Ser Leu
                355                 360                 365

Lys Lys Ser Lys Lys Glu Asn Asp Phe Ala Gln Ser Gly Gln Asp Ala
                370                 375                 380

Val Pro Glu Ser Pro Ser Lys Leu Ser Ser Lys Arg Pro Lys Gly Ile
385                 390                 395                 400

Leu Lys Lys Arg Ser Asn Ser Glu His Arg Ser His Ser Thr Gly Phe
                405                 410                 415

Ile Glu Gly Val Val Gly Pro Ala Leu Pro Ser Thr Phe Lys Met Glu
                420                 425                 430

Gln Asp Leu Cys Arg Thr Gly Val Leu Leu Pro Ser Ser Pro Glu Ala
                435                 440                 445

Glu Val Pro Gly Lys Leu Ser Pro Lys Gln Ser Ala Thr Met Pro Lys
                450                 455                 460

Lys Gly Ile Leu Lys Lys Thr Gln Gln Arg Glu Ser Gly Tyr Tyr Ser
465                 470                 475                 480

Ser Pro Glu Arg Ser Glu Ser Ser Glu Leu Leu Asp Ser Asn Asp Val
                485                 490                 495

Met Gly Ser Ser Ile Pro Ser Pro Ser Pro Asp Pro Ala Arg Val
                500                 505                 510

Thr Ser His Ser Leu Ser Cys Arg Arg Lys Gly Ile Leu Lys His Ser
                515                 520                 525

Ser Lys Tyr Ser Ala Gly Thr Met Asp Pro Ala Leu Val Ser Pro Glu
                530                 535                 540

Met Pro Thr Leu Glu Ser Leu Ser Glu Pro Gly Val Pro Ala Glu Gly
545                 550                 555                 560

Leu Ser Arg Ser Tyr Ser Arg Pro Ser Ser Val Ile Ser Asp Asp Ser
                565                 570                 575
```

Val Leu Ser Ser Asp Ser Phe Asp Leu Leu Asp Leu Gln Glu Asn Arg
            580                 585                 590

Pro Ala Arg Gln Arg Ile Arg Ser Cys Val Ser Ala Glu Asn Phe Leu
            595                 600                 605

Gln Ile Gln Asp Phe Glu Gly Leu Gln Asn Arg Pro Arg Pro Gln Tyr
    610                 615                 620

Leu Lys Arg Tyr Arg Asn Arg Leu Ala Asp Ser Ser Phe Ser Leu Leu
625                 630                 635                 640

Thr Asp Met Asp Asp Val Thr Gln Val Tyr Lys Gln Ala Leu Glu Ile
                645                 650                 655

Cys Ser Lys Leu Asn
            660

<210> SEQ ID NO 113
<211> LENGTH: 724
<212> TYPE: PRT
<213> ORGANISM: Homo sapiens

<400> SEQUENCE: 113

Met Ser Ser Ala Arg Thr Pro Leu Pro Thr Leu Asn Glu Arg Asp Thr
1               5                   10                  15

Glu Gln Pro Thr Leu Gly His Leu Asp Ser Lys Pro Ser Ser Lys Ser
            20                  25                  30

Asn Met Ile Arg Gly Arg Asn Ser Ala Thr Ser Ala Asp Glu Gln Pro
        35                  40                  45

His Ile Gly Asn Tyr Arg Leu Leu Lys Thr Ile Gly Lys Gly Asn Phe
    50                  55                  60

Ala Lys Val Lys Leu Ala Arg His Ile Leu Thr Gly Lys Glu Val Ala
65                  70                  75                  80

Val Lys Ile Ile Asp Lys Thr Gln Leu Asn Ser Ser Ser Leu Gln Lys
                85                  90                  95

Leu Phe Arg Glu Val Arg Ile Met Lys Val Leu Asn His Pro Asn Ile
            100                 105                 110

Val Lys Leu Phe Glu Val Ile Glu Thr Glu Lys Thr Leu Tyr Leu Val
        115                 120                 125

Met Glu Tyr Ala Ser Gly Gly Glu Val Phe Asp Tyr Leu Val Ala His
    130                 135                 140

Gly Arg Met Lys Glu Lys Glu Ala Arg Ala Lys Phe Arg Gln Ile Val
145                 150                 155                 160

Ser Ala Val Gln Tyr Cys His Gln Lys Phe Ile Val His Arg Asp Leu
                165                 170                 175

Lys Ala Glu Asn Leu Leu Leu Asp Ala Asp Met Asn Ile Lys Ile Ala
            180                 185                 190

Asp Phe Gly Phe Ser Asn Glu Phe Thr Phe Gly Asn Lys Leu Asp Thr
        195                 200                 205

Phe Cys Gly Ser Pro Pro Tyr Ala Ala Pro Glu Leu Phe Gln Gly Lys
    210                 215                 220

Lys Tyr Asp Gly Pro Glu Val Asp Val Trp Ser Leu Gly Val Ile Leu
225                 230                 235                 240

Tyr Thr Leu Val Ser Gly Ser Leu Pro Phe Asp Gly Gln Asn Leu Lys
                245                 250                 255

Glu Leu Arg Glu Arg Val Leu Arg Gly Lys Tyr Arg Ile Pro Phe Tyr
            260                 265                 270

Met Ser Thr Asp Cys Glu Asn Leu Leu Lys Lys Phe Leu Ile Leu Asn

```
                275                 280                 285
Pro Ser Lys Arg Gly Thr Leu Glu Gln Ile Met Lys Asp Arg Trp Met
290                 295                 300

Asn Val Gly His Glu Asp Asp Glu Leu Lys Pro Tyr Val Glu Pro Leu
305                 310                 315                 320

Pro Asp Tyr Lys Asp Pro Arg Arg Thr Glu Leu Met Val Ser Met Gly
                325                 330                 335

Tyr Thr Arg Glu Glu Ile Gln Asp Ser Leu Val Gly Gln Arg Tyr Asn
            340                 345                 350

Glu Val Met Ala Thr Tyr Leu Leu Gly Tyr Lys Ser Ser Glu Leu
        355                 360                 365

Glu Gly Asp Thr Ile Thr Leu Lys Pro Arg Pro Ser Ala Asp Leu Thr
        370                 375                 380

Asn Ser Ser Ala Pro Ser Pro Ser His Lys Val Gln Arg Ser Val Ser
385                 390                 395                 400

Ala Asn Pro Lys Gln Arg Arg Phe Ser Asp Gln Ala Gly Pro Ala Ile
                405                 410                 415

Pro Thr Ser Asn Ser Tyr Ser Lys Lys Thr Gln Ser Asn Asn Ala Glu
            420                 425                 430

Asn Lys Arg Pro Glu Glu Asp Arg Glu Ser Gly Arg Lys Ala Ser Ser
        435                 440                 445

Thr Ala Lys Val Pro Ala Ser Pro Leu Pro Gly Leu Glu Arg Lys Lys
    450                 455                 460

Thr Thr Pro Thr Pro Ser Thr Asn Ser Val Leu Ser Thr Ser Thr Asn
465                 470                 475                 480

Arg Ser Arg Asn Ser Pro Leu Leu Glu Arg Ala Ser Leu Gly Gln Ala
                485                 490                 495

Ser Ile Gln Asn Gly Lys Asp Ser Thr Ala Pro Gln Arg Val Pro Val
            500                 505                 510

Ala Ser Pro Ser Ala His Asn Ile Ser Ser Gly Gly Ala Pro Asp
        515                 520                 525

Arg Thr Asn Phe Pro Arg Gly Val Ser Ser Arg Ser Thr Phe His Ala
    530                 535                 540

Gly Gln Leu Arg Gln Val Arg Asp Gln Gln Asn Leu Pro Tyr Gly Val
545                 550                 555                 560

Thr Pro Ala Ser Pro Ser Gly His Ser Gln Gly Arg Arg Gly Ala Ser
                565                 570                 575

Gly Ser Ile Phe Ser Lys Phe Thr Ser Lys Phe Val Arg Arg Asn Leu
            580                 585                 590

Asn Glu Pro Glu Ser Lys Asp Arg Val Glu Thr Leu Arg Pro His Val
        595                 600                 605

Val Gly Ser Gly Asn Asp Lys Glu Lys Glu Glu Phe Arg Glu Ala
    610                 615                 620

Lys Pro Arg Ser Leu Arg Phe Thr Trp Ser Met Lys Thr Thr Ser Ser
625                 630                 635                 640

Met Glu Pro Asn Glu Met Met Arg Glu Ile Arg Lys Val Leu Asp Ala
                645                 650                 655

Asn Ser Cys Gln Ser Glu Leu His Glu Lys Tyr Met Leu Leu Cys Met
            660                 665                 670

His Gly Thr Pro Gly His Glu Asp Phe Val Gln Trp Glu Met Glu Val
        675                 680                 685

Cys Lys Leu Pro Arg Leu Ser Leu Asn Gly Val Arg Phe Lys Arg Ile
    690                 695                 700
```

```
Ser Gly Thr Ser Met Ala Phe Lys Asn Ile Ala Ser Lys Ile Ala Asn
705                 710                 715                 720

Glu Leu Lys Leu

<210> SEQ ID NO 114
<211> LENGTH: 885
<212> TYPE: PRT
<213> ORGANISM: Homo sapiens

<400> SEQUENCE: 114

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
                180                 185                 190

His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
        210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
                260                 265                 270

Ala Gly Glu Pro Asp Pro Pro Glu Glu Pro Leu Thr Ser Gln Ala Ser
            275                 280                 285

Val Pro Pro His Gln Leu Arg Leu Gly Ser Leu His Pro His Thr Pro
        290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
                340                 345                 350
```

-continued

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Val Lys Glu Pro
            420                 425                 430

Ser Thr Pro Ala Phe Ser Trp Pro Trp Trp Tyr Val Leu Leu Gly Ala
        435                 440                 445

Val Val Ala Ala Cys Val Leu Ile Leu Ala Leu Phe Leu Val His
        450                 455                 460

Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
                485                 490                 495

Arg Arg Thr Thr Glu Ala Thr Leu Asn Ser Leu Gly Ile Ser Glu Glu
            500                 505                 510

Leu Lys Glu Lys Leu Arg Asp Val Met Val Asp Arg His Lys Val Ala
        515                 520                 525

Leu Gly Lys Thr Leu Gly Glu Gly Glu Phe Gly Ala Val Met Glu Gly
        530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
            580                 585                 590

Gly Val Cys Phe Gln Gly Ser Glu Arg Glu Ser Phe Pro Ala Pro Val
        595                 600                 605

Val Ile Leu Pro Phe Met Lys His Gly Asp Leu His Ser Phe Leu Leu
        610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
            660                 665                 670

Glu Asn Met Ser Val Cys Val Ala Asp Phe Gly Leu Ser Lys Lys Ile
        675                 680                 685

Tyr Asn Gly Asp Tyr Tyr Arg Gln Gly Arg Ile Ala Lys Met Pro Val
        690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735

Gly Gln Thr Pro Tyr Pro Gly Val Glu Asn Ser Glu Ile Tyr Asp Tyr
            740                 745                 750

Leu Arg Gln Gly Asn Arg Leu Lys Gln Pro Ala Asp Cys Leu Asp Gly
        755                 760                 765

```
Leu Tyr Ala Leu Met Ser Arg Cys Trp Glu Leu Asn Pro Gln Asp Arg
    770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815

Glu Gly Gly Tyr Pro Glu Pro Pro Gly Ala Ala Gly Gly Ala Asp
            820                 825                 830

Pro Pro Thr Gln Pro Asp Pro Lys Asp Ser Cys Ser Cys Leu Thr Ala
                835                 840                 845

Ala Glu Val His Pro Ala Gly Arg Tyr Val Leu Cys Pro Ser Thr Thr
850                 855                 860

Pro Ser Pro Ala Gln Pro Ala Asp Arg Gly Ser Pro Ala Ala Pro Gly
865                 870                 875                 880

Gln Glu Asp Gly Ala
                885

<210> SEQ ID NO 115
<211> LENGTH: 297
<212> TYPE: PRT
<213> ORGANISM: Homo sapiens

<400> SEQUENCE: 115

Met Glu Asp Tyr Thr Lys Ile Glu Lys Ile Gly Glu Gly Thr Tyr Gly
1               5                   10                  15

Val Val Tyr Lys Gly Arg His Lys Thr Thr Gly Gln Val Val Ala Met
            20                  25                  30

Lys Lys Ile Arg Leu Glu Ser Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80

Glu Phe Leu Ser Met Asp Leu Lys Lys Tyr Leu Asp Ser Ile Pro Pro
                85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255
```

```
Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
            275                 280                 285

Asp Leu Asp Asn Gln Ile Lys Lys Met
            290                 295

<210> SEQ ID NO 116
<211> LENGTH: 466
<212> TYPE: PRT
<213> ORGANISM: Homo sapiens

<400> SEQUENCE: 116

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
            115                 120                 125

Asp Ile Phe Arg Tyr Gln Asp Glu Val Phe Gly Gly Phe Val Thr Glu
    130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
            275                 280                 285

Glu Ser Gln Ile Pro Pro Gln Arg Pro Gln Arg Asp Gln Arg Val Arg
        290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
```

```
                    325                 330                 335
Pro Asp Ser His Gln Leu Phe Ile Gly Asn Leu Pro His Glu Val Asp
                340                 345                 350

Lys Ser Glu Leu Lys Asp Phe Phe Gln Ser Tyr Gly Asn Val Val Glu
            355                 360                 365

Leu Arg Ile Asn Ser Gly Gly Lys Leu Pro Asn Phe Gly Phe Val Val
        370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Glu Lys Lys Thr Arg
                405                 410                 415

Ala Ala Arg Glu Gly Asp Arg Arg Asp Asn Arg Leu Arg Gly Pro Gly
                420                 425                 430

Gly Pro Arg Gly Gly Leu Gly Gly Met Arg Gly Pro Pro Arg Gly
                435                 440                 445

Gly Met Val Gln Lys Pro Gly Phe Gly Val Gly Arg Gly Leu Ala Pro
            450                 455                 460

Arg Gln
465

<210> SEQ ID NO 117
<211> LENGTH: 298
<212> TYPE: PRT
<213> ORGANISM: Homo sapiens

<400> SEQUENCE: 117

Met Val Thr Pro Ala Leu Gln Met Lys Lys Pro Lys Gln Phe Cys Arg
1               5                   10                  15

Arg Met Gly Gln Lys Lys Gln Arg Pro Ala Arg Ala Gly Gln Pro His
                20                  25                  30

Ser Ser Ser Asp Ala Ala Gln Ala Pro Ala Glu Gln Pro His Ser Ser
            35                  40                  45

Ser Asp Ala Ala Gln Ala Pro Cys Pro Arg Glu Arg Cys Leu Gly Pro
50                  55                  60

Pro Thr Thr Pro Gly Pro Tyr Arg Ser Ile Tyr Phe Ser Pro Lys
65                  70                  75                  80

Gly His Leu Thr Arg Leu Gly Leu Glu Phe Phe Asp Gln Pro Ala Val
                85                  90                  95

Pro Leu Ala Arg Ala Phe Leu Gly Gln Val Leu Val Arg Arg Leu Pro
                100                 105                 110

Asn Gly Thr Glu Leu Arg Gly Arg Ile Val Glu Thr Glu Ala Tyr Leu
            115                 120                 125

Gly Pro Glu Asp Glu Ala Ala His Ser Arg Gly Arg Gln Thr Pro
130                 135                 140

Arg Asn Arg Gly Met Phe Met Lys Pro Gly Thr Leu Tyr Val Tyr Ile
145                 150                 155                 160

Ile Tyr Gly Met Tyr Phe Cys Met Asn Ile Ser Ser Gln Gly Asp Gly
                165                 170                 175

Ala Cys Val Leu Leu Arg Ala Leu Glu Pro Leu Glu Gly Leu Glu Thr
            180                 185                 190

Met Arg Gln Leu Arg Ser Thr Leu Arg Lys Gly Thr Ala Ser Arg Val
            195                 200                 205

Leu Lys Asp Arg Glu Leu Cys Ser Gly Pro Ser Lys Leu Cys Gln Ala
    210                 215                 220
```

```
Leu Ala Ile Asn Lys Ser Phe Asp Gln Arg Asp Leu Ala Gln Asp Glu
225                 230                 235                 240

Ala Val Trp Leu Glu Arg Gly Pro Leu Glu Pro Ser Glu Pro Ala Val
            245                 250                 255

Val Ala Ala Ala Arg Val Gly Val Gly His Ala Gly Glu Trp Ala Arg
            260                 265                 270

Lys Pro Leu Arg Phe Tyr Val Arg Gly Ser Pro Trp Val Ser Val Val
            275                 280                 285

Asp Arg Val Ala Glu Gln Asp Thr Gln Ala
            290                 295
```

<210> SEQ ID NO 118
<211> LENGTH: 581
<212> TYPE: PRT
<213> ORGANISM: Homo sapiens

<400> SEQUENCE: 118

```
Met Glu Asp Val Asn Ser Asn Val Asn Ala Asp Gln Glu Val Arg Lys
1               5                   10                  15

Leu Gln Glu Leu Val Lys Lys Leu Glu Lys Gln Asn Glu Gln Leu Arg
            20                  25                  30

Ser Arg Ser Gly Ala Val Gln Gly Ala Gly Ser Leu Gly Pro Gly Ser
        35                  40                  45

Pro Val Arg Ala Gly Ala Ser Ile Pro Ser Ser Gly Ala Ala Ser Pro
    50                  55                  60

Arg Gly Phe Pro Leu Gly Leu Ser Ala Lys Ser Gly Gly Pro Gly Gly
65                  70                  75                  80

Ser Gly Pro Arg Arg Thr Ser Ser Glu Glu Leu Arg Asp Ala Thr Ser
                85                  90                  95

Leu Leu Ala Ala Gly Glu Gly Leu Leu Asp Glu Val Glu Pro Leu
            100                 105                 110

Arg Pro Asp Glu Leu Glu Arg Leu Ser Gly Trp Glu Glu Glu Glu Glu
            115                 120                 125

Ser Trp Leu Tyr Ser Ser Pro Lys Lys Lys Leu Thr Pro Met Gln Lys
130                 135                 140

Ser Val Ser Pro Leu Val Trp Cys Arg Gln Val Leu Asp Tyr Pro Ser
145                 150                 155                 160

Pro Asp Val Glu Cys Ala Lys Lys Ser Leu Ile His Lys Leu Asp Gln
                165                 170                 175

Thr Met Ser Ala Leu Lys Arg Gln Asn Leu Tyr Asn Asn Pro Phe Asn
            180                 185                 190

Ser Met Ser Tyr Thr Ser Pro Tyr Ser Pro Asn Ala Ser Ser Pro Tyr
        195                 200                 205

Ser Ser Gly Phe Asn Ser Pro Ser Ser Thr Pro Val Arg Pro Pro Ile
    210                 215                 220

Val Lys Gln Leu Ile Leu Pro Gly Asn Ser Gly Asn Leu Lys Ser Ser
225                 230                 235                 240

Asp Arg Asn Pro Pro Leu Ser Pro Gln Ser Ser Ile Asp Ser Glu Leu
                245                 250                 255

Ser Ala Ser Glu Leu Asp Glu Ser Ile Gly Ser Asn Tyr Lys Leu
            260                 265                 270

Asn Asp Val Thr Asp Val Gln Ile Leu Ala Arg Met Gln Glu Glu Ser
            275                 280                 285

Leu Arg Gln Glu Tyr Ala Ala Thr Thr Ser Arg Arg Ser Gly Ser
        290                 295                 300
```

```
Ser Cys Asn Ser Thr Arg Arg Gly Thr Phe Ser Asp Gln Glu Leu Asp
305                 310                 315                 320

Ala Gln Ser Leu Asp Asp Glu Asp Asn Met His His Ala Val Tyr
            325                 330                 335

Pro Ala Val Asn Arg Phe Ser Pro Ser Pro Arg Asn Ser Pro Arg Pro
            340                 345                 350

Ser Pro Lys Gln Ser Pro Arg Asn Ser Pro Arg Ser Arg Ser Pro Ala
            355                 360                 365

Arg Gly Ile Glu Tyr Ser Arg Val Ser Pro Gln Pro Met Ile Ser Arg
370                 375                 380

Leu Gln Gln Pro Arg Leu Ser Leu Gln Gly His Pro Thr Asp Leu Gln
385                 390                 395                 400

Thr Ser Asn Val Lys Asn Glu Glu Lys Leu Arg Arg Ser Leu Pro Asn
                405                 410                 415

Leu Ser Arg Thr Ser Asn Thr Gln Val Asp Ser Val Lys Ser Ser Arg
            420                 425                 430

Ser Asp Ser Asn Phe Gln Val Pro Asn Gly Gly Ile Pro Arg Met Gln
            435                 440                 445

Pro Gln Ala Ser Ala Ile Pro Ser Pro Gly Lys Phe Arg Ser Pro Ala
    450                 455                 460

Ala Pro Ser Pro Leu Ala Leu Arg Gln Pro Val Lys Ala Phe Ser Asn
465                 470                 475                 480

His Gly Ser Gly Ser Pro Gly Ser Gln Glu Ile Thr Gln Leu Thr Gln
                485                 490                 495

Thr Thr Ser Ser Pro Gly Pro Pro Met Val Gln Ser Thr Val Ser Ala
            500                 505                 510

Asn Pro Pro Ser Asn Ile Asn Ser Ala Thr Leu Thr Arg Pro Ala Gly
            515                 520                 525

Thr Thr Ala Met Arg Ser Gly Leu Pro Arg Pro Ser Ala Pro Ser Ala
    530                 535                 540

Gly Gly Ile Pro Val Pro Arg Ser Lys Leu Ala Gln Pro Val Arg Arg
545                 550                 555                 560

Ser Leu Pro Ala Pro Lys Thr Tyr Gly Ser Met Lys Asp Asp Ser Trp
                565                 570                 575

Lys Asp Gly Cys Tyr
            580

<210> SEQ ID NO 119
<211> LENGTH: 370
<212> TYPE: PRT
<213> ORGANISM: Homo sapiens

<400> SEQUENCE: 119

Met Ser His Pro Ser Pro Gln Ala Lys Pro Ser Asn Pro Ser Asn Pro
1               5                   10                  15

Arg Val Phe Phe Asp Val Asp Ile Gly Gly Glu Arg Val Gly Arg Ile
                20                  25                  30

Val Leu Glu Leu Phe Ala Asp Ile Val Pro Lys Thr Ala Glu Asn Phe
            35                  40                  45

Arg Ala Leu Cys Thr Gly Glu Lys Gly Ile Gly His Thr Thr Gly Lys
        50                  55                  60

Pro Leu His Phe Lys Gly Cys Pro Phe His Arg Ile Ile Lys Lys Phe
65                  70                  75                  80

Met Ile Gln Gly Gly Asp Phe Ser Asn Gln Asn Gly Thr Gly Gly Glu
```

```
                    85                  90                  95
Ser Ile Tyr Gly Glu Lys Phe Glu Asp Glu Asn Phe His Tyr Lys His
            100                 105                 110

Asp Arg Glu Gly Leu Leu Ser Met Ala Asn Ala Gly Arg Asn Thr Asn
        115                 120                 125

Gly Ser Gln Phe Phe Ile Thr Thr Val Pro Thr Pro His Leu Asp Gly
    130                 135                 140

Lys His Val Val Phe Gly Gln Val Ile Lys Gly Ile Gly Val Ala Arg
145                 150                 155                 160

Ile Leu Glu Asn Val Glu Val Lys Gly Glu Lys Pro Ala Lys Leu Cys
                165                 170                 175

Val Ile Ala Glu Cys Gly Glu Leu Lys Glu Gly Asp Asp Gly Gly Ile
            180                 185                 190

Phe Pro Lys Asp Gly Ser Gly Asp Ser His Pro Asp Phe Pro Glu Asp
        195                 200                 205

Ala Asp Ile Asp Leu Lys Asp Val Asp Lys Ile Leu Leu Ile Thr Glu
    210                 215                 220

Asp Leu Lys Asn Ile Gly Asn Thr Phe Phe Lys Ser Gln Asn Trp Glu
225                 230                 235                 240

Met Ala Ile Lys Lys Tyr Ala Glu Val Leu Arg Tyr Val Asp Ser Ser
                245                 250                 255

Lys Ala Val Ile Glu Thr Ala Asp Arg Ala Lys Leu Gln Pro Ile Ala
            260                 265                 270

Leu Ser Cys Val Leu Asn Ile Gly Ala Cys Lys Leu Lys Met Ser Asn
        275                 280                 285

Trp Gln Gly Ala Ile Asp Ser Cys Leu Glu Ala Leu Glu Leu Asp Pro
    290                 295                 300

Ser Asn Thr Lys Ala Leu Tyr Arg Arg Ala Gln Gly Trp Gln Gly Leu
305                 310                 315                 320

Lys Glu Tyr Asp Gln Ala Leu Ala Asp Leu Lys Lys Ala Gln Gly Ile
                325                 330                 335

Ala Pro Glu Asp Lys Ala Ile Gln Ala Glu Leu Leu Lys Val Lys Gln
            340                 345                 350

Lys Ile Lys Ala Gln Lys Asp Lys Glu Lys Ala Val Tyr Ala Lys Met
        355                 360                 365

Phe Ala
    370

<210> SEQ ID NO 120
<211> LENGTH: 354
<212> TYPE: PRT
<213> ORGANISM: Homo sapiens

<400> SEQUENCE: 120

Met Cys Gly Arg Thr Ser Cys His Leu Pro Arg Asp Val Leu Thr Arg
1               5                   10                  15

Ala Cys Ala Tyr Gln Asp Arg Arg Gly Gln Gln Arg Leu Pro Glu Trp
            20                  25                  30

Arg Asp Pro Asp Lys Tyr Cys Pro Ser Tyr Asn Lys Ser Pro Gln Ser
        35                  40                  45

Asn Ser Pro Val Leu Leu Ser Arg Leu His Phe Glu Lys Asp Ala Asp
    50                  55                  60

Ser Ser Glu Arg Ile Ile Ala Pro Met Arg Trp Gly Leu Val Pro Ser
65                  70                  75                  80
```

```
Trp Phe Lys Glu Ser Asp Pro Ser Lys Leu Gln Phe Asn Thr Thr Asn
                85                  90                  95

Cys Arg Ser Asp Thr Val Met Glu Lys Arg Ser Phe Lys Val Pro Leu
            100                 105                 110

Gly Lys Gly Arg Arg Cys Val Val Leu Ala Asp Gly Phe Tyr Glu Trp
        115                 120                 125

Gln Arg Cys Gln Gly Thr Asn Gln Arg Gln Pro Tyr Phe Ile Tyr Phe
    130                 135                 140

Pro Gln Ile Lys Thr Glu Lys Ser Gly Ser Ile Gly Ala Ala Asp Ser
145                 150                 155                 160

Pro Glu Asn Trp Glu Lys Val Trp Asp Asn Trp Arg Leu Leu Thr Met
                165                 170                 175

Ala Gly Ile Phe Asp Cys Trp Glu Pro Pro Glu Gly Gly Asp Val Leu
            180                 185                 190

Tyr Ser Tyr Thr Ile Ile Thr Val Asp Ser Cys Lys Gly Leu Ser Asp
        195                 200                 205

Ile His His Arg Met Pro Ala Ile Leu Asp Gly Glu Glu Ala Val Ser
    210                 215                 220

Lys Trp Leu Asp Phe Gly Glu Val Ser Thr Gln Glu Ala Leu Lys Leu
225                 230                 235                 240

Ile His Pro Thr Glu Asn Ile Thr Phe His Ala Val Ser Ser Val Val
                245                 250                 255

Asn Asn Ser Arg Asn Asn Thr Pro Glu Cys Leu Ala Pro Val Asp Leu
            260                 265                 270

Val Val Lys Lys Glu Leu Arg Ala Ser Gly Ser Ser Gln Arg Met Leu
        275                 280                 285

Gln Trp Leu Ala Thr Lys Ser Pro Lys Glu Asp Ser Lys Thr Pro
    290                 295                 300

Gln Lys Glu Glu Ser Asp Val Pro Gln Trp Ser Ser Gln Phe Leu Gln
305                 310                 315                 320

Lys Ser Pro Leu Pro Thr Lys Arg Gly Thr Ala Gly Leu Leu Glu Gln
                325                 330                 335

Trp Leu Lys Arg Glu Lys Glu Glu Pro Val Ala Lys Arg Pro Tyr
            340                 345                 350

Ser Gln

<210> SEQ ID NO 121
<211> LENGTH: 365
<212> TYPE: PRT
<213> ORGANISM: Homo sapiens

<400> SEQUENCE: 121

Met Ser Leu Ile Arg Lys Lys Gly Phe Tyr Lys Gln Asp Val Asn Lys
1               5                   10                  15

Thr Ala Trp Glu Leu Pro Lys Thr Tyr Val Ser Pro Thr His Val Gly
                20                  25                  30

Ser Gly Ala Tyr Gly Ser Val Cys Ser Ala Ile Asp Lys Arg Ser Gly
            35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Leu Lys His Met Gln
65                  70                  75                  80

His Glu Asn Val Ile Gly Leu Leu Asp Val Phe Thr Pro Ala Ser Ser
                85                  90                  95
```

```
Leu Arg Asn Phe Tyr Asp Phe Tyr Leu Val Met Pro Phe Met Gln Thr
                100                 105                 110

Asp Leu Gln Lys Ile Met Gly Met Glu Phe Ser Glu Glu Lys Ile Gln
            115                 120                 125

Tyr Leu Val Tyr Gln Met Leu Lys Gly Leu Lys Tyr Ile His Ser Ala
        130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Ala Gln Ala Leu Thr
290                 295                 300

His Pro Phe Phe Glu Pro Phe Arg Asp Pro Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
            340                 345                 350

Ala Arg Lys Asp Ser Arg Arg Ser Gly Met Lys Leu
        355                 360                 365

<210> SEQ ID NO 122
<211> LENGTH: 70
<212> TYPE: PRT
<213> ORGANISM: Homo sapiens

<400> SEQUENCE: 122

Met Ser Glu Val Lys Ser Arg Lys Ser Gly Pro Lys Gly Ala Pro
1               5                   10                  15

Ala Ala Glu Pro Gly Lys Arg Ser Glu Gly Gly Lys Thr Pro Val Ala
            20                  25                  30

Arg Ser Ser Gly Gly Gly Gly Trp Ala Asp Pro Arg Thr Cys Leu Ser
        35                  40                  45

Leu Leu Ser Leu Gly Thr Cys Leu Gly Leu Ala Cys Gly Arg Asn Leu
    50                  55                  60

Lys Leu Ser Trp Asn Asn
65                  70

<210> SEQ ID NO 123
<211> LENGTH: 352
<212> TYPE: PRT
<213> ORGANISM: Homo sapiens
```

<400> SEQUENCE: 123

| | | | | | | | | | | | | | | |
|---|---|---|---|---|---|---|---|---|---|---|---|---|---|---|
|Met|Ala|Pro|Lys|Leu|Ile|Thr|Val|Leu|Cys|Leu|Gly|Phe|Cys|Leu|Asn|
|1| | | |5| | | | |10| | | | |15| |

Gln Lys Ile Cys Pro His Ala Gly Ala Gln Asp Lys Phe Ser Leu Ser
            20                  25                  30

Ala Trp Pro Ser Pro Val Val Pro Leu Gly Gly Arg Val Thr Leu Ser
        35                  40                  45

Cys His Ser His Leu Arg Phe Val Ile Trp Thr Ile Phe Gln Thr Thr
    50                  55                  60

Gly Thr Arg Ser His Glu Leu His Thr Gly Leu Ser Asn Asn Ile Thr
65                  70                  75                  80

Ile Ser Pro Val Thr Pro Glu His Ala Gly Thr Tyr Arg Cys Val Gly
                85                  90                  95

Ile Tyr Lys His Ala Ser Lys Trp Ser Ala Glu Ser Asn Ser Leu Lys
            100                 105                 110

Ile Ile Val Thr Gly Leu Phe Thr Lys Pro Ser Ile Ser Ala His Pro
            115                 120                 125

Ser Ser Leu Val His Ala Gly Ala Arg Val Ser Leu Arg Cys His Ser
130                 135                 140

Glu Leu Ala Phe Asp Glu Phe Ile Leu Tyr Lys Glu Gly His Ile Gln
145                 150                 155                 160

His Ser Gln Gln Leu Asp Gln Gly Met Glu Ala Gly Ile His Tyr Val
                165                 170                 175

Glu Ala Val Phe Ser Met Gly Pro Val Thr Pro Ala His Ala Gly Ala
            180                 185                 190

Tyr Arg Cys Cys Gly Cys Phe Ser His Ser Arg Tyr Glu Trp Ser Ala
        195                 200                 205

Pro Ser Asp Pro Leu Asp Ile Val Ile Thr Gly Lys Tyr Lys Lys Pro
    210                 215                 220

Ser Leu Ser Thr Gln Val Asp Pro Met Met Arg Leu Gly Glu Lys Leu
225                 230                 235                 240

Thr Leu Phe Cys Ser Ser Glu Ile Ser Phe Asp Gln Tyr His Leu Phe
                245                 250                 255

Arg His Gly Val Ala His Gly Gln Trp Leu Ser Gly Gly Gln Arg His
            260                 265                 270

Arg Glu Ala Phe Gln Ala Asn Phe Ser Val Gly Arg Ala Thr Pro Val
            275                 280                 285

Pro Gly Gly Thr Tyr Arg Cys Tyr Gly Ser Phe Asn Asp Ser Pro Tyr
        290                 295                 300

Lys Pro Pro Val Thr Arg Cys Asn Phe Thr Pro Gln Glu Thr Leu Arg
305                 310                 315                 320

Val Leu Leu Cys His Ser Gln Asn Pro Pro Leu Asn Leu Thr His Leu
                325                 330                 335

Ala Leu Lys Asp Ser Pro Ala Thr Cys Ile Cys Ser Leu Asp Ser Gln
            340                 345                 350

<210> SEQ ID NO 124
<211> LENGTH: 365
<212> TYPE: PRT
<213> ORGANISM: Homo sapiens

<400> SEQUENCE: 124

Met Ala Lys Val Ala Lys Asp Leu Asn Pro Gly Val Lys Lys Met Ser
1               5                   10                  15

```
Leu Gly Gln Leu Gln Ser Ala Arg Gly Val Ala Cys Leu Gly Cys Lys
        20                  25                  30

Gly Thr Cys Ser Gly Phe Glu Pro His Ser Trp Arg Lys Ile Cys Lys
            35                  40                  45

Ser Cys Lys Cys Ser Gln Glu Asp His Cys Leu Thr Ser Asp Leu Glu
50                  55                  60

Asp Asp Arg Lys Ile Gly Arg Leu Leu Met Asp Ser Lys Tyr Ser Thr
65                  70                  75                  80

Leu Thr Ala Arg Val Lys Gly Asp Gly Ile Arg Ile Tyr Lys Arg
                85                  90                  95

Asn Arg Met Ile Met Thr Asn Pro Ile Ala Thr Gly Lys Asp Pro Thr
            100                 105                 110

Phe Asp Thr Ile Thr Tyr Glu Trp Ala Pro Pro Gly Val Thr Gln Lys
        115                 120                 125

Leu Gly Leu Gln Tyr Met Glu Leu Ile Pro Lys Glu Lys Gln Pro Val
    130                 135                 140

Thr Gly Thr Glu Gly Ala Phe Tyr Arg Arg Gln Leu Met His Gln
145                 150                 155                 160

Leu Pro Ile Tyr Asp Gln Asp Pro Ser Arg Cys Arg Gly Leu Leu Glu
                165                 170                 175

Asn Glu Leu Lys Leu Met Glu Glu Phe Val Lys Gln Tyr Lys Ser Glu
            180                 185                 190

Ala Leu Gly Val Gly Glu Val Ala Leu Pro Gly Gln Gly Leu Pro
        195                 200                 205

Lys Glu Glu Gly Lys Gln Gln Glu Lys Pro Glu Gly Ala Glu Thr Thr
    210                 215                 220

Ala Ala Thr Thr Asn Gly Ser Leu Ser Asp Pro Ser Lys Glu Val Glu
225                 230                 235                 240

Tyr Val Cys Glu Leu Cys Lys Gly Ala Ala Pro Pro Asp Ser Pro Val
                245                 250                 255

Val Tyr Ser Asp Arg Ala Gly Tyr Asn Lys Gln Trp His Pro Thr Cys
            260                 265                 270

Phe Val Cys Ala Lys Cys Ser Glu Pro Leu Val Asp Leu Ile Tyr Phe
        275                 280                 285

Trp Lys Asp Gly Ala Pro Trp Cys Gly Arg His Tyr Cys Glu Ser Leu
    290                 295                 300

Arg Pro Arg Cys Ser Gly Cys Asp Glu Ile Ile Phe Ala Glu Asp Tyr
305                 310                 315                 320

Gln Arg Val Glu Asp Leu Ala Trp His Arg Lys His Phe Val Cys Glu
                325                 330                 335

Gly Cys Glu Gln Leu Leu Ser Gly Arg Ala Tyr Ile Val Thr Lys Gly
            340                 345                 350

Gln Leu Leu Cys Pro Thr Cys Ser Lys Ser Lys Arg Ser
        355                 360                 365

<210> SEQ ID NO 125
<211> LENGTH: 601
<212> TYPE: PRT
<213> ORGANISM: Homo sapiens

<400> SEQUENCE: 125

Met Pro Glu Arg Glu Leu Trp Pro Ala Gly Thr Gly Ser Glu Pro Val
1               5                   10                  15

Thr Arg Val Gly Ser Cys Asp Ser Met Met Ser Ser Thr Ser Thr Arg
```

-continued

```
                20                  25                  30
Ser Gly Ser Ser Asp Ser Ser Tyr Asp Phe Leu Ser Thr Glu Glu Lys
            35                  40                  45
Glu Cys Leu Leu Phe Leu Glu Glu Thr Ile Gly Ser Leu Asp Thr Glu
        50                  55                  60
Ala Asp Ser Gly Leu Ser Thr Asp Glu Ser Glu Pro Ala Thr Thr Pro
 65                  70                  75                  80
Arg Gly Phe Arg Ala Leu Pro Ile Thr Gln Pro Thr Pro Arg Gly Gly
                85                  90                  95
Pro Glu Glu Thr Ile Thr Gln Gln Gly Arg Thr Pro Arg Thr Val Thr
            100                 105                 110
Glu Ser Ser Ser Ser His Pro Pro Glu Pro Gln Gly Leu Gly Leu Arg
        115                 120                 125
Ser Gly Ser Tyr Ser Leu Pro Arg Asn Ile His Ile Ala Arg Ser Gln
        130                 135                 140
Asn Phe Arg Lys Ser Thr Thr Gln Ala Ser Ser His Asn Pro Gly Glu
145                 150                 155                 160
Pro Gly Arg Leu Ala Pro Glu Pro Glu Lys Glu Gln Val Ser Gln Ser
                165                 170                 175
Ser Gln Pro Arg Gln Ala Pro Ala Ser Pro Gln Glu Ala Ala Leu Asp
            180                 185                 190
Leu Asp Val Val Leu Ile Pro Pro Glu Ala Phe Arg Asp Thr Gln
        195                 200                 205
Pro Glu Gln Cys Arg Glu Ala Ser Leu Pro Glu Gly Pro Gly Gln Gln
        210                 215                 220
Gly His Thr Pro Gln Leu His Thr Pro Ser Ser Gln Glu Arg Glu
225                 230                 235                 240
Gln Thr Pro Ser Glu Ala Met Ser Gln Lys Ala Lys Glu Thr Val Ser
                245                 250                 255
Thr Arg Tyr Thr Gln Pro Gln Pro Pro Ala Gly Leu Pro Gln Asn
            260                 265                 270
Ala Arg Ala Glu Asp Ala Pro Leu Ser Ser Gly Glu Asp Pro Asn Ser
        275                 280                 285
Arg Leu Ala Pro Leu Thr Thr Pro Lys Pro Arg Lys Leu Pro Pro Asn
        290                 295                 300
Ile Val Leu Lys Ser Ser Arg Ser Ser Phe His Ser Asp Pro Gln His
305                 310                 315                 320
Trp Leu Ser Arg His Thr Glu Ala Ala Pro Gly Asp Ser Gly Leu Ile
                325                 330                 335
Ser Cys Ser Leu Gln Glu Gln Arg Lys Ala Arg Lys Glu Ala Leu Glu
            340                 345                 350
Lys Leu Gly Leu Pro Gln Asp Gln Asp Glu Pro Gly Leu His Leu Ser
        355                 360                 365
Lys Pro Thr Ser Ser Ile Arg Pro Lys Glu Thr Arg Ala Gln His Leu
        370                 375                 380
Ser Pro Ala Pro Gly Leu Ala Gln Pro Ala Ala Pro Ala Gln Ala Ser
385                 390                 395                 400
Ala Ala Ile Pro Ala Gly Lys Ala Leu Ala Gln Ala Pro Ala Pro
                405                 410                 415
Ala Pro Gly Pro Ala Gln Gly Pro Leu Pro Met Lys Ser Pro Ala Pro
            420                 425                 430
Gly Asn Val Ala Ala Ser Lys Ser Met Pro Ile Ser Ile Pro Lys Ala
        435                 440                 445
```

```
Pro Arg Ala Asn Ser Ala Leu Thr Pro Pro Lys Pro Glu Ser Gly Leu
    450                 455                 460

Thr Leu Gln Glu Ser Asn Thr Pro Gly Leu Arg Gln Met Asn Phe Lys
465                 470                 475                 480

Ser Asn Thr Leu Glu Arg Ser Gly Val Gly Leu Ser Ser Tyr Leu Ser
                485                 490                 495

Thr Glu Lys Asp Ala Ser Pro Lys Thr Ser Thr Ser Leu Gly Lys Gly
            500                 505                 510

Ser Phe Leu Asp Lys Ile Ser Pro Ser Val Leu Arg Asn Ser Arg Pro
        515                 520                 525

Arg Pro Ala Ser Leu Gly Thr Gly Lys Asp Phe Ala Gly Ile Gln Val
    530                 535                 540

Gly Lys Leu Ala Asp Leu Glu Gln Gln Ser Ser Lys Arg Leu Ser
545                 550                 555                 560

Tyr Gln Gly Gln Ser Arg Asp Lys Leu Pro Arg Pro Cys Val Ser
                565                 570                 575

Val Lys Ile Ser Pro Lys Gly Val Pro Asn Glu His Arg Arg Glu Ala
            580                 585                 590

Leu Lys Lys Leu Gly Leu Leu Lys Glu
            595                 600

<210> SEQ ID NO 126
<211> LENGTH: 433
<212> TYPE: PRT
<213> ORGANISM: Homo sapiens

<400> SEQUENCE: 126

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
```

```
                210                 215                 220

Pro Glu Leu Ile Phe Gly Ala Thr Asp Tyr Thr Ser Ile Asp Val
225                 230                 235                 240

Trp Ser Ala Gly Cys Val Leu Ala Glu Leu Leu Gly Gln Pro Ile
                245                 250                 255

Phe Pro Gly Asp Ser Gly Val Asp Gln Leu Val Glu Ile Lys Val
                260                 265                 270

Leu Gly Thr Pro Thr Arg Glu Gln Ile Arg Glu Met Asn Pro Asn Tyr
            275                 280                 285

Thr Glu Phe Lys Phe Pro Gln Ile Lys Ala His Pro Trp Thr Lys Asp
        290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
                340                 345                 350

Phe Asp Glu Leu Arg Asp Pro Asn Val Lys Leu Pro Asn Gly Arg Asp
            355                 360                 365

Thr Pro Ala Leu Phe Asn Phe Thr Gln Glu Leu Ser Ser Asn Pro
370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
                420                 425                 430

Thr

<210> SEQ ID NO 127
<211> LENGTH: 40
<212> TYPE: PRT
<213> ORGANISM: Homo sapiens

<400> SEQUENCE: 127

Leu Arg Ser Cys Gln Gly Tyr Lys Gln Cys Asn Pro Arg Pro Lys Asn
1               5                   10                  15

Leu Asp Val Gly Asn Lys Asp Gly Gly Ser Tyr Asp Leu His Arg Gly
                20                  25                  30

Gln Leu Trp Asp Gly Trp Glu Gly
            35                  40

<210> SEQ ID NO 128
<211> LENGTH: 637
<212> TYPE: PRT
<213> ORGANISM: Homo sapiens

<400> SEQUENCE: 128

Met Thr Lys Arg Lys Lys Leu Arg Thr Ser Gly Glu Gly Leu Cys Pro
1               5                   10                  15

Pro Lys Pro Leu Lys Asn Pro Arg Leu Gly Asp Phe Tyr Gly Asp Pro
                20                  25                  30

Gln Ser Ser Met Leu Gly Cys Leu His His Pro Glu Glu Pro Glu Gly
            35                  40                  45

Lys Leu Gly Pro Val Pro Ser Thr Gln Gln His Gly Glu Glu Pro Gly
        50                  55                  60
```

-continued

```
Lys Ala Val Ser Ser Pro Asp Glu Glu Thr Gly Ser Pro Cys Arg
 65                  70                  75                  80

Leu Leu Arg Gln Pro Glu Lys Glu Pro Ala Pro Leu Pro Pro Ser Gln
                 85                  90                  95

Asn Ser Phe Gly Arg Phe Val Pro Gln Phe Ala Lys Ser Arg Lys Thr
            100                 105                 110

Val Thr Arg Lys Glu Glu Met Lys Asp Glu Asp Arg Gly Ser Gly Ala
        115                 120                 125

Phe Ser Leu Glu Thr Ile Ala Glu Ser Ser Ala Gln Ser Pro Gly Cys
130                 135                 140

Gln Leu Leu Val Glu Thr Leu Gly Val Pro Leu Gln Glu Ala Thr Glu
145                 150                 155                 160

Leu Gly Asp Pro Thr Gln Ala Asp Ser Ala Arg Pro Glu Gln Ser Ser
                165                 170                 175

Gln Ser Pro Val Gln Ala Val Pro Gly Ser Gly Asp Ser Gln Pro Asp
            180                 185                 190

Asp Pro Pro Asp Arg Gly Thr Gly Leu Ser Ala Ser Gln Arg Ala Ser
        195                 200                 205

Gln Asp His Leu Ser Glu Gln Gly Ala Asp Asp Ser Lys Pro Glu Thr
    210                 215                 220

Asp Arg Val Pro Gly Asp Gly Gly Gln Lys Glu His Leu Pro Ser Ile
225                 230                 235                 240

Asp Ser Glu Gly Glu Lys Pro Asp Arg Gly Ala Pro Gln Glu Gly Gly
                245                 250                 255

Ala Gln Arg Thr Ala Gly Ala Gly Leu Pro Gly Gly Pro Gln Glu Glu
            260                 265                 270

Gly Asp Gly Val Pro Cys Thr Pro Ala Ser Ala Pro Thr Ser Gly Pro
        275                 280                 285

Ala Pro Gly Leu Gly Pro Ala Ser Trp Cys Leu Glu Pro Gly Ser Val
    290                 295                 300

Ala Gln Gly Ser Pro Asp Pro Gln Gln Thr Pro Ser Arg Met Gly Arg
305                 310                 315                 320

Glu Gly Glu Gly Thr His Ser Ser Leu Gly Cys Ser Ser Leu Gly Met
                325                 330                 335

Val Val Ile Ala Asp Leu Ser Thr Asp Pro Thr Glu Leu Glu Glu Arg
            340                 345                 350

Ala Leu Glu Val Ala Gly Pro Asp Gly Gln Ala Ser Ala Ile Ser Pro
        355                 360                 365

Ala Ser Pro Arg Arg Lys Ala Ala Asp Gly Gly His Arg Arg Ala Leu
    370                 375                 380

Pro Gly Cys Thr Ser Leu Thr Gly Glu Thr Thr Gly Glu Ser Gly Glu
385                 390                 395                 400

Ala Gly Gln Asp Gly Lys Pro Pro Gly Asp Val Leu Val Gly Pro Thr
                405                 410                 415

Ala Ser Leu Ala Leu Ala Pro Gly Ser Gly Glu Ser Met Met Gly Ala
            420                 425                 430

Gly Asp Ser Gly His Ala Ser Pro Asp Thr Gly Pro Cys Val Asn Gln
        435                 440                 445

Lys Gln Glu Pro Gly Pro Ala Gln Glu Glu Ala Glu Leu Gly Gly Gln
    450                 455                 460

Asn Leu Glu Arg Asp Leu Glu Gly Phe Arg Val Ser Pro Gln Ala Ser
465                 470                 475                 480
```

```
Val Val Leu Glu His Arg Glu Ile Ala Asp Asp Pro Leu Gln Glu Pro
                485                 490                 495

Gly Ala Gln Gln Gly Ile Pro Asp Thr Thr Ser Glu Leu Ala Gly Gln
            500                 505                 510

Arg Asp His Leu Pro His Ser Ala Asp Gln Gly Thr Trp Ala Asp Ser
            515                 520                 525

Leu Ala Val Glu Leu Asp Phe Leu Leu Asp Ser Gln Ile Gln Asp Ala
            530                 535                 540

Leu Asp Ala Ser Asp Phe Glu Ala Pro Pro Glu Gln Leu Phe Pro Ser
545                 550                 555                 560

Gly Asn Lys Pro Gly Pro Cys Trp Pro Gly Pro Ser Ser His Ala Asn
                565                 570                 575

Gly Asp Pro Val Ala Val Ala Lys Ala Gln Pro Ser Arg Leu Ile Met
            580                 585                 590

Gly Thr His Arg Asp Leu Glu Ala Phe Lys Arg Leu Asn Tyr Arg Lys
            595                 600                 605

Thr Lys Leu Gly Gly Lys Ala Pro Leu Pro Tyr Pro Ser Lys Gly Pro
    610                 615                 620

Gly Asn Ile Pro Arg Gly Asp Pro Pro Trp Arg Glu Leu
625                 630                 635

<210> SEQ ID NO 129
<211> LENGTH: 553
<212> TYPE: PRT
<213> ORGANISM: Homo sapiens

<400> SEQUENCE: 129

Met Ala Ala Pro Ala Gly Gly Gly Ser Ala Val Ser Val Leu Ala
1               5                   10                  15

Pro Asn Gly Arg Arg His Thr Val Lys Val Thr Pro Ser Thr Val Leu
                20                  25                  30

Leu Gln Val Leu Glu Asp Thr Cys Arg Arg Gln Asp Phe Asn Pro Cys
            35                  40                  45

Glu Tyr Asp Leu Lys Phe Gln Arg Ser Val Leu Asp Leu Ser Leu Gln
50                  55                  60

Trp Arg Phe Ala Asn Leu Pro Asn Asn Ala Lys Leu Glu Met Val Pro
65                  70                  75                  80

Ala Ser Arg Ser Arg Glu Gly Pro Glu Asn Met Val Arg Ile Ala Leu
                85                  90                  95

Gln Leu Asp Asp Gly Ser Arg Leu Gln Asp Ser Phe Cys Ser Gly Gln
            100                 105                 110

Thr Leu Trp Glu Leu Leu Ser His Phe Pro Gln Ile Arg Glu Cys Leu
        115                 120                 125

Gln His Pro Gly Gly Ala Thr Pro Val Cys Val Tyr Thr Arg Asp Glu
    130                 135                 140

Val Thr Gly Glu Ala Ala Leu Arg Gly Thr Thr Leu Gln Ser Leu Gly
145                 150                 155                 160

Leu Thr Gly Gly Ser Ala Thr Ile Arg Phe Val Met Lys Cys Tyr Asp
                165                 170                 175

Pro Val Gly Lys Thr Pro Gly Ser Leu Gly Ser Ser Ala Ser Ala Gly
            180                 185                 190

Gln Ala Ala Ala Ser Ala Pro Leu Pro Leu Glu Ser Gly Glu Leu Ser
        195                 200                 205

Arg Gly Asp Leu Ser Arg Pro Glu Asp Ala Asp Thr Ser Gly Pro Cys
    210                 215                 220
```

Cys Glu His Thr Gln Glu Lys Gln Ser Thr Arg Ala Pro Ala Ala
225                 230                 235                 240

Pro Phe Val Pro Phe Ser Gly Gly Gly Gln Arg Gln Gly Pro Pro
            245                 250                 255

Gly Pro Thr Arg Pro Leu Thr Ser Ser Ala Lys Leu Pro Lys Ser
        260                 265                 270

Leu Ser Ser Pro Gly Gly Pro Ser Lys Pro Lys Lys Ser Lys Ser Gly
    275                 280                 285

Gln Asp Pro Gln Gln Glu Gln Glu Gln Glu Arg Glu Arg Asp Pro Gln
    290                 295                 300

Gln Glu Gln Glu Arg Glu Arg Pro Val Asp Arg Glu Pro Val Asp Arg
305                 310                 315                 320

Glu Pro Val Val Cys His Pro Asp Leu Glu Glu Arg Leu Gln Ala Trp
            325                 330                 335

Pro Ala Glu Leu Pro Asp Glu Phe Phe Glu Leu Thr Val Asp Asp Val
            340                 345                 350

Arg Arg Arg Leu Ala Gln Leu Lys Ser Glu Arg Lys Arg Leu Glu Glu
            355                 360                 365

Ala Pro Leu Val Thr Lys Ala Phe Arg Glu Ala Gln Ile Lys Glu Lys
370                 375                 380

Leu Glu Arg Tyr Pro Lys Val Ala Leu Arg Val Leu Phe Pro Asp Arg
385                 390                 395                 400

Tyr Val Leu Gln Gly Phe Phe Arg Pro Ser Glu Thr Val Gly Asp Leu
            405                 410                 415

Arg Asp Phe Val Arg Ser His Leu Gly Asn Pro Glu Leu Ser Phe Tyr
            420                 425                 430

Leu Phe Ile Thr Pro Pro Lys Thr Val Leu Asp Asp His Thr Gln Thr
            435                 440                 445

Leu Phe Gln Ala Asn Leu Phe Pro Ala Ala Leu Val His Leu Gly Ala
    450                 455                 460

Glu Glu Pro Ala Gly Val Tyr Leu Glu Pro Gly Leu Leu Glu His Ala
465                 470                 475                 480

Ile Ser Pro Ser Ala Ala Asp Val Leu Val Ala Arg Tyr Met Ser Arg
            485                 490                 495

Ala Ala Gly Ser Pro Ser Pro Leu Pro Ala Pro Asp Pro Ala Pro Lys
            500                 505                 510

Ser Glu Pro Ala Ala Glu Glu Gly Ala Leu Val Pro Pro Glu Pro Ile
        515                 520                 525

Pro Gly Thr Ala Gln Pro Val Lys Arg Ser Leu Gly Lys Val Pro Lys
        530                 535                 540

Trp Leu Lys Leu Pro Ala Ser Lys Arg
545                 550

<210> SEQ ID NO 130
<211> LENGTH: 553
<212> TYPE: PRT
<213> ORGANISM: Homo sapiens

<400> SEQUENCE: 130

Met Ala Ala Pro Ala Gly Gly Gly Gly Ser Ala Val Ser Val Leu Ala
1               5                   10                  15

Pro Asn Gly Arg Arg His Thr Val Lys Val Thr Pro Ser Thr Val Leu
            20                  25                  30

Leu Gln Val Leu Glu Asp Thr Cys Arg Arg Gln Asp Phe Asn Pro Cys

-continued

```
               35                  40                  45
Glu Tyr Asp Leu Lys Phe Gln Arg Ser Val Leu Asp Leu Ser Leu Gln
 50                  55                  60

Trp Arg Phe Ala Asn Leu Pro Asn Asn Ala Lys Leu Glu Met Val Pro
 65                  70                  75                  80

Ala Ser Arg Ser Arg Glu Gly Pro Glu Asn Met Val Arg Ile Ala Leu
                 85                  90                  95

Gln Leu Asp Asp Gly Ser Arg Leu Gln Asp Ser Phe Cys Ser Gly Gln
                100                 105                 110

Thr Leu Trp Glu Leu Leu Ser His Phe Pro Gln Ile Arg Glu Cys Leu
            115                 120                 125

Gln His Pro Gly Gly Ala Thr Pro Val Cys Val Tyr Thr Arg Asp Glu
        130                 135                 140

Val Thr Gly Glu Ala Ala Leu Arg Gly Thr Thr Leu Gln Ser Leu Gly
145                 150                 155                 160

Leu Thr Gly Gly Ser Ala Thr Ile Arg Phe Val Met Lys Cys Tyr Asp
                165                 170                 175

Pro Val Gly Lys Thr Pro Gly Ser Leu Gly Ser Ser Ala Ser Ala Gly
            180                 185                 190

Gln Ala Ala Ser Ala Pro Leu Pro Leu Glu Ser Gly Glu Leu Ser
        195                 200                 205

Arg Gly Asp Leu Ser Arg Pro Glu Asp Ala Asp Thr Ser Gly Pro Cys
    210                 215                 220

Cys Glu His Thr Gln Glu Lys Gln Ser Thr Arg Ala Pro Ala Ala Ala
225                 230                 235                 240

Pro Phe Val Pro Phe Ser Gly Gly Gln Arg Leu Gly Gly Pro Pro
                245                 250                 255

Gly Pro Thr Arg Pro Leu Thr Ser Ser Ala Lys Leu Pro Lys Ser
            260                 265                 270

Leu Ser Ser Pro Gly Gly Pro Ser Lys Pro Lys Lys Ser Lys Ser Gly
        275                 280                 285

Gln Asp Pro Gln Gln Glu Gln Glu Gln Glu Arg Glu Arg Asp Pro Gln
290                 295                 300

Gln Glu Gln Glu Arg Glu Arg Pro Val Asp Arg Glu Pro Val Asp Arg
305                 310                 315                 320

Glu Pro Val Val Cys His Pro Asp Leu Glu Glu Arg Leu Gln Ala Trp
                325                 330                 335

Pro Ala Glu Leu Pro Asp Glu Phe Phe Glu Leu Thr Val Asp Asp Val
            340                 345                 350

Arg Arg Arg Leu Ala Gln Leu Lys Ser Glu Arg Lys Arg Leu Glu Glu
        355                 360                 365

Ala Pro Leu Val Thr Lys Ala Phe Arg Glu Ala Gln Ile Lys Glu Lys
    370                 375                 380

Leu Glu Arg Tyr Pro Lys Val Ala Leu Arg Val Leu Phe Pro Asp Arg
385                 390                 395                 400

Tyr Val Leu Gln Gly Phe Phe Arg Pro Ser Glu Thr Val Gly Asp Leu
                405                 410                 415

Arg Asp Phe Val Arg Ser His Leu Gly Asn Pro Glu Leu Ser Phe Tyr
            420                 425                 430

Leu Phe Ile Thr Pro Pro Lys Thr Val Leu Asp Asp His Thr Gln Thr
        435                 440                 445

Leu Phe Gln Ala Asn Leu Phe Pro Ala Ala Leu Val His Leu Gly Ala
    450                 455                 460
```

```
Glu Pro Ala Gly Val Tyr Leu Glu Pro Gly Leu Leu Glu His Ala
465                 470                 475                 480

Ile Ser Pro Ser Ala Ala Asp Val Leu Val Ala Arg Tyr Met Ser Arg
            485                 490                 495

Ala Ala Gly Ser Pro Ser Pro Leu Pro Ala Pro Asp Pro Ala Pro Lys
                500                 505                 510

Ser Glu Pro Ala Ala Glu Glu Gly Ala Leu Val Pro Pro Glu Pro Ile
            515                 520                 525

Pro Gly Thr Ala Gln Pro Val Lys Arg Ser Leu Gly Lys Val Pro Lys
        530                 535                 540

Trp Leu Lys Leu Pro Ala Ser Lys Arg
545                 550

<210> SEQ ID NO 131
<211> LENGTH: 483
<212> TYPE: PRT
<213> ORGANISM: Homo sapiens

<400> SEQUENCE: 131

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
        115                 120                 125

Ser Phe Gly Val Val Tyr Gln Ala Arg Leu Ala Glu Thr Arg Glu Leu
    130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
        195                 200                 205

Phe Thr Lys Ala Lys Leu Thr Ile Pro Ile Leu Tyr Val Lys Val Tyr
    210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
            260                 265                 270

Gly Glu Pro Asn Val Ser Tyr Ile Cys Ser Arg Tyr Tyr Arg Ala Pro
```

```
            275                 280                 285
Glu Leu Ile Phe Gly Ala Thr Asp Tyr Thr Ser Ser Ile Asp Val Trp
290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
                340                 345                 350

Glu Phe Lys Phe Pro Gln Ile Lys Ala His Pro Trp Thr Lys Val Phe
                355                 360                 365

Lys Ser Arg Thr Pro Pro Glu Ala Ile Ala Leu Cys Ser Ser Leu Leu
370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
                420                 425                 430

Gln Pro Ser Leu Asn Ala Ile Leu Ile Pro Pro His Leu Arg Ser Pro
                435                 440                 445

Ala Gly Thr Thr Thr Leu Thr Pro Ser Ser Gln Ala Leu Thr Glu Thr
                450                 455                 460

Pro Thr Ser Ser Asp Trp Gln Ser Thr Asp Ala Thr Pro Thr Leu Thr
465                 470                 475                 480

Asn Ser Ser

<210> SEQ ID NO 132
<211> LENGTH: 744
<212> TYPE: PRT
<213> ORGANISM: Homo sapiens

<400> SEQUENCE: 132

Met Glu Gln Asp Pro Lys Pro Pro Arg Leu Arg Leu Trp Ala Leu Ile
1               5                   10                  15

Pro Trp Leu Pro Arg Lys Gln Arg Pro Arg Ile Ser Gln Thr Ser Leu
                20                  25                  30

Pro Val Pro Gly Pro Gly Ser Gly Pro Gln Arg Asp Ser Asp Glu Gly
                35                  40                  45

Val Leu Lys Glu Ile Ser Ile Thr His His Val Lys Ala Gly Ser Glu
50                  55                  60

Lys Ala Asp Pro Ser His Phe Glu Leu Leu Lys Val Leu Gly Gln Gly
65                  70                  75                  80

Ser Phe Gly Lys Val Phe Leu Val Arg Lys Val Thr Arg Pro Asp Ser
                85                  90                  95

Gly His Leu Tyr Ala Met Lys Val Leu Lys Lys Ala Thr Leu Lys Val
                100                 105                 110

Arg Asp Arg Val Arg Thr Lys Met Glu Arg Asp Ile Leu Ala Asp Val
                115                 120                 125

Asn His Pro Phe Val Val Lys Leu His Tyr Ala Phe Gln Thr Glu Gly
                130                 135                 140

Lys Leu Tyr Leu Ile Leu Asp Phe Leu Arg Gly Gly Asp Leu Phe Thr
145                 150                 155                 160

Arg Leu Ser Lys Glu Val Met Phe Thr Glu Glu Asp Val Lys Phe Tyr
```

```
                165                 170                 175
Leu Ala Glu Leu Ala Leu Gly Leu Asp His Leu His Ser Leu Gly Ile
            180                 185                 190
Ile Tyr Arg Asp Leu Lys Pro Glu Asn Ile Leu Leu Asp Glu Glu Gly
            195                 200                 205
His Ile Lys Leu Thr Asp Phe Gly Leu Ser Lys Glu Ala Ile Asp His
210                 215                 220
Glu Lys Lys Ala Tyr Ser Phe Cys Gly Thr Val Glu Tyr Met Ala Pro
225                 230                 235                 240
Glu Val Val Asn Arg Gln Gly His Ser His Ser Ala Asp Trp Trp Ser
            245                 250                 255
Tyr Gly Val Leu Met Phe Glu Met Leu Thr Gly Ser Leu Pro Phe Gln
            260                 265                 270
Gly Lys Asp Arg Lys Glu Thr Met Thr Leu Ile Leu Lys Ala Lys Leu
            275                 280                 285
Gly Met Pro Gln Phe Leu Ser Thr Glu Ala Gln Ser Leu Leu Arg Ala
            290                 295                 300
Leu Phe Lys Arg Asn Pro Ala Asn Arg Leu Gly Ser Gly Pro Asp Gly
305                 310                 315                 320
Ala Glu Glu Ile Lys Arg His Val Phe Tyr Ser Thr Ile Asp Trp Asn
            325                 330                 335
Lys Leu Tyr Arg Arg Glu Ile Lys Pro Pro Phe Lys Pro Ala Val Ala
            340                 345                 350
Gln Pro Asp Asp Thr Phe Tyr Phe Asp Thr Glu Phe Thr Ser Arg Thr
            355                 360                 365
Pro Lys Asp Ser Pro Gly Ile Pro Pro Ser Ala Gly Ala His Gln Leu
            370                 375                 380
Phe Arg Gly Phe Ser Phe Val Ala Thr Gly Leu Met Glu Asp Asp Gly
385                 390                 395                 400
Lys Pro Arg Ala Pro Gln Ala Pro Leu His Ser Val Val Gln Gln Leu
            405                 410                 415
His Gly Lys Asn Leu Val Phe Ser Asp Gly Tyr Val Val Lys Glu Thr
            420                 425                 430
Ile Gly Val Gly Ser Tyr Ser Glu Cys Lys Arg Cys Val His Lys Ala
            435                 440                 445
Thr Asn Met Glu Tyr Ala Val Lys Val Ile Asp Lys Ser Lys Arg Asp
450                 455                 460
Pro Ser Glu Glu Ile Glu Ile Leu Leu Arg Tyr Gly Gln His Pro Asn
465                 470                 475                 480
Ile Ile Thr Leu Lys Asp Val Tyr Asp Asp Gly Lys His Val Tyr Leu
            485                 490                 495
Val Thr Glu Leu Met Arg Gly Gly Glu Leu Leu Asp Lys Ile Leu Arg
            500                 505                 510
Gln Lys Phe Phe Ser Glu Arg Glu Ala Ser Phe Val Leu His Thr Ile
            515                 520                 525
Gly Lys Thr Val Glu Tyr Leu His Ser Gln Gly Val Val His Arg Asp
            530                 535                 540
Leu Lys Pro Ser Asn Ile Leu Tyr Val Asp Glu Ser Gly Asn Pro Glu
545                 550                 555                 560
Cys Leu Arg Ile Cys Asp Phe Gly Phe Ala Lys Gln Leu Arg Ala Glu
            565                 570                 575
Asn Gly Leu Leu Met Thr Pro Cys Tyr Thr Ala Asn Phe Val Ala Pro
            580                 585                 590
```

```
Glu Val Leu Lys Arg Gln Gly Tyr Asp Glu Gly Cys Asp Ile Trp Ser
            595                 600                 605

Leu Gly Ile Leu Leu Tyr Thr Met Leu Ala Gly Tyr Thr Pro Phe Ala
        610                 615                 620

Asn Gly Pro Ser Asp Thr Pro Glu Glu Ile Leu Thr Arg Ile Gly Ser
625                 630                 635                 640

Gly Lys Phe Thr Leu Ser Gly Gly Asn Trp Asn Thr Val Ser Glu Thr
            645                 650                 655

Ala Lys Asp Leu Val Ser Lys Met Leu His Val Asp Pro His Gln Arg
        660                 665                 670

Leu Thr Ala Lys Gln Val Leu Gln His Pro Trp Val Thr Gln Lys Asp
            675                 680                 685

Lys Leu Pro Gln Ser Gln Leu Ser His Gln Asp Leu Gln Leu Val Lys
        690                 695                 700

Gly Ala Met Ala Ala Thr Tyr Ser Ala Leu Asn Ser Ser Lys Pro Thr
705                 710                 715                 720

Pro Gln Leu Lys Pro Ile Glu Ser Ser Ile Leu Ala Gln Arg Arg Val
            725                 730                 735

Arg Lys Leu Pro Ser Thr Thr Leu
            740

<210> SEQ ID NO 133
<211> LENGTH: 209
<212> TYPE: PRT
<213> ORGANISM: Homo sapiens

<400> SEQUENCE: 133

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
            85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 134
<211> LENGTH: 151
<212> TYPE: PRT
<213> ORGANISM: Homo sapiens

<400> SEQUENCE: 134

```
Met Asp Ser Ala Ala Cys Ala Ala Ala Thr Pro Val Pro Ala Leu
1               5                   10                  15

Ala Leu Ala Leu Ala Pro Asp Leu Ala Gln Ala Pro Leu Ala Leu Pro
                20                  25                  30

Gly Leu Leu Ser Pro Ser Cys Leu Leu Ser Ser Gly Gln Glu Val Asn
                35                  40                  45

Gly Ser Glu Arg Gly Thr Cys Leu Trp Arg Pro Trp Leu Ser Ser Thr
        50                  55                  60

Asn Asp Ser Pro Arg Gln Met Arg Lys Leu Val Asp Leu Ala Ala Gly
65                  70                  75                  80

Gly Ala Thr Ala Ala Glu Val Thr Lys Ala Glu Ser Lys Phe His His
                85                  90                  95

Pro Val Arg Leu Phe Trp Pro Lys Ser Arg Ser Phe Asp Tyr Leu Tyr
                100                 105                 110

Ser Ala Gly Glu Ile Leu Leu Gln Asn Phe Pro Val Gln Ala Thr Ile
                115                 120                 125

Asn Leu Tyr Glu Asp Ser Asp Ser Glu Glu Glu Glu Glu Asp Glu Glu
                130                 135                 140

Gln Glu Asp Glu Glu Lys
145                 150
```

<210> SEQ ID NO 135
<211> LENGTH: 539
<212> TYPE: PRT
<213> ORGANISM: Homo sapiens

<400> SEQUENCE: 135

```
Met Trp Arg Leu Pro Arg Ala Leu Cys Val His Ala Ala Lys Thr Ser
1               5                   10                  15

Lys Leu Ser Gly Pro Trp Ser Arg Pro Ala Ala Phe Met Ser Thr Leu
                20                  25                  30

Leu Ile Asn Gln Pro Gln Tyr Ala Trp Leu Lys Glu Leu Gly Leu Arg
                35                  40                  45

Glu Glu Asn Glu Gly Val Tyr Asn Gly Ser Trp Gly Gly Arg Gly Glu
        50                  55                  60

Val Ile Thr Thr Tyr Cys Pro Ala Asn Asn Glu Pro Ile Ala Arg Val
65                  70                  75                  80

Arg Gln Ala Ser Val Ala Asp Tyr Glu Glu Thr Val Lys Lys Ala Arg
                85                  90                  95

Glu Ala Trp Lys Ile Trp Ala Asp Ile Pro Ala Pro Lys Arg Gly Glu
                100                 105                 110

Ile Val Arg Gln Ile Gly Asp Ala Leu Arg Glu Lys Ile Gln Val Leu
                115                 120                 125

Gly Ser Leu Val Ser Leu Glu Met Gly Lys Ile Leu Val Glu Gly Val
                130                 135                 140

Gly Glu Val Gln Glu Tyr Val Asp Ile Cys Asp Tyr Ala Val Gly Leu
145                 150                 155                 160

Ser Arg Met Ile Gly Gly Pro Ile Leu Pro Ser Glu Arg Ser Gly His
                165                 170                 175
```

Ala Leu Ile Glu Gln Trp Asn Pro Val Gly Leu Val Gly Ile Ile Thr
                180                 185                 190

Ala Phe Asn Phe Pro Val Ala Val Tyr Gly Trp Asn Ala Ile Ala
            195                 200                 205

Met Ile Cys Gly Asn Val Cys Leu Trp Lys Gly Ala Pro Thr Thr Ser
    210                 215                 220

Leu Ile Ser Val Ala Val Thr Lys Ile Ile Ala Lys Val Leu Glu Asp
225                 230                 235                 240

Asn Lys Leu Pro Gly Ala Ile Cys Ser Leu Thr Cys Gly Gly Ala Asp
                245                 250                 255

Ile Gly Thr Ala Met Ala Lys Asp Glu Arg Val Asn Leu Leu Ser Phe
            260                 265                 270

Thr Gly Ser Thr Gln Val Gly Lys Gln Val Gly Leu Met Val Gln Glu
        275                 280                 285

Arg Phe Gly Arg Ser Leu Leu Glu Leu Gly Gly Asn Asn Ala Ile Ile
    290                 295                 300

Ala Phe Glu Asp Ala Asp Leu Ser Leu Val Val Pro Ser Ala Leu Phe
305                 310                 315                 320

Ala Ala Val Gly Thr Ala Gly Gln Arg Cys Thr Thr Ala Arg Arg Leu
                325                 330                 335

Phe Ile His Glu Ser Ile His Asp Glu Val Val Asn Arg Leu Lys Lys
            340                 345                 350

Ala Tyr Ala Gln Ile Arg Val Gly Asn Pro Trp Asp Pro Asn Val Leu
        355                 360                 365

Tyr Gly Pro Leu His Thr Lys Gln Ala Val Ser Met Phe Leu Gly Ala
    370                 375                 380

Val Glu Glu Ala Lys Lys Glu Gly Gly Thr Val Val Tyr Gly Gly Lys
385                 390                 395                 400

Val Met Asp Arg Pro Gly Asn Tyr Val Glu Pro Thr Ile Val Thr Gly
                405                 410                 415

Leu Gly His Asp Ala Ser Ile Ala His Thr Glu Thr Phe Ala Pro Ile
            420                 425                 430

Leu Tyr Val Phe Lys Phe Lys Asn Glu Glu Val Phe Ala Trp Asn
        435                 440                 445

Asn Glu Val Lys Gln Gly Leu Ser Ser Ser Ile Phe Thr Lys Asp Leu
    450                 455                 460

Gly Arg Ile Phe Arg Trp Leu Gly Pro Lys Gly Ser Asp Cys Gly Ile
465                 470                 475                 480

Val Asn Val Asn Ile Pro Thr Ser Gly Ala Glu Ile Gly Gly Ala Phe
                485                 490                 495

Gly Gly Glu Lys His Thr Gly Gly Arg Glu Ser Gly Ser Asp Ala
            500                 505                 510

Trp Lys Gln Tyr Met Arg Arg Ser Thr Cys Thr Ile Asn Tyr Ser Lys
        515                 520                 525

Asp Leu Pro Leu Ala Gln Gly Ile Lys Phe Gln
    530                 535

<210> SEQ ID NO 136
<211> LENGTH: 280
<212> TYPE: PRT
<213> ORGANISM: Homo sapiens

<400> SEQUENCE: 136

Met Ala Thr Glu Ala Pro Val Asn Ile Ala Pro Pro Glu Cys Ser Thr

```
1               5                   10                  15
Val Val Ser Thr Ala Val Asp Ser Leu Ile Trp Gln Pro Asn Ser Leu
                20                  25                  30

Asn Met His Met Ile Arg Pro Lys Ser Ala Lys Gly Arg Thr Arg Pro
                35                  40                  45

Ser Leu Gln Lys Ser Gln Gly Val Glu Val Cys Ala His His Ile Pro
    50                  55                  60

Ser Pro Pro Ala Ile Pro Tyr Glu Leu Pro Ser Ser Gln Lys Pro
65              70                  75                  80

Gly Ala Cys Ala Pro Lys Ser Pro Asn Gln Gly Ala Ser Asp Glu Ile
                85                  90                  95

Pro Glu Leu Gln Gln Gln Val Pro Thr Gly Ala Ser Ser Ser Leu Asn
                100                 105                 110

Lys Tyr Pro Val Leu Pro Ser Ile Asn Arg Lys Asn Leu Glu Glu Glu
                115                 120                 125

Ala Val Glu Thr Val Ala Lys Lys Ala Ser Ser Leu Gln Leu Ser Ser
                130                 135                 140

Ile Arg Ala Leu Tyr Gln Asp Glu Thr Gly Thr Met Lys Thr Ser Glu
145                 150                 155                 160

Glu Asp Ser Arg Ala Arg Ala Cys Ala Val Glu Arg Lys Phe Ile Val
                165                 170                 175

Arg Thr Lys Lys Gln Gly Ser Ser Arg Ala Gly Asn Leu Glu Glu Pro
                180                 185                 190

Ser Asp Gln Glu Pro Arg Leu Leu Leu Ala Val Arg Ser Pro Thr Gly
                195                 200                 205

Gln Arg Phe Val Arg His Phe Arg Pro Thr Asp Leu Gln Thr Ile
                210                 215                 220

Val Ala Val Ala Glu Gln Lys Asn Lys Thr Ser Tyr Arg His Cys Ser
225                 230                 235                 240

Ile Glu Thr Met Glu Val Pro Arg Arg Arg Phe Ser Asp Leu Thr Lys
                245                 250                 255

Ser Leu Gln Glu Cys Arg Ile Pro His Lys Ser Val Leu Gly Ile Ser
                260                 265                 270

Leu Glu Asp Gly Glu Gly Trp Pro
                275                 280

<210> SEQ ID NO 137
<211> LENGTH: 666
<212> TYPE: PRT
<213> ORGANISM: Homo sapiens

<400> SEQUENCE: 137

Met Ala Thr Thr Val Thr Cys Thr Arg Phe Thr Asp Glu Tyr Gln Leu
1               5                   10                  15

Tyr Glu Asp Ile Gly Lys Gly Ala Phe Ser Val Val Arg Arg Cys Val
                20                  25                  30

Lys Leu Cys Thr Gly His Glu Tyr Ala Ala Lys Ile Ile Asn Thr Lys
                35                  40                  45

Lys Leu Ser Ala Arg Asp His Gln Lys Leu Glu Arg Glu Ala Arg Ile
                50                  55                  60

Cys Arg Leu Leu Lys His Ser Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95
```

-continued

```
Glu Leu Phe Glu Asp Ile Val Ala Arg Glu Tyr Tyr Ser Glu Ala Asp
                100                 105                 110

Ala Ser His Cys Ile Gln Gln Ile Leu Glu Ala Val Leu His Cys His
            115                 120                 125

Gln Met Gly Val Val His Arg Asp Leu Lys Pro Glu Asn Leu Leu Leu
        130                 135                 140

Ala Ser Lys Cys Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Glu Ala Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala His Glu Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Lys Lys Phe Asn Ala Arg Arg Lys Leu Lys Gly Ala Ile
290                 295                 300

Leu Thr Thr Met Leu Ala Thr Arg Asn Phe Ser Val Gly Arg Gln Thr
305                 310                 315                 320

Thr Ala Pro Ala Thr Met Ser Thr Ala Ala Ser Gly Thr Thr Met Gly
                325                 330                 335

Leu Val Glu Gln Ala Lys Ser Leu Leu Asn Lys Lys Ala Asp Gly Val
            340                 345                 350

Lys Pro Gln Thr Asn Ser Thr Lys Asn Ser Ala Ala Ala Thr Ser Pro
        355                 360                 365

Lys Gly Thr Leu Pro Pro Ala Ala Leu Glu Pro Gln Thr Thr Val Ile
370                 375                 380

His Asn Pro Val Asp Gly Ile Lys Glu Ser Ser Asp Ser Ala Asn Thr
385                 390                 395                 400

Thr Ile Glu Asp Glu Asp Ala Lys Ala Pro Arg Val Pro Asp Ile Leu
                405                 410                 415

Ser Ser Val Arg Arg Gly Ser Gly Ala Pro Glu Ala Glu Gly Pro Leu
            420                 425                 430

Pro Cys Pro Ser Pro Ala Pro Phe Ser Pro Leu Pro Ala Pro Ser Pro
        435                 440                 445

Arg Ile Ser Asp Ile Leu Asn Ser Val Arg Arg Gly Ser Gly Thr Pro
450                 455                 460

Glu Ala Glu Gly Pro Leu Ser Ala Gly Pro Pro Cys Leu Ser Pro
465                 470                 475                 480

Ala Leu Leu Gly Pro Leu Ser Ser Pro Arg Ile Ser Asp Ile
                485                 490                 495

Leu Asn Ser Val Arg Arg Gly Ser Gly Thr Pro Glu Ala Glu Gly Pro
            500                 505                 510

Ser Pro Val Gly Pro Pro Pro Cys Pro Ser Pro Thr Ile Pro Gly Pro
```

```
            515                 520                 525
Leu Pro Thr Pro Ser Arg Lys Gln Glu Ile Ile Lys Thr Thr Glu Gln
    530                 535                 540

Leu Ile Glu Ala Val Asn Asn Gly Asp Phe Glu Ala Tyr Ala Lys Ile
545                 550                 555                 560

Cys Asp Pro Gly Leu Thr Ser Phe Glu Pro Glu Ala Leu Gly Asn Leu
                565                 570                 575

Val Glu Gly Met Asp Phe His Arg Phe Tyr Phe Glu Asn Leu Leu Ala
            580                 585                 590

Lys Asn Ser Lys Pro Ile His Thr Thr Ile Leu Asn Pro His Val His
        595                 600                 605

Val Ile Gly Glu Asp Ala Ala Cys Ile Ala Tyr Ile Arg Leu Thr Gln
    610                 615                 620

Tyr Ile Asp Gly Gln Gly Arg Pro Arg Thr Ser Gln Ser Glu Glu Thr
625                 630                 635                 640

Arg Val Trp His Arg Arg Asp Gly Lys Trp Gln Asn Val His Phe His
                645                 650                 655

Cys Ser Gly Ala Pro Val Ala Pro Leu Gln
            660                 665

<210> SEQ ID NO 138
<211> LENGTH: 488
<212> TYPE: PRT
<213> ORGANISM: Homo sapiens

<400> SEQUENCE: 138

Met Arg Phe His Trp Leu Pro Thr Leu Ser Glu Pro Phe Asp Arg Asn
1               5                   10                  15

Gln Glu Leu Glu Thr Cys Ile Arg Pro Leu Trp Thr Pro Ser Gly Ser
            20                  25                  30

Ala Cys Glu Thr Glu His Asn Lys Ser Met Asp Met Gly Asn Gln His
        35                  40                  45

Pro Ser Ile Ser Arg Leu Gln Glu Ile Gln Lys Glu Val Lys Ser Val
    50                  55                  60

Glu Gln Gln Val Ile Gly Phe Ser Gly Leu Ser Asp Asp Lys Asn Tyr
65                  70                  75                  80

Lys Lys Leu Glu Arg Ile Leu Thr Lys Gln Leu Phe Glu Ile Asp Ser
                85                  90                  95

Val Asp Thr Glu Gly Lys Gly Asp Ile Gln Gln Ala Arg Lys Arg Ala
            100                 105                 110

Ala Gln Glu Thr Glu Arg Leu Leu Lys Glu Leu Glu Gln Asn Ala Asn
        115                 120                 125

His Pro His Arg Ile Glu Ile Gln Asn Ile Phe Glu Glu Ala Gln Ser
    130                 135                 140

Leu Val Arg Glu Lys Ile Val Pro Phe Tyr Asn Gly Asn Cys Val
145                 150                 155                 160

Thr Asp Glu Phe Glu Glu Gly Ile Gln Asp Ile Ile Leu Arg Leu Thr
                165                 170                 175

His Val Lys Thr Gly Gly Lys Ile Ser Leu Arg Lys Ala Arg Tyr His
            180                 185                 190

Thr Leu Thr Lys Ile Cys Ala Val Gln Glu Ile Ile Glu Asp Cys Met
        195                 200                 205

Lys Lys Gln Pro Ser Leu Pro Leu Ser Glu Asp Ala His Pro Ser Val
    210                 215                 220
```

```
Ala Lys Ile Asn Phe Val Met Cys Glu Val Asn Lys Ala Arg Gly Val
225                 230                 235                 240

Leu Ile Ala Leu Leu Met Gly Val Asn Asn Glu Thr Cys Arg His
            245                 250                 255

Leu Ser Cys Val Leu Ser Gly Leu Ile Ala Asp Leu Asp Ala Leu Asp
                260                 265                 270

Val Cys Gly Arg Thr Glu Ile Arg Asn Tyr Arg Arg Glu Val Val Glu
                275                 280                 285

Asp Ile Asn Lys Leu Leu Lys Tyr Leu Asp Leu Glu Glu Ala Asp
        290                 295                 300

Thr Thr Lys Ala Phe Asp Leu Arg Gln Asn His Ser Ile Leu Lys Ile
305                 310                 315                 320

Glu Lys Val Leu Lys Arg Met Arg Glu Ile Lys Asn Glu Leu Leu Gln
                325                 330                 335

Ala Gln Asn Pro Ser Glu Leu Tyr Leu Ser Ser Lys Thr Glu Leu Gln
                340                 345                 350

Gly Leu Ile Gly Gln Leu Asp Glu Val Ser Leu Glu Lys Asn Pro Cys
            355                 360                 365

Ile Arg Glu Ala Arg Arg Ala Val Ile Glu Val Gln Thr Leu Ile
        370                 375                 380

Thr Tyr Ile Asp Leu Lys Glu Ala Leu Glu Lys Arg Lys Leu Phe Ala
385                 390                 395                 400

Cys Glu Glu His Pro Ser His Lys Ala Val Trp Asn Val Leu Gly Asn
                405                 410                 415

Leu Ser Glu Ile Gln Gly Glu Val Leu Ser Phe Asp Gly Asn Arg Thr
            420                 425                 430

Asp Lys Asn Tyr Ile Arg Leu Glu Leu Leu Thr Lys Gln Leu Leu
        435                 440                 445

Ala Leu Asp Ala Val Asp Pro Gln Gly Glu Glu Lys Cys Lys Ala Ala
            450                 455                 460

Arg Lys Gln Ala Val Arg Leu Ala Gln Asn Ile Leu Ser Tyr Leu Asp
465                 470                 475                 480

Leu Lys Ser Asp Glu Trp Glu Tyr
                485

<210> SEQ ID NO 139
<211> LENGTH: 928
<212> TYPE: PRT
<213> ORGANISM: Homo sapiens

<400> SEQUENCE: 139

Met Gly Gly Ser Ala Ser Ser Gln Leu Asp Glu Gly Lys Cys Ala Tyr
1               5                   10                  15

Ile Arg Gly Lys Thr Glu Ala Ala Ile Lys Asn Phe Ser Pro Tyr Tyr
                20                  25                  30

Ser Arg Gln Tyr Ser Val Ala Phe Cys Asn His Val Arg Thr Glu Val
            35                  40                  45

Glu Gln Gln Arg Asp Leu Thr Ser Gln Phe Leu Lys Thr Lys Pro Pro
        50                  55                  60

Leu Ala Pro Gly Thr Ile Leu Tyr Glu Ala Glu Leu Ser Gln Phe Ser
65                  70                  75                  80

Glu Asp Ile Lys Lys Trp Lys Glu Arg Tyr Val Val Val Lys Asn Asp
                85                  90                  95

Tyr Ala Val Glu Ser Tyr Glu Asn Lys Glu Ala Tyr Gln Arg Gly Ala
                100                 105                 110
```

```
Ala Pro Lys Cys Arg Ile Leu Pro Ala Gly Lys Val Leu Thr Ser
            115                 120                 125

Glu Asp Glu Tyr Asn Leu Leu Ser Asp Arg His Phe Pro Asp Pro Leu
            130                 135                 140

Ala Ser Ser Glu Lys Glu Asn Thr Gln Pro Phe Val Val Leu Pro Lys
145                 150                 155                 160

Glu Phe Pro Val Tyr Leu Trp Gln Pro Phe Phe Arg His Gly Tyr Phe
                    165                 170                 175

Cys Phe His Glu Ala Ala Asp Gln Lys Arg Phe Ser Ala Leu Leu Ser
            180                 185                 190

Asp Cys Val Arg His Leu Asn His Asp Tyr Met Lys Gln Met Thr Phe
            195                 200                 205

Glu Ala Gln Ala Phe Leu Glu Ala Val Gln Phe Phe Arg Gln Glu Lys
            210                 215                 220

Gly His Tyr Gly Ser Trp Glu Met Ile Thr Gly Asp Glu Ile Gln Ile
225                 230                 235                 240

Leu Ser Asn Leu Val Met Glu Leu Leu Pro Thr Leu Gln Thr Asp
                    245                 250                 255

Leu Leu Pro Lys Met Lys Gly Lys Lys Asn Asp Arg Lys Arg Thr Trp
            260                 265                 270

Leu Gly Leu Leu Glu Glu Ala Tyr Thr Leu Val Gln His Gln Val Ser
            275                 280                 285

Glu Gly Leu Ser Ala Leu Lys Glu Glu Cys Arg Ala Leu Thr Lys Gly
            290                 295                 300

Leu Glu Gly Thr Ile Arg Ser Asp Met Asp Gln Ile Val Asn Ser Lys
305                 310                 315                 320

Asn Tyr Leu Ile Gly Lys Ile Lys Ala Met Val Ala Gln Pro Ala Glu
                    325                 330                 335

Lys Ser Cys Leu Glu Ser Val Gln Pro Phe Leu Ala Ser Ile Leu Glu
            340                 345                 350

Glu Leu Met Gly Pro Val Ser Ser Gly Phe Ser Glu Val Arg Val Leu
            355                 360                 365

Phe Glu Lys Glu Val Asn Glu Val Ser Gln Asn Phe Gln Thr Thr Lys
            370                 375                 380

Asp Ser Val Gln Leu Lys Glu His Leu Asp Arg Leu Met Asn Leu Pro
385                 390                 395                 400

Leu His Ser Val Lys Met Glu Pro Cys Tyr Thr Lys Val Asn Leu Leu
                    405                 410                 415

His Glu Arg Leu Gln Asp Leu Lys Ser Arg Phe Arg Phe Pro His Ile
            420                 425                 430

Asp Leu Val Val Gln Arg Thr Gln Asn Tyr Met Gln Glu Leu Met Glu
            435                 440                 445

Asn Ala Val Phe Thr Phe Glu Gln Leu Leu Ser Pro His Leu Gln Gly
            450                 455                 460

Glu Ala Ser Lys Thr Ala Val Ala Ile Glu Lys Val Lys Leu Arg Val
465                 470                 475                 480

Leu Lys Gln Tyr Asp Tyr Asp Ser Ser Thr Ile Arg Lys Lys Ile Phe
                    485                 490                 495

Gln Glu Ala Leu Val Gln Ile Thr Leu Pro Thr Val Gln Lys Ala Leu
            500                 505                 510

Ala Ser Thr Cys Lys Pro Glu Leu Gln Lys Tyr Glu Gln Phe Ile Phe
            515                 520                 525
```

```
Ala Asp His Thr Asn Met Ile His Val Glu Asn Val Tyr Glu Glu Ile
    530                 535                 540
Leu His Gln Ile Leu Leu Asp Glu Thr Leu Lys Val Ile Lys Glu Ala
545                 550                 555                 560
Ala Ile Leu Lys Lys His Asn Leu Phe Glu Asp Asn Met Ala Leu Pro
                565                 570                 575
Ser Glu Ser Val Ser Ser Leu Thr Asp Leu Lys Pro Pro Thr Gly Ser
            580                 585                 590
Asn Gln Ala Ser Pro Ala Arg Arg Ala Ser Ala Ile Leu Pro Gly Val
        595                 600                 605
Leu Gly Ser Glu Thr Leu Ser Asn Glu Val Phe Gln Glu Ser Glu Glu
    610                 615                 620
Glu Lys Gln Pro Glu Val Pro Ser Ser Leu Ala Lys Gly Glu Ser Leu
625                 630                 635                 640
Ser Leu Pro Gly Pro Ser Pro Pro Asp Gly Thr Glu Gln Val Ile
                645                 650                 655
Ile Ser Arg Val Asp Asp Pro Val Val Asn Pro Val Ala Thr Glu Asp
            660                 665                 670
Thr Ala Gly Leu Pro Gly Thr Cys Ser Ser Glu Leu Glu Phe Gly Gly
        675                 680                 685
Thr Leu Glu Asp Glu Glu Pro Ala Gln Glu Glu Pro Glu Pro Ile Thr
    690                 695                 700
Ala Ser Gly Ser Leu Lys Ala Leu Arg Lys Leu Leu Thr Ala Ser Val
705                 710                 715                 720
Glu Val Pro Val Asp Ser Ala Pro Val Met Glu Glu Asp Thr Asn Gly
                725                 730                 735
Glu Ser His Val Pro Gln Glu Asn Glu Glu Glu Glu Lys Glu Pro
            740                 745                 750
Ser Gln Ala Ala Ala Ile His Pro Asp Asn Cys Glu Glu Ser Glu Val
        755                 760                 765
Ser Glu Arg Glu Ala Gln Pro Pro Cys Pro Glu Ala His Gly Glu Glu
    770                 775                 780
Leu Gly Gly Phe Pro Glu Val Gly Ser Pro Ala Ser Pro Ala Ser
785                 790                 795                 800
Gly Gly Leu Thr Glu Glu Pro Leu Gly Pro Met Glu Gly Glu Leu Pro
                805                 810                 815
Gly Glu Ala Cys Thr Leu Thr Ala His Glu Gly Arg Gly Gly Lys Cys
            820                 825                 830
Thr Glu Glu Gly Asp Ala Ser Gln Gln Glu Gly Cys Thr Leu Gly Ser
        835                 840                 845
Asp Pro Ile Cys Leu Ser Glu Ser Gln Val Ser Glu Glu Gln Glu
    850                 855                 860
Met Gly Gly Gln Ser Ser Ala Ala Gln Ala Thr Ala Ser Val Asn Ala
865                 870                 875                 880
Glu Glu Ile Lys Val Ala Arg Ile His Glu Cys Gln Trp Val Val Glu
                885                 890                 895
Asp Ala Pro Asn Pro Asp Val Leu Leu Ser His Lys Asp Asp Val Lys
            900                 905                 910
Glu Gly Glu Gly Gly Gln Glu Ser Phe Pro Glu Leu Pro Ser Glu Glu
        915                 920                 925

<210> SEQ ID NO 140
<211> LENGTH: 550
<212> TYPE: PRT
```

```
<213> ORGANISM: Homo sapiens

<400> SEQUENCE: 140

Met Trp Lys Ala Ser Ala Gly His Ala Val Ser Ile Ala Gln Asp
1               5                   10                  15

Ala Gly Ala Asp Asp Trp Glu Thr Asp Pro Asp Phe Val Asn Asp Val
            20                  25                  30

Ser Glu Lys Glu Gln Arg Trp Gly Ala Lys Thr Val Gln Gly Ser Gly
        35                  40                  45

His Gln Glu His Ile Asn Ile His Lys Leu Arg Glu Asn Val Phe Gln
    50                  55                  60

Glu His Gln Thr Leu Lys Glu Lys Glu Leu Thr Gly Pro Lys Ala
65                  70                  75                  80

Ser His Gly Tyr Gly Gly Lys Phe Gly Val Glu Gln Asp Arg Met Asp
                85                  90                  95

Lys Ser Ala Val Gly His Glu Tyr Gln Ser Lys Leu Ser Lys His Cys
            100                 105                 110

Ser Gln Val Asp Ser Val Arg Gly Phe Gly Gly Lys Phe Gly Val Gln
        115                 120                 125

Met Asp Arg Val Asp Gln Ser Ala Val Gly Phe Glu Tyr Gln Gly Lys
130                 135                 140

Thr Glu Lys His Ala Ser Gln Lys Asp Tyr Ser Ser Gly Phe Gly Gly
145                 150                 155                 160

Lys Tyr Gly Val Gln Ala Asp Arg Val Asp Lys Ser Ala Val Gly Phe
                165                 170                 175

Asp Tyr Gln Gly Lys Thr Glu Lys His Glu Ser Gln Arg Asp Tyr Ser
            180                 185                 190

Lys Gly Phe Gly Gly Lys Tyr Gly Ile Asp Lys Asp Lys Val Asp Lys
        195                 200                 205

Ser Ala Val Gly Phe Glu Tyr Gln Gly Lys Thr Glu Lys His Glu Ser
210                 215                 220

Gln Lys Asp Tyr Val Lys Gly Phe Gly Gly Lys Phe Gly Val Gln Thr
225                 230                 235                 240

Asp Arg Gln Asp Lys Cys Ala Leu Gly Trp Asp His Gln Glu Lys Leu
                245                 250                 255

Gln Leu His Glu Ser Gln Lys Asp Tyr Lys Thr Gly Phe Gly Gly Lys
            260                 265                 270

Phe Gly Val Gln Ser Glu Arg Gln Asp Ser Ala Ala Val Gly Phe Asp
        275                 280                 285

Tyr Lys Glu Lys Leu Ala Lys His Glu Ser Gln Gln Asp Tyr Ser Lys
290                 295                 300

Gly Phe Gly Gly Lys Tyr Gly Val Gln Lys Asp Arg Met Asp Lys Asn
305                 310                 315                 320

Ala Ser Thr Phe Glu Asp Val Thr Gln Val Ser Ser Ala Tyr Gln Lys
                325                 330                 335

Thr Val Pro Val Glu Ala Val Thr Ser Lys Thr Ser Asn Ile Arg Ala
            340                 345                 350

Asn Phe Glu Asn Leu Ala Lys Glu Lys Glu Gln Glu Asp Arg Arg Lys
        355                 360                 365

Ala Glu Ala Glu Arg Ala Gln Arg Met Ala Lys Glu Arg Gln Glu Gln
370                 375                 380

Glu Glu Ala Arg Arg Lys Leu Glu Glu Gln Ala Arg Ala Lys Thr Gln
385                 390                 395                 400
```

```
Thr Pro Pro Val Ser Pro Ala Pro Gln Pro Thr Glu Glu Arg Leu Pro
                405                 410                 415

Ser Ser Pro Val Tyr Glu Asp Ala Ala Ser Phe Lys Ala Glu Leu Ser
            420                 425                 430

Tyr Arg Gly Pro Val Ser Gly Thr Glu Pro Glu Pro Val Tyr Ser Met
        435                 440                 445

Glu Ala Ala Asp Tyr Arg Glu Ala Ser Ser Gln Gln Gly Leu Ala Tyr
    450                 455                 460

Ala Thr Glu Ala Val Tyr Glu Ser Ala Glu Ala Pro Gly His Tyr Pro
465                 470                 475                 480

Ala Glu Asp Ser Thr Tyr Asp Glu Tyr Glu Asn Asp Leu Gly Ile Thr
                485                 490                 495

Ala Val Ala Leu Tyr Asp Tyr Gln Ala Ala Gly Asp Asp Glu Ile Ser
            500                 505                 510

Phe Asp Pro Asp Asp Ile Ile Thr Asn Ile Glu Met Ile Asp Asp Gly
        515                 520                 525

Trp Trp Arg Gly Val Cys Lys Gly Arg Tyr Gly Leu Phe Pro Ala Asn
    530                 535                 540

Tyr Val Glu Leu Arg Gln
545                 550

<210> SEQ ID NO 141
<211> LENGTH: 1255
<212> TYPE: PRT
<213> ORGANISM: Homo sapiens

<400> SEQUENCE: 141

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640
```

-continued

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Phe Gly
    660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg

-continued

```
                1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
        1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
                1140                1145                1150

Arg Glu Gly Pro Leu Pro Ala Ala Arg Pro Ala Gly Ala Thr Leu Glu
                1155                1160                1165

Arg Pro Lys Thr Leu Ser Pro Gly Lys Asn Gly Val Val Lys Asp Val
        1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
        1220                1225                1230

Pro Pro Ser Thr Phe Lys Gly Thr Pro Thr Ala Glu Asn Pro Glu Tyr
        1235                1240                1245

Leu Gly Leu Asp Val Pro Val
        1250                1255

<210> SEQ ID NO 142
<211> LENGTH: 284
<212> TYPE: PRT
<213> ORGANISM: Homo sapiens

<400> SEQUENCE: 142

Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

Glu Asp Arg Ser Lys Gln Leu Glu Asp Glu Leu Val Ser Leu Gln Lys
        35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175
```

Glu Arg Ala Glu Glu Arg Ala Glu Leu Ser Glu Gly Lys Cys Ala Glu
            180                 185                 190

Leu Glu Glu Glu Leu Lys Thr Val Thr Asn Asn Leu Lys Ser Leu Glu
        195                 200                 205

Ala Gln Ala Glu Lys Tyr Ser Gln Lys Glu Asp Arg Tyr Glu Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Asp Glu Leu Tyr Ala Gln Lys Leu Lys Tyr Lys Ala Ile Ser Glu
            260                 265                 270

Glu Leu Asp His Ala Leu Asn Asp Met Thr Ser Ile
        275                 280

<210> SEQ ID NO 143
<211> LENGTH: 471
<212> TYPE: PRT
<213> ORGANISM: Homo sapiens

<400> SEQUENCE: 143

Met Leu Leu Asn Asp Pro Asp Thr Glu Leu Val Arg Leu Leu Ala Ser
1               5                   10                  15

Val Cys Met Gln Val Asn Lys Asp Lys Gly Arg Pro Ser His Gln Pro
            20                  25                  30

Pro Leu Pro His Ser Lys Val Arg Gln Pro Trp Ser Ile Pro Val Leu
        35                  40                  45

Pro Asp Asp Lys Gly Gly Leu Lys Ser Trp Trp Asn Arg Met Ser Asn
50                  55                  60

Arg Phe Arg Lys Leu Lys Leu Met Gln Thr Leu Pro Arg Gly Leu Ser
65                  70                  75                  80

Ser Asn Gln Pro Leu Pro Phe Ser Asp Glu Pro Glu Pro Ala Leu Asp
                85                  90                  95

Ser Thr Met Arg Ala Ala Pro Gln Asp Lys Thr Ser Arg Ser Ala Leu
            100                 105                 110

Pro Asp Ala Ala Pro Val Thr Lys Asp Asn Gly Pro Gly Ser Thr Arg
        115                 120                 125

Gly Glu Lys Glu Asp Thr Leu Leu Thr Thr Met Leu Arg Asn Gly Ala
    130                 135                 140

Pro Leu Thr Arg Leu Pro Ser Asp Lys Leu Lys Ala Val Ile Pro Pro
145                 150                 155                 160

Phe Leu Pro Pro Ser Ser Phe Glu Leu Trp Ser Ser Asp Arg Ser Arg
                165                 170                 175

Thr Arg His Asn Gly Lys Ala Asp Pro Met Lys Thr Ala Leu Pro Gln
            180                 185                 190

Arg Ala Ser Arg Gly His Pro Val Gly Gly Gly Thr Asp Thr Thr
        195                 200                 205

Pro Val Arg Pro Val Lys Phe Pro Ser Leu Pro Arg Ser Pro Ala Ser
    210                 215                 220

Ser Ala Asn Ser Gly Asn Phe Asn His Ser Pro His Ser Ser Gly Gly
225                 230                 235                 240

Ser Ser Gly Ile Gly Val Ser Arg His Gly Glu Leu Leu Asn Arg
                245                 250                 255

Ser Gly Gly Ser Ile Asp Asn Val Leu Ser Gln Ile Ala Ala Gln Arg
            260                 265                 270

```
Lys Lys Ala Ala Gly Leu Leu Glu Gln Lys Pro Ser His Arg Ser Ser
        275                 280                 285

Pro Val Gly Pro Ala Pro Gly Ser Ser Pro Ser Glu Leu Pro Ala Ser
    290                 295                 300

Pro Ala Gly Gly Ser Ala Pro Val Gly Lys Lys Leu Glu Thr Ser Lys
305                 310                 315                 320

Arg Pro Pro Ser Gly Thr Ser Thr Thr Ser Lys Ser Thr Ser Pro Thr
                325                 330                 335

Leu Thr Pro Ser Pro Ser Pro Lys Gly His Thr Ala Glu Ser Ser Val
                340                 345                 350

Ser Ser Ser Ser Ser His Arg Gln Ser Lys Ser Ser Gly Gly Ser Ser
            355                 360                 365

Ser Gly Thr Ile Thr Asp Glu Asp Leu Thr Gly Ile Leu Lys Lys
    370                 375                 380

Leu Ser Leu Glu Lys Tyr Gln Pro Ile Phe Glu Gln Gln Val Asp
385                 390                 395                 400

Met Glu Ala Phe Leu Thr Leu Thr Asp Gly Asp Leu Lys Glu Leu Gly
                405                 410                 415

Ile Lys Thr Asp Gly Ser Arg Gln Gln Ile Leu Ala Ala Ile Ser Glu
                420                 425                 430

Leu Asn Ala Gly Lys Gly Arg Glu Arg Gln Ile Leu Gln Glu Thr Ile
            435                 440                 445

His Asn Phe His Ser Ser Phe Glu Ser Ser Ala Ser Asn Thr Arg Ala
    450                 455                 460

Pro Gly Asn Ser Pro Cys Ala
465                 470

<210> SEQ ID NO 144
<211> LENGTH: 1073
<212> TYPE: PRT
<213> ORGANISM: Homo sapiens

<400> SEQUENCE: 144

Met Ala Ala Ala Gly Gln Leu Cys Leu Leu Tyr Leu Ser Ala Gly Leu
1               5                   10                  15

Leu Ser Arg Leu Gly Ala Ala Phe Asn Leu Asp Thr Arg Glu Asp Asn
            20                  25                  30

Val Ile Arg Lys Tyr Gly Asp Pro Gly Ser Leu Phe Gly Phe Ser Leu
        35                  40                  45

Ala Met His Trp Gln Leu Gln Pro Glu Asp Lys Arg Leu Leu Leu Val
    50                  55                  60

Gly Ala Pro Arg Ala Glu Ala Leu Pro Leu Gln Arg Ala Asn Arg Thr
65                  70                  75                  80

Gly Gly Leu Tyr Ser Cys Asp Ile Thr Ala Arg Gly Pro Cys Thr Arg
                85                  90                  95

Ile Glu Phe Asp Asn Asp Ala Asp Pro Thr Ser Glu Ser Lys Glu Asp
                100                 105                 110

Gln Trp Met Gly Val Thr Val Gln Ser Gln Gly Pro Gly Gly Lys Val
            115                 120                 125

Val Thr Cys Ala His Arg Tyr Glu Lys Arg Gln His Val Asn Thr Lys
    130                 135                 140

Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
```

-continued

```
                165                 170                 175
Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
            195                 200                 205

Gly Thr Tyr Asn Trp Lys Gly Ile Val Arg Val Glu Gln Lys Asn Asn
            210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Phe Ser Leu Asp Ser Gly Lys Gly Ile Val Ser Lys Asp
            260                 265                 270

Glu Ile Thr Phe Val Ser Gly Ala Pro Arg Ala Asn His Ser Gly Ala
            275                 280                 285

Val Val Leu Leu Lys Arg Asp Met Lys Ser Ala His Leu Leu Pro Glu
            290                 295                 300

His Ile Phe Asp Gly Glu Gly Leu Ala Ser Ser Phe Gly Tyr Asp Val
305                 310                 315                 320

Ala Val Val Asp Leu Asn Lys Asp Gly Trp Gln Asp Ile Val Ile Gly
                325                 330                 335

Ala Pro Gln Tyr Phe Asp Arg Asp Gly Glu Val Gly Gly Ala Val Tyr
            340                 345                 350

Val Tyr Met Asn Gln Gln Gly Arg Trp Asn Asn Val Lys Pro Ile Arg
            355                 360                 365

Leu Asn Gly Thr Lys Asp Ser Met Phe Gly Ile Ala Val Lys Asn Ile
            370                 375                 380

Gly Asp Ile Asn Gln Asp Gly Tyr Pro Asp Ile Ala Val Gly Ala Pro
385                 390                 395                 400

Tyr Asp Asp Leu Gly Lys Val Phe Ile Tyr His Gly Ser Ala Asn Gly
                405                 410                 415

Ile Asn Thr Lys Pro Thr Gln Val Leu Lys Gly Ile Ser Pro Tyr Phe
            420                 425                 430

Gly Tyr Ser Ile Ala Gly Asn Met Asp Leu Asp Arg Asn Ser Tyr Pro
            435                 440                 445

Asp Val Ala Val Gly Ser Leu Ser Asp Ser Val Thr Ile Phe Arg Ser
450                 455                 460

Arg Pro Val Ile Asn Ile Gln Lys Thr Ile Thr Val Thr Pro Asn Arg
465                 470                 475                 480

Ile Asp Leu Arg Gln Lys Thr Ala Cys Gly Ala Pro Ser Gly Ile Cys
                485                 490                 495

Leu Gln Val Lys Ser Cys Phe Glu Tyr Thr Ala Asn Pro Ala Gly Tyr
            500                 505                 510

Asn Pro Ser Ile Ser Ile Val Gly Thr Leu Glu Ala Glu Lys Glu Arg
            515                 520                 525

Arg Lys Ser Gly Leu Ser Ser Arg Val Gln Phe Arg Asn Gln Gly Ser
            530                 535                 540

Glu Pro Lys Tyr Thr Gln Glu Leu Thr Leu Lys Arg Gln Lys Gln Lys
545                 550                 555                 560

Val Cys Met Glu Glu Thr Leu Trp Leu Gln Asp Asn Ile Arg Asp Lys
                565                 570                 575

Leu Arg Pro Ile Pro Ile Thr Ala Ser Val Glu Ile Gln Glu Pro Ser
            580                 585                 590
```

```
Ser Arg Arg Arg Val Asn Ser Leu Pro Glu Val Pro Ile Leu Asn
        595                 600             605

Ser Asp Glu Pro Lys Thr Ala His Ile Asp Val His Phe Leu Lys Glu
    610                 615             620

Gly Cys Gly Asp Asp Asn Val Cys Asn Ser Asn Leu Lys Leu Glu Tyr
625                 630                 635                 640

Lys Phe Cys Thr Arg Glu Gly Asn Gln Asp Lys Phe Ser Tyr Leu Pro
                645                 650                 655

Ile Gln Lys Gly Val Pro Glu Leu Val Leu Lys Asp Gln Lys Asp Ile
                660                 665                 670

Ala Leu Glu Ile Thr Val Thr Asn Ser Pro Ser Asn Pro Arg Asn Pro
            675                 680                 685

Thr Lys Asp Gly Asp Asp Ala His Glu Ala Lys Leu Ile Ala Thr Phe
    690                 695                 700

Pro Asp Thr Leu Thr Tyr Ser Ala Tyr Arg Glu Leu Arg Ala Phe Pro
705                 710                 715                 720

Glu Lys Gln Leu Ser Cys Val Ala Asn Gln Asn Gly Ser Gln Ala Asp
                725                 730                 735

Cys Glu Leu Gly Asn Pro Phe Lys Arg Asn Ser Asn Val Thr Phe Tyr
                740                 745                 750

Leu Val Leu Ser Thr Thr Glu Val Thr Phe Asp Thr Pro Asp Leu Asp
            755                 760                 765

Ile Asn Leu Lys Leu Glu Thr Thr Ser Asn Gln Asp Asn Leu Ala Pro
770                 775                 780

Ile Thr Ala Lys Ala Lys Val Val Ile Glu Leu Leu Ser Val Ser
785                 790                 795                 800

Gly Val Ala Lys Pro Ser Gln Val Tyr Phe Gly Gly Thr Val Val Gly
                805                 810                 815

Glu Gln Ala Met Lys Ser Glu Asp Glu Val Gly Ser Leu Ile Glu Tyr
                820                 825                 830

Glu Phe Arg Val Ile Asn Leu Gly Lys Pro Leu Thr Asn Leu Gly Thr
            835                 840                 845

Ala Thr Leu Asn Ile Gln Trp Pro Lys Glu Ile Ser Asn Gly Lys Trp
    850                 855                 860

Leu Leu Tyr Leu Val Lys Val Glu Ser Lys Gly Leu Glu Lys Val Thr
865                 870                 875                 880

Cys Glu Pro Gln Lys Glu Ile Asn Ser Leu Asn Leu Thr Glu Ser His
                885                 890                 895

Asn Ser Arg Lys Lys Arg Glu Ile Thr Glu Lys Gln Ile Asp Asp Asn
                900                 905                 910

Arg Lys Phe Ser Leu Phe Ala Glu Arg Lys Tyr Gln Thr Leu Asn Cys
            915                 920                 925

Ser Val Asn Val Asn Cys Val Asn Ile Arg Cys Pro Leu Arg Gly Leu
    930                 935                 940

Asp Ser Lys Ala Ser Leu Ile Leu Arg Ser Arg Leu Trp Asn Ser Thr
945                 950                 955                 960

Phe Leu Glu Glu Tyr Ser Lys Leu Asn Tyr Leu Asp Ile Leu Met Arg
                965                 970                 975

Ala Phe Ile Asp Val Thr Ala Ala Glu Asn Ile Arg Leu Pro Asn
                980                 985                 990

Ala Gly Thr Gln Val Arg Val Thr Val Phe Pro Ser Lys Thr Val Ala
            995                 1000                1005
```

```
Gln Tyr Ser Gly Val Pro Trp Trp Ile Ile Leu Val Ala Ile Leu Ala
    1010                1015                1020

Gly Ile Leu Met Leu Ala Leu Leu Val Phe Ile Leu Trp Lys Cys Gly
        1025                1030                1035                1040

Phe Phe Lys Arg Asn Lys Lys Asp His Tyr Asp Ala Thr Tyr His Lys
                1045                1050                1055

Ala Glu Ile His Ala Gln Pro Ser Asp Lys Glu Arg Leu Thr Ser Asp
            1060                1065                1070

Ala
```

<210> SEQ ID NO 145
<211> LENGTH: 227
<212> TYPE: PRT
<213> ORGANISM: Homo sapiens

<400> SEQUENCE: 145

```
Met Glu Lys Leu Phe Asn Glu Asn Glu Gly Met Pro Ser Asn Gln Gly
1               5                   10                  15

Lys Ile Asp Asn Glu Glu Gln Pro His Glu Gly Lys Pro Glu Val
            20                  25                  30

Ala Cys Ile Leu Glu Asp Lys Lys Leu Glu Asn Glu Gly Asn Thr Glu
        35                  40                  45

Asn Thr Gly Lys Arg Val Glu Glu Pro Leu Lys Asp Lys Glu Lys Pro
    50                  55                  60

Glu Ser Ala Gly Lys Ala Lys Gly Glu Gly Lys Ser Glu Arg Lys Gly
65                  70                  75                  80

Lys Ser Glu Met Gln Gly Gly Ser Lys Thr Glu Gly Lys Pro Glu Arg
                85                  90                  95

Gly Gly Arg Ala Glu Gly Glu Gly Glu Pro Asp Ser Glu Arg Glu Pro
            100                 105                 110

Glu Ser Glu Gly Glu Pro Glu Ser Glu Thr Arg Ala Ala Gly Lys Arg
        115                 120                 125

Pro Ala Glu Asp Asp Ile Pro Arg Lys Ala Lys Arg Lys Thr Asn Lys
    130                 135                 140

Gly Leu Ala Gln Tyr Leu Lys Gln Tyr Lys Glu Ala Ile His Asp Met
145                 150                 155                 160

Asn Phe Ser Asn Glu Asp Met Ile Arg Glu Phe Asp Asn Met Ala Arg
                165                 170                 175

Val Glu Asp Lys Arg Arg Lys Ser Lys Gln Lys Leu Gly Ala Phe Leu
            180                 185                 190

Trp Met Gln Arg Asn Leu Gln Asp Pro Phe Tyr Pro Arg Gly Pro Arg
        195                 200                 205

Glu Phe Arg Gly Gly Cys Arg Ala Pro Arg Arg Asp Thr Glu Asp Ile
    210                 215                 220

Pro Tyr Val
225
```

<210> SEQ ID NO 146
<211> LENGTH: 117
<212> TYPE: PRT
<213> ORGANISM: Homo sapiens

<400> SEQUENCE: 146

```
Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
```

```
                    20                  25                  30

Leu Ser Ala Ser Val Gly Asp Arg Val Thr Ile Thr Cys Arg Ala Ser
            35                  40                  45

Gln Ser Ile Ser Ser Trp Leu Ala Trp Tyr Gln Gln Lys Pro Gly Lys
        50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Asp Asp Phe Ala Thr Tyr Tyr Cys Gln Gln
            100                 105                 110

Tyr Asn Ser Tyr Ser
        115

<210> SEQ ID NO 147
<211> LENGTH: 284
<212> TYPE: PRT
<213> ORGANISM: Homo sapiens

<400> SEQUENCE: 147

Met Asp Ala Ile Lys Lys Lys Met Gln Met Leu Lys Leu Asp Lys Glu
1               5                   10                  15

Asn Ala Ile Asp Arg Ala Glu Gln Ala Glu Ala Asp Lys Lys Gln Ala
            20                  25                  30

Glu Asp Arg Cys Lys Gln Leu Glu Glu Glu Gln Gln Ala Leu Gln Lys
        35                  40                  45

Lys Leu Lys Gly Thr Glu Asp Glu Val Glu Lys Tyr Ser Glu Ser Val
    50                  55                  60

Lys Glu Ala Gln Glu Lys Leu Glu Gln Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Asn Arg Ala Met Lys Asp Glu Glu Lys Met Glu Leu Gln
    130                 135                 140

Glu Met Gln Leu Lys Glu Ala Lys His Ile Ala Glu Asp Ser Asp Arg
145                 150                 155                 160

Lys Tyr Glu Glu Val Ala Arg Lys Leu Val Ile Leu Glu Gly Glu Leu
                165                 170                 175

Glu Arg Ser Glu Glu Arg Ala Glu Val Ala Glu Ser Arg Ala Arg Gln
            180                 185                 190

Leu Glu Glu Glu Leu Arg Thr Met Asp Gln Ala Leu Lys Ser Leu Met
        195                 200                 205

Ala Ser Glu Glu Glu Tyr Ser Thr Lys Glu Asp Lys Tyr Glu Glu Glu
    210                 215                 220

Ile Lys Leu Leu Glu Glu Lys Leu Lys Glu Ala Glu Thr Arg Ala Glu
225                 230                 235                 240

Phe Ala Glu Arg Ser Val Ala Lys Leu Glu Lys Thr Ile Asp Asp Leu
                245                 250                 255

Glu Glu Thr Leu Ala Ser Ala Lys Glu Glu Asn Val Glu Ile His Gln
            260                 265                 270
```

Thr Leu Asp Gln Thr Leu Leu Glu Leu Asn Asn Leu
            275                 280

<210> SEQ ID NO 148
<211> LENGTH: 460
<212> TYPE: PRT
<213> ORGANISM: Homo sapiens

<400> SEQUENCE: 148

Met Asn Lys Pro Ile Thr Pro Ser Thr Tyr Val Arg Cys Leu Asn Val
1               5                   10                  15

Gly Leu Ile Arg Lys Leu Ser Asp Phe Ile Asp Pro Gln Glu Gly Trp
            20                  25                  30

Lys Lys Leu Ala Val Ala Ile Lys Lys Pro Ser Gly Asp Asp Arg Tyr
        35                  40                  45

Asn Gln Phe His Ile Arg Arg Phe Glu Ala Leu Leu Thr Gly Lys
    50                  55                  60

Ser Pro Thr Ser Glu Leu Leu Phe Asp Trp Gly Thr Thr Asn Cys Thr
65                  70                  75                  80

Val Gly Asp Leu Val Asp Leu Ile Gln Asn Glu Phe Phe Ala Pro
                85                  90                  95

Ala Ser Leu Leu Leu Pro Asp Ala Val Pro Lys Thr Ala Asn Thr Leu
            100                 105                 110

Pro Ser Lys Glu Ala Ile Thr Val Gln Gln Lys Gln Met Pro Phe Cys
        115                 120                 125

Asp Lys Asp Arg Thr Leu Met Thr Pro Val Gln Asn Leu Glu Gln Ser
    130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
                165                 170                 175

Thr Asn Asn Phe Asp Glu Arg Pro Ile Ser Val Gly Gly Asn Lys Met
            180                 185                 190

Gly Glu Gly Gly Phe Gly Val Val Tyr Lys Gly Tyr Val Asn Asn Thr
        195                 200                 205

Thr Val Ala Val Lys Lys Leu Ala Ala Met Val Asp Ile Thr Thr Glu
    210                 215                 220

Glu Leu Lys Gln Gln Phe Asp Gln Glu Ile Lys Val Met Ala Lys Cys
225                 230                 235                 240

Gln His Glu Asn Leu Val Glu Leu Leu Gly Phe Ser Ser Asp Gly Asp
                245                 250                 255

Asp Leu Cys Leu Val Tyr Val Tyr Met Pro Asn Gly Ser Leu Leu Asp
            260                 265                 270

Arg Leu Ser Cys Leu Asp Gly Thr Pro Pro Leu Ser Trp His Met Arg
        275                 280                 285

Cys Lys Ile Ala Gln Gly Ala Ala Asn Gly Ile Asn Phe Leu His Glu
    290                 295                 300

Asn His His Ile His Arg Asp Ile Lys Ser Ala Asn Ile Leu Leu Asp
305                 310                 315                 320

Glu Ala Phe Thr Ala Lys Ile Ser Asp Phe Gly Leu Ala Arg Ala Ser
                325                 330                 335

Glu Lys Phe Ala Gln Thr Val Met Thr Ser Arg Ile Val Gly Thr Thr
            340                 345                 350

Ala Tyr Met Ala Pro Glu Ala Leu Arg Gly Glu Ile Thr Pro Lys Ser
        355                 360                 365

```
Asp Ile Tyr Ser Phe Gly Val Leu Leu Glu Ile Thr Gly Leu
        370                 375                 380

Pro Ala Val Asp Glu His Arg Glu Pro Gln Leu Leu Asp Ile Lys
385                 390                 395                 400

Glu Glu Ile Glu Asp Glu Glu Lys Thr Ile Glu Asp Tyr Ile Asp Lys
                405                 410                 415

Lys Met Asn Asp Ala Asp Ser Thr Ser Val Glu Ala Met Tyr Ser Val
                420                 425                 430

Ala Ser Gln Cys Leu His Glu Lys Lys Asn Lys Arg Pro Asp Ile Lys
            435                 440                 445

Lys Val Gln Gln Leu Leu Gln Glu Met Thr Ala Ser
        450                 455                 460

<210> SEQ ID NO 149
<211> LENGTH: 120
<212> TYPE: PRT
<213> ORGANISM: Homo sapiens

<400> SEQUENCE: 149

Met Trp Ala Ser Glu Leu Arg Gly Pro Gly Cys Ala Asp Ser Leu Asn
1               5                   10                  15

Ala Ala Leu Ala His Ser Pro Leu Arg Asn Arg Gln Cys Arg Gly Phe
            20                  25                  30

Pro Gly Gly Gly His Ser Ile Gln Pro Leu Tyr Thr Pro Arg Ala Pro
        35                  40                  45

Ala Ala Ala Pro Pro Pro Pro His Lys Met Ala Ala Pro Ile Glu Glu
    50                  55                  60

Thr Ala Ala Ala Ser Pro Ala Pro Phe Cys Gly Arg Arg Glu Ile Cys
65                  70                  75                  80

Gln His Gly Lys Pro Leu Leu Arg Met His Pro Ser Leu Glu Thr Pro
                85                  90                  95

Leu Lys Gly Trp Ser Leu Gly Asp His Ile Lys Arg Lys Met Pro Thr
            100                 105                 110

Thr Ser Thr Thr Ser Thr Arg Phe
        115                 120

<210> SEQ ID NO 150
<211> LENGTH: 527
<212> TYPE: PRT
<213> ORGANISM: Homo sapiens

<400> SEQUENCE: 150

Met Ser Leu Cys Gly Ala Arg Ala Asn Ala Lys Met Met Ala Ala Tyr
1               5                   10                  15

Asn Gly Gly Thr Ser Ala Ala Ala Gly His His His His His His
            20                  25                  30

His His Leu Pro His Leu Pro Pro His Leu His His His His
        35                  40                  45

Pro Gln His His Leu His Pro Gly Ser Ala Ala Val His Pro Val
    50                  55                  60

Gln Gln His Thr Ser Ala Ala Ala Ala Ala Ala Ala Ala
65                  70                  75                  80

Ala Ala Ala Met Leu Asn Pro Gly Gln Gln Pro Tyr Phe Pro Ser
                85                  90                  95

Pro Ala Pro Gly Gln Ala Pro Gly Pro Ala Ala Ala Pro Ala Gln
            100                 105                 110
```

```
Val Gln Ala Ala Ala Ala Thr Val Lys Ala His His Gln His
        115                 120             125

Ser His His Pro Gln Gln Leu Asp Ile Glu Pro Asp Arg Pro Ile
    130             135                 140

Gly Tyr Gly Ala Phe Gly Val Val Trp Ser Val Thr Asp Pro Arg Asp
145             150                 155                 160

Gly Lys Arg Val Ala Leu Lys Lys Met Pro Asn Val Phe Gln Asn Leu
                165             170                 175

Val Ser Cys Lys Arg Val Phe Arg Glu Leu Lys Met Leu Cys Phe Phe
            180                 185                 190

Lys His Asp Asn Val Leu Ser Ala Leu Asp Ile Leu Gln Pro Pro His
                195                 200             205

Ile Asp Tyr Phe Glu Glu Ile Tyr Val Val Thr Glu Leu Met Gln Ser
    210                 215                 220

Asp Leu His Lys Ile Ile Val Ser Pro Gln Pro Leu Ser Ser Asp His
225                 230                 235                 240

Val Lys Val Phe Leu Tyr Gln Ile Leu Arg Gly Leu Lys Tyr Leu His
                245                 250                 255

Ser Ala Gly Ile Leu His Arg Asp Ile Lys Pro Gly Asn Leu Leu Val
            260                 265                 270

Asn Ser Asn Cys Val Leu Lys Ile Cys Asp Phe Gly Leu Ala Arg Val
    275                 280                 285

Glu Glu Leu Asp Glu Ser Arg His Met Thr Gln Glu Val Val Thr Gln
290                 295                 300

Tyr Tyr Arg Ala Pro Glu Ile Leu Met Gly Ser Arg His Tyr Ser Asn
305                 310                 315                 320

Ala Ile Asp Ile Trp Ser Val Gly Cys Ile Phe Ala Glu Leu Leu Gly
                325                 330                 335

Arg Arg Ile Leu Phe Gln Ala Gln Ser Pro Ile Gln Gln Leu Asp Leu
            340                 345                 350

Ile Thr Asp Leu Leu Gly Thr Pro Ser Leu Glu Ala Met Arg Thr Ala
        355                 360                 365

Cys Glu Gly Ala Lys Ala His Ile Leu Arg Gly Pro His Lys Gln Pro
370                 375                 380

Ser Leu Pro Val Leu Tyr Thr Leu Ser Ser Gln Ala Thr His Glu Ala
385                 390                 395                 400

Val His Leu Leu Cys Arg Met Leu Val Phe Asp Pro Ser Lys Arg Ile
                405                 410                 415

Ser Ala Lys Asp Ala Leu Ala His Pro Tyr Leu Asp Glu Gly Arg Leu
            420                 425                 430

Arg Tyr His Thr Cys Met Cys Lys Cys Cys Phe Ser Thr Ser Thr Gly
        435                 440                 445

Arg Val Tyr Thr Ser Asp Phe Glu Pro Val Thr Asn Pro Lys Phe Asp
    450                 455                 460

Asp Thr Phe Glu Lys Asn Leu Ser Ser Val Arg Gln Val Lys Glu Ile
465                 470                 475                 480

Ile His Gln Phe Ile Leu Glu Gln Gln Lys Gly Asn Arg Val Pro Leu
                485                 490                 495

Cys Ile Asn Pro Gln Ser Ala Ala Phe Lys Ser Phe Ile Ser Ser Thr
            500                 505                 510

Val Ala Gln Pro Ser Glu Met Pro Pro Ser Pro Leu Val Trp Glu
        515                 520                 525
```

```
<210> SEQ ID NO 151
<211> LENGTH: 248
<212> TYPE: PRT
<213> ORGANISM: Homo sapiens

<400> SEQUENCE: 151

Met Arg Leu Ile Gln Asn Met Cys Thr Ile Ala Glu Tyr Pro Ala Pro
1               5                   10                  15

Gly Asn Ala Ala Ala Ser Asp Cys Cys Val Gly Ala Ala Gly Arg Arg
            20                  25                  30

Leu Val Lys Ile Ala Val Val Gly Ala Ser Gly Val Gly Lys Thr Ala
        35                  40                  45

Leu Val Val Arg Phe Leu Thr Lys Arg Phe Ile Gly Asp Tyr Glu Arg
    50                  55                  60

Asn Ala Gly Asn Leu Tyr Thr Arg Gln Val Gln Ile Glu Gly Glu Thr
65                  70                  75                  80

Leu Ala Leu Gln Val Gln Asp Thr Pro Gly Ile Gln Val His Glu Asn
                85                  90                  95

Ser Leu Ser Cys Ser Glu Gln Leu Asn Arg Cys Ile Arg Trp Ala Asp
            100                 105                 110

Ala Val Ile Val Phe Ser Ile Thr Asp Tyr Lys Ser Tyr Glu Leu
        115                 120                 125

Ile Ser Gln Leu His Gln His Val Gln Gln Leu His Leu Gly Thr Arg
    130                 135                 140

Leu Pro Val Val Val Ala Asn Lys Ala Asp Leu Leu His Ile Lys
145                 150                 155                 160

Gln Val Asp Pro Gln Leu Gly Leu Gln Leu Ala Ser Met Leu Gly Cys
                165                 170                 175

Ser Phe Tyr Glu Val Ser Val Ser Glu Asn Tyr Asn Asp Val Tyr Ser
            180                 185                 190

Ala Phe His Val Leu Cys Lys Glu Val Ser His Lys Gln Pro Ser
        195                 200                 205

Ser Thr Pro Glu Lys Arg Arg Thr Ser Leu Ile Pro Arg Pro Lys Ser
    210                 215                 220

Pro Asn Met Gln Asp Leu Lys Arg Arg Phe Lys Gln Ala Leu Ser Ala
225                 230                 235                 240

Lys Val Arg Thr Val Thr Ser Val
                245

<210> SEQ ID NO 152
<211> LENGTH: 592
<212> TYPE: PRT
<213> ORGANISM: Homo sapiens

<400> SEQUENCE: 152

Met Pro Ser Arg Thr Gly Pro Lys Met Glu Gly Ser Gly Gly Arg Val
1               5                   10                  15

Arg Leu Lys Ala His Tyr Gly Gly Asp Ile Phe Ile Thr Ser Val Asp
            20                  25                  30

Ala Ala Thr Thr Phe Glu Glu Leu Cys Glu Glu Val Arg Asp Met Cys
        35                  40                  45

Arg Leu His Gln Gln His Pro Leu Thr Leu Lys Trp Val Asp Ser Glu
    50                  55                  60

Gly Asp Pro Cys Thr Val Ser Ser Gln Met Glu Leu Glu Glu Ala Phe
65                  70                  75                  80
```

```
Arg Leu Ala Arg Gln Cys Arg Asp Glu Gly Leu Ile Ile His Val Phe
                85                  90                  95

Pro Ser Thr Pro Glu Gln Pro Gly Leu Pro Cys Pro Gly Glu Asp Lys
            100                 105                 110

Ser Ile Tyr Arg Arg Gly Ala Arg Arg Trp Arg Lys Leu Tyr Arg Ala
            115                 120                 125

Asn Gly His Leu Phe Gln Ala Lys Arg Phe Asn Arg Arg Ala Tyr Cys
            130                 135                 140

Gly Gln Cys Ser Glu Arg Ile Trp Gly Leu Ala Arg Gln Gly Tyr Arg
145                 150                 155                 160

Cys Ile Asn Cys Lys Leu Leu Val His Lys Arg Cys His Gly Leu Val
                165                 170                 175

Pro Leu Thr Cys Arg Lys His Met Asp Ser Val Met Pro Ser Gln Glu
            180                 185                 190

Pro Pro Val Asp Asp Lys Asn Glu Asp Ala Asp Leu Pro Ser Glu Glu
            195                 200                 205

Thr Asp Gly Ile Ala Tyr Ile Ser Ser Arg Lys His Asp Ser Ile
210                 215                 220

Lys Asp Asp Ser Glu Asp Leu Lys Pro Val Ile Asp Gly Met Asp Gly
225                 230                 235                 240

Ile Lys Ile Ser Gln Gly Leu Gly Leu Gln Asp Phe Asp Leu Ile Arg
                245                 250                 255

Val Ile Gly Arg Gly Ser Tyr Ala Lys Val Leu Leu Val Arg Leu Lys
            260                 265                 270

Lys Asn Asp Gln Ile Tyr Ala Met Lys Val Val Lys Lys Glu Leu Val
            275                 280                 285

His Asp Asp Glu Asp Ile Asp Trp Val Gln Thr Glu Lys His Val Phe
            290                 295                 300

Glu Gln Ala Ser Ser Asn Pro Phe Leu Val Gly Leu His Ser Cys Phe
305                 310                 315                 320

Gln Thr Thr Ser Arg Leu Phe Leu Val Ile Glu Tyr Val Asn Gly Gly
                325                 330                 335

Asp Leu Met Phe His Met Gln Arg Gln Arg Lys Leu Pro Glu Glu His
            340                 345                 350

Ala Arg Phe Tyr Ala Ala Glu Ile Cys Ile Ala Leu Asn Phe Leu His
            355                 360                 365

Glu Arg Gly Ile Ile Tyr Arg Asp Leu Lys Leu Asp Asn Val Leu Leu
            370                 375                 380

Asp Ala Asp Gly His Ile Lys Leu Thr Asp Tyr Gly Met Cys Lys Glu
385                 390                 395                 400

Gly Leu Gly Pro Gly Asp Thr Thr Ser Thr Phe Cys Gly Thr Pro Asn
                405                 410                 415

Tyr Ile Ala Pro Glu Ile Leu Arg Gly Glu Glu Tyr Gly Phe Ser Val
            420                 425                 430

Asp Trp Trp Ala Leu Gly Val Leu Met Phe Glu Met Met Ala Gly Arg
            435                 440                 445

Ser Pro Phe Asp Ile Ile Thr Asp Asn Pro Asp Met Asn Thr Glu Asp
450                 455                 460

Tyr Leu Phe Gln Val Ile Leu Glu Lys Pro Ile Arg Ile Pro Arg Phe
465                 470                 475                 480

Leu Ser Val Lys Ala Ser His Val Leu Lys Gly Phe Leu Asn Lys Asp
                485                 490                 495

Pro Lys Glu Arg Leu Gly Cys Arg Pro Gln Thr Gly Phe Ser Asp Ile
```

```
            500                 505                 510
Lys Ser His Ala Phe Arg Ser Ile Asp Trp Asp Leu Leu Glu Lys
        515                 520                 525

Lys Gln Ala Leu Pro Phe Gln Pro Gln Ile Thr Asp Asp Tyr Gly
        530                 535                 540

Leu Asp Asn Phe Asp Thr Gln Phe Thr Ser Glu Pro Val Gln Leu Thr
545                 550                 555                 560

Pro Asp Asp Glu Asp Ala Ile Lys Arg Ile Asp Gln Ser Glu Phe Glu
                565                 570                 575

Gly Phe Glu Tyr Ile Asn Pro Leu Leu Leu Ser Thr Glu Glu Ser Val
                580                 585                 590

<210> SEQ ID NO 153
<211> LENGTH: 673
<212> TYPE: PRT
<213> ORGANISM: Homo sapiens

<400> SEQUENCE: 153

Met Ala Asp Pro Ala Gly Pro Pro Ser Glu Gly Glu Glu Ser
1               5                   10                  15

Thr Val Arg Phe Ala Arg Lys Gly Ala Leu Arg Gln Lys Asn Val His
            20                  25                  30

Glu Val Lys Asn His Lys Phe Thr Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Met Met Asn Val His Lys Arg Cys Val
    130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
        195                 200                 205

Lys Gln Lys Thr Lys Thr Ile Lys Cys Ser Leu Asn Pro Glu Trp Asn
    210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
        275                 280                 285
```

```
Pro Val Pro Pro Glu Gly Ser Glu Ala Asn Glu Glu Leu Arg Gln Lys
    290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
        355                 360                 365

Ala Val Lys Ile Leu Lys Lys Asp Val Val Ile Gln Asp Asp Asp Val
    370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
        435                 440                 445

Glu Ile Ala Ile Gly Leu Phe Phe Leu Gln Ser Lys Gly Ile Ile Tyr
    450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Cys Gly Arg
    610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Glu Phe Leu Lys Pro Glu Val Lys
            660                 665                 670

Ser

<210> SEQ ID NO 154
<211> LENGTH: 312
<212> TYPE: PRT
<213> ORGANISM: Homo sapiens
```

```
<400> SEQUENCE: 154

Met Ala Asp Phe Gly Ile Ser Ala Gly Gln Phe Val Ala Val Val Trp
1               5                   10                  15

Asp Lys Ser Ser Pro Val Glu Ala Leu Lys Gly Leu Val Asp Lys Leu
            20                  25                  30

Gln Ala Leu Thr Gly Asn Glu Gly Arg Val Ser Val Glu Asn Ile Lys
        35                  40                  45

Gln Leu Leu Gln Ser Ala His Lys Glu Ser Ser Phe Asp Ile Ile Leu
    50                  55                  60

Ser Gly Leu Val Pro Gly Ser Thr Thr Leu His Ser Ala Glu Ile Leu
65                  70                  75                  80

Ala Glu Ile Ala Arg Ile Leu Arg Pro Gly Gly Cys Leu Phe Leu Lys
                85                  90                  95

Glu Pro Val Glu Thr Ala Val Asp Asn Asn Ser Lys Val Lys Thr Ala
            100                 105                 110

Ser Lys Leu Cys Ser Ala Leu Thr Leu Ser Gly Leu Val Glu Val Lys
        115                 120                 125

Glu Leu Gln Arg Glu Pro Leu Thr Pro Glu Glu Val Gln Ser Val Arg
    130                 135                 140

Glu His Leu Gly His Glu Ser Asp Asn Leu Leu Phe Val Gln Ile Thr
145                 150                 155                 160

Gly Lys Lys Pro Asn Phe Glu Val Gly Ser Arg Gln Leu Lys Leu
                165                 170                 175

Ser Ile Thr Lys Lys Ser Ser Pro Ser Val Lys Pro Ala Val Asp Pro
        180                 185                 190

Ala Ala Ala Lys Leu Trp Thr Leu Ser Ala Asn Asp Met Glu Asp Asp
    195                 200                 205

Ser Met Asp Leu Ile Asp Ser Asp Glu Leu Leu Asp Pro Glu Asp Leu
210                 215                 220

Lys Lys Pro Asp Pro Ala Ser Leu Arg Ala Ala Ser Cys Gly Glu Gly
225                 230                 235                 240

Lys Lys Arg Lys Ala Cys Lys Asn Cys Thr Cys Gly Leu Ala Glu Glu
                245                 250                 255

Leu Glu Lys Glu Lys Ser Arg Glu Gln Met Ser Ser Gln Pro Lys Ser
            260                 265                 270

Ala Cys Gly Asn Cys Tyr Leu Gly Asp Ala Phe Arg Cys Ala Ser Cys
        275                 280                 285

Pro Tyr Leu Gly Met Pro Ala Phe Lys Pro Gly Glu Lys Val Leu Leu
    290                 295                 300

Ser Asp Ser Asn Leu His Asp Ala
305                 310

<210> SEQ ID NO 155
<211> LENGTH: 546
<212> TYPE: PRT
<213> ORGANISM: Homo sapiens

<400> SEQUENCE: 155

Asp Arg Gly Ser Gly Ala Phe Ser Leu Glu Thr Ile Ala Glu Ser Ser
1               5                   10                  15

Ala Gln Ser Pro Gly Cys Gln Leu Leu Val Glu Thr Leu Gly Val Pro
            20                  25                  30

Leu Gln Glu Ala Thr Glu Leu Gly Asp Pro Thr Gln Ala Asp Ser Ala
        35                  40                  45
```

Arg Pro Glu Gln Ser Ser Gln Ser Pro Val Gln Ala Val Pro Gly Ser
        50                  55                  60

Gly Asp Ser Gln Pro Asp Pro Pro Asp Arg Gly Thr Gly Leu Ser
 65                  70                  75                  80

Ala Ser Gln Arg Ala Ser Gln Asp His Leu Ser Glu Gln Gly Ala Asp
                 85                  90                  95

Asp Ser Lys Pro Glu Thr Asp Arg Val Pro Gly Asp Gly Gln Lys
                100                 105                 110

Glu His Leu Pro Ser Ile Asp Ser Glu Gly Glu Lys Pro Asp Arg Gly
            115                 120                 125

Ala Pro Gln Glu Gly Gly Ala Gln Arg Thr Ala Gly Ala Gly Leu Pro
        130                 135                 140

Arg Gly Pro Gln Glu Glu Gly Asp Gly Val Pro Cys Thr Pro Ala Ser
145                 150                 155                 160

Ala Pro Thr Ser Gly Pro Ala Pro Gly Leu Gly Pro Ala Ser Trp Cys
                165                 170                 175

Leu Glu Pro Gly Ser Val Ala Gln Gly Ser Pro Asp Pro Gln Gln Thr
            180                 185                 190

Pro Ser Arg Met Gly Arg Glu Gly Glu Gly Thr His Ser Ser Leu Gly
        195                 200                 205

Cys Ser Ser Leu Gly Met Val Val Ile Ala Asp Leu Ser Thr Asp Pro
210                 215                 220

Thr Glu Leu Glu Glu Arg Ala Leu Glu Val Ala Gly Pro Asp Gly Gln
225                 230                 235                 240

Ala Ser Ala Ile Ser Pro Ala Ser Pro Arg Arg Lys Ala Ala Asp Gly
                245                 250                 255

Gly His Arg Arg Ala Leu Pro Gly Cys Thr Ser Leu Thr Gly Glu Thr
            260                 265                 270

Thr Gly Glu Ser Gly Glu Ala Gly Gln Asp Gly Lys Pro Pro Gly Asp
        275                 280                 285

Val Leu Val Gly Pro Thr Ala Ser Leu Ala Leu Ala Pro Gly Ser Gly
        290                 295                 300

Glu Ser Met Met Gly Ala Gly Asp Ser Gly His Ala Ser Pro Asp Thr
305                 310                 315                 320

Gly Pro Cys Val Asn Gln Lys Gln Glu Pro Gly Pro Ala Gln Glu Glu
                325                 330                 335

Ala Glu Leu Gly Gly Gln Asn Leu Glu Arg Asp Leu Glu Gly Phe Arg
            340                 345                 350

Val Ser Pro Gln Ala Ser Val Val Leu Glu His Arg Glu Ile Ala Asp
        355                 360                 365

Asp Pro Leu Gln Glu Pro Gly Ala Gln Arg Gly Ile Pro Asp Thr Thr
        370                 375                 380

Ser Glu Leu Ala Gly Gln Arg Asp His Leu Pro His Ser Ala Asp Gln
385                 390                 395                 400

Gly Thr Trp Ala Asp Ser Leu Ala Val Glu Leu Asp Phe Leu Leu Asp
                405                 410                 415

Ser Gln Ile Gln Asp Ala Leu Asp Ala Ser Asp Phe Glu Ala Pro Pro
            420                 425                 430

Glu Gln Leu Phe Pro Ser Gly Asn Lys Pro Gly Pro Cys Trp Pro Gly
        435                 440                 445

Pro Ser Ser His Ala Asn Gly Asp Pro Val Ala Val Ala Lys Ala Gln
    450                 455                 460

-continued

```
Pro Arg Thr Phe Val Gly Ile Gln Ala Ser Glu Ala Ser Arg Met Glu
465                 470                 475                 480

Asp Ala Thr Asn Val Val Arg Gly Leu Ile Val Glu Leu Ser Asn Leu
                485                 490                 495

Asn Arg Leu Ile Met Gly Thr His Arg Asp Leu Glu Ala Phe Lys Arg
            500                 505                 510

Leu Asn Tyr Arg Lys Thr Lys Leu Gly Gly Lys Ala Pro Leu Pro Tyr
        515                 520                 525

Pro Ser Lys Gly Pro Gly Asn Ile Pro Arg Gly Asp Pro Pro Trp Arg
    530                 535                 540

Glu Leu
545
```